US009416382B2

(12) United States Patent
Bostick et al.

(10) Patent No.: US 9,416,382 B2
(45) **Date of Patent: *Aug. 16, 2016**

(54) PRODUCTION OF POLYUNSATURATED FATTY ACIDS BY COEXPRESSION OF ACYL-COA:LYSOPHOSPHATIDYLCHOLINE ACYLTRANSFERASES AND PHOSPHOLIPID:DIACYLGLYCEROL ACYLTRANSFERASES

(71) Applicant: E I DU PONT DE NEMOURS AND COMPANY, Wilmington, DE (US)

(72) Inventors: Michael W Bostick, Wilmington, DE (US); Narendra S Yadav, Wilmington, DE (US); Hongxiang Zhang, Chadds Ford, PA (US); Quinn Qun Zhu, West Chester, PA (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 219 days.

This patent is subject to a terminal disclaimer.

(21) Appl. No.: 13/916,628

(22) Filed: Jun. 13, 2013

(65) Prior Publication Data

US 2013/0337514 A1 Dec. 19, 2013

Related U.S. Application Data

(60) Provisional application No. 61/661,615, filed on Jun. 19, 2012, provisional application No. 61/661,623, filed on Jun. 19, 2012.

(51) Int. Cl.

| | |
|---|---|
| ***C12N 1/21*** | (2006.01) |
| ***C12N 1/15*** | (2006.01) |
| ***C12P 7/64*** | (2006.01) |
| ***C12N 15/81*** | (2006.01) |
| ***C12N 9/10*** | (2006.01) |

(52) U.S. Cl.
CPC ............. *C12P 7/6427* (2013.01); *C12N 9/1029* (2013.01); *C12N 15/815* (2013.01); *Y02P 20/52* (2015.11)

(58) Field of Classification Search
CPC .... C12N 15/815; C12N 9/1029; C12P 7/6427
See application file for complete search history.

(56) References Cited

U.S. PATENT DOCUMENTS

| | | | | |
|---|---|---|---|---|
| 7,267,976 | B2 | 9/2007 | Yadav et al. | |
| 7,588,931 | B2 * | 9/2009 | Damude et al. | 435/254.2 |
| 7,732,155 | B2 | 6/2010 | Zou et al. | |
| 7,901,928 | B2 | 3/2011 | Yadav et al. | |
| 7,932,077 | B2 | 4/2011 | Damude et al. | |
| 2006/0094092 | A1 * | 5/2006 | Damude et al. | 435/134 |
| 2008/0145867 | A1 | 6/2008 | Zou et al. | |
| 2010/0022647 | A1 | 1/2010 | Damude et al. | |
| 2010/0317882 | A1 | 12/2010 | Yadav et al. | |
| 2010/0323085 | A1 | 12/2010 | Ochiai | |
| 2012/0052537 | A1 | 3/2012 | Hong et al. | |

FOREIGN PATENT DOCUMENTS

| | | | |
|---|---|---|---|
| CA | 2517253 | A1 | 9/2004 |
| CA | 2520795 | A1 | 10/2004 |
| CA | 2591599 | A1 | 7/2006 |
| WO | 2004076617 | A2 | 9/2004 |
| WO | 2004087902 | A2 | 10/2004 |
| WO | 2006052870 | A2 | 5/2006 |
| WO | 2006069936 | A2 | 7/2006 |
| WO | 2006127655 | A2 | 11/2006 |
| WO | 2009001315 | A2 | 12/2008 |
| WO | 2009014140 | A1 | 1/2009 |
| WO | 2009129582 | A1 | 10/2009 |

OTHER PUBLICATIONS

Branden et al., Introduction to Protein Structure, Garland Publishing Inc., New York, p. 247, 1991.*

Seffernick et al., J. Bacteriol. 183(8):2405-2410, 2001.*

Witkowski et al., Biochemistry 38:11643-11650, 1999.*

Guo et al., PNAS 101(25):9205-9210, 2004.*

International Search Report, Related PCT International Application No. PCT/US2012/045628, Mailed Sep. 30, 2013.

Soupene et al., Phosphatidylcholine Formation by LPCAT1 Is Regulated by CA2+ and the Redox Status of the Cell, BMC Biochemistry, Biomed Central, London, GB, vol. 13, No. 1 (2012), pp. 1-11.

Paramesvaran et al., Distributions of Enzyme Residues Yielding Mutants With Different Directed Evolution Strategies, Protein Engineering Design and Selection, vol. 22, No. 7 (209), pp. 401-411.

Related U.S. Appl. No. 13/916,644, Michael E. Bostick, filed Jun. 13, 2013.

Abbadi et al., Biosynthesis of Very-Long-Chain Polyunsaturated Fatty Acids in Transgenic Oilseeds; Contraints on Their Accumulation, The Plant Cell, vol. 16 (2004), pp. 2734-2748.

Benghezal et al., SLC1 and SLC4 Encode Partially Redundant Acyl-Coenzyme A 1-Acylglycerol-3-Phosphate O-Acyltransferases of Budding Yeast, The Journal of Biological Chemistry, vol. 282, No. 42 (2007), pp. 30845-30855.

(Continued)

*Primary Examiner* — Delia Ramirez

(57) ABSTRACT

Acyl-CoA:lysophosphatidylcholine acyltransferase ["LPCAT"] having the ability to convert acyl-CoA+1-acyl-sn-glycero-3-phosphocholine to CoA+1,2-diacyl-sn-glycero-3-phosphocholine (EC 2.3.1.23) is disclosed herein to be over-expressed along with the over-expression of phospholipid: diacylglycerol acyltransferase ["PDAT"] having the ability to transfer a fatty acyl group from the sn-2 position of a phospholipid (e.g., phosphatidylcholine) to the sn-3 position of 1,2-diacylglycerol [E.C.2.3.1.158], thus resulting in a lysophospholipid and TAG. Co-expression of these enzymes in a recombinant microbial host cell resulted in increased production of long chain polyunsaturated fatty acids ["PUFAs"].

12 Claims, 4 Drawing Sheets

(56) References Cited

OTHER PUBLICATIONS

Chen et al., The Yeast Acylglycerol Acyltransferase LCA1 Is a Key Component of Lands Cycle for Phosphatidylcholine Turnover, FEBS Letters, vol. 581 (2007), pp. 5511-5516.
Dahlqvist et al., Phospholipid: Diacylglycerol Acyltransferase: An Enzyme That Catalyzes the Acyl-CoA-Independent Formation of Triacylglycerol in Yeast and Plants, PNAS, vol. 97, No. 12 (2000), pp. 6487-6492.
Domergue et al., Acyl Carriers Used as Substrates by the Desaturases and Elongases Involved in Very Long-Chain Polyunsaturated Fatty Acids Biosynthesis Reconstituted in Yeast, The Journal of Biological Chemistry, vol. 278, No. 37 (2003), pp. 35115-35126.
Hishikawa et al., Discovery of a Lysophospholipid acyltransferese Family Essential for Membrane Asymmetry and Diversity, PNAS, vol. 105, No. 8 (2008), pp. 2830-2835.
Lands, Metabolism of Glycerolipides: A Comparison of Leithin and Triglyceride Synthesis, J. Biological Chemistry, vol. 231 (1958), pp. 883-888.
Lee et al., Caenorhabditis elegans MBOA-7, A Member of the MBOAT Family, Is Required for Selective Incorporation of Polyunsaturated Fatty Acids Into Phosphatidylinositol, Molecular Biology of the Cell, vol. 19 (2008), pp. 1174-1184.
Lewin et al., Analysis of Amino Acids Motifs Diagnostic for the Sn-Glycerol-3-Phosphate Acyltransferase Reaction, Biochemistry, vol. 38 (1999), pp. 5764-5771.
Oelkers et al., A Lecithin Cholesterol Acyltransferase-Like Gene Mediates Diacylglycerol Esterification in Yeast, Accelerated Publication the Journal of Biological Chemistry, vol. 275, No. 21 (2000), pp. 15509-15612.
Riekhof et al., Identification and Characterization of the Major Lysophosphatidylethanolamine Acyltransferase in *Saccharomyces cerevisiae*, The Journal of Biological Chemistry, vol. 282, No. 39 (2007), pp. 28344-28352.
Shindou et al., Identification of Membrane O-Acyltransferase Family Motifs, Biochemical and Biophysical Research Communications, vol. 383 (2009), pp. 320-325.
Stahl et al., A Family of Eukaryotic Lysophospholipid Acyltransferases With Broad Specificity, FEBS Letters, vol. 582 (2008), pp. 305-309.
Stymne et al., Evidence for the Reversibility of the Acyl-CoA: Lysophosphatidylcholine Acyltransferase in Microsomal Preparation From Developing Safflower (*Carthamus tinctorius* L.) Cotyledons and Rat Liver, Biochem J., vol. 223 (1984), pp. 305-314.
Tamaki et al., LPT1 Encodes a Membrane-Bound O-Acyltransferase Involved in the Acylation of Lysophospholipids in the Yeast *Saccharomyces cerevisiae*, The Journal of Biological Chemistry, vol. 282, No. 47 (2007), pp. 34288-34298.
Yamashita et al., Topology of Acyltransferase Motifs and Substrate Specificity and Accessibility in 1-Acyl-Sn-Glycero-3-Phosphate Acyltransferase 1, Biochimica Et Biophysica, vol. 1771 (2007).
International Search Report, PCT International Application No. PCT/US2013/045592, Mailed Aug. 8, 2013.
Snyder et al., Acyltransferase Action in the Modification of Seed Oil Biosynthesis, New Biotechology, vol. 26, No. 1-2 (2009), pp. 11-16.
Xu et al., Triacylglycerol Synthesis by PDAT1 in the Absence of DGAT1 Activity Is Dependent on Re-Acylation of LPC by LPCAT2, BMC Plant Biology, vol. 12, No. 1 (2012), pp. 1-22.

* cited by examiner

A)

B)

PRODUCTION OF POLYUNSATURATED FATTY ACIDS BY COEXPRESSION OF ACYL-COA:LYSOPHOSPHATIDYLCHOLINE ACYLTRANSFERASES AND PHOSPHOLIPID:DIACYLGLYCEROL ACYLTRANSFERASES

This application claims the benefit of U.S. Provisional Application Nos. 61/661,615 and 61/661,623, each filed Jun. 19, 2012, both of which are incorporated herein by reference in their entirety.

FIELD OF THE INVENTION

This invention is in the field of biotechnology. More specifically, this invention pertains to over-expression of both a polynucleotide sequence encoding acyl-CoA:lysophosphatidylcholine acyltransferase and a polynucleotide sequence encoding phospholipid:diacylglycerol acyltransferase as a means to improve production of long-chain polyunsaturated fatty acids ["PUFAs"] in a recombinant microbial cell.

BACKGROUND OF THE INVENTION

Glycerophospholipids, the main component of biological membranes, contain a glycerol core with fatty acids attached as R groups at the sn-1 position and sn-2 position, and a polar head group joined at the sn-3 position via a phosphodiester bond. The specific polar head group determines the name given to a particular glycerophospholipid (e.g., a chloline head group results in a phosphatidylcholine). Glycerophospholipids possess tremendous diversity, not only resulting from variable phosphoryl head groups, but also as a result of differing chain lengths and degrees of saturation of their fatty acids. Generally, saturated and monounsaturated fatty acids are esterified at the sn-1 position, while polyunsaturated fatty acids are esterified at the sn-2 position.

Glycerophospholipid biosynthesis, summarized in U.S. Pat. Appl. Publ. No. 2010-0317882-A1, requires a variety of acyltransferases, including glycerol-3-phosphate acyltransferase (GPAT) [E.C. 2.3.1.15], acyl-CoA:lysophosphatidic acid acyltransferase (LPAAT) [E.C. 2.3.1.51], diacylglycerol acyltransferase (DGAT) [E.C. 2.3.1.20] and phospholipid: diacylglycerol acyltransferase (PDAT) [E.C.2.3.1.158].

Following their de novo synthesis, glycerophospholipids can undergo rapid turnover of the fatty acyl composition at the sn-2 position. This "remodeling", or "acyl editing", is important for membrane structure and function, biological response to stress conditions, and manipulation of fatty acid composition and quantity in biotechnological applications. Specifically, the remodeling has been attributed to a combination of deacylation and reacylation of glycerophospholipid. For example, in the Lands' cycle (Lands, *J. Biol. Chem.,* 231:883-888 (1958)), remodeling occurs through the concerted action of: 1) a phospholipase, such as phospholipase $A_2$, that releases fatty acids from the sn-2 position of phosphatidylcholine; and 2) acyl-CoA:lysophospholipid acyltransferases ["LPLATs"], such as acyl-CoA:lysophosphatidylcholine acyltransferase ["LPCAT"] that reacylates the lysophosphatidylcholine ["LPC"] at the sn-2 position (thereby removing acyl-CoA fatty acids from the cellular acyl-CoA pool and acylating lysophospholipid substrates at the sn-2 position in the phospholipid pool). Remodeling has also been attributed to reversible LPCAT activity (Stymne and Stobart (*Biochem J.,* 223(2):305-314 (1984))

The effect of LPCATs (and other LPLATs that have LPCAT activity) on polyunsaturated fatty acid ["PUFA"] production has been contemplated, since fatty acid biosynthesis requires rapid exchange of acyl groups between the acyl-CoA pool and the phospholipid pool. Specifically, desaturations occur mainly at the sn-2 position of phospholipids, while elongation occurs in the acyl-CoA pool. More specifically, U.S. Pat. No. 7,932,077 hypothesized that acyltransferases, including PDAT and LPCAT, could be important in the accumulation of PUFAs (e.g., eicosapentaenoic acid ["EPA"], 20:5 omega-3) in the TAG fraction of *Yarrowia lipolytica*. As described therein, this was based on the following studies: 1) Stymne and Stobart (*Biochem J.,* 223(2):305-314 (1984)), who hypothesized that the exchange between the acyl-CoA pool and PC pool may be attributed to the forward and backward reaction of LPCAT; 2) Domergue et al. (*J. Biol. Chem.,* 278:35115-35126 (2003)), who suggested that accumulation of gamma-linolenic acid ["GLA"] at the sn-2 position of phosphatidylcholine ["PC"] and the inability to efficiently synthesize arachidonic acid ["ARA"] (20:4 omega-6) in yeast was a result of the elongation step involved in PUFA biosynthesis occurring within the acyl-CoA pool, while delta-5 and delta-6 desaturation steps occurred predominantly at the sn-2 position of PC; 3) Abbadi et al. (*The Plant Cell,* 16:2734-2748 (2004)), who suggested that LPCAT plays a critical role in the successful reconstitution of a delta-6 desaturase/delta-6 elongase pathway, based on analysis of the constraints of PUFA accumulation in transgenic oilseed plants; and 4) Intl. Appl. Publ. No. WO 2004/076617 A2 (Renz et al.), who provided a gene encoding LPCAT from *Caenorhabditis elegans* (T06E8.1) that substantially improved the efficiency of elongation in a genetically introduced delta-6 desaturase/delta-6 elongase pathway in *S. cerevisiae* fed with exogenous fatty acid substrates suitable for delta-6 elongation. Renz et al. concluded that LPCAT allowed efficient and continuous exchange of the newly synthesized fatty acids between phospholipids and the acyl-CoA pool, since desaturases catalyze the introduction of double bonds in PC-coupled fatty acids while elongases exclusively catalyze the elongation of CoA-esterified fatty acids (acyl-CoA).

U.S. Pat. Appl. Publ. No. 2010-0317882-A1 provided further support that LPCAT is indeed important in the accumulation of EPA and docosahexaenoic acid ["DHA"] (22:6 omega-3) in the TAG fraction of *Yarrowia lipolytica*. It was found that over-expression of LPCATs can result in an improvement in the delta-9 elongase conversion efficiency and/or delta-4 desaturase conversion efficiency (wherein conversion efficiency is a term that refers to the efficiency by which a particular enzyme can convert substrate to product). Thus, in a strain engineered to produce EPA, improvement in delta-9 elongase conversion efficiency was demonstrated to result in increased EPA % TFAs or EPA % DCW. Similarly, improvement in delta-9 elongase and/or delta-4 desaturase conversion efficiency in a strain engineered to produce DHA was demonstrated to result in increased DHA % TFAs or DHA % DCW.

Numerous other references generally describe benefits of co-expressing LPLATs with PUFA biosynthetic genes to increase the amount of a desired fatty acid in the oil of a transgenic organism, increase total oil content, or selectively increase the content of desired fatty acids (e.g., Intl. Appl. Publication Nos. WO 2004/087902, WO 2006/069936, WO 2006/052870, WO 2009/001315, WO 2009/014140). However, none of these references describe the benefits achieved in an organism engineered for high-level production of LC-PUFAs when an LPCAT and a phospholipid:diacylglycerol acyltransferase (PDAT) are both over-expressed. PDAT is an enzyme responsible for transferring a fatty acyl-group from the sn-2 position of a phospholipid (e.g., phosphatidylcholine) to the sn-3 position of 1,2-diacylglycerol to produce a lysophospholipid and TAG via an acyl-CoA-independent mechanism.

Furthermore, despite reports of a variety of conserved membrane bound O-acyltransferase ["MBOAT"] family protein motif sequences within LPCATs in both public and patent literature, a detailed investigation concerning specific mutations within these motifs has not been previously conducted.

SUMMARY OF THE INVENTION

In one embodiment, the invention concerns a recombinant microbial cell for the production of at least one long-chain polyunsaturated fatty acid (PUFA). The recombinant microbial cell comprises:

(a) at least one polypeptide having acyl CoA:lysophosphatidylcholine acyltransferase (LPCAT) activity;

(b) at least one polypeptide having phospholipid:diacylglycerol acyltransferase (PDAT) activity; and (c) a polyunsaturated fatty acid biosynthetic pathway capable of producing at least one long-chain polyunsaturated fatty acid;

wherein the polypeptides of (a) and (b) are over-expressed in the recombinant microbial cell. The recombinant microbial cell also comprises an increased amount of a PUFA measured as a weight percent of total fatty acids, when compared to the amount of the PUFA measured as a weight percent of total fatty acids in a control cell.

In a second embodiment, the recombinant microbial cell further comprises at least one of the following:

(i) an increased $C_{18}$ to $C_{20}$ elongation conversion efficiency with respect to the $C_{18}$ to $C_{20}$ elongation conversion efficiency of a control cell, or (ii) an increased amount of total fatty acids measured as a weight percent of dry cell weight, in comparison to the amount of total fatty acids measured as a weight percent of dry cell weight in a control cell.

Preferably, the increased $C_{18}$ to $C_{20}$ elongation conversion efficiency is an effect of increased delta-9 elongase conversion efficiency or increased delta-6 elongase conversion efficiency in the recombinant microbial cell.

In a third embodiment, the polypeptide having PDAT activity has at least 90% or 95% amino acid identity, based on the Clustal W method of alignment, when compared to an amino acid sequence selected from the group consisting of SEQ ID NO:32 (YlPDAT) and SEQ ID NO:30 (ScPDAT).

In a fourth embodiment, the polypeptide having LPCAT activity is selected from the group consisting of:

(a) a polypeptide having at least 45% amino acid identity, based on the Clustal W method of alignment, when compared to an amino acid sequence selected from the group consisting of SEQ ID NO:2 (ScLPCAT) and SEQ ID NO:4 (YlLPCAT);

(b) a polypeptide comprising at least one membrane-bound O-acyltransferase protein family motif selected from the group consisting of: SEQ ID NO:5 (WHG-$X_3$-GY-$X_3$-F), SEQ ID NO:6 (Y-$X_4$-F), SEQ ID NO:7 (Y-$X_3$-YF-$X_2$-H), SEQ ID NO:8 (M-[V/I]-[L/I]-$X_2$-K-[L/V/I]-$X_8$-DG), SEQ ID NO:9 (RxKYY-$X_2$-W-$X_3$-[E/D]-[A/G]-$X_5$-GxG-[F/Y]-xG), SEQ ID NO:10 (E$X_{11}$WN-$X_2$-[T/V]-$X_2$-W), SEQ ID NO:11 (SAxWHG-$X_2$-PGY-$X_2$-[T/F]-F), SEQ ID NO:12 (M-[V/I]-[L/I/V]-[V/C/A/THM/L/Q]-K-[L/V/I/M]-[S/T/Y/I]-[S/T/A/M/G]-[F/L/C/Y]-[C/A/G/S]-[W/Y/M/I/F/C]-[N/S/E/Q/D]-[V/Y/L/I]-[H/Y/A/N/S/T]-DG), SEQ ID NO:13 (R-[L/M/F/W/P/Y]-KYY-[G/A/F/H/S]-[V/A/I/C]-W-[Y/E/T/M/S/L]-[L/I/N]-[T/S/A]-[E/D]-[G/A]-[A/S/I/V]-[C/S/I/N/H/L]-[V/I/N]-[L/I/N/A/C]-[S/C/W/A/I]-G-[M/I/L/A/F]-G-[Y/F]-[N/E/S/T/R/K]-G), SEQ ID NO:14 (E-[T/F/L/M]-[A/S]-[Q/D/P/K/T]-[N/S]-[S/I/T/L/A/M/F]-[H/K/R/V]-[G/C/E/T/Q/D/M]-[Y/A/M/L/I/F]-[L/S/P/I]-[G/E/A/L/N/D]-[S/A/V/F/M/N]-WN-[K/M/I/C]-[N/K/Q/G]-[T/V]-[N/A/S]-[H/K/N/T/R/L]-W), SEQ ID NO:15 (SA-[F/M/V/I]-WHG-[F/V/T/L]-[Y/S/R]-PGY-[Y/M/I]-[L/M/I/F]-[T/F]-F), SEQ ID NO:16 (M-[V/I]-L-$X_2$-KL), SEQ ID NO:17 (RxKYY-$X_2$-W), and SEQ ID NO:18 (SAxWHG);

(c) a polypeptide comprising at least one mutant membrane-bound O-acyltransferase protein family motif selected from the group consisting of:

(i) a mutant motif comprising an amino acid sequence as set forth in SEQ ID NO:38, wherein SEQ ID NO:38 differs from SEQ ID NO:16 (M-[V/I]-L-$X_2$-KL) by at least one amino acid mutation selected from the group consisting of: V2C, I2C, L3A, L3C, L3G, K6H, K6G, K6N, K6Y, L7A, L7N, L7G, L7H, L7I and L7M;

(ii) a mutant motif comprising an amino acid sequence as set forth in SEQ ID NO:39, wherein SEQ ID NO:39 differs from SEQ ID NO:8 (M-[V/I]-[L/I]-$X_2$-K-[L/V/I]-$X_8$-DG) by at least one amino acid mutation selected from the group consisting of: V2C, I2C, L3A, L3C, L3G, I3A, I3G, I3G, K6H, K6G, K6N, K6Y, L7A, L7N, L7G, L7H, L7M, V7A, V7N, V7G, V7H, V7M, I7A, I7N, I7G, I7H, I7M, D16Q, D16N, D16H, G17A, G17V and G17N;

(iii) a mutant motif comprising an amino acid sequence as set forth in SEQ ID NO:40, wherein SEQ ID NO:40 differs from SEQ ID NO:5 (WHG-$X_3$-GY-$X_3$-F) by at least one amino acid mutation selected from the group consisting of: F12N, F12C, F12G and F12T; and (iv) a mutant motif comprising an amino acid sequence as set forth in SEQ ID NO:41, wherein SEQ ID NO:41 differs from SEQ ID NO:11 (SAxWHG-$X_2$-PGY-$X_2$-[T/F]-F) by at least one amino acid mutation selected from the group consisting of: T14A, T14C, T145, F14A, F14C, F145, F15N, F15C, F15G and F15T;

(d) a polypeptide having at least 43.9% amino acid identity, based on the Clustal W method of alignment, when compared to an amino acid sequence selected from the group consisting of SEQ ID NO:21 (MaLPAAT1), SEQ ID NO:23 (YlLPAAT1) and SEQ ID NO:24 (ScLPAAT); and (e) a polypeptide comprising at least one 1-acyl-sn-glycerol-3-phosphate acyltransferase family motif selected from the group consisting of: SEQ ID NO:25 (NHxxxxD) and SEQ ID NO:26 (EGTR).

In a fifth embodiment, the long-chain PUFA is selected from the group consisting of: eicosadienoic acid, dihomo-gamma-linolenic acid, arachidonic acid, docosatetraenoic acid, omega-6 docosapentaenoic acid, eicosatrienoic acid, eicosatetraenoic acid, eicosapentaenoic acid, omega-3 docosapentaenoic acid and docosahexaenoic acid. Preferably, the PUFA is eicosapentaenoic acid.

In a sixth embodiment, the recombinant microbial cell is selected from the group consisting of: algae, yeast, euglenoids, stramenopiles, oomycetes and fungi. Preferably, the recombinant microbial cell is an oleaginous yeast. The oleaginous yeast may be of the genus *Yarrowia*.

Another embodiment of the invention concerns a method for improving the production of at least one long-chain PUFA. This method comprises:

(a) growing the recombinant microbial cell of the invention in the presence of a fermentable carbon source; and (b) optionally, recovering the long-chain PUFA.

In one aspect of the method, the recombinant microbial cell is an oleaginous yeast and the long-chain PUFA is selected from the group consisting of: eicosadienoic acid, dihomo-gamma-linolenic acid, arachidonic acid, docosatetraenoic acid, omega-6 docosapentaenoic acid, eicosatrienoic acid, eicosatetraenoic acid, eicosapentaenoic acid, omega-3 docosapentaenoic acid and docosahexaenoic acid. Preferably, the PUFA is eicosapentaenoic acid. In another aspect of the method, the oleaginous yeast is of the genus *Yarrowia*.

BRIEF DESCRIPTION OF THE DRAWINGS AND SEQUENCE LISTING

Figure 3:
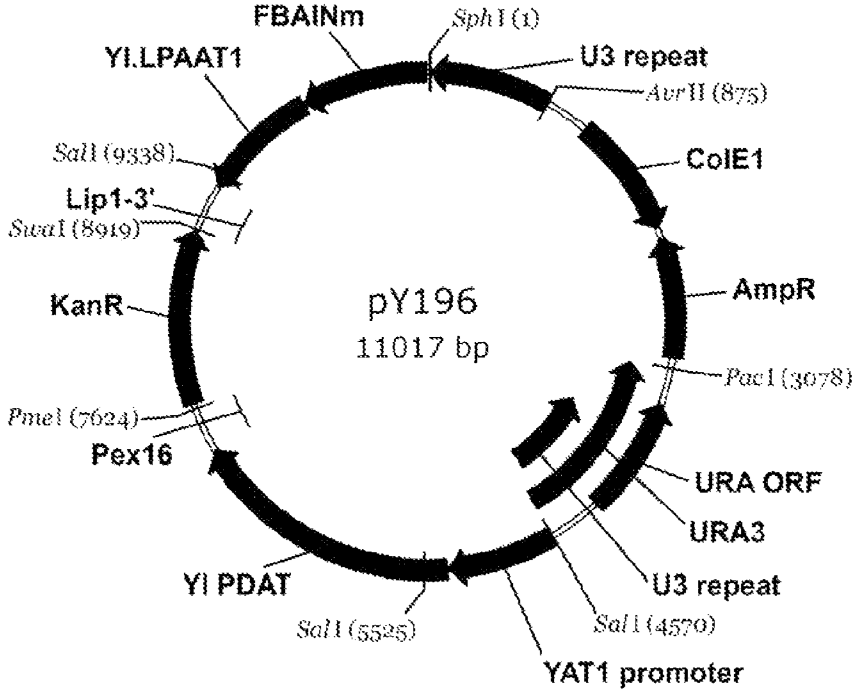
Figure 3:
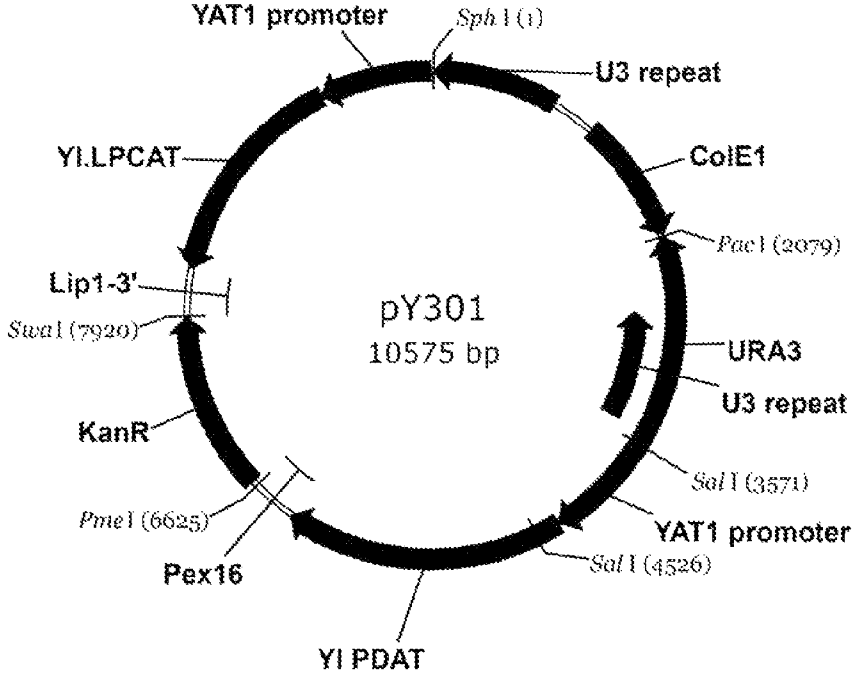

FIG. 3 provides plasmid maps for the following: (A) pY196 and (B) pY301.

Figure 4:
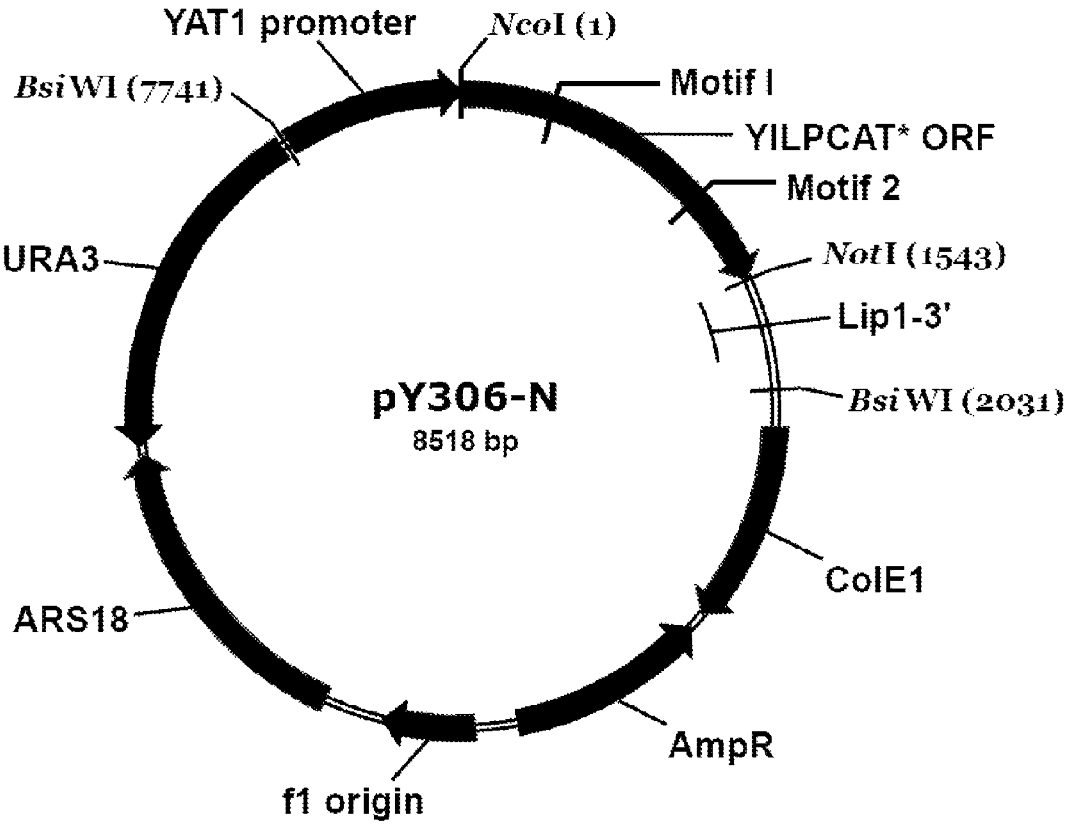

FIG. 4 provides a plasmid map for pY306-N.

The invention can be more fully understood from the following detailed description and the accompanying sequence descriptions (Table 1), which form a part of this application.

TABLE 1

Summary of Gene and Protein SEQ ID NOs

| Description | Nucleic acid SEQ ID NO. | Protein SEQ ID NO. |
|---|---|---|
| *Saccharomyces cerevisiae* Ale1 (“ScAle1” or “ScLPAAT”; also ORF “YOR175C”) | 1 (1860 bp) | 2 (619 AA) |
| *Yarrowia lipolytica* Ale1 (“YlAle1” or “YlLPCAT”) (YALI0F19514p) | 3 (1539 bp) | 4 (512 AA) |
| Shindou et al. WHG-$X_3$-GY-$X_3$-F motif | — | 5 |
| Shindou et al. Y-$X_4$-F motif | — | 6 |
| Shindou et al. Y-$X_3$-YF-$X_2$-H motif | — | 7 |
| U.S. Pat. Appl. Publ. No. 2008-0145867-A1 M-[V/I]-[L/I]-$X_2$-K-[L/V/I]-$X_8$-DG motif | — | 8 |
| U.S. Pat. Appl. Publ. No. 2008-0145867-A1 RxKYY-$X_2$-W-$X_3$-[E/D]-[A/G]-$X_5$-GxG-[F/Y]-xG motif | — | 9 |
| U.S. Pat. Appl. Publ. No. 2008-0145867-A1 E$X_{11}$WN-$X_2$-[T/V]-$X_2$-W motif | — | 10 |
| U.S. Pat. Appl. Publ. No. 2008-0145867-A1 SAxWHG-$X_2$-PGY-$X_2$-[T/F]-F motif | — | 11 |
| U.S. Pat. No. 7,732,155 motif | — | 12 |
| U.S. Pat. No. 7,732,155 motif | — | 13 |
| U.S. Pat. No. 7,732,155 motif | — | 14 |
| U.S. Pat. No. 7,732,155 motif | — | 15 |
| U.S. Pat. Appl. Publ. No. 2010-0317882-A1 M-[V/I]-L-$X_2$-KL motif | — | 16 |
| U.S. Pat. Appl. Publ. No. 2010-0317882-A1 RxKYY-$X_2$-W motif | — | 17 |
| U.S. Pat. Appl. Publ. No. 2010-0317882-A1 SAxWHG motif | — | 18 |
| Mutant YlLPCAT, comprising a mutant Motif I motif and/or a mutant Motif II motif | — | 19 (512 AA) |
| *Mortierella alpina* LPAAT1 (“MaLPAAT1”) | 20 (945 bp) | 21 (314 AA) |
| *Yarrowia lipolytica* LPAAT1 (“YlLPAAT1”) | 22 (1549 bp) | 23 (282 AA) |
| *Saccharomyces cerevisiae* LPAAT (“ScLPAAT”; also ORF “YDL052C”) | — | 24 (303 AA) |
| 1-acyl-sn-glycerol-3-phosphate acyltransferase motif NHxxxxD | — | 25 |
| 1-acyl-sn-glycerol-3-phosphate acyltransferase motif EGTR | — | 26 |
| Lewin et al. and Yamashita et al. 1-acyl-sn-glycerol-3-phosphate acyltransferase motif GxxFI-[D/R]-R | — | 27 |
| Yamashita et al. 1-acyl-sn-glycerol-3-phosphate acyltransferase motif [V/I]-[P/X]-[I/V/L]-[I/V]-P-[V/I] | — | 28 |
| Yamashita et al. 1-acyl-sn-glycerol-3-phosphate acyltransferase motif IVPIVM | — | 29 |
| *Saccharomyces cerevisiae* PDAT (GenBank Accession No. P40345) | — | 30 (661 AA) |
| *Yarrowia lipolytica* phospholipid:diacylglycerol acyltransferase (“YlPDAT”) | 31 (1947 bp) | 32 (648 AA) |
| Mutant M-[V/I]-L-$X_2$-KL motif | — | 33 |
| Mutant M-[V/I]-[L/I]-$X_2$-K-[L/V/I]-$X_8$-DG motif | — | 34 |
| Mutant WHG-$X_3$-GY-$X_3$-F motif | — | 35 |
| Mutant SAxWHG-$X_2$-PGY-$X_2$-[T/F]-F motif | — | 36 |
| Mutant YlLPCAT, comprising single mutations in Motif I and/or Motif II | — | 37 (512 AA) |
| Mutant M-[V/I]-L-$X_2$-KL motif | — | 38 |
| Mutant M-[V/I]-[L/I]-$X_2$-K-[L/V/I]-$X_8$-DG motif | — | 39 |

TABLE 1-continued

| Summary of Gene and Protein SEQ ID NOs | | |
|---|---|---|
| Description | Nucleic acid SEQ ID NO. | Protein SEQ ID NO. |
| Mutant WHG-$X_3$-GY-$X_3$-F motif | — | 40 |
| Mutant SAxWHG-$X_2$-PGY-$X_2$-[T/F]-F motif | — | 41 |
| Mutant YlLPCAT, comprising a single mutation in Motif I and a single mutation in Motif II | — | 42 (512 AA) |
| Plasmid pY196 for co-expressing PDAT and LPAAT | 43 (11017 bp) | |
| Plasmid pY301 for co-expressing PDAT and LPCAT | 44 (10575 bp) | |
| "YlLPCAT*", YlLPCAT lacking two internal NcoI restriction sites with respect to SEQ ID NO: 3, but encoding wild type YlLPCAT protein | 45 (1549 bp) | 46 (512 AA) |
| Plasmid pY306, containing YlLPCAT | 47 (8518 bp) | |
| Plasmid pY306-N, containing YlLPCAT* | 48 (8518 bp) | |
| YlLPCAT_M132X, comprising M132A, M132N, M132C, M132G, M132Q, M132H, M132I, M132L, M132F, M132P, M132S, M132T, M132W, M132Y or M132V mutation in Motif I | — | 49 |
| YlLPCAT_V133X, comprising V133A, V133N, V133C, V133G, V133Q, V133H, V133L, V133M, V133F, V133P, V133S, V133T, V133W or V133Y mutation in Motif I | — | 50 |
| YlLPCAT_L134X, comprising L134A, L134N, L134C, L134G, L134Q, L134H, L134M, L134F, L134P, L134S, L134T, L134W, L134Y or L134V mutation in Motif I | — | 51 |
| YlLPCAT_C135X, comprising C135R, C135N, C135D, C135G, C135E, C135Q, C135H, C135I, C135L, C135K, C135M, C135F, C135P, C135S, C135W or C135Y mutation in Motif I | — | 52 |
| YlLPCAT_M136X, comprising M136A, M136N, M136C, M136G, M136H, M136I, M136F, M136P, M136S, M136T, M136W, M136Y or M136V mutation in Motif I | — | 53 |
| YlLPCAT_K137X, comprising K137A, K137R, K137N, K137G, K137H, K137P, K137S, K137T, or K137Y mutation in Motif I | — | 54 |
| YlLPCAT_L138X, comprising L138A, L138N, L138C, L138G, L138Q, L138H, L138I, L138M, L138F, L138P, L138S, L138T, L138W, or L138Y mutation in Motif I | — | 55 |
| YlLPCAT_S139X, comprising S139A, S139N, S139C, S139G, S139H, S139L, S139M, S139F, S139P, S139W, or S139V mutation in Motif I | — | 56 |
| YlLPCAT_S140X, comprising S140N, S140C, S140H, S140I, S140L, S140F, S140P, S140W, S140Y or S140V mutation in Motif I | — | 57 |
| YlLPCAT_F141X, comprising F141A, F141N, F141G, F141H, F141I, F141M, F141P, F141S, F141T, F141W, or F141V mutation in Motif I | — | 58 |
| YlLPCAT_G142X, comprising G142N, G142H, G142I, G142L, G142M, G142F, G142P, G142T, G142W, G142Y or G142V mutation in Motif I | — | 59 |
| YlLPCAT_W143X, comprising W143A, W143G, W143H, W143L, W143K, W143P, W143S, W143T or W143V mutation in Motif I | — | 60 |
| YlLPCAT_N144X, comprising N144A, N144R, N144G, N144H, N144K, N144F, N144P, N144T or N144V mutation in Motif I | — | 61 |
| YlLPCAT_V145X, comprising V145A, V145C, V145G, V145E, V145H, V145M, V145F, V145P, V145S, V145T, or V145W mutation in Motif I | — | 62 |
| YlLPCAT_Y146X, comprising Y146R, Y146N, Y146D, Y146G, Y146E, Y146Q, Y146I, Y146L, Y146M, Y146F, Y146P, Y146W or Y146V mutation in Motif I | — | 63 |
| YlLPCAT_D147X, comprising D147A, D147N, D147G, D147E, D147Q, D147H, D147F, D147S, or D147T mutation in Motif I | — | 64 |
| YlLPCAT_G148X, comprising G148A, G148N, G148H, G148L, G148M, G148F, G148S, G148T or G148V mutation in Motif I | — | 65 |

TABLE 1-continued

| Summary of Gene and Protein SEQ ID NOs | | |
|---|---|---|
| Description | Nucleic acid SEQ ID NO. | Protein SEQ ID NO. |
| YlLPCAT_S376X, comprising S376A, S376G, S376H, S376L, S376F, S376P, S376T or S376V mutation in Motif II | — | 66 |
| YlLPCAT_A377X, comprising A377N, A377G, A377H, A377L, A377F, A377P, A377S, A377T or A377V mutation in Motif II | — | 67 |
| YlLPCAT_F378X, comprising F378A, F378N, F378C, F378G, F378H, F378L, F378P, F378S, F378T, F378W, or F378Y mutation in Motif II | — | 68 |
| YlLPCAT_T382X, comprising T382A, T382N, T382G, T382Q, T382H, T382I, T382M, T382P, T382S, T382W and or T382Y mutation in Motif II | — | 69 |
| YlLPCAT_R383X, comprising R383A, R383N, R383D, R383G, R383E, R383Q, R383H, R383I, R383L, R383K, R383M, R383F, R383P, R383T, R383W or R383V mutation in Motif II | — | 70 |
| YlLPCAT_P384X, comprising P384A, P384R, P384G, P384H, P384I, P384L, P384K, P384M, P384F, P384S, P384T, P384W, P384Y or P384V mutation in Motif II | — | 71 |
| YlLPCAT_G385X, comprising G385A, G385N, G385C, G385G, G385H, G385I, G385L, G385K, G385M, G385F, G385S, G385T, G385W, G385Y or G385V mutation in Motif II | — | 72 |
| YlLPCAT_Y386X, comprising Y386A, Y386G, Y386H, Y386L, Y386F, Y386P, Y386S, Y386T or Y386V mutation in Motif II | — | 73 |
| YlLPCAT_Y387X, comprising Y387A, Y387G, Y387H, Y387L, Y387F, Y387P, Y387S, Y387T, Y387W or Y387V mutation in Motif II | — | 74 |
| YlLPCAT_L388X, comprising L388A, L388G, L388H, L388P, L388S, L388T, L388W, L388Y or L388V mutation in Motif II | — | 75 |
| YlLPCAT_T389X, comprising T389A, T389C, T389G, T389H, T389I, T389L, T389M, T389F, T389P, T389S, T389W, T389Y or T389V mutation in Motif II | — | 76 |
| YlLPCAT_F390X, comprising F390A, F390N, F390C, F390G, F390H, F390L, F390M, F390P, F390S, F390T or F390V mutation in Motif II | — | 77 |
| YlLPCAT comprising M136S_T389A | 78 | 79 |
| YlLPCAT comprising M136S_T389C | 80 | 81 |
| YlLPCAT comprising M136S_T389S | 82 | 83 |
| YlLPCAT comprising M136V_T389C | 84 | 85 |
| YlLPCAT comprising N144A_F390S | 86 | 87 |
| YlLPCAT comprising G148A_F390S | 88 | 89 |
| YlLPCAT comprising G148N_T382I | 90 | 91 |
| YlLPCAT comprising G148N_F390S | 92 | 93 |

DETAILED DESCRIPTION OF THE INVENTION

All patents, patent applications and publications cited herein are incorporated herein by reference in their entirety.

When an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

As used herein the term "invention" or "present invention" is intended to refer to all aspects and embodiments of the invention as described in the claims and specification herein and should not be read so as to be limited to any particular embodiment or aspect.

In this disclosure, a number of terms and abbreviations are used. Amino acids are identified by either the one-letter code or the three-letter codes for amino acids, in conformity with the IUPAC-IYUB standards described in *Nucleic Acids Research,* 13:3021-3030 (1985) and in the *Biochemical Journal,* 219 (2):345-373 (1984), which are herein incorporated by reference.

"Open reading frame" is abbreviated as "ORF".

"Polymerase chain reaction" is abbreviated as "PCR".

"American Type Culture Collection" is abbreviated as "ATCC".

"Polyunsaturated fatty acid(s)" is abbreviated as "PUFA(s)".

"Long-chain polyunsaturated fatty acid(s)" is abbreviated as "LC-PU FA(s)".

"Triacylglycerols" are abbreviated as "TAGs".

"Total fatty acids" are abbreviated as "TFAs".

"Fatty acid methyl esters" are abbreviated as "FAMEs".

"Dry cell weight" is abbreviated as "DCW".

"Acyl-CoA:lysophospholipid acyltransferase(s)" or "lysophospholipid acyltransferase(s)" is abbreviated as "LPLAT(s)".

"Lysophosphatidylcholine acyltransferase(s)" is abbreviated as "LPCAT(s)".

"Membrane bound O-acyltransferase" is abbreviated as "MBOAT".

"Phospholipid:diacylglycerol acyltransferase(s)" is abbreviated as "PDAT(s)".

The term "glycerophospholipids" refers to a broad class of molecules, having a glycerol core with fatty acids at the sn-1 position and sn-2 position, and a polar head group (e.g., phosphate, choline, ethanolamine, glycerol, inositol, serine, cardiolipin) joined at the sn-3 position via a phosphodiester bond. Glycerophospholipids thus include phosphatidylcholine ["PC"], phosphatidylethanolamine ["PE"], phosphatidylglycerol ["PG"], phosphatidylinositol ["PI"], phosphatidylserine ["PS"] and cardiolipin ["CL"].

"Lysophospholipids" are derived from glycerophospholipids by deacylation of the sn-2 position. Lysophospholipids include, e.g., lysophosphatidic acid ["LPA"], lysophosphatidylcholine ["LPC"], lysophosphatidylethanolamine ["LPE"], lysophosphatidylserine ["LPS"], lysophosphatidylglycerol ["LPG"] and lysophosphatidylinositol ["LPI"].

The term "acyltransferase" refers to an enzyme responsible for transferring an acyl group from a donor lipid to an acceptor lipid molecule.

The term "acyl-CoA:lysophospholipid acyltransferase" or "lysophospholipid acyltransferase" ["LPLAT"] refers to a broad class of acyltransferases having the ability to acylate a variety of lysophospholipid substrates at the sn-2 position. A variety of LPLATs have been identified, including LPAATs (catalyzing conversion of LPA to PA), LPEATs (catalyzing conversion of LPE to PE), LPLATs (catalyzing conversion of LPS to PS), LPGATs (catalyzing conversion of LPG to PG), and LPIATs (catalyzing conversion of LPI to PI). LPC acyltransferases ["LPCATs"] are the focus of the present application, having the ability to catalyze conversion of LPC to PC. Standardization of LPLAT nomenclature has not been formalized, so various other designations are used in the art (for example, LPCATs are often referred to as acyl-CoA:1-acyl lysophosphatidyl-choline acyltransferases). Additionally, it is important to note that some LPLATs, such as the *Saccharomyces cerevisiae* Ale1 (ORF YOR175c, SEQ ID NO:2), have broad specificity and thus a single enzyme may be capable of catalyzing several LPLAT reactions, including LPAAT, LPCAT and LPEAT reactions (Tamaki et al., *J. Biol. Chem.,* 282:34288-34298 (2007); Stahl et al., *FEBS Letters,* 582:305-309 (2008); Chen et al., *FEBS Letters,* 581:5511-5516 (2007); Benghezal et al., *J. Biol. Chem.,* 282:30845-30855 (2007); Riekhof et al., *J. Biol. Chem.,* 282:28344-28352 (2007)).

More specifically, the term "polypeptide having lysophosphatidylcholine acyltransferase ["LPCAT"] activity" will refer to those enzymes capable of catalyzing the reaction: acyl-CoA+1-acyl-sn-glycero-3-phosphocholine CoA+1,2-diacyl-sn-glycero-3-phosphocholine (EC 2.3.1.23). LPCAT activity has been described in two structurally distinct protein families, i.e., the LPAAT protein family (Hishikawa et al., *Proc. Natl. Acad. Sci. U.S.A.,* 105:2830-2835 (2008); Intl. Appl. Publ. No. WO 2004/076617) and the ALE1 protein family (Tamaki et al., Ståahl et al., Chen et al., Benghezal et al., Riekhof et al.).

The term "LPCAT" refers to a protein of the ALE1 protein family that: 1) has LPCAT activity (EC 2.3.1.23) and shares at least about 45% amino acid identity, based on the Clustal W method of alignment, when compared to an amino acid sequence selected from the group consisting of SEQ ID NO:2 (ScAle1) and SEQ ID NO:4 (YlAle1); and/or 2) has LPCAT activity (EC 2.3.1.23) and has at least one membrane bound O-acyltransferase ["MBOAT"] protein family motif, described below. Examples of ALE1 polypeptides include ScAle1 and YlLPCAT.

The term "ScAle1" refers to an LPCAT isolated from *Saccharomyces cerevisiae* (ORF "YOR175C"). ScAle1 may have the amino acid sequence of SEQ ID NO:2, encoded by the nucleotide sequence set forth as SEQ ID NO:1.

The term "YlAle1" or "YlLPCAT" refers to a LPCAT isolated from *Yarrowia lipolytica*. YlLPCAT may have the amino acid sequence of SEQ ID NO:4, encoded by the nucleotide sequence set forth as SEQ ID NO:3.

The term "conserved domain" or "motif" means a set of amino acids conserved at specific positions along an aligned sequence of evolutionarily related proteins. While amino acids at other positions can vary between homologous proteins, amino acids that are highly conserved at specific positions likely indicate amino acids that are essential in the structure, the stability, or the activity of a protein. Because they are identified by their high degree of conservation in aligned sequences of a family of protein homologues, they can be used as identifiers, or "signatures", to determine if a protein with a newly determined sequence belongs to a previously identified protein family.

A variety of membrane bound O-acyltransferase ["MBOAT"] family motifs have been proposed. These motifs are summarized in Table 2 below and discussed further in U.S. Pat. Appl. Publ. No. 2010-0317882-A1.

TABLE 2

Membrane Bound O-Acyltransferase ["MBOAT"] Family Motifs

| Reference | Organisms Analyzed | Motif (X represents any amino acid) | SEQ ID NO |
|---|---|---|---|
| Shindou et al. (Biochem. Biophys. Res. Comm., 383: 320-325 (2009)) | *Homo sapiens, Gallus gallus, Danio rerio Caenorhabditis elegans* | WD | — |
| | | WHG-$X_3$-GY-$X_3$-F | 5 |
| | | Y-$X_4$-F | 6 |
| | | Y-$X_3$-YF-$X_2$-H | 7 |
| U.S. Patent Application Publ. No. 2008-0145867-A1 | Non-plants | M-[V/I]-[L/I]-$X_2$-K-[L/V/I]-$X_8$-DG | 8 |
| | | RxKYY-$X_2$-W-$X_3$-[E/D]-[A/G]-$X_5$-GxG-[F/Y]-xG | 9 |
| | | E$X_{11}$WN-$X_2$-[T/V]-$X_2$-W | 10 |
| | | SAxWHG-$X_2$-PGY-$X_2$-[T/F]-F | 11 |

TABLE 2-continued

| Membrane Bound O-Acyltransferase ["MBOAT"] Family Motifs | | | |
|---|---|---|---|
| Reference | Organisms Analyzed | Motif (X represents any amino acid) | SEQ ID NO |
| U.S. Pat. No. 7,732,155 | Non-plants | M-[V/I]-[L/I/V]-[V/C/A/T]-[M/L/Q]-K-[L/V/I/M]-[S/T/Y/I]-[S/T/A/M/G]-[F/L/C/Y]-[C/A/G/S]-[W/Y/M/I/F/C]-[N/S/E/Q/D]-[V/Y/L/I]-[H/Y/A/N/S/T]-DG | 12 |
| | | R-[L/M/F/W/P/Y]-KYY-[G/A/F/H/S]-[V/A/I/C]-W-[Y/E/T/M/S/L]-[L/I/N]-[T/S/A]-[E/D]-[G/A]-[A/S/I/V]-[C/S/I/N/H/L]-[V/I/N]-[L/I/N/A/C]-[S/C/W/A/I]-G-[M/I/L/A/F]-G-[Y/F]-[N/E/S/T/R/K]-G | 13 |
| | | E-[T/F/L/M]-[A/S]-[Q/D/P/K/T]-[N/S]-[S/I/T/L/A/M/F]-[H/K/R/V]-[G/C/E/T/Q/D/M]-[Y/A/M/L/I/F]-[L/S/P/I]-[G/E/A/L/N/D]-[S/A/V/F/M/N]-WN-[K/M/I/C]-[N/K/Q/G]-[T/V]-[N/A/S]-[H/K/N/T/R/L]-W | 14 |
| | | SA-[F/M/V/I]-WHG-[F/V/T/L]-[Y/S/R]-PGY-[Y/M/I]-[L/M/I/F]-[T/F]-F | 15 |
| U.S. Patent Application Publ. No. 2010-0317882-A1 | Yeast and Fungi | M-[V/I]-L-$X_2$-KL | 16 |
| | | RxKYY-$X_2$-W | 17 |
| | | E-$X_{11}$-WN-$X_2$-[T/V]-$X_2$-W | 10 |
| | | SAxWHG | 18 |

The term "mutant polypeptide having LPCAT activity comprising at least one mutant membrane bound O-acyltransferase ["MBOAT"] protein family motif" or "mutant polypeptide having LPCAT activity comprising at least one mutant MBOAT motif" refers to a polypeptide of the present invention comprising at least one amino acid mutation with respect to SEQ ID NOs:5-18.

For each amino acid substitution in an MBOAT motif disclosed herein, the first letter corresponds to the amino acid in the wild type MBOAT motif and the second letter corresponds to the amino acid found in the same position in the mutant MBOAT motif, e.g., an L3A mutation in SEQ ID NO:16 [M-[V/I]-L-$X_2$-KL] indicates a change from Leu [L] in SEQ ID NO:16 at position 3 to Ala [A] in the MBOAT mutant. This nomenclature is used throughout the specification to refer to mutations within the LPCAT motifs and proteins described herein; similar notation is used to describe substitutions within nucleotide sequences (e.g., A9G indicates a change from adenine [A] at base position 9 in the nucleotide sequence encoding an MBOAT motif to guanine [G]).

Preferably, a mutant polypeptide having at least LPCAT activity comprising at least one mutant MBOAT motif (e.g., a mutated form of one of SEQ ID NOs:5-8) will have equivalent or improved LPCAT activity when compared to a control polypeptide having LPCAT activity comprising at least one MBOAT motif (e.g., one of SEQ ID NOs:5-18) that is the wild type version of the mutated MBOAT motif in the mutant polypeptide.

Although "mutations" may include any deletions, insertions and point mutations (or combinations thereof), in a preferred embodiment, a mutant LPCAT having lysophosphatidylcholine acyltransferase ["LPCAT"] activity comprising at least one mutant MBOAT motif is set forth in SEQ ID NO:19, wherein SEQ ID NO:19 differs from SEQ ID NO:4 [YlLPCAT] by at least one amino acid mutation, wherein:

(a) one of the at least one amino acid mutations is in an amino acid residue selected from the group consisting of: residue 133, residue 134, residue 135, residue 136, residue 137, residue 138, residue 139, residue 140, residue 141, residue 142, residue 143, residue 144, residue 145, residue 146, residue 147, residue 148;

(b) one of the at least one amino acid mutations is in an amino acid residue selected from the group consisting of: residue 378, residue 382, residue 383, residue 385, residue 388, residue 389 and residue 390; and/or (c) said at least one amino acid mutation comprises at least two amino acid mutations, wherein:

(i) the first amino acid mutation is in an amino acid residue selected from the group set forth in part (a), and (ii) the second amino acid mutation is in an amino acid residue selected from the group set forth in part (b).

The term "LPCAT" also refers to a protein that has LPCAT activity (EC 2.3.1.23) and which may also have an alternate acyl-CoA:lysophospholipid acyltransferase activity (e.g., LPAAT activity, LPEAT activity, LPSAT activity, LPGAT activity, LPIAT activity). For example, a polypeptide may have both LPCAT and LPAAT activity and should thus be considered as an LPCAT herein, despite being classified in previous literature as an LPAAT polypeptide. These LPCATs may possess structural characteristics of LPAAT proteins.

The term "polypeptide having lysophosphatidic acid acyltransferase ["LPAAT"] activity" will refer to those enzymes capable of catalyzing the reaction: acyl-CoA+1-acyl-sn-glycerol 3-phosphate→CoA+1,2-diacyl-sn-glycerol 3-phosphate (EC 2.3.1.51).

The term "LPAAT" refers to a protein that: 1) has LPAAT activity and shares at least about 43.9% amino acid identity, based on the Clustal W method of alignment, when compared to an amino acid sequence selected from the group consisting of SEQ ID NO:21 (MaLPAAT1), SEQ ID NO:23 (YlLPAAT1) and SEQ ID NO:24 (ScLPAAT1); and/or 2) has LPAAT activity and has at least one 1-acyl-sn-glycerol-3-phosphate acyltransferase family motif selected from the group consisting of: NHxxxxD (SEQ ID NO:25) and EGTR (SEQ ID NO:26). More specifically, Lewin et al. (*Biochemistry,* 38:5764-5771 (1999)) and Yamashita et al. (*Biochim, Biophys. Acta,* 1771:1202-1215 (2007)) proposed the following 1-acyl-sn-glycerol-3-phosphate acyltransferase ["LPAAT"] family motifs to be important for "acyl-CoA: lysophospholipid acyltransferase" or "lysophospholipid acyltransferase" ["LPAAT"] activity, based on alignment of sequences from bacteria, yeast, nematodes and mammals: NHxxxxD (SEQ ID NO:25), GxxFI-[D/R]-R (SEQ ID NO:27), EGTR (SEQ ID NO:26) and either [V/I]-[P/X]-[I/V/L]-[I/V]-P-[V/I] (SEQ ID NO:28) or IVPIVM (SEQ ID NO:29). Examples of LPAAT polypeptides include ScLPAAT, MaLPAAT1 and YILPAAT1.

The term "ScLPAAT" refers to an LPAAT isolated from *Saccharomyces cerevisiae* (e.g., ORF "YDL052C", SEQ ID NO:24).

The term "MaLPAAT1" refers to an LPAAT isolated from *Mortierella alpina*. MaLPAAT1 may have the amino acid sequence of SEQ ID NO:21, encoded by the nucleotide sequence set forth as SEQ ID NO:20. The NHxxxxD (SEQ ID NO:25) and EGTR (SEQ ID NO:26) motifs are present in MaLPAAT1, but the other LPAAT motifs are not.

The terms "YILPAAT1" and "YILPAAT2" refer to LPAATs isolated from *Yarrowia lipolytica*. An YILPAAT may have the amino acid sequence of SEQ ID NO:23, encoded by the nucleotide sequence set forth as SEQ ID NO:22. The NHxxxxD (SEQ ID NO:25) and EGTR (SEQ ID NO:26) motifs are present in YILPAAT1, but the other LPAAT motifs are not.

The term "polypeptide having phospholipid:diacylglycerol acyltransferase ["PDAT"] activity" will refer to those enzymes capable of transferring a fatty acyl group from the sn-2 position of a phospholipid (e.g., phosphatidylcholine) to the sn-3 position of 1,2-diacylglycerol [E.C.2.3.1.158], thus resulting in a lysophospholipid and TAG. Although both PDATs and acyl-CoA:diacylglycerol acyltransferases (DGATs) [E.C. 2.3.1.20] are involved in the terminal step of TAG biosynthesis, only PDAT may synthesize TAGs via an acyl-CoA-independent mechanism. A representative PDAT enzyme, as set forth in SEQ ID NO:30, is encoded by the LRO1 gene in *Saccharomyces cerevisiae* (Dahlqvist et al., Proc. Natl. Acad. Sci. U.S.A., 97:6487 (2000)).

The term "YIPDAT" refers to a PDAT isolated from *Yarrowia lipolytica*. YIPDAT may have the amino acid sequence of SEQ ID NO:32, encoded by the nucleotide sequence set forth as SEQ ID NO:31 (U.S. Pat. No. 7,901,928 which is incorporated herein by reference).

The term "ortholog" refers to a homologous protein from a different species that evolved from a common ancestor protein as evidenced by being in one Glade of a phylogenetic tree analysis and that catalyzes the same enzymatic reaction.

The term "oil" refers to a lipid substance that is liquid at 25° C. and usually polyunsaturated. In oleaginous organisms, oil constitutes a major part of the total lipid. "Oil" is composed primarily of triacylglycerols ["TAGs"] but may also contain other neutral lipids, phospholipids and free fatty acids. The fatty acid composition in the oil and the fatty acid composition of the total lipid are generally similar; thus, an increase or decrease in the concentration of PUFAs in the total lipid will correspond with an increase or decrease in the concentration of PUFAs in the oil, and vice versa.

"Neutral lipids" refer to those lipids commonly found in cells in lipid bodies as storage fats and are so called because at cellular pH, the lipids bear no charged groups. Generally, they are completely non-polar with no affinity for water. Neutral lipids generally refer to mono-, di-, and/or triesters of glycerol with fatty acids, also called monoacylglycerol, diacylglycerol or triacylglycerol, respectively, or collectively, acylglycerols. A hydrolysis reaction must occur to release free fatty acids from acylglycerols.

The term "triacylglycerols" ["TAGs"] refers to neutral lipids composed of three fatty acyl residues esterified to a glycerol molecule. TAGs can contain LC-PUFAs and saturated fatty acids, as well as shorter chain saturated and unsaturated fatty acids.

The term "total fatty acids" ["TFAs"] herein refers to the sum of all cellular fatty acids that can be derivatized to fatty acid methyl esters ["FAMEs"] by the base transesterification method (as known in the art) in a given sample, which may be the biomass or oil, for example. Thus, total fatty acids include fatty acids from neutral lipid fractions (including diacylglycerols, monoacylglycerols and TAGs) and from polar lipid fractions (including the PC and the PE fractions), but not free fatty acids.

The term "total lipid content" of cells is a measure of TFAs as a percent of the dry cell weight ["DCW"], although total lipid content can be approximated as a measure of FAMEs as a percent of the DCW ["FAMEs % DCW"]. Thus, total lipid content ["TFAs % DCW"] is equivalent to, e.g., milligrams of total fatty acids per 100 milligrams of DCW. The total lipid content can also refer to the oil content.

The concentration of a fatty acid in the total lipid is expressed herein as a weight percent of TFAs ["% TFAs"], e.g., milligrams of the given fatty acid per 100 milligrams of TFAs. Unless otherwise specifically stated herein, reference to the percent of a given fatty acid with respect to total lipids is equivalent to concentration of the fatty acid as % TFAs (e.g., % EPA of total lipids is equivalent to EPA % TFAs).

In some cases, it is useful to express the content of a given fatty acid(s) in a cell as its weight percent of the dry cell weight ["% DCW"]. Thus, for example, EPA % DCW would be determined according to the following formula: (EPA % TFAs)*(TFAs % DCW)]/100. The content of a given fatty acid(s) in a cell as its weight percent of the dry cell weight ["% DCW"] can be approximated, however, as: (EPA % TFAs)*(FAMEs % DCW)]/100.

The terms "lipid profile" and "lipid composition" are interchangeable and refer to the amount of individual fatty acids contained in a particular lipid fraction, such as in the total lipids or the oil, wherein the amount is expressed as a weight percent of TFAs. The sum of each individual fatty acid present in the mixture should be 100.

The term "fatty acids" refers to long chain aliphatic acids (alkanoic acids) of varying chain lengths, from about $C_{12}$ to $C_{22}$, although both longer and shorter chain-length acids are known. The predominant chain lengths are between $C_{16}$ and $C_{22}$. The structure of a fatty acid is represented by a simple notation system of "X:Y", where X is the total number of carbon ["C"] atoms in the particular fatty acid and Y is the number of double bonds. Additional details concerning the differentiation between "saturated fatty acids" versus "unsaturated fatty acids", "monounsaturated fatty acids" versus "polyunsaturated fatty acids" ["PUFAs"], and "omega-6 fatty acids" ["n-6"] versus "omega-3 fatty acids" ["n-3"] are provided in U.S. Pat. No. 7,238,482, which is incorporated herein by reference.

Nomenclature used to describe PUFAs herein is given in Table 3. In the column titled "Shorthand Notation", the omega-reference system is used to indicate the number of carbons, the number of double bonds and the position of the double bond closest to the omega carbon, counting from the omega carbon, which is numbered 1 for this purpose. The remainder of Table 3 summarizes the common names of omega-3 and omega-6 fatty acids and their precursors, the abbreviations that will be used throughout the specification and the chemical name of each compound.

TABLE 3

Nomenclature of Polyunsaturated Fatty Acids and Precursors

| Common Name | Abbreviation | Chemical Name | Shorthand Notation |
|---|---|---|---|
| Myristic | — | tetradecanoic | 14:0 |
| Palmitic | Palmitate | hexadecanoic | 16:0 |
| Palmitoleic | — | 9-hexadecenoic | 16:1 |
| Stearic | — | octadecanoic | 18:0 |
| Oleic | — | cis-9-octadecenoic | 18:1 |
| Linoleic | LA | cis-9,12-octadecadienoic | 18:2 omega-6 |
| Gamma-Linolenic | GLA | cis-6,9,12-octadecatrienoic | 18:3 omega-6 |
| Eicosadienoic | EDA | cis-11,14-eicosadienoic | 20:2 omega-6 |
| Dihomo-Gamma-Linolenic | DGLA | cis-8,11,14-eicosatrienoic | 20:3 omega-6 |
| Arachidonic | ARA | cis-5,8,11,14-eicosatetraenoic | 20:4 omega-6 |
| Alpha-Linolenic | ALA | cis-9,12,15-octadecatrienoic | 18:3 omega-3 |
| Stearidonic | STA | cis-6,9,12,15-octadecatetraenoic | 18:4 omega-3 |
| Eicosatrienoic | ETrA | cis-11,14,17-eicosatrienoic | 20:3 omega-3 |
| Eicosa-tetraenoic | ETA | cis-8,11,14,17-eicosatetraenoic | 20:4 omega-3 |
| Eicosa-pentaenoic | EPA | cis-5,8,11,14,17-eicosapentaenoic | 20:5 omega-3 |
| Docosa-tetraenoic | DTA | cis-7,10,13,16-docosatetraenoic | 22:4 omega-6 |
| Docosa-pentaenoic | DPAn-6 | cis-4,7,10,13,16-docosapentaenoic | 22:5 omega-6 |
| Docosa-pentaenoic | DPA | cis-7,10,13,16,19-docosapentaenoic | 22:5 omega-3 |
| Docosa-hexaenoic | DHA | cis-4,7,10,13,16,19-docosahexaenoic | 22:6 omega-3 |

Although the omega-3/omega-6 PUFAs listed in Table 3 are the most likely to be accumulated in the oil fractions of microbial and plant hosts using the methods described herein, this list should not be construed as limiting or as complete.

The term "long-chain polyunsaturated fatty acid" ["LC-PUFA"] refers to those PUFAs that have chain lengths of $C_{20}$ or greater. Thus, the term LC-PUFA includes at least EDA, DGLA, ARA, ETrA, ETA, EPA, DTA, DPAn-6, DPA and DHA.

The term "PUFA biosynthetic pathway" refers to a metabolic process that converts oleic acid to omega-6 fatty acids such as LA, EDA, GLA, DGLA, ARA, DTA and DPAn-6 and omega-3 fatty acids such as ALA, STA, ETrA, ETA, EPA, DPA and DHA. This process is well described in the literature (e.g., see U.S. Pat. No. 7,7932,077 which is incorporated herein by reference). Briefly, this process involves elongation of the carbon chain through the addition of carbon atoms and desaturation of the molecule through the addition of double bonds, via a series of special elongation and desaturation enzymes termed "PUFA biosynthetic pathway enzymes" that are present in the endoplasmic reticulum membrane. More specifically, "PUFA biosynthetic pathway enzymes" refer to any of the following enzymes (and genes which encode said enzymes) associated with the biosynthesis of a PUFA, including: delta-4 desaturases, delta-5 desaturases, delta-6 desaturases, delta-12 desaturases, delta-15 desaturases, delta-17 desaturases, delta-9 desaturases, delta-8 desaturases, delta-9 elongases, $C_{14/16}$ elongases, $C_{16/18}$ elongases, $C_{18/20}$ elongases and/or $C_{20/22}$ elongases.

Figure 2:
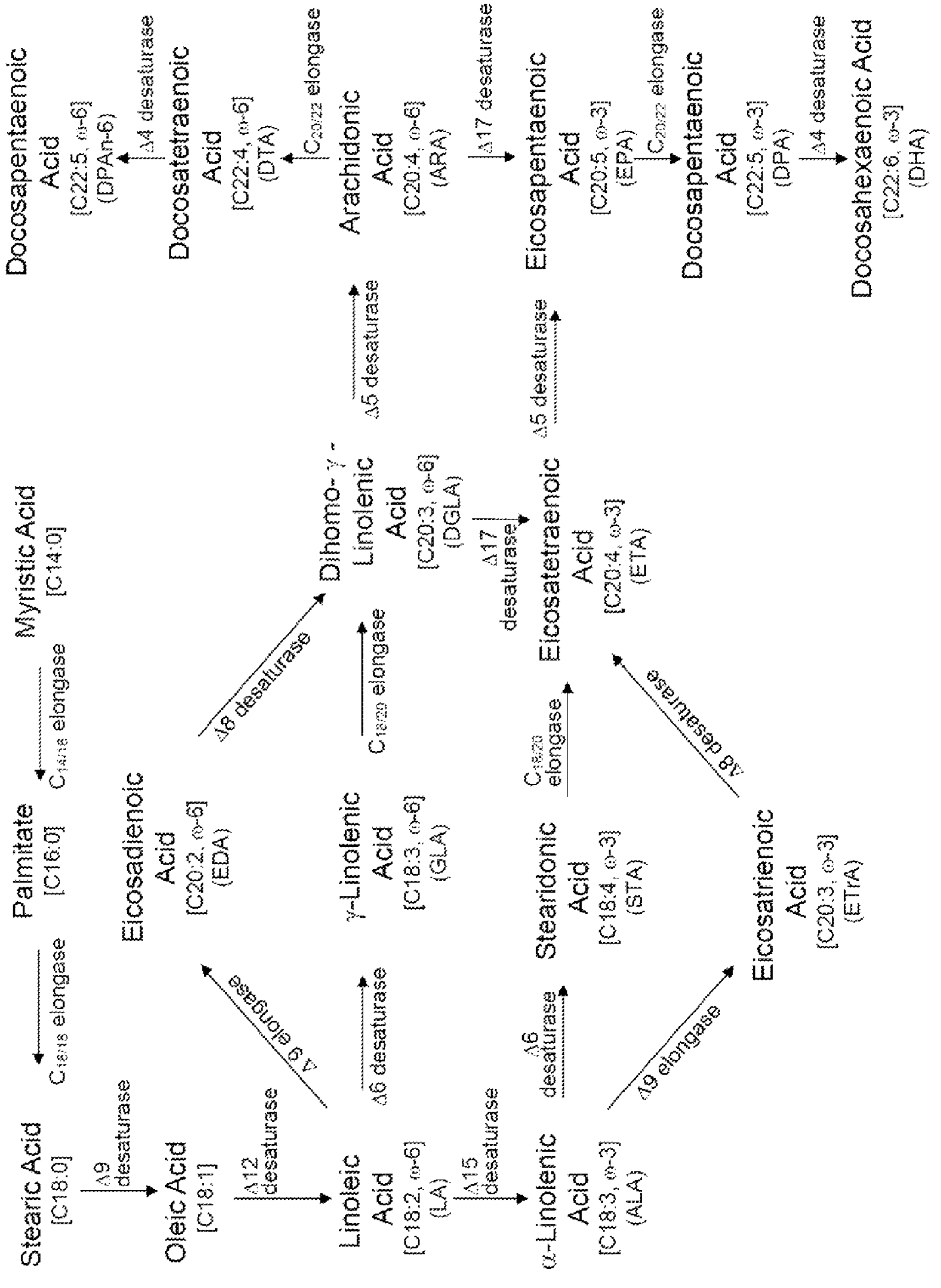
FIG. 2 illustrates the omega-3/omega-6 fatty acid biosynthetic pathway, and should be viewed together when considering the description of this pathway.

The term "PUFA biosynthetic pathway capable of producing at least one long-chain polyunsaturated product fatty acid" refers to a PUFA biosynthetic pathway comprising PUFA biosynthetic pathway enzymes that enables production of at least one long-chain polyunsaturated product fatty acid. FIG. 2. depicts examples of PUFA biosynthetic pathways.

The terms "conversion efficiency" and "percent substrate conversion" refer to the efficiency by which a particular enzyme, such as a desaturase or elongase, can convert substrate to product. The conversion efficiency is measured according to the following formula: ([product]/[substrate+product])*100, where 'product' includes the immediate product and all products derived from it. More specifically, since each PUFA biosynthetic pathway enzyme rarely functions with 100% efficiency to convert substrate to product, the final lipid profile of unpurified oils produced in a host cell will typically be a mixture of various PUFAs consisting of the desired omega-3/omega-6 fatty acid, as well as various upstream intermediary PUFAs. Thus, each enzyme's conversion efficiency is often considered, when optimizing biosynthesis of a desired fatty acid in a specific host organism.

The term "$C_{18}$ to $C_{20}$ elongation conversion efficiency" refers to the efficiency by which $C_{18/20}$ elongases can convert $O_{18}$ substrates (i.e., LA, ALA, GLA, STA, etc.) to $O_{20}$ products (i.e., EDA, ETrA, DGLA, ETA, EPA, etc.). These $C_{18/20}$ elongases can be either delta-9 elongases or delta-6 elongases.

The terms "delta-9 elongation conversion efficiency" and "delta-9 elongase conversion efficiency" refer to the efficiency by which delta-9 elongase can convert $C_{18}$ substrates (i.e., LA, ALA) to $C_{20}$ products (such as EDA, ETrA, DGLA, ETA, ARA, EPA). Delta-9 elongase conversion efficiency is referred to herein as "% Conv." or "d9e CE (%)".

The terms "delta-6 elongation conversion efficiency" and "delta-6 elongase conversion efficiency" refer to the efficiency by which delta-6 elongase can convert $C_{18}$ substrates (such as GLA, STA) to $C_{20}$ products (such as DGLA, ETA, ARA, EPA, etc.).

The term "increased" herein means having a greater quantity or activity, for example a quantity or activity only slightly greater than the original quantity or activity, or for example a quantity or activity in large excess compared to the original quantity or activity, and including all quantities or activities in between. Alternatively, "increased" may refer to a quantity or activity that is at least 1%, 2%, 3%, 4%, 5%, 6%, 7%, 8%, 9%, 10%, 11%, 12%, 13%, 14%, 15%, 16%, 17%, 18%, 19% or 20% more than the quantity or activity for which the increased quantity or activity is being compared.

The terms "microbial cell" and "microbial organism" are used interchangeably herein and refer to a microorganism capable of receiving foreign or heterologous genes and capable of expressing those genes. A "recombinant microbial cell" refers to a microbial host cell that has been recombinantly engineered.

Generally, the term "oleaginous" refers to those organisms that tend to store their energy source in the form of oil (Weete, In: Fungal Lipid Biochemistry, 2nd Ed., Plenum, 1980). For the purposes of the present application, the term "oleaginous" refers to those microorganisms that can accumulate at least about 25% of their dry cell weight ["DCW"] as oil.

The term "oleaginous yeast" refers to those oleaginous microorganisms classified as yeasts that can make oil, i.e., wherein the oil can accumulate in excess of about 25% of their DCW. Examples of oleaginous yeast include the following genera: *Yarrowia, Candida, Rhodotorula, Rhodosporidium, Cryptococcus, Trichosporon* and *Lipomyces*. The ability to accumulate oil in excess of about 25% of the DCW of the yeast may be through efforts of recombinant engineering or through the natural abilities of the organism.

The term "conservative amino acid substitution" refers to a substitution of an amino acid residue in a given protein with another amino acid, without altering the chemical or functional nature of that protein. For example, it is well known in the art that alterations in a gene that result in the production of a chemically equivalent amino acid at a given site (but do not affect the structural and functional properties of the encoded, folded protein) are common. For the purposes herein, "conservative amino acid substitutions" are defined as exchanges within one of the following five groups:

1. Small aliphatic, nonpolar or slightly polar residues: Ala [A], Ser [S], Thr [T] (Pro [P], Gly [G]);
2. Polar, negatively charged residues and their amides: Asp [D], Asn [N], Glu [E], Gln [Q];
3. Polar, positively charged residues: His [H], Arg [R], Lys [K];
4. Large aliphatic, nonpolar residues: Met [M], Leu [L], Ile [I], Val [V] (Cys [C]); and
5. Large aromatic residues: Phe [F], Tyr [Y], Trp [W].

Thus, Ala, a slightly hydrophobic amino acid, may be substituted by another less hydrophobic residue (e.g., Gly). Similarly, changes which result in substitution of one negatively charged residue for another (e.g., Asp for Glu) or one positively charged residue for another (e.g., Lys for Arg) can also be used to produce a functionally equivalent product. As such, conservative amino acid substitutions generally maintain: 1) the structure of the polypeptide backbone in the area of the substitution; 2) the charge or hydrophobicity of the molecule at the target site; or, 3) the bulk of the side chain. Additionally, in many cases, alterations of the N-terminal and C-terminal portions of the protein molecule would also not be expected to alter the activity of the protein.

The term "non-conservative amino acid substitution" refers to an amino acid substitution that is used to produce the greatest change in protein properties. Thus, for example, a non-conservative amino acid substitution would be one whereby: 1) a hydrophilic residue is substituted for/by a hydrophobic residue (e.g., Ser or Thr for/by Leu, Ile, Val); 2) a Cys or Pro is substituted for/by any other residue; 3) a residue having an electropositive side chain is substituted for/by an electronegative residue (e.g., Lys, Arg or His for/by Asp or Glu); or 4) a residue having a bulky side chain is substituted for/by one not having a side chain (e.g., Phe for/by Gly). Sometimes, non-conservative amino acid substitutions between two of the five groups will not affect the activity of the encoded protein.

The term "silent mutation" refers to a mutation in a DNA sequence that does not result in an amino acid change in the encoded polypeptide. These mutations often occur as a result of the degeneracy of the genetic code, wherein more than one codon may specify an amino acid. For example, TCT, TCA, TCG and TCC all encode the amino acid Ser; thus, a TCT to TCA mutation in the DNA sequence will only be detected by sequencing the gene (or its mRNA), since there is no alteration in the amino acid in the synthesized protein.

The terms "polynucleotide", "polynucleotide sequence", "nucleic acid sequence", "nucleic acid molecule", "nucleic acid fragment" and "isolated nucleic acid fragment" are used interchangeably herein. As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

As used herein, a nucleic acid fragment is "hybridizable" to another nucleic acid fragment, such as a cDNA, genomic DNA, or RNA molecule, when a single-stranded form of the nucleic acid fragment can anneal to the other nucleic acid fragment under the appropriate conditions of temperature and solution ionic strength. Hybridization and washing conditions are well known and exemplified in Sambrook, J., Fritsch, E. F. and Maniatis, T. *Molecular Cloning: A Laboratory Manual,* 2nd ed., Cold Spring Harbor Laboratory: Cold Spring Harbor, N.Y. (1989), which is incorporated herein by reference, particularly Chapter 11 and Table 11.1.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., *J. Mol. Biol.,* 215: 403-410 (1993)). In general, a sequence of ten or more contiguous amino acids or thirty or more nucleotides is necessary in order to identify putatively a polypeptide or nucleic acid sequence as homologous to a known protein or gene. Moreover, with respect to nucleotide sequences, gene-specific oligonucleotide probes comprising 20-30 contiguous nucleotides may be used in sequence-dependent methods of gene identification (e.g., Southern hybridization) and isolation, such as in situ hybridization of bacterial colonies or bacteriophage plaques. In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The disclosure herein teaches the complete amino acid and nucleotide sequences encoding particular LPCATs and PDATs. The skilled artisan, having the benefit of the sequences as reported herein, may now use all or a substantial portion of the disclosed sequences for purposes known to those skilled in this art.

The term "complementary" is used to describe the relationship between nucleotide bases that are capable of hybridizing to one another. For example, with respect to DNA, adenosine is complementary to thymine and cytosine is complementary to guanine.

The terms "homology", "homologous", "substantially similar" and "corresponding substantially" are used interchangeably herein. They refer to nucleic acid fragments or polypeptides that have similar, but not identical sequences These terms sometimes also refer to modifications of the nucleic acid fragments (e.g., via deletion or insertion of one or more nucleotides) that do not substantially alter the functional properties of the resulting nucleic acid fragment relative to the initial, unmodified fragment. It is therefore understood, as those skilled in the art will appreciate, that the invention encompasses more than the specific exemplary sequences.

"Sequence identity" or "identity" in the context of nucleic acid or polypeptide sequences refers to the nucleic acid bases or amino acid residues in two sequences that are the same when aligned for maximum correspondence over a specified comparison window Thus, "percentage of sequence identity" or "percent identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity.

Methods to determine "percent identity" and "percent similarity" are codified in publicly available computer programs. Percent identity and percent similarity can be readily calculated by known methods, including but not limited to those described in: 1) *Computational Molecular Biology* (Lesk, A. M., Ed.) Oxford University: NY (1988); 2) *Biocomputing: Informatics and Genome Projects* (Smith, D. W., Ed.) Academic: NY (1993); 3) *Computer Analysis of Sequence Data, Part I* (Griffin, A. M., and Griffin, H. G., Eds.) Humana: NJ (1994); 4) *Sequence Analysis in Molecular Biology* (von Heinje, G., Ed.) Academic (1987); and, 5) *Sequence Analysis Primer* (Gribskov, M. and Devereux, J., Eds.) Stockton: NY (1991).

Sequence alignments and percent identity or similarity calculations may be determined using a variety of comparison methods designed to detect homologous sequences including, but not limited to, the MegAlign™ program of the LASERGENE bioinformatics computing suite (DNASTAR Inc., Madison, Wis.). Multiple alignment of the sequences is performed using the "Clustal method of alignment" which encompasses several varieties of the algorithm including the "Clustal V method of alignment" and the "Clustal W method of alignment" (described by Higgins and Sharp, *CABIOS,* 5:151-153 (1989); Higgins, D. G. et al., *Comput. Appl. Biosci.,* 8:189-191 (1992)) and found in the MegAlign™ (version 8.0.2) program of the LASERGENE bioinformatics computing suite (DNASTAR Inc.). Default parameters for multiple protein alignment using the Clustal W method of alignment correspond to GAP PENALTY=10, GAP LENGTH PENALTY=0.2, Delay Divergent Seqs (%)=30, DNA Transition Weight=0.5, Protein Weight Matrix=Gonnet Series, DNA Weight Matrix=IUB with the 'slow-accurate' option. After alignment of the sequences using either Clustal program, it is possible to obtain a "percent identity" by viewing the "sequence distances" table in the program.

It is well understood by one skilled in the art that many levels of sequence identity are useful in identifying polypeptides, from other species, wherein such polypeptides have the same or similar function or activity. Suitable nucleic acid fragments, i.e., isolated polynucleotides according to the disclosure herein, encode polypeptides that are at least about 70-85% identical, while more preferred nucleic acid fragments encode amino acid sequences that are at least about 85-95% identical to the amino acid sequences reported herein. Although preferred ranges are described above, useful examples of amino acid sequence percent identities include any integer percentage from 45% to 100%, such as 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. Also, of interest is any full-length or partial complement of this isolated nucleotide fragment.

Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

"Codon degeneracy" refers to the nature in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These oligonucleotide building blocks are annealed and then ligated to form gene segments that are then enzymatically assembled to construct the entire gene. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell, where sequence information is available. For example, the codon usage profile for *Yarrowia lipolytica* is provided in U.S. Pat. No. 7,125,672 which is incorporated herein by reference.

"Gene" refers to a nucleic acid sequence that expresses a specific protein, and that may refer to the coding region alone or may include regulatory sequences upstream and/or downstream to the coding region (e.g., 5'-untranslated regions upstream of the transcription start site of the coding region, 3' non-coding regions). "Native gene" refers to a gene as found in nature with its own regulatory sequences. "Chimeric gene" refers to any gene that is not a native gene, comprising regulatory and coding sequences that are not found together in nature (i.e., heterologous with respect to each other). Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene that is introduced into the host organism by gene transfer. Foreign genes can comprise native genes inserted into a non-native organism, native genes introduced into a new location within the native host, or chimeric genes. A "transgene" is a gene that has been introduced into the genome by a transformation procedure. A "codon-optimized gene" is a gene having its frequency of codon usage designed to mimic the frequency of preferred codon usage of the host cell.

"Coding sequence" refers to a DNA sequence that codes for a specific amino acid sequence. "Regulatory sequences" refer to nucleotide sequences located upstream of the coding sequence's transcription start site, 5'-untranslated regions and 3' non-coding regions, and which may influence the transcription, RNA processing or stability, or translation of the associated coding sequence. Regulatory sequences may include, but are not limited to: promoters, enhancers, silencers, 5'-untranslated leader sequence, introns, polyadenylation recognition sequences, RNA processing sites, effector binding sites, stem-loop structures and terminators.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters". It is further recognized that since in most cases the exact boundaries of regulatory sequences (especially at their 5' end) have not been completely defined, DNA fragments of different lengths may have identical promoter activity.

The terms "3' non-coding sequences", "transcription terminator", "terminator" and "termination sequences" refer to DNA sequences located 3' downstream of a coding sequence. This includes polyadenylation recognition sequences and other sequences encoding regulatory signals capable of affecting mRNA processing or gene expression. The polyadenylation signal is usually characterized by affecting the addition of polyadenylic acid tracts to the 3'-end of the mRNA precursor. The 3' region can influence the transcription, RNA processing or stability, or translation of the associated coding sequence.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA" or "mRNA" refers to the RNA that is without introns and which can be translated into protein by the cell. "cDNA" refers to a double-stranded DNA that is complementary to, and derived from, mRNA.

The term "operably linked" refers to the association of nucleic acid sequences on a single nucleic acid fragment so that the function of one is affected by the other. For example, a promoter is operably linked with a coding sequence when it is capable of affecting the expression of that coding sequence. That is, the coding sequence is under the transcriptional control of the promoter. Regulatory sequences can be operably linked to coding sequences in sense or antisense orientation.

The term "recombinant" or "heterologous" refers to an artificial combination of two otherwise separated segments of sequence, e.g., by chemical synthesis or by the manipulation of isolated segments of nucleic acids by genetic engineering techniques.

The term "expression", as used herein, refers to the transcription and stable accumulation of sense (mRNA) or antisense RNA. Expression may also refer to translation of mRNA into a protein (either precursor or mature).

"Transformation" refers to the transfer of a nucleic acid molecule into a host organism, resulting in genetically stable inheritance. The nucleic acid molecule may be a plasmid that replicates autonomously, for example, or it may integrate into the genome of the host organism. Host organisms containing the transformed nucleic acid fragments are referred to as "transgenic" or "recombinant" or "transformed" or "transformant" organisms.

The terms "plasmid" and "vector" refer to an extrachromosomal element often carrying genes that are not part of the central metabolism of the cell, and usually in the form of circular double-stranded DNA fragments. Such elements may have autonomously replicating sequences, genome integrating sequences, phage or nucleotide sequences, and may be linear or circular, of a single- or double-stranded DNA or RNA, derived from any source, in which a number of nucleotide sequences have been joined or recombined into a unique construction that is capable of introducing an expression cassette(s) into a cell.

The term "expression cassette" refers to a fragment of DNA containing a foreign gene and having elements in addition to the foreign gene that allow for expression of that gene in a foreign host. Generally, an expression cassette will comprise the coding sequence of a selected gene and regulatory sequences preceding (5' non-coding sequences) and following (3' non-coding sequences) the coding sequence that are required for expression of the selected gene product. Thus, an expression cassette is typically composed of: 1) a promoter sequence; 2) a coding sequence (i.e., ORF); and 3) a terminator that usually contains a polyadenylation site in eukaryotes. The expression cassette(s) is usually included within a vector to facilitate cloning and transformation. Different expression cassettes can be transformed into different organisms including bacteria, yeast, plants and mammalian cells, as long as the correct regulatory sequences are used for each host.

The terms "recombinant construct", "expression construct", "chimeric construct", "construct", and "recombinant DNA construct" are used interchangeably herein. A recombinant construct comprises an artificial combination of nucleic acid fragments, e.g., regulatory and coding sequences that are not found together in nature. For example, a recombinant DNA construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments described herein. The skilled artisan will also recognize that different independent transformation events will result in different levels and patterns of expression (Jones et al., *EMBO J.,* 4:2411-2418 (1985); De Almeida et al., *Mol. Gen. Genetics,* 218:78-86 (1989)), and thus that multiple events must be screened in order to obtain strains or lines displaying the desired expression level and pattern. Such screening may be accomplished by Southern analysis of DNA, northern analysis of mRNA expression, western and/or ELISA analyses of protein expression, formation of a specific product, phenotypic analysis or GC analysis of the PUFA products, among others.

The terms "host cell" and "host organism" are used interchangeably herein and refer to any organism such as a microorganism or a plant (e.g., an oilseed plant) that is capable of receiving foreign or heterologous genes and capable of expressing those genes. A "recombinant host cell" refers to a host cell that has been recombinantly engineered.

Standard recombinant DNA and molecular cloning techniques used herein are well known in the art and are described more fully in Sambrook, J., Fritsch, E. F. and Maniatis, T. Molecular Cloning: A Laboratory Manual; Cold Spring Harbor Laboratory: Cold Spring Harbor, N.Y. (1989); by Silhavy, T. J., Bennan, M. L. and Enquist, L. W., *Experiments with Gene Fusions*, Cold Spring Harbor Laboratory: Cold Spring Harbor, N.Y. (1984); and by Ausubel, F. M. et al., *Current Protocols in Molecular Biology*, published by Greene Publishing Assoc. and Wiley-Interscience, Hoboken, N.J. (1987).

In a first embodiment, described herein is a recombinant microbial cell for the production of at least one long-chain (LC) polyunsaturated fatty acid (PUFA), said recombinant microbial cell comprising:

(a) at least one polypeptide having LPCAT activity;

(b) at least one polypeptide having PDAT activity; and (c) a PUFA biosynthetic pathway capable of producing at least one long-chain polyunsaturated fatty acid;

wherein the polypeptides of (a) and (b) are over-expressed, and wherein the recombinant microbial cell has an increased amount ofat least one long-chain polyunsaturated fatty acid measured as a weight percent of total fatty acids ["wt. % TFAs"], when compared to a control cell.

Over-expression of PDAT and LPCAT can be achieved, for example, by introducing polynucleotides encoding these enzymes (i.e., transgenes) to cells. Preferably, such polynucleotides are operably linked to a regulatory sequence such as a promoter that allows gene expression in the cells modified to contain the polynucleotides. Over-expression of PDAT and LPCAT is with respect to the expression of PDAT and LPCAT in a control cell.

An increase in the amount of the at least one long-chain PUFA (e.g., EPA) measured as a weight percent of total fatty acids ["wt. % TFAs"] of the recombinant microbial cell over-expressing PDAT and LPCAT may be at least about 1%, 2%, 3%, 4%, 5%, 6%, 7%, 8%, 9%, 10%, 11%, 12%, 13%, 14%, 15%, 16%, 17%, 18%, 19%, or 20% over the amount of the at least one long-chain PUFA measured as a weight percent of total fatty acids of a control cell.

With respect to over-expressing PDAT and LPCAT, a control cell, corresponding control cell, or suitable control cell may be a wild type or recombinant cell that corresponds to the recombinant microbial cell, but does not comprise the over-expressed PDAT and LPCAT polypeptides. For example, the control cell does not over-express the PDAT and LPCAT polypeptides by virtue of not comprising recombinant polynucleotide sequences encoding the PDAT and LPCAT polypeptides. Also for example, the control cell does not over-express the PDAT and LPCAT polypeptides by virtue of comprising, but not expressing, recombinant polynucleotide sequences encoding the PDAT and LPCAT polypeptides. The control cell may be the recombinant microbial cell as it existed before it was modified to over-express the PDAT and LPCAT polypeptides (i.e., a parent cell), or may be a recombinant microbial cell that has been modified to contain the recombinant polynucleotides encoding PDAT and LPCAT, but does not over-express the recombinant PDAT and LPCAT polypeptides (e.g., a cell prepared in parallel with the recombinant microbial cell that over-expresses the PDAT and LPCAT polypeptides).

Figure 1:
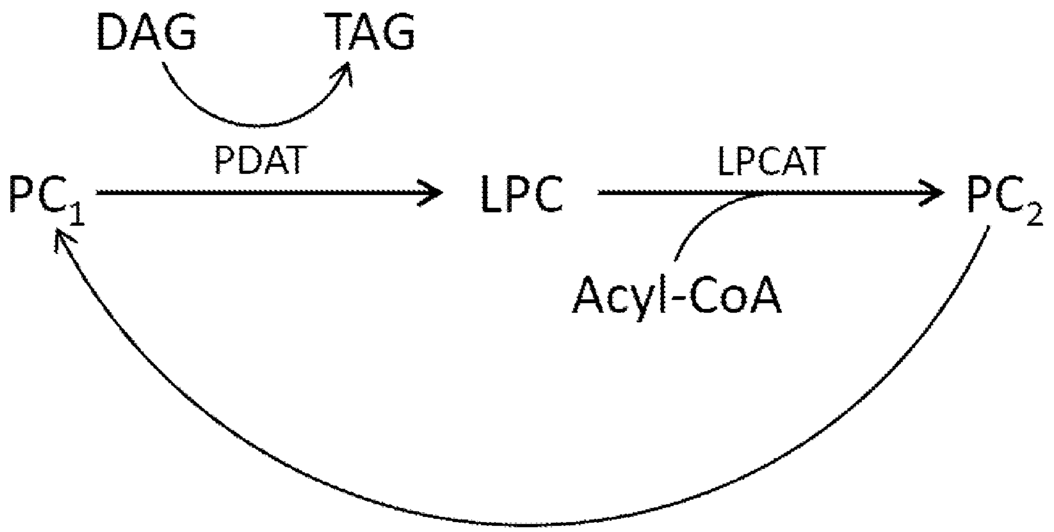
FIG. 1 illustrates the cycle of phosphatidylcholine (PC) substrate use by PDAT and regeneration by LPCAT. $PC_1$ and $PC_2$ may differ in that the fatty acid removed from $PC_1$ by PDAT to yield lysophosphatidylcholine (LPC) may differ from the fatty acid added to LPC by LPCAT in yielding $PC_2$.

PDAT catalyzes TAG biosynthesis by transferring an acyl group from the sn-2 position of phospholipids such as phosphatidylcholine ["PC"], phosphatidylethanolamine ["PE"], and phosphatidic acid ["PA"] to the sn-3 position of 1,2-diacylglycerol ["DAG"]. This reaction results in lysophospholipids such as lysophosphatidylcholine ["LPC"], lysophosphatidylethanolamine ["LPE"], lysophosphatidic acid ["LPA"] and lysophosphatidylglycerol ["LPG"]. LPCAT can regenerate PC by transferring an acyl group from acyl-CoA to the sn-2 position of its substrate LPC. Fatty acid remodeling may occur in this manner, since $PC_1$ (FIG. 1) may not be equivalent to $PC_2$, depending on which fatty acid from the acyl-CoA pool is used to replace the fatty acid that was removed by PDAT. This cycle of PC substrate use ($PC_1$) by PDAT and regeneration ($PC_2$) by LPCAT is diagrammed in FIG. 1.

While the recombinant microbial cell over-expressing LPCAT and PDAT produces an increased amount of long-chain polyunsaturated fatty acid measured as a wt. % TFAs when compared to a control cell, the recombinant microbial cell may also have: (i) an increased $O_{18}$ to $C_{20}$ elongation conversion efficiency; and/or (ii) an increased total lipid content (i.e., the amount of total fatty acids, measured as a weight percent of the dry cell weight ["TFAs % DCW"]), compared to a control cell.

The increased $C_{18}$ to $C_{20}$ elongation conversion efficiency may be either the effect of increased delta-9 elongase conversion efficiency, i.e., when the recombinant microbial cell's PUFA biosynthetic pathway comprises a delta-9 elongase, and/or the effect of increased delta-6 elongase conversion efficiency, i.e., when the recombinant microbial cell's PUFA biosynthetic pathway comprises a delta-6 elongase. The increase in the $C_{18}$ to $C_{20}$ elongation conversion efficiency, delta-9 elongase conversion efficiency, and/or delta-6 elongase conversion efficiency of the recombinant microbial cell over-expressing PDAT and LPCAT may be at least about 1%, 2%, 3%, 4%, 5%, 6%, 7%, 8%, 9%, or 10% over the $O_{18}$ to $O_{20}$ elongation conversion efficiency, delta-9 elongase conversion efficiency, and/or delta-6 elongase conversion efficiency, respectively, of a control cell.

Total lipid content ["TFAs % DCW"] may be increased in the recombinant microbial cell over-expressing LPCAT and PDAT. As is well known to one of skill in the art, economical commercial production of a LC polyunsaturated fatty acid in a recombinant microbial host cell requires consideration of a variety of variables, including the LC polyunsaturated fatty acid concentration ["LC polyunsaturated fatty acid % TFAs"], total lipid content ["TFAs % DCW"] and LC polyunsaturated fatty acid productivity ["LC polyunsaturated fatty acid % DCW"]. Selection of a preferred strain for commercial purposes will consider both the LC polyunsaturated fatty acid TFAs) and TFAs % DCW, as both factors affect the cellular content of the LC polyunsaturated fatty acid as a percent of the dry cell weight.

The increase in the total lipid content (TFAs % DCW) of the recombinant microbial cell over-expressing PDAT and LPCAT may be at least about 1%, 2%, 3%, 4%, or 5% over the total lipid content of a control cell. The increase in total lipid content can coincide with an increase in EPA TFAs.

The recombinant microbial cells of the present invention over-express at least one polypeptide having PDAT activity. Dahlqvist et al. (*Proc. Natl. Acad. Sci. U.S.A.,* 97:6487-6492 (2000)) and Oelkers et al. (*J. Biol. Chem.,* 275:15609-15612 (2000)) were the first to appreciate that TAG synthesis can occur in the absence of acyl-CoA, via the acyl-CoA-independent PDAT enzyme (structurally related to the lecithin:cholesterol acyltransferase family of proteins). More specifically, Dahlqvist et al. and Oelkers et al. demonstrated that overexpression of the *Saccharomyces cerevisiae* LRO1 gene encoding PDAT (SEQ ID NO:30; "ScPDAT") resulted in an increased TAG content, while deletion of ScPDAT caused significant reduction of TAG synthesis. Following this work, U.S. Pat. No. 7,267,976 described the cloning, overexpression and knockout of the *Yarrowia lipolytica* ATCC #90812 gene encoding PDAT (SEQ ID NOs:31 and 32 herein), which was determined to share 47.1% amino acid sequence identity with ScPDAT. *Y. lipolytica* strains having disrupted PDAT were found to have lower oil content ["TFAs % DCW"] as compared to the wild type strain (ca. 29-38%), while strains having a disruption in both PDAT2 and DGAT2 were determined to have only 17-27% oil content when compared to the control. The *Y. lipolytica* PDAT was then expressed in an *S. cerevisiae* strain having a disruption in its native PDAT and DGAT2 genes; TFAs % DCW was doubled in the transformant strains as compared to the control.

For purposes herein, a polypeptide having PDAT activity may be selected from the group consisting of: (a) a sequence consisting essentially of a sequence selected from the group consisting of SEQ ID NO:30 and SEQ ID NO:32; and (b) a polypeptide having at least 90% or 95% amino acid identity, based on the Clustal W method of alignment, when compared to an amino acid sequence selected from the group consisting of SEQ ID NO:30 and SEQ ID NO:32. In this sense, the polypeptide having PDAT activity may be derived from a yeast for example; preferably the yeast PDAT polypeptide is derived from *Saccharomyces cerevisiae* or *Yarrowia lipolytica.*

One of skill in the art will appreciate that either of the sequences set forth as SEQ ID NOs:30 and 32, or portions thereof, may be used to search for PDAT homologs in the same or other algal, fungal, oomycete, euglenoid, stramenopiles, yeast or plant species using sequence analysis software. In general, such computer software matches similar sequences by assigning degrees of homology to various substitutions, deletions, and other modifications. Use of software algorithms, such as the BLASTP method of alignment with a low complexity filter and the following parameters: Expect value=10, matrix=Blosum 62 (Altschul, et al., *Nucleic Acids Res.,* 25:3389-3402 (1997)), is well-known for comparing any PDAT protein against a database of nucleic or protein sequences and thereby identifying similar known sequences within a preferred host organism.

Alternatively, publicly available PDAT sequences or their motifs may be hybridization reagents for the identification of homologs. Hybridization methods are well known to those of ordinary skill in the art as noted above.

Isolation of homologous genes using sequence-dependent protocols is well known in the art. Examples of sequence-dependent protocols include, but are not limited to: 1) methods of nucleic acid hybridization; 2) methods of DNA and RNA amplification, as exemplified by various uses of nucleic acid amplification technologies, such as polymerase chain reaction ["PCR"] (U.S. Pat. No. 4,683,202); ligase chain reaction ["LCR"] (Tabor et al., *Proc. Natl. Acad. Sci. U.S.A.,* 82:1074 (1985)); or strand displacement amplification ["SDA"] (Walker et al., *Proc. Natl. Acad. Sci. U.S.A.,* 89:392 (1992)); and 3) methods of library construction and screening by complementation.

Based on well-known methods available to one of skill in the art, it would be possible to identify and/or isolate PDAT gene homologs in any preferred eukaryotic organism of choice. The activity of any putative PDAT gene can readily be confirmed by expression of the gene within a LC-PUFA-producing host organism, since the LC-polyunsaturated fatty acids measured as a wt. % of TFAs are increased (when co-expressed with a suitable PDAT) relative to those within a control not over-expressing the LPCAT and PDAT transgenes.

The recombinant microbial cells of the present invention over-express at least one polypeptide having LPCAT activity, wherein the polypeptide can be a wild type protein or a mutant protein that is synthetically created (i.e., not naturally occurring). This polypeptide is preferably selected from the group consisting of:

(a) a polypeptide having at least 45% amino acid identity, based on the Clustal W method of alignment, when compared to an amino acid sequence selected from the group consisting of SEQ ID NO:2 (ScLPCAT) and SEQ ID NO:4 (YlLPCAT);

(b) a polypeptide comprising at least one membrane bound O-acyltransferase protein family motif selected from the group consisting of: SEQ ID NO:5 (WHG-$X_3$-GY-$X_3$-F), SEQ ID NO:6 (Y-$X_4$-F), SEQ ID NO:7 (Y-$X_3$-YF-$X_2$-H), SEQ ID NO:8 (M-[V/I]-[L/I]-$X_2$-K-[L/V/I]-$X_8$-DG), SEQ ID NO:9 (RxKYY-$X_2$-W-$X_3$-[E/D]-[A/G]-$X_5$-GxG-[F/Y]-xG), SEQ ID NO:10 (E$X_{11}$WN-$X_2$-[T/V]-$X_2$-W), SEQ ID NO:11 (SAxWHG-$X_2$-PGY-$X_2$-[T/F]-F), SEQ ID NO:12 (M-[V/I]-[L/I/V]-[V/C/A/T]-[M/L/Q]-K-[L/V/I/M]-[S/T/Y/I]-[S/T/A/M/G]-[F/L/C/Y]-[C/A/G/S]-[W/Y/M/I/F/C]-[N/S/E/Q/D]-[V/Y/L/I]-[H/Y/A/N/S/T]-DG), SEQ ID NO:13 (R-[L/M/F/W/P/Y]-KYY-[G/A/F/H/S]-[V/A/I/C]-W-[Y/E/T/M/S/L]-[L/I/N]-[T/S/A]-[E/D]-[G/A]-[A/S/I/V]-[C/S/I/N/H/L]-[V/I/N]-[L/I/N/A/C]-[S/C/W/A/I]-G-[M/I/L/A/F]-G-[Y/F]-[N/E/S/T/R/K]-G), SEQ ID NO:14 (E-[T/F/L/M]-[A/S]-[Q/D/P/K/T]-[N/S]-[S/I/T/L/A/M/F]-[H/K/R/V]-[G/C/E/T/Q/D/M]-[Y/A/M/L/I/F]-[L/S/P/I]-[G/E/A/L/N/D]-[S/A/V/F/M/N]-WN-[K/M/I/C]-[N/K/Q/G]-[T/V]-[N/A/S]-[H/K/N/T/R/L]-W), SEQ ID NO:15 (SA-[F/M/V/I]-WHG-[F/V/T/L]-[Y/S/R]-PGY-[Y/M/I]-[L/M/I/F]-[T/F]-F), SEQ ID NO:16 (M-[V/I]-L-$X_2$-KL), SEQ ID NO:17 (RxKYY-$X_2$-W), and SEQ ID NO:18 (SAxWHG);

(c) a polypeptide comprising at least one mutant membrane bound O-acyltransferase protein family motif, as described below;

(d) a polypeptide having at least 43.9% amino acid identity, based on the Clustal W method of alignment, when compared to an amino acid sequence selected from the group consisting of SEQ ID NO:21 (MaLPAAT1), SEQ ID NO:23 (YlLPAAT1) and SEQ ID NO:24 (ScLPAAT); and (e) a polypeptide comprising at least one 1-acyl-sn-glycerol-3-phosphate acyltransferase family motif selected from the group consisting of: SEQ ID NO:25 (NHxxxxD) and SEQ ID NO:26 (EGTR).

Alternatively, the polypeptide having LPCAT activity may have at least 90%, or 95% amino acid identity, based on the Clustal W method of alignment, when compared to an amino acid sequence selected from the group consisting of SEQ ID NO:2 (ScLPCAT) and SEQ ID NO:4 (YlLPCAT). In this sense, the polypeptide having LPCAT activity may be derived from a yeast for example; preferably the yeast LPCAT polypeptide is derived from *Saccharomyces cerevisiae* or *Yarrowia lipolytica.*

Either the LPCAT sequences set forth herein as SEQ ID NO:2 [ScLPCAT] and SEQ ID NO:4 [YlLPCAT], or portions thereof, or the LPAATs set forth herein as SEQ ID NO:24 [ScLPAAT], SEQ ID NO:21 [MaLPAAT1] and SEQ ID NO:23 [YlLPAAT1], or portions of them, may be used to search for LPCAT homologs in the same or other species using sequence analysis software, as described above with respect to PDATs.

Use of a software algorithm to comb through databases of known sequences is particularly suitable for the isolation of homologs having a relatively low percent identity to publicly available LPCAT sequences, such as those described in SEQ ID NOs:2 and 4. It is predictable that isolation would be relatively easier for LPCAT homologs of at least about 70%-85% identity to publicly available LPCAT sequences. Further, those sequences that are at least about 85%-90% identical would be particularly suitable for isolation and those sequences that are at least about 90%-95% identical would be the most facilely isolated.

LPCAT homologs can also be identified by the use of motifs unique to the LPCAT enzymes, e.g., membrane bound O-acyltransferase ["MBOAT"] family motifs such as described in Table 2. LPCATs that have both LPCAT and LPAAT activity may also be identified by the use of motifs unique to the LPAAT enzymes, e.g., 1-acyl-sn-glycerol-3-phosphate acyltransferase family motifs selected from the group consisting of: NHxxxxD (SEQ ID NO:25) and EGTR (SEQ ID NO:26).

Based on well-known methods available to one of skill in the art, it would be possible to identify and/or isolate LPCAT gene homologs in any preferred eukaryotic organism of choice. The activity of any putative LPCAT gene can readily be confirmed by expression of the gene within a LC-PUFA-producing host organism, since the LC-PUFAs, measured as a wt. % of TFAs, are increased (when co-expressed with a suitable PDAT) relative to those within an organism not over-expressing both the LPCAT and PDAT transgenes (above).

In one aspect of the present invention, considerable effort was invested toward the identification of an isolated polynucleotide encoding a non-naturally occurring mutant polypeptide having LPCAT activity, wherein said mutant polypeptide comprises at least one mutant membrane-bound O-acyltransferase protein motif, said mutant motif selected from the group consisting of:

(a) a mutant motif comprising an amino acid sequence as set forth in SEQ ID NO:33, wherein SEQ ID NO:33 differs from SEQ ID NO:16 (M-[V/I]-L-$X_2$-KL) by at least one amino acid mutation, said mutation selected from the group consisting of: M1A, M1N, M1C, M1G, M1Q, M1H, M1I, M1L, M1F, M1P, M1S, M1T, M1W, M1Y, M1V, V2A, V2N, V2C, V2G, V2Q, V2H, V2L, V2M, V2F, V2P, V2S, V2T, V2W, V2Y, I2A, I2N, I2C, I2G, I2Q, I2H, I2L, I2M, I2F, I2P, I2S, I2T, I2W, I2Y, L3A, L3N, L3C, L3G, L3Q, L3H, L3M, L3F, L3P, L3S, L3T, L3W, L3Y, L3V, K6A, K6R, K6N, K6G, K6H, K6P, K6S, K6T, K6Y, L7A, L7N, L7C, L7G, L7Q, L7H, L7I, L7M, L7F, L7P, L7S, L7T, L7W and L7Y;

(b) a mutant motif comprising an amino acid sequence as set forth in SEQ ID NO:34, wherein SEQ ID NO:34 differs from SEQ ID NO:8 (M-[V/I]-[L/I]-$X_2$-K-[L/V/I]-$X_8$-DG) by at least amino acid mutation, said mutation selected from the group consisting of: M1A, M1N, M1C, M1G, M1Q, M1H, M1I, M1L, M1F, M1P, M1S, M1T, M1W, M1Y, M1V, V2A, V2N, V2C, V2G, V2Q, V2H, V2L, V2M, V2F, V2P, V2S, V2T, V2W, V2Y, 12A, I2N, I2C, I2G, I2Q, I2H, I2L, I2M, I2F, I2P, I2S, I2T, I2W, I2Y, L3A, L3N, L3C, L3G, L3Q, L3H, L3M, L3F, L3P, L3S, L3T, L3W, L3Y, L3V, I3A, I3N, I3C, I3G, I3Q, I3H, I3M, I13F, I3P, I3S, I3T, I3W, 13Y, 13V, K6A, K6R, K6N, K6G, K6H, K6P, K6S, K6T, K6Y, L7A, L7N, L7C, L7G, L7Q, L7H, L7I, L7M, L7F, L7P, L7S, L7T, L7W, L7Y, V7A, V7N, V7C, V7G, V7Q, V7H, V7I, V7M, V7F, V7P, V7S, V7T, V7W, V7Y, I7A, I7N, I7C, I7G, I7Q, I7H, I7M, I7F, I7P, I7S, I7T, I7W, I7Y, D16A, D16N, D16G, D16E, D16Q, D16H, D16F, D16S, D16T, G17A, G17N, G17H, G17L, G17M, G17F, G17S, G17T and G17V;

(c) a mutant motif comprising an amino acid sequence as set forth in SEQ ID NO:35, wherein SEQ ID NO:35 differs from SEQ ID NO:5 (WHG-$X_3$-GY-$X_3$-F) by at least one amino acid mutation, said mutation selected from the group consisting of: G7A, G7N, G7C, G7H, G7I, G7L, G7K, G7M, G7F, G7S, G7T, G7W, G7Y, G7V, Y8A, Y8G, Y8H, Y8L, Y8F, Y8P, Y8S, Y8T, Y8V, F12A, F12N, F12C, F12G, F12H, F12L, F12M, F12P, F12S, F12T and F12V;

(d) a mutant motif comprising an amino acid sequence as set forth in SEQ ID NO:36, wherein SEQ ID NO:36 differs from SEQ ID NO:11 (SAxWHG-$X_2$-PGY-$X_2$-[T/F]-F) by at least one amino acid mutation, said mutation selected from the group consisting of: S1A, S1G, S1N, S1L, S1F, S1P, S1T, S1V, A2N, A2G, A2H, A2L, A2F, A2P, 2S, A2T, A2V, P9A, P9R, P9G, P9H, P9I, P9L, P9K, P9M, P9F, P9S, P9T, P9W, P9Y, P9V, G10A, G10N, G10C, G10H, G10I, G10L, G10K, G10M, G10F, G10S, G10T, G10W, G10Y, G10V, Y11A, Y11G, Y11H, Y11L, Y11F, Y11P, Y11S, Y11T, Y11V, T14A, T14C, T14G, T14H, T14I, T14L, T14M, T14F, T14P, T145, T14W, T14Y, T14V, F14A, F140, F14G, F14H, F14I, F14L, F14M, F14P, F14S, F14W, F14Y, F14V, F15A, F15N, F15C, F15G, F15H, F15L, F15M, F15P, F15S, F15T and F15V; and (e) a complement of the nucleotide sequence of part (a), (b), (c) or (d), wherein the complement and the nucleotide sequence consist of the same number of nucleotides and are 100% complementary.

Therefore, one aspect of the invention concerns an isolated polynucleotide encoding a mutant polypeptide having acyl-CoA:lysophosphatidylcholine acyltransferase (LPCAT) activity, wherein the mutant polypeptide comprises at least one mutant membrane-bound O-acyltransferase protein motif, and the polynucleotide is operably linked to at least one regulatory sequence.

For example, the polynucleotide may encode a mutant yeast (e.g., *Yarrowia*) LPCAT polypeptide having a mutation in Motif I and/or Motif II. Alternatively, the polynucleotide may encode an amino acid sequence that has LPCAT activity and that is at least 90%, or 95%, identical to SEQ ID NO:4 (wild type YlLPCAT) based on the Clustal W method of alignment, and that has one or more mutations (e.g., amino acid substitution, deletion, and/or insertion) in Motif I (SEQ ID NO:4 residues 132, 133, 134, 135, 136, 137, 138, 139, 140, 141, 142, 143, 144, 145, 146, 147, 148) and/or Motif II (SEQ ID NO:4 residues 376, 377, 378, 382, 383, 384, 385, 386, 387, 389, 390). Substitution mutations may be any of those described herein, for example. Preferably, the activity of a mutant LPCAT polypeptide encoded by a polynucleotide is equal to or greater than the activity of wild type YlLPCAT (e.g., SEQ ID NO:4). Such activity can be determined by comparing the EPA % TFAs and/or d9e CE (%) in recombinant cells (e.g., microbial cells) over-expressing a mutant LPCAT with the EPA % TFAs and/or d9e CE (%) in a control cell.

As another example, the polynucleotide may encode a polypeptide that has LPCAT activity and that is at least 90% or 95% identical to: SEQ ID NO:79, where the polypeptide has a serine at position 136 and an alanine at position 389; SEQ ID NO:81, where the polypeptide has a serine at position 136 and a cysteine at position 389; SEQ ID NO:83, where the polypeptide has a serine at position 136 and a serine at position 389; SEQ ID NO:85, where the polypeptide has a valine at position 136 and a cysteine at position 389; SEQ ID NO:87, where the polypeptide has an alanine at position 144 and a serine at position 390; SEQ ID NO:89, where the polypeptide has an alanine at position 148 and a serine at position 390; SEQ ID NO:91, where the polypeptide has an asparagine at position 148 and an isoleucine at position 382; or SEQ ID NO:93, where the polypeptide has an asparagine at position 148 and a serine at position 390.

Methods for synthesizing sequences and bringing sequences together are well established in the literature. Many techniques are commonly employed to obtain mutations of naturally occurring genes (wherein such mutations may include deletions, insertions and point mutations, or combinations thereof). The present work was conducted with the goal of identifying suitable mutation(s) within an LPCAT (e.g., YlLPCAT [e.g., SEQ ID NO:4]) that would be tolerated within the enzyme when it was expressed in a microbial cell engineered to produce at least one LC-polyunsaturated fatty acid. More preferably, identification of mutations that increased the amount of LC-polyunsaturated fatty acid, measured as a wt. % of TFAs, and/or the $C_{18}$ to $C_{20}$ elongation conversion efficiency was especially desirable as a means to increase the overall rate and quantity of PUFA biosynthesis.

A variety of LPCAT mutations are described herein within two specific conserved motifs within the *Yarrowia lipolytica* LPCAT polypeptide. Specifically, a suite of site-saturation libraries were created within the 17 amino acid residues within Motif I, corresponding to SEQ ID NO:8 (M-[V/I]-[L/I]-$X_2$-K-[L/V/I]-$X_8$-DG) and within 12 of the 15 amino acid residues of Motif II, corresponding to SEQ ID NO:11 (SAx-WHG-$X_2$-PGY-$X_2$-[T/F]-F), using YlLPCAT (SEQ ID NO:4) as a template, wherein YlLPCAT was contained within a plasmid construct comprising a chimeric YAT1::YlLPCAT::Lip1 gene. The site-saturation libraries, each comprising a single amino acid change with respect to the YlLPCAT polypeptide, were then transformed into *Yarrowia lipolytica*, and screened for improved delta-9 elongase conversion efficiency ["% Conv."] (i.e., based on conversion of C18 PUFAs to C20 PUFAs) and/or improved production of EPA as a weight percent of TFAs ["EPA % TFAs"] based on GC analyses. These indirect means were utilized to analyze LPCAT activity, as opposed to a direct method.

More specifically, amino acid residues 132 to 148 (Motif I) and amino acid residues 376 to 378 and 382 to 390 (Motif II) within YlLPCAT were individually mutated. All 329 of the mutants performed such that the EPA TFAs was at least 75% of that of the control YlLPCAT polypeptide; and all of the mutants performed with a % Conv. that was at least 87.6% of that of the control YlLPCAT polypeptide. Fifty-six (56) YlLPCAT mutants were found to exhibit equivalent or improved EPA % TFAs and equivalent or improved Conv. An additional 14 YlLPCAT* mutants were determined to have an equivalent or improved EPA % TFAs when compared to the control (but did not have an equivalent or improved % Conv.); an additional 12 YlLPCAT mutants were determined to have an equivalent or improved % Conv., when compared to the control (but did not have an equivalent or improved EPA TFAs). Thus, this work demonstrated that the LPCAT activity of YlLPCAT could indeed be modified without negative implications and even improved by protein engineering.

Mutants resulting in equivalent or improved LPCAT activity were generated at amino acid residues 133, 134, 135, 136, 137, 138, 139, 140, 141, 142, 143, 144, 145, 146, 147 and 148 within Motif I, thereby demonstrating that only the methionine [M] residue of SEQ ID NO:8 (M-[V/I]-[L/I]-$X_2$-K-[L/V/I]-$X_8$-DG) appears unable to tolerate variation. Similarly, mutants resulting in equivalent or improved LPCAT activity were generated at amino acid residues 378, 382, 383, 385, 388, 389 and 390 within Motif II, thereby demonstrating that the serine [S], alanine [A], proline [P] and tyrosine [Y] of SEQ ID NO:11 (SAxWHG-$X_2$-PGY-$X_2$-[T/F]-F) appear unable to tolerate variation. The amino acids at residues 379-381, (i.e., WHG) were not subjected to mutation, since the histidine of other LPCATs corresponding to H380 of YlLPCAT has been reported to be a likely active site residue (Lee et al., 2008, *Mol. Biol. Cell* 19:1174-1184).

Thus, in one embodiment herein, disclosed is an isolated polynucleotide encoding a non-naturally occurring mutant polypeptide having lysophosphatidylcholine acyltransferase ["LPCAT"] activity comprising at least one mutant membrane bound O-acyltransferase protein motif, wherein:

(a) the mutant polypeptide comprises an amino acid sequence as set forth in SEQ ID NO:19, wherein SEQ ID NO:19 differs from SEQ ID NO:4 (YlLPCAT) by at least one amino acid mutation, wherein:
  (i) the amino acid mutation is an amino acid substitution at a residue selected from the group consisting of: residue 133, residue 134, residue 135, residue 136, residue 137, residue 138, residue 139, residue 140, residue 141, residue 142, residue 143, residue 144, residue 145, residue 146, residue 147 and residue 148;
  (ii) the amino acid mutation is in an amino acid substitution at a residue selected from the group consisting of: residue 378, residue 382, residue 383, residue 385, residue 388, residue 389 and residue 390; or
  (iii) there are at least two amino acid mutations, wherein:
    (1) a first amino acid mutation is an amino acid substitution selected from the group set forth in part (i), and
    (2) the second amino acid mutation is an amino acid substitution selected from the group set forth in part (ii);
(b) overexpression of the mutant polypeptide in a recombinant *Yarrowia* cell comprising a polyunsaturated fatty acid biosynthetic pathway that is capable of producing at least one long-chain polyunsaturated fatty acid produces a result selected from the group consisting of:
  (i) an amount of at least one long-chain polyunsaturated fatty acid, measured as a weight percent of total fatty acids that is at least the same as or greater than the amount produced by a control *Yarrowia* cell; and
  (ii) a $C_{18}$ to $C_{20}$ elongation conversion efficiency that is at least the same as or greater than the conversion efficiency of a control *Yarrowia* cell.

Mutant polypeptides having LPCAT activity encoded by the isolated polynucleotide described above are also envisioned by the Applicants herein.

In one preferred embodiment, the amino acid sequence of a mutant YlLPCAT polypeptide comprises an amino acid sequence as set forth in SEQ ID NO:37, wherein SEQ ID NO:37 differs from SEQ ID NO:4 (YlLPCAT) and wherein said difference is an amino acid mutation selected from the group consisting of: L134A, L134C, L134G, C135D, C135I, M136G, M136P, M1365, M136V, K137N, K137G, K137H, K137Y, L138A, L138H, L138M, S139L, S139W, S140N, S140H, S140P, S140W, F141A, F141M, F141W, G142H, W143L, N144A, N144K, N144F, N144T, N144V, V145A, V145G, V145E, V145M, V145F, V145W, Y146G, Y146L, Y146M, D147N, D147Q, D147H, G148A, G148N, T382I, T382P, R383M, L388G, L388Y, T389A, T389C, T389S, F390C, V133C, M136N, L138G, L1381, L138N, S139G, S139N, W143H, G148V, L388H, L388T, F390G, F390N, F390T, C135F, M136T, S140Y, S1401, F141V, G142I, G142V, D147E, F378Y, T382Y, R383A and F390S.

More specifically, and of applicability for use in any recombinant microbial cell (e.g., wherein said LC-polyunsaturated product fatty acid-producing cell is over-expressing both a PDAT and LPCAT), also described herein is a polypeptide having LPCAT activity comprising at least one mutant membrane bound O-acyltransferase protein motif, wherein the mutant motif is selected from the group consisting of:

(a) a mutant motif comprising an amino acid sequence as set forth in SEQ ID NO:38, wherein SEQ ID NO:38 differs from SEQ ID NO:16 (M-[V/I]-L-$X_2$-KL) by at least one amino acid mutation selected from the group consisting of: V2C, I2C, L3A, L3C, L3G, K6H, K6G, K6N, K6Y, L7A, L7N, L7G, L7H, L7I and L7M;

(b) a mutant motif comprising an amino acid sequence as set forth in SEQ ID NO:39, wherein SEQ ID NO:39 differs from SEQ ID NO:8 (M-[V/I]-[L/I]-$X_2$-K-[L/V/I]-$X_8$-DG) by at least one amino acid mutation selected from the group consisting of: V2C, I2C, L3A, L3C, L3G, I3A, I3C, I3G, K6H, K6G, K6N, K6Y, L7A, L7N, L7G, L7H, L7I, L7M, V7A, V7N, V7G, V7H, V7M, I7A, I7N, I7G, I7H, I7M, D16Q, D16N, D16H, G17A, G17V and G17N;

(c) a mutant motif comprising an amino acid sequence as set forth in SEQ ID NO:40, wherein SEQ ID NO:40 differs from SEQ ID NO:5 (WHG-$X_3$-GY-$X_3$-F) by at least one amino acid mutation selected from the group consisting of: F12N, F12C, F12G, and F12T; and (d) a mutant motif comprising an amino acid sequence as set forth in SEQ ID NO:41, wherein SEQ ID NO:41 differs from SEQ ID NO:11 (SAxWHG-$X_2$-PGY-$X_2$-[T/F]-F) by at least one amino acid mutation selected from the group consisting of: T14A, T14C, T145, F15N, F15C, F15G and F15T.

The specific mutations set forth above correspond to mutations identified within YlLPCAT according to the methodologies described above, and that were demonstrated to result in mutants having equivalent or improved EPA % TFAs and/or equivalent or improved % Conv.

Following the work set forth above, wherein single amino acid mutations were created within either Motif I or Motif II of YlLPCAT (SEQ ID NO:4), 18 different single Motif I mutations were then combined with one of 16 preferred single Motif II mutations, resulting in the generation of 167 double mutants (i.e., wherein the LPCAT comprises both a single mutation within Motif I and a single mutation within Motif II). These double mutants were transformed into *Yarrowia lipolytica* strain Y8406U2, and then the lipid profiles of the double mutants were compared to that of the parent YlLPCAT.

Again, the effect of each double mutation on the LPCAT activity of the resulting mutant YlLPCAT protein was screened, based on EPA % TFAs and % delta-9 conversion efficiency. Most of the 167 YlLPCAT mutants functioned with approximately equal or improved activity when compared to YlLPCAT. More specifically, 106 of the double mutants exhibited equivalent or improved EPA % TFAs and equivalent or improved % Conv., 15 of the double mutants had an equivalent or improved EPA % TFAs when compared to the control, while an additional 6 of the double mutants were determined to have an equivalent or improved % Conv. when compared to the control.

Twenty-five (25) of these double mutants were then subjected to flask assays for a detailed analysis of the total lipid content and composition. Seventeen (17) of these double mutants were observed to have equivalent or improved EPA % TFAs and equivalent or improved % Conv., while the remaining 8 had equivalent or improved % Conv. Furthermore, 22 of these 25 mutants were demonstrated to have improved EPA productivity ["EPA DOW"] when compared to the control strain that was not expressing a mutant YlLPCAT comprising a single mutation within Motif I and a single mutation within Motif II.

Thus, disclosed herein is the amino acid sequence of a mutant YlLPCAT polypeptide comprising an amino acid sequence as set forth in SEQ ID NO:42, wherein SEQ ID NO:42 differs from SEQ ID NO:4 (YlLPCAT) and wherein said difference is any one of the pairs of mutations set forth in Table 4 (e.g., an L134A mutation in Motif I may be combined with either a T382I mutation, an L388G mutation, an F390G mutation or an F390T mutation in Motif II, thereby generating mutants L134A_T382I, L134A_L388G, L134A_F390G and L134A_F390T).

TABLE 4

YlLPCAT Double Mutations Demonstrating Equivalent or Improved EPA % TFAs and/or Equivalent or Improved % Delta-9 Conversion

| Amino Acid Mutation in Motif I | Amino Acid Mutation in Motif II |
|---|---|
| L134A | T382I[b], L388G, F390G[a], F390T |
| L134G | L388G[a], F390G[a], F390T[a] |
| M136S | F378Y, T382I, T382P, T382Y, R383M, P384A, L388Y, T389A, T389C, T389S |
| M136V | T382P, T382Y, P384A, L388Y, T389A, T389C, T389S |
| K137H | T382I[a], P384G, L388G[b], L388T, F390G[a], F390S, F390T |
| K137N | F378Y, T382P, R383M, P384G, L388G, L388T, T389A, T389C[b], T389S, F390G[b], F390S, F390T |
| S140H | T382I[b], P384G, L388G[b], L388T, F390G, F390S |
| S140W | T382I, T382P, T382Y, R383M, P384A, L388Y, T389A, T389C, T389S[a] |
| F141M | F378Y, T382P[b], T382Y, R383M, P384A, T389A[a], T389C |
| F141W | F378Y, T382I[b], T382P, T382Y, R383M, P384A, L388Y[b], T389A, T389C, T389S |
| N144A | T382I[a], P384G, L388G, L388T, F390G, F390S, F390T |
| N144T | F378Y, T382P, T382Y, R383M, P384A, L388Y, T389A, T389C, T389S |
| V145M | F378Y[b], T382Y[b], T382I, R383M, T389A, T389C |
| V145W | F378Y[b], T382I, T389A[a], T389S[a] |
| D147H | T382I[b], L388G, L388T, F390S, F390T[a] |
| D147Q | T382I, L388G[a], L388T[a], F390S |
| G148A | F378Y, T382I, T382Y, R383M, P384A[b], P384G, L388G, L388Y, T389A, T389C, F390S, F390T |
| G148N | T382I, P384G[a], L388T, F390G, F390S |

Notes:
Pairs of mutations comprising a first mutation in Motif I and a second mutation in Motif II lacking a superscript (a or b) resulted in equivalent or improved EPA % TFAs and equivalent or improved % Conv.
[a]Indicates a pair of mutations comprising a first mutation in Motif I and a second mutation in Motif II that resulted in equivalent or improved EPA % TFAs (but not equivalent or improved % Conv.).
[b]Indicates a pair of mutations comprising a first mutation in Motif I and a second mutation in Motif II that resulted in equivalent or improved % Conv. (but not equivalent or improved EPA % TFAs).

Based on the above, it will be understood by one of skill in the art that a variety of other double mutations could be generated by combining alternate single mutations within Motif I and single mutations within Motif II, wherein the single mutations are preferably selected from those that existed within the 14 YlLPCAT mutants found to exhibit equivalent or improved EPA % TFAs with respect to the control or from those that existed within the 12 YlLPCAT mutants found to exhibit equivalent or improved % Conv. when compared to the control. More preferably, the single mutations are those that existed within the 56 YlLPCAT mutants found to exhibit equivalent or improved EPA % TFAs and equivalent or improved % Conv.

In one aspect of the invention, a mutant LPCAT polypeptide encoded by the isolated polynucleotide comprises a sequence selected from the group consisting of: SEQ ID NOs:79, 81, 83, 85, 87, 89, 91 and 93.

Although certain combinations of LPCAT amino acid mutations are disclosed herein, one of skill in the art would readily recognize that other combinations of the Motif I and Motif II mutations disclosed herein may be combined as well. Accordingly, one or more of the disclosed Motif I mutations may be used in combination with one or more of the disclosed Motif II mutations in preparing a polynucleotide encoding a mutant LPCAT polypeptide.

The mutant polypeptides described herein (i.e., having at least LPCAT activity) are useful for over-expression along with over-expression of a polypeptide having PDAT activity in a recombinant microbial cell for the improved production of at least one long-chain ["LC"] polyunsaturated fatty acid, wherein over-expression of PDAT and a mutant LPCAT results in an increase in the at least one long-chain polyunsaturated fatty acid, measured as a wt. % TFAs, when compared to a control cell. It should also be noted that these results are also achieved upon over-expression of mutant LPCAT polypeptides described herein without over-expression of PDAT.

Specifically, disclosed herein is a recombinant cell comprising any one of the isolated polynucleotides described herein, encoding a non-naturally occurring mutant polypeptide having LPCAT activity, wherein said recombinant cell further comprises a PUFA biosynthetic pathway capable of producing at least one long-chain polyunsaturated fatty acid, and wherein the isolated polynucleotide is over-expressed, and wherein the recombinant cell comprises at least one of the following:

(a) an amount of at least one long-chain polyunsaturated fatty acid measured as a weight percent of total fatty acids that is at least the same as or greater than the amount produced by a control cell, or (b) a $C_{18}$ to $C_{20}$ elongation conversion efficiency (e.g., delta-9 elongase conversion efficiency or delta-6 elongase conversion efficiency) that is at least the same as or greater than the conversion efficiency of a control cell.

With respect to over-expressing a mutant LPCAT (containing a mutation in Motif I and/or Motif II) in a recombinant cell, over-expression of a mutant LPCAT can be achieved, for example, by introducing a polynucleotide encoding mutant LPCAT (i.e., transgene) to cells. Preferably, such a polynucleotide is operably linked to a regulatory sequence such as a promoter that allows gene expression in the cells (e.g., microbial cells) modified to contain the polynucleotides. Over-expression of mutant LPCAT is with respect to the expression of LPCAT in a control cell.

An increase in the amount of the at least one long-chain PUFA (e.g., EPA) measured as a weight percent of total fatty acids ["wt. % TFAs"] of the recombinant cell over-expressing a mutant LPCAT (containing a mutation in Motif I and/or Motif II) may be at least about 1%, 2%, 3%, 4%, 5%, 6%, 7%, 8%, 9%, 10%, 11%, 12%, 13%, 14%, 15%, 16%, 17%, 18%, 19%, or 20% over the amount of the at least one long-chain PUFA measured as a weight percent of total fatty acids of a control cell.

An increase in the $C_{18}$ to $C_{20}$ elongation conversion efficiency, delta-9 elongase conversion efficiency, and/or delta-6 elongase conversion efficiency of the recombinant cell over-expressing a mutant LPCAT (containing a mutation in Motif I and/or Motif II) may be at least about 1%, 2%, 3%, 4%, 5%, 6%, 7%, 8%, 9%, 10%, 11%, 12%, 13%, 14%, or 15% over the $C_{18}$ to $C_{20}$ elongation conversion efficiency, delta-9 elongase conversion efficiency, and/or delta-6 elongase conversion efficiency, respectively, of a control cell.

Total lipid content (TFAs % DCW) may be increased in the recombinant cell over-expressing mutant LPCAT. The increase in the total lipid content of the recombinant cell may be at least about 1%, 2%, 3%, 4%, 5%, 6%, 7%, 8%, 9%, 10%, 11%, or 12% over the total lipid content of a control cell. The increase in total lipid content can coincide with an increase in EPA % TFAs.

With respect to over-expressing a mutant LPCAT, a control cell, corresponding control cell, or suitable control cell may be a wild type or recombinant cell that corresponds to the recombinant cell, but does not comprise the over-expressed mutant LPCAT polypeptide. For example, the control cell does not over-express a mutant LPCAT polypeptide by virtue of not comprising recombinant polynucleotide sequences encoding mutant LPCAT. Also for example, the control cell does not over-express mutant LPCAT polypeptides by virtue of comprising, but not expressing, a recombinant polynucleotide sequence encoding mutant LPCAT. The control cell may be the recombinant cell as it existed before it was modified to over-express a mutant LPCAT polypeptide (i.e., a parent cell), or may be a recombinant cell that has been modified to contain a recombinant polynucleotide encoding mutant LPCAT, but does not over-express the mutant LPCAT polypeptide (e.g., a cell prepared in parallel with the recombinant cell that over-expresses a mutant LPCAT).

One of ordinary skill in the art is aware of standard resource materials that describe: 1) specific conditions and procedures for construction, manipulation and isolation of macromolecules, such as DNA molecules, plasmids, etc.; 2) generation of recombinant DNA fragments and recombinant expression constructs; and, 3) screening and isolating of clones. See, Maniatis, Silhavy, and Ausubel, as cited above.

In general, the choice of sequences included in a recombinant expression construct depends on the desired expression products, the nature of the host cell and the proposed means of separating transformed cells versus non-transformed cells. Typically, a vector contains at least one expression cassette, a selectable marker and sequences allowing autonomous replication or chromosomal integration. Suitable expression cassettes typically comprise a promoter, the coding sequence of a selected gene (e.g., encoding a polypeptide having at least LPCAT or PDAT activity), and a terminator (i.e., a chimeric gene). Preferably, both control regions are derived from genes from the transformed host cell.

Virtually any promoter (i.e., native, synthetic, or chimeric) capable of directing expression of an ORF encoding a polypeptide of the invention herein will be suitable, although transcriptional and translational regions from the host species are particularly useful. Expression in a host cell can occur in an induced or constitutive fashion. Induced expression occurs by inducing the activity of a regulatable promoter operably linked to the LPCAT and/or PDAT gene(s) of interest, while constitutive expression occurs by the use of a constitutive promoter operably linked to the gene(s) of interest.

A terminator can be derived from the 3' region of a gene from which the promoter was obtained or from a different gene. A large number of termination regions are known and function satisfactorily in a variety of hosts when utilized in both the same and different genera and species from which they were derived. The terminator usually is selected more as a matter of convenience rather than because of any particular property. Preferably, the terminator is derived from a yeast gene. The terminator can also be synthetic, as one of skill in the art can utilize available information to design and synthesize a terminator. A terminator may be unnecessary, but it is highly preferred.

Many specialized expression vectors have been created to obtain a high expression rate. Such vectors are made by adjusting certain properties that govern transcription, RNA stability, translation, protein stability and location, and secretion from the host cell. These properties include: the nature of the relevant transcriptional promoter and terminator sequences; the number of copies of the cloned gene (wherein additional copies may be cloned within a single expression construct and/or additional copies may be introduced into the host cell by increasing the plasmid copy number or by multiple integration of the cloned gene into the genome); whether the gene is plasmid-borne or integrated into the host cell genome; the final cellular location of the synthesized protein; the efficiency of translation and correct folding of the protein in the host organism; the intrinsic stability of the mRNA and protein of the cloned gene within the host cell; and, the codon usage within the cloned gene, such that its frequency approaches the frequency of preferred codon usage of the host cell.

Once a DNA cassette (e.g., comprising a chimeric gene comprising a promoter, an ORF encoding a polypeptide having LPCAT activity or PDAT activity, and a terminator) suitable for expression in an appropriate cell has been obtained, it is placed in a plasmid vector capable of autonomous replication in the host cell or it is directly integrated into the genome of the host cell. Integration of expression cassettes can occur randomly within the host genome or can be targeted through the use of constructs containing regions of homology with the host genome sufficient to target recombination with the host locus. Where constructs are targeted to an endogenous locus, all or some of the transcriptional and translational regulatory regions can be provided by the endogenous locus.

Constructs comprising a chimeric gene(s) of interest may be introduced into e.g., oleaginous yeast by any standard technique. These techniques include transformation (e.g., lithium acetate transformation [*Methods in Enzymology,* 194: 186-187 (1991)]), biolistic impact, electroporation, microinjection, or any other method that introduces the gene(s) of interest into the host cell. More specific teachings applicable for *Y. lipolytica* include U.S. Pat. No. 4,880,741 and U.S. Pat. No. 5,071,764 and Chen et al. (*Appl. Microbiol. Biotechnol.,* 48(2):232-235 (1997)), which are incorporated herein by reference. Integration of a linear DNA fragment into the genome of the host is favored in transformation of *Y. lipolytica* host cells. Integration into multiple locations within the genome can be particularly useful when high level expression of genes are desired. Preferred loci include those taught in U.S. Pat. Appl. Publ. No. 2009-0093543-A1.

The transformed host cell can be identified by selection for a marker contained on the introduced construct. Alternatively, a separate marker construct may be co-transformed with the desired construct, as many transformation techniques introduce many DNA molecules into host cells.

Stability of an integrated DNA fragment in a microbial host cell is often dependent on the individual transformants, the recipient strain and the targeting platform used. Thus, multiple transformants of a particular recombinant microbial host should be screened in order to obtain a strain displaying the desired expression level and pattern. Southern analysis of DNA blots (Southern, *J. Mol. Biol.,* 98:503 (1975)), northern analysis of mRNA expression (Kroczek, *J. Chromatogr. Biomed. Appl.,* 618(1-2):133-145 (1993)), western analysis of protein expression, phenotypic analysis or GC analysis are suitable screening methods.

Disclosed herein are recombinant constructs that comprise the isolated polynucleotides of the invention. For example, a recombinant construct may comprise an isolated polynucleotide encoding a non-naturally occurring mutant polypeptide having LPCAT activity, wherein the mutant polypeptide comprises at least one mutant membrane MBOAT protein motif, operably linked to at least one regulatory sequence.

Disclosed herein are recombinant cells that comprise the recombinant constructs of the invention. The recombinant cells described herein all comprise a PUFA biosynthetic pathway capable of producing at least one LC polyunsaturated fatty acid. Preferably, the long-chain polyunsaturated fatty acid is selected from the group consisting of: eicosadienoic acid, dihomo-gamma-linolenic acid, arachidonic acid, docosatetraenoic acid, omega-6 docosapentaenoic acid, eicosatrienoic acid, eicosatetraenoic acid, eicosapentaenoic acid, omega-3 docosapentaenoic acid and docosahexaenoic acid.

The metabolic process wherein oleic acid is converted to LC-PUFAs involves elongation of the carbon chain through the addition of carbon atoms and desaturation of the molecule through the addition of double bonds. This requires a series of special desaturation and elongation enzymes present in the endoplasmic reticulum membrane. However, as seen in FIG. 2 and as described below, multiple alternate pathways exist for LC-PUFA production.

Specifically, FIG. 2 depicts the pathways described below. All pathways require the initial conversion of oleic acid to linoleic acid ["LA"], the first of the omega-6 fatty acids, by a delta-12 desaturase. Then, using the "delta-9 elongase/delta-8 desaturase pathway" and LA as substrate, long-chain omega-6 fatty acids are formed as follows: 1) LA is converted to eicosadienoic acid ["EDA"] by a delta-9 elongase; 2) EDA is converted to dihomo-gamma-linolenic acid ["DGLA"] by a delta-8 desaturase; 3) DGLA is converted to arachidonic acid ["ARA"] by a delta-5 desaturase; 4) ARA is converted to docosatetraenoic acid ["DTA"] by a $C_{20/22}$ elongase; and 5) DTA is converted to docosapentaenoic acid ["DPAn-6"] by a delta-4 desaturase.

The "delta-9 elongase/delta-8 desaturase pathway" can also use alpha-linolenic acid ["ALA"] as substrate to produce long-chain omega-3 fatty acids as follows: 1) LA is converted to ALA by a delta-15 desaturase; 2) ALA is converted to eicosatrienoic acid ["ETrA"] by a delta-9 elongase; 3) ETrA is converted to eicosatetraenoic acid ["ETA"] by a delta-8 desaturase; 4) ETA is converted to eicosapentaenoic acid ["EPA"] by a delta-5 desaturase; 5) EPA is converted to docosapentaenoic acid ["DPA"] by a $C_{20/22}$ elongase; and 6) DPA is converted to docosahexaenoic acid ["DHA"] by a delta-4 desaturase. Optionally, omega-6 fatty acids may be converted to omega-3 fatty acids. For example, ETA and EPA are produced from DGLA and ARA, respectively, by delta-17 desaturase activity.

Alternate pathways for the biosynthesis of omega-3/omega-6 fatty acids utilize a delta-6 desaturase and $C_{18/20}$ elongase, that is, the "delta-6 desaturase/delta-6 elongase pathway". More specifically, LA and ALA may be converted to GLA and stearidonic acid ["STA"], respectively, by a delta-6 desaturase; then, a $C_{18/20}$ elongase converts GLA to DGLA and/or STA to ETA.

A LC-PUFA-producing recombinant cell will possess at least one of the biosynthetic pathways described above, whether this pathway is native to the cell or is genetically engineered. Preferably, the recombinant cell will be capable of producing at least about 2-5% LC-PUFAs in the total lipids of the recombinant cell, more preferably at least about 5-15% LC-PUFAs in the total lipids, more preferably at least about 15-35% LC-PUFAs in the total lipids, more preferably at least about 35-50% LC-PUFAs in the total lipids, more preferably at least about 50-65% LC-PUFAs in the total lipids and most preferably at least about 65-75% LC-PUFAs in the total lipids. The structural form of the LC-PUFAs is not limiting; thus, for example, the EPA or DHA may exist in the total lipids as free fatty acids or in esterified forms such as acylglycerols, phospholipids, sulfolipids or glycolipids.

An "LC polyunsaturated fatty acid" refers to the PUFA that the PUFA biosynthetic pathway is designed to produce. Thus, for example, in the present examples, a *Yarrowia lipolytica* strain engineered to express a PUFA biosynthetic pathway comprising delta-12 desaturase, delta-9 elongase, delta-8 desaturase, delta-5 desaturase and delta-17 desaturase genes produced a variety of fatty acids in the lipids including palmitate, palmitoleic acid, stearic acid, oleic acid, LA, ALA, EDA, DGLA, ARA, ETrA, ETA, EPA. However, since the strain was designed to primarily produce EPA as the product of the PUFA biosynthetic pathway, this fatty acid should be considered as the LC polyunsaturated product fatty acid.

A variety of eukaryotes such as plants, fungi and microbial organisms, including yeast, algae, stramenopiles, oomycetes and euglenoids can be used herein to produce (or can be engineered to produce) LC-PUFAs. These may include cells that grow on a variety of feedstocks, including simple or complex carbohydrates, fatty acids, organic acids, oils, glycerols and alcohols, and/or hydrocarbons over a wide range of temperature and pH values. Thus, any of these organisms are suitable host cells for transformation with the polynucleotides of the invention.

Preferred microbes are oleaginous organisms. These oleaginous organisms are naturally capable of oil synthesis and accumulation, wherein the total oil content can comprise greater than about 25% of the dry cell weight, more preferably greater than about 30% of the dry cell weight, and most preferably greater than about 40% of the dry cell weight. Various bacteria, algae, euglenoids, moss, fungi, yeast and stramenopiles are naturally classified as oleaginous. Within this broad group of microbes, of particular interest are those organisms that naturally produce omega-3/omega-6 fatty acids. For example, ARA, EPA and/or DHA is produced by *Cyclotella* sp., *Crypthecodinium* sp., *Mortierella* sp., *Nitzschia* sp., *Pythium, Thraustochytrium* sp. and *Schizochytrium* sp. Thus, for example, transformation of *Mortierella alpina*, which is commercially used for production of ARA, with any of the present LPCAT genes (optionally with co-expression of PDAT) under the control of inducible or regulated promoters could yield a transformant organism capable of synthesizing increased quantities of ARA. The method of transformation of *M. alpina* is described by Mackenzie et al. (*Appl. Environ. Microbiol.*, 66:4655 (2000)). Similarly, methods for transformation of Thraustochytriales microorganisms (e.g., *Thraustochytrium, Schizochytrium*) are disclosed in U.S. Pat. No. 7,001,772. In alternate embodiments, a non-oleaginous organism can be genetically modified to become oleaginous, e.g., yeast such as *Saccharomyces cerevisiae* (U.S. Pat. Appl. Publ. No. 2007/0015237-A1).

In more preferred embodiments, the microbial cells are oleaginous yeast. Genera typically identified as oleaginous yeast include, but are not limited to: *Yarrowia, Candida, Rhodotorula, Rhodosporidium, Cryptococcus, Trichosporon* and *Lipomyces*. More specifically, illustrative oil-synthesizing yeast include: *Rhodosporidium toruloides, Lipomyces starkeyii, L. lipoferus, Candida revkaufi, C. pulcherrima, C. tropicalis, C. utilis, Trichosporon pullans, T. cutaneum, Rhodotorula glutinus, R. graminis* and *Yarrowia lipolytica* (formerly classified as *Candida lipolytica*). Most preferred is the oleaginous yeast *Yarrowia lipolytica*; and in a further embodiment, most preferred are the *Y. lipolytica* strains designated as ATCC #76982, ATCC #20362, ATCC #8862, ATCC #18944 and/or LGAM S(7)1 (Papanikolaou S., and Aggelis G., Bioresour. Technol., 82(1):43-9 (2002)).

Specific teachings applicable for engineering ARA, EPA and DHA production in *Y. lipolytica* are provided in U.S. Pat. No. 7,588,931, U.S. Pat. No. 7,932,077, U.S. Pat. Appl. Publications No. 2009-0993543-A1, No. 2010-0317072-A1 and No. 2012-0052537-A1, and U.S. Pat. No. 7,550,286, respectively, all of which are incorporated herein by reference. These references also describe the preferred method of expressing genes in *Yarrowia lipolytica* by integration of linear DNA fragments into the genome of the host, preferred promoters, termination regions, integration loci and disruptions, and preferred selection methods when using this particular host species.

Similarly, a variety of plants may produce (or be engineered to produce) at least one LC polyunsaturated fatty acid (see, e.g., PCT Publ. No. WO 1998/46764, U.S. Pat. Appl. Publ. No. 2004-0172682-A1) and thus are suitable host cells for transformation with the polynucleotides described herein. For example, U.S. Pat. Appl. Publ. No. 2008-0254191-A1 provides a detailed discussion concerning oleaginous plants, which are commonly referred to as "oilseed" plants (which include, e.g., soybean [Glycine and *Soja* sp.], rapeseed [*Brassica* sp.], sunflower [*Helianthus* sp.], maize, cotton, flax [*Linum* sp.] and safflower [*Carthamus* sp.]), as well as means to engineer suitable recombinant constructs for these species and enable transformations and regeneration of the transformed plant tissue and cells.

The transformed recombinant cell is grown under conditions that optimize expression of chimeric genes of the invention and produce the greatest and the most economical yield of the LC polyunsaturated fatty acid(s). In general, media conditions may be optimized by modifying the type and amount of carbon source, the type and amount of nitrogen source, the carbon-to-nitrogen ratio, the amount of different mineral ions, the oxygen level, growth temperature, pH, length of the biomass production phase, length of the oil accumulation phase and the time and method of cell harvest.

*Yarrowia lipolytica* is generally grown in a complex media such as yeast extract-peptone-dextrose broth ["YPD"] or a defined minimal media that lacks a component necessary for growth and thereby forces selection of the desired expression cassettes (e.g., Yeast Nitrogen Base (DIFCO Laboratories, Detroit, Mich.)).

Fermentation media for the methods and host cells described herein must contain a suitable carbon source, such as are taught in U.S. Pat. No. 7,238,482 and U.S. Pat. Appl. Publ. No. 2011-0059204-A1. Although it is contemplated that the source of carbon utilized may encompass a wide variety of carbon-containing sources, preferred carbon sources are sugars, glycerol and/or fatty acids. Most preferred is glucose, sucrose, invert sucrose, fructose and/or fatty acids containing between 10-22 carbons. For example, the fermentable carbon source can be selected from the group consisting of invert sucrose, glucose, fructose and combinations of these, provided that glucose is used in combination with invert sucrose and/or fructose.

Nitrogen may be supplied from an inorganic (e.g., $(NH_4)_2SO_4$) or organic (e.g., urea or glutamate) source. In addition to appropriate carbon and nitrogen sources, the fermentation media must also contain suitable minerals, salts, cofactors, buffers, vitamins and/or other components known to those skilled in the art suitable for the growth of the host cells and the promotion of the enzymatic pathways for LC polyunsaturated fatty acid production. Particular attention is given to several metal ions, such as $Fe^{+2}$, $Cu^{+2}$, $Mn^{+2}$, $Co^{+2}$, $Zn^{+2}$ and $Mg^{+2}$ that promote synthesis of lipids and PUFAs (Nakahara, T. et al., *Ind. Appl. Single Cell Oils*, D. J. Kyle and R. Colin, eds. pp 61-97 (1992)).

Preferred growth media for the methods and host cells described herein are common commercially prepared media, such as Yeast Nitrogen Base (DIFCO Laboratories, Detroit, Mich.). Other defined or synthetic growth media may also be used and the appropriate medium for growth of *Yarrowia lipolytica* will be known by one skilled in the art of microbiology or fermentation science. A suitable pH range for the fermentation is typically between about pH 4.0 to pH 8.0, wherein pH 5.5 to pH 7.5 is preferred as the range for the initial growth conditions. The fermentation may be conducted under aerobic or anaerobic conditions, wherein microaerobic conditions are preferred.

Typically, accumulation of high levels of PUFAs in oleaginous yeast cells requires a two-stage process, since the metabolic state must be "balanced" between growth and synthesis/storage of fats. Thus, most preferably, a two-stage fermentation process is necessary for the production of LC polyunsaturated fatty acid(s) in *Yarrowia lipolytica*. This approach is described in U.S. Pat. No. 7,238,482, as are various suitable fermentation process designs (i.e., batch, fed-batch and continuous) and considerations during growth.

Thus, in one aspect, the present invention is directed toward a method for improving the production of at least one LC polyunsaturated fatty acid, comprising:

(a) growing the recombinant microbial cell of the invention in the presence of a fermentable carbon source; and (b) optionally recovering the LC polyunsaturated fatty acid.

Preferably, the recombinant microbial cell grown in this method is an oleaginous yeast such as one of the genus *Yarrowia* (e.g., *Y. lipolytica*). The LC PUFA produced by the method is preferably selected from the group consisting of: eicosadienoic acid, dihomo-gamma-linolenic acid, arachidonic acid, docosatetraenoic acid, omega-6 docosapentaenoic acid, eicosatrienoic acid, eicosatetraenoic acid, eicosapentaenoic acid, omega-3 docosapentaenoic acid and docosahexaenoic acid.

EXAMPLES

The present invention is further described in the following Examples, which illustrate reductions to practice of the invention but do not completely define all of its possible variations.

General Methods

Standard recombinant DNA and molecular cloning techniques used in the Examples are well known in the art and are described by: 1) Sambrook, J., Fritsch, E. F. and Maniatis, T. *Molecular Cloning: A Laboratory Manual*; Cold Spring Harbor Laboratory: Cold Spring Harbor, N.Y. (1989); 2) T. J. Silhavy, M. L. Bennan, and L. W. Enquist, Experiments with Gene Fusions; Cold Spring Harbor Laboratory: Cold Spring Harbor, N.Y. (1984); and, 3) Ausubel, F. M. et al., Current Protocols in Molecular Biology, published by Greene Publishing Assoc. and Wiley-Interscience, Hoboken, N.J. (1987).

Materials and Methods suitable for the maintenance and growth of microbial cultures are well known in the art. Techniques suitable for use in the following examples may be found as set out in Manual of Methods for General Bacteriology (Phillipp Gerhardt, R. G. E. Murray, Ralph N. Costilow, Eugene W. Nester, Willis A. Wood, Noel R. Krieg and G. Briggs Phillips, Eds, American Society for Microbiology: Washington, D.C. (1994)); or by Thomas D. Brock in Biotechnology: A Textbook of Industrial Microbiology, 2nd ed., Sinauer Associates Sunderland, Mass. (1989). All reagents, restriction enzymes and materials used for the growth and maintenance of microbial cells were obtained from Aldrich Chemicals (Milwaukee, Wis.), DIFCO Laboratories (Detroit, Mich.), New England Biolabs, Inc. (Beverly, Mass.), GIBCO/BRL (Gaithersburg, Md.), or Sigma Chemical Company (St. Louis, Mo.), unless otherwise specified. *E. coli* strains were typically grown at 37° C. on Luria Bertani ["LB"] plates.

General molecular cloning was performed according to standard methods (Sambrook et al., above). DNA sequence was generated on an ABI Automatic sequencer using dye terminator technology using a combination of vector and insert-specific primers. Sequence editing was performed in Sequencher (Gene Codes Corporation, Ann Arbor, Mich.).

*Yarrowia lipolytica* strain ATCC #20362 was purchased from the American Type Culture Collection (Manassas, Va.). *Y. lipolytica* strains were routinely grown at 28-30° C. in several media (e.g., Basic Minimal Media ["MM"], Minimal Media+5-Fluoroorotic Acid ["MM+5-FOA"], High Glucose Media ["HGM"] and Fermentation medium ["FM"]), as described in U.S. Pat. Appl. Publ. No. 2009-0093543-A1, which is incorporated herein by reference.

Transformation of *Y. lipolytica* was performed as described in U.S. Pat. Appl. Publ. No. 2009-0093543-A1, which is incorporated herein by reference.

For fatty acid ["FA"] analysis, cells were collected by centrifugation and lipids were extracted as described by Bligh and Dyer (*Can. J. Biochem. Physiol.,* 37:911-917 (1959)). Fatty acid methyl esters ["FAMEs"] were prepared by transesterification of the lipid extract with sodium methoxide (Roughan and Nishida, *Arch Biochem Biophys.,* 276(1):38-46 (1990)) and subsequently analyzed with a Hewlett-Packard 6890 GC fitted with a 30-m×0.25 mm (i.d.) HP-INNOWAX (Hewlett-Packard) column. The oven temperature was from 170° C. (25 min hold) to 185° C. at 3.5° C./min.

For direct base transesterification, *Yarrowia* cells (0.5 mL culture) were harvested, washed once in distilled water, and dried under vacuum in a Speed-Vac for 5-10 min. Sodium methoxide (100 μl of 1%) and a known amount of C15:0 triacylglycerol (C15:0 TAG; Cat. No. T-145, Nu-Check Prep, Elysian, Minn.) was added to the sample, and then the sample was vortexed and rocked for 30 min at 50° C. After adding 3 drops of 1 M NaCl and 400 μl hexane, the sample was vortexed and spun. The upper layer was removed and analyzed by GC.

Alternately, a modification of the base-catalyzed transesterification method described in *Lipid Analysis*, William W. Christie, 2003 was used for routine analysis of the broth samples from either fermentation or flask samples. Specifically, broth samples were rapidly thawed in room temperature water, then weighed to 0.1 mg into a tarred 2-mL microcentrifuge tube with a 0.22-μm Corning® Costar® Spin-X® centrifuge tube filter (Cat. No. 8161). Sample (75-800 μl) was used, depending on the previously determined DCW. Using an Eppendorf 5430 centrifuge, samples are centrifuged for 5-7 min at 14,000 rpm or as long as necessary to remove the broth. The filter was removed, liquid was drained, and ~500 μl of deionized water was added to the filter to wash the sample. After centrifugation to remove the water, the filter was again removed, the liquid drained and the filter re-inserted. The tube was then re-inserted into the centrifuge, this time with the top open, for ~3-5 min to dry. The filter was then cut approximately half-way up the tube and inserted into a fresh 2-mL round bottom Eppendorf tube (Cat. No. 22 36 335-2).

The filter was pressed to the bottom of the tube with an appropriate tool that only touches the rim of the cut filter container and not the sample or filter material. A known amount of C15:0 TAG (above) in toluene was added and 500 μl of freshly made 1% sodium methoxide in methanol solution. The sample pellet was firmly broken up and the tubes were closed and placed in a 50° C. heat block (VWR Cat. No. 12621-088) for 30 min. The tubes were then allowed to cool for at least 5 min. Then, 400 μl of hexane and 500 μl of a 1 M NaCl in water solution were added, the tubes were vortexed for 2×6 sec and centrifuged for 1 min. Approximately 150 μl of the top (organic) layer was placed into a GC vial with an insert and analyzed by GC.

FAME peaks recorded via GC analysis were identified by their retention times, when compared to that of known fatty acids, and quantitated by comparing the FAME peak areas with that of the internal standard (C15:0 TAG) of known amount. Thus, the approximate amount (μg) of any fatty acid FAME ["μg FAME"] is calculated according to the formula:

(area of the FAME peak for the specified fatty acid/area of the standard FAME peak)*(μg of the standard C15:0 TAG), while the amount (μg) of any fatty acid ["μg FA"] is calculated according to the formula: (area of the FAME peak for the specified fatty acid/area of the standard FAME peak)*(μg of the standard C15:0 TAG)*0.9503, since 1 μg of C15:0 TAG is equal to 0.9503 μg fatty acids. Note that the 0.9503 conversion factor is an approximation of the value determined for most fatty acids, which range between 0.95 and 0.96.

The lipid profile, summarizing the amount of each individual fatty acid as a weight percent of TFAs (i.e., FA % TFAs), was determined by dividing the individual FAME peak area by the sum of all FAME peak areas and multiplying by 100.

For quantitating the amount of an individual fatty acid or the total fatty acids as a weight percent of the dry cell weight ["% DCW"], cells from 10 mL of the culture were collected by centrifugation, washed once with 10 mL water and collected by centrifugation again. Cells were resuspended in 1-2 mL water, poured into a pre-weighed aluminum weighing pan, and rinsed with 1-2 mL water that was also added to the same weighing pan. The pan was placed under vacuum at 80° C. overnight. The pan was weighed and the DCW calculated by subtracting the weight of the empty pan. Determination of the fatty acid as a % DCW can then be calculated based on either μg FAME or μg FA as a fraction of the μg DCW (for example, FAME % DCW was calculated as μg FAME/μg DCW*100).

For a detailed analysis of the total lipid content and composition in a particular strain of *Y. lipolytica*, flask assays were conducted as followed. Specifically, one loop of freshly streaked cells was inoculated into 3 mL FM medium and grown overnight at 250 rpm and 30° C. The $OD_{600nm}$ was measured and an aliquot of the cells were added to a final $OD_{600nm}$ of 0.3 in 25 mL FM medium in a 125 mL flask. After 2 days in a shaking incubator at 250 rpm and at 30° C., 6 mL of the culture was harvested by centrifugation and resuspended in 25 mL HGM in a 125 mL flask. After 5 days in a shaking incubator at 250 rpm and at 30° C., a 1 mL aliquot was used for fatty acid analysis and 10 mL dried for dry cell weight determination.

Example 1

Isolation of *Yarrowia lipolytica* LPCAT

U.S. Pat. Appl. Publ. No. 2010-0317882-A1, incorporated herein by reference, describes the identification of a *Y. lipolytica* homolog to the *Saccharomyces cerevisiae* Ale1 (i.e., "ScAleI"; SEQ ID NO:2; GenBank Accession No. NP_014818; U.S. Pat. No. 7,732,155; Intl. Appl. Publ. No. WO 2009/001315). This homolog, designated therein as either YIAleI or YILPCAT (SEQ ID NO:4) and corresponding to ORF YALI0F19514p (GenBank Accession No. XP_505624; Intl. Appl. Publ. No. WO 2009/001315) was found to be 45% identical to ScAleI.

YILPCAT was analyzed to determine the presence or absence of non-plant motifs present in Ale1 homologs, as identified in U.S. Pat. No. 7,732,155 and U.S. Pat. Appl. Publ. No. 2008-0145867-A1, which are herein incorporated by reference. Specifically, these motifs are SEQ ID NOs:8-15 (Table 2). The H is residue in SEQ ID NO:11 (SAxWHG-$X_2$-PGY-$X_2$-[T/F]-F) may be an active site residue within the protein, given studies of other LPCATs (Lee et al., 2008, *Mol. Biol. Cell* 19:1174-1184). It was determined that YILPCAT comprises at least the motifs SEQ ID NOs:8-11. It is hypothesized herein that these conserved motifs are likely involved in catalysis.

Overexpression of YILPLAT in a strain of *Y. lipolytica* that had been engineered to produce EPA resulted in a significant reduction of the concentration of LA (18:2) as a weight % of TFAs ["LA % TFAs"], an increase in the concentration of EPA as a weight % of TFAs ["EPA % TFAs"], and an increase in the conversion efficiency of delta-9 elongase (U.S. Pat. Appl. Publ. No. 2010-0317882-A1).

Example 2

Co-Expression of PDAT with LPCAT or LPAAT in *Yarrowia lipolytica*

The present Example describes overexpression of a *Y. lipolytica* PDAT (phospholipid:diacylglycerol acyltransferase [EC 2.3.1.158]) with either a *Y. lipolytica* LPCAT (acyl-CoA:lysophosphatidylcholine acyltransferase [EC 2.3.1.23]) or a *Y. lipolytica* LPAAT (acyl CoA:lysophosphatidic acid acyltransferase [EC 2.3.1.51]) in a *Y. lipolytica* strain that had been engineered to produce a high level of lipids containing eicosapentaenoic acid ["EPA"]. Compared to *Yarrowia* transformants co-expressing PDAT and LPAAT, transformants co-expressing PDAT and LPCAT produced an increased amount of EPA, measured as a weight percent of total fatty acids (EPA % TFAs). Furthermore, PDAT and LPCAT co-expression resulted in an increased $C_{18}$ to $C_{20}$ elongation conversion efficiency, measured as increased delta-9 elongase percent conversion efficiency, and an increased amount of total fatty acids, measured as a weight percent of the dry cell weight (TFAs % DCW).

Construction of Vectors for Overexpression of PDAT with LPAAT or LPCAT

To test if the enzymatic activities of PDAT and LPCAT could function synergistically to improve oil and EPA production in *Yarrowia*, the effects of co-expressing PDAT with LPAAT were compared to the effects of co-expressing PDAT with LPCAT.

Plasmids pY196 (FIG. 3A, SEQ ID NO:43) and pY301 (FIG. 3B, SEQ ID NO:44) were constructed to co-express these enzyme pairs in *Y. lipolytica*. As listed in Tables 5 and 6, respectively, both of these plasmids contained a chimeric YAT1::YIPDAT::Pex16 gene for expressing wild type *Y. lipolytica* PDAT (SEQ ID NO:32). pY196 also contained a chimeric FBAINm::YILPAAT1::Lip1 gene for expressing wild type *Y. lipolytica* LPAAT1 (SEQ ID NO:23), while pY301 also contained a chimeric YAT1::YILPCAT::Lip1 gene for expressing wild type *Y. lipolytica* LPCAT (SEQ ID NO:4).

TABLE 5

Components of Plasmid pY196 (SEQ ID NO: 43)

| RE Sites and Nucleotides within SEQ ID NO: 43 | Description of Fragment and Chimeric Gene Components |
|---|---|
| SphI/AvrII 1-875 | Fragment of *Y. lipolytica* URA3 gene (GenBank Accession No. AJ306421; labeled as "U3 repeat" in FIG. 3A) |
| AvrII/PacI 875-3078 | ColE1 plasmid origin of replication Ampicillin-resistance gene |
| PacI/SalI 3078-4570 | *Y. lipolytica* URA3 gene (GenBank Accession No. AJ306421) |

TABLE 5-continued

| Components of Plasmid pY196 (SEQ ID NO: 43) | |
|---|---|
| RE Sites and Nucleotides within SEQ ID NO: 43 | Description of Fragment and Chimeric Gene Components |
| SalI/PmeI 4570-7624 | YAT1::YlPDAT::PEX16, comprising: YAT1: *Y. lipolytica* YAT1 promoter (U.S. Pat. Appl. Publ. No. 2010/0068789); YlPDAT: *Y. lipolytica* phospholipid:diacylglycerol acyltransferase gene (SEQ ID NO: 32; U.S. Pat. No. 7,901,928; GenBank Accession No. XM_504038); PEX16 terminator sequence from *Yarrowia* PEX16 gene (GenBank Accession No. YLU75433) |
| PmeI/SwaI 7624-8919 | Kanamycin-resistance gene from plasmid pBHR1 (GenBank Accession No. Y14439) |
| SwaI/SphI 8919-1 | FBAINm::YlLPAAT1::Lip1 (complementary), comprising: FBAINm: *Y. lipolytica* FBAINm promoter (U.S. Pat. No. 7,202,356); YlLPAAT1: *Y. lipolytica* acyl-CoA:lysophosphatidic acid acyltransferase gene (SEQ ID NO: 23; U.S. Pat. No. 7,189,559; GenBank Accession No. XP_504127); Lip1: terminator sequence from *Yarrowia* Lip1 gene (GenBank Accession No. Z50020) |

TABLE 6

| Components of Plasmid pY301 (SEQ ID NO: 44) | |
|---|---|
| RE Sites and Nucleotides within SEQ ID NO: 44 | Description of Fragment and Chimeric Gene Components |
| SphI/AvrII 1-875 | Fragment of Y. lipolytica URA3 gene (GenBank Accession No. AJ306421; labeled as "U3 repeat" in Figure) |
| AvrII/PacI 875-2079 | ColE1 plasmid origin of replication |
| PacI/SalI 2079-3571 | *Y. lipolytica* URA3 gene (GenBank Accession No. AJ306421) |
| SalI/PmeI 3571-6625 | YAT1::YlPDAT::PEX16 (as described in Table 5 for pY196) |
| PmeI/SwaI 6625-7920 | Kanamycin-resistance gene from plasmid pBHR1 (GenBank Accession No. Y14439) |
| SwaI/SphI 7920-1 | YAT1::YlLPCAT::Lip1 (complementary), comprising: YAT1: *Y. lipolytica* YAT1 promoter (U.S. Pat. Appl. Publ. No. 2010-0068789-A1); YlLPCAT: *Y. lipolytica* lysophosphatidylcholine acyltransferase gene (SEQ ID NO: 4; U.S. Pat. Appl. Publ. No. 2010/0317882); Lip1: terminator sequence from *Yarrowia* Lip1 gene (GenBank Accession No. Z50020) |

Lipid Production in *Y. lipolytica* Strain Z5567U19 Transformed with pY196 or pY301

Plasmids pY196 and pY301 were digested with PmeI and SwaI. The larger fragment in each digestion was agarose-purified away from the kanamycin-resistance gene fragment and used to transform *Yarrowia* strain Z5567U19 by chromosomal integration. Z5567U19 is a Ura[−] strain of Z5567 and produces an increased amount of lipids containing long-chain polyunsaturated fatty acids. Details regarding the development of strains Z5567 and Z5567U19 are provided in U.S. Pat. Appl. Publ. No. 2012-0052537 A1, which is incorporated herein by reference. A control transformation was also performed in which no plasmid DNA was included.

The transformed cells were plated onto MM plates and maintained at 30° C. for 5 days (MM comprises per liter: 20 g glucose, 1.7 g yeast nitrogen base without amino acids, 1.0 g proline, pH 6.1 (do not need to adjust)). Eleven colonies for each experimental transformation (i.e., either PDAT+LPCAT [pY301] or PDAT+LPAAT [pY196]) were then re-streaked onto MM plates and subsequently analyzed for lipid content.

Table 7 summarizes the total dry cell weight ["DCW"], TFAs % DCW, the concentration of EPA as a weight percent of TFAs ["EPA % TFAs"], EPA % DCW, and the total delta-9 elongase percent conversion efficiency ["d9E CE"] of LA and ALA to EPA in each transformant and the control. Calculation of d9e CE was made following the formula: (EDA+HGLA+ARA+ERA+ETA+EPA)/(C18:2+C18:3+EDA+HGLA+ARA+ERA+ETA+EPA)*100.

TABLE 7

Lipid Analysis of pY196 and pY301 Transformants of *Yarrowia* Strain Z5567U19, by Flask Assay

| Z5567U19 transformant | Trans-formation plasmid | DCW, (g/L) | TFAs % DCW | EPA % TFAs | EPA % DCW | d9e CE (%) |
|---|---|---|---|---|---|---|
| L313 | Control | 5.9 | 46.1 | 45 | 21 | 76 |
| L313 | | 5.7 | 48.9 | 46 | 23 | 77 |
| Average | | 5.8 | 47.5 | 46 | 22 | 76 |
| Standard deviation | | 0.1 | 2.0 | 0.4 | 1.1 | 0.6 |
| | pY196 | 3.1 | 39.7 | 49 | 19 | 79 |
| | (PDAT + | 3.2 | 41.9 | 51 | 21 | 81 |
| L314 | LPAAT) | 4.1 | 48.4 | 49 | 24 | 79 |
| | | 3.7 | 47.0 | 50 | 23 | 79 |
| | | 3.4 | 39.5 | 46 | 18 | 77 |
| | | 5.1 | 42.9 | 46 | 20 | 77 |
| | | 3.6 | 46.8 | 48 | 22 | 78 |
| | | 4.3 | 43.7 | 49 | 22 | 78 |
| | | 4.2 | 46.6 | 49 | 23 | 79 |
| | | 3.8 | 45.9 | 49 | 22 | 78 |
| | | 4.7 | 46.4 | 47 | 22 | 79 |
| Average | | 3.9 | 44.5 | 48 | 22 | 79 |
| Standard deviation | | 0.6 | 3.1 | 1.6 | 1.8 | 1.2 |
| | pY301 | 4.3 | 37.7 | 45 | 17 | 78 |
| | (PDAT + | 4.9 | 48.2 | 51 | 25 | 83 |
| L317 | LPCAT) | 4.7 | 49.0 | 51 | 25 | 82 |
| | | 4.6 | 48.1 | 51 | 24 | 82 |
| | | 4.2 | 44.6 | 50 | 22 | 81 |
| | | 5.5 | 43.6 | 51 | 22 | 82 |
| | | 4.8 | 44.8 | 50 | 22 | 80 |
| | | 4.7 | 46.0 | 49 | 23 | 81 |
| | | 4.1 | 41.2 | 46 | 19 | 79 |
| | | 4.3 | 46.5 | 49 | 23 | 81 |
| | | 5.2 | 47.4 | 51 | 24 | 81 |
| Average | | 4.7 | 45.2 | 49 | 22 | 81 |
| Standard deviation | | 0.4 | 3.4 | 2.0 | 2.4 | 1.5 |

Both the pY196 and pY301 transformants had improved EPA % TFAs and d9e CE compared to the control. Specifically regarding the pY301 transformants (PDAT+LPCAT), they exhibited an average increase in EPA % TFAs and d9e CE of about 6.5% and 6.6%, respectively, over the control. Furthermore, the pY301 transformants had average DCW, TFAs % DCW, EPA % TFAs and d9E CE values that, respectively, were 20.5%, 1.6%, 2.1% and 2.5% greater than the respective average values measured for the pY196 transformants.

Differences in the lipids of certain individual transformants were also compared. Specifically, the lipid profiles of the pY196 transformant L314 and the pY301 transformant L317 were further analyzed (Table 8) in comparison to each other and the control, strain L313.

TABLE 8

Comparison of Lipid Production in Transformants L314 and L317

| Z5567U19 transformant | DCW, (g/L) | TFAs % DCW | EPA % TFAs | EPA % DCW | d9e CE (%) |
|---|---|---|---|---|---|
| L313 control, average | 5.8 | 47.5 | 45.8 | 21.7 | 76.2 |
| L314 (pY196, PDAT + LPAAT) | 4.1 | 48.4 | 49.3 | 23.9 | 78.6 |
| L314, % change over control: | −30 | 1.9 | 7.7 | 9.7 | 3.2 |
| L317 (pY301, PDAT + LPCAT) | 4.7 | 49.0 | 51.0 | 25.0 | 81.9 |
| L317, % change over control: | −19 | 3.2 | 11.4 | 15.2 | 7.5 |
| L317, % change over L314: | 14.6 | 1.2 | 3.4 | 4.6 | 4.2 |

Transformant L317 had improved TFAs % DCW, EPA % TFAs, EPA % DCW and d9e CE compared to both the control and transformant L314.

Previous attempts to enhance lipids in *Yarrowia* by other strategies have mostly yielded increased total lipid content [TFAs % DCW], but with a decrease in the EPA concentration as a weight percent of TFAs [EPA % TFAs], or vice versa (i.e., lower TFAs % DCW with higher EPA % TFAs). In transformant L317, however, both of these factors increased with respect to the control and L314. Therefore, the concomitant overexpression of PDAT and LPCAT in transformant L317 may allow a balanced movement of EPA from acyl-CoA stores (i.e., EPA-CoA) to TAG by increasing the rate at which EPA contained in phosphatidylcholine ["PC"] is transferred to DAG while also increasing the rate at which PC is restored from lysophosphatidylcholine using EPA-CoA.

Overexpression of PDAT and LPCAT (strain L317) appears to have advantages when compared to overexpression of PDAT and LPAAT (strain L314). This may point to a greater synergy between PDAT and LPCAT than between PDAT and LPAAT in the synthesis of TAG using phospholipid-derived fatty acids. In both overexpression systems, PDAT transferred fatty acids from PC and phosphatidic acid ["PA"] stores to DAG. The higher level of lipid production observed using PDAT and LPCAT, as compared to PDAT and LPAAT, may reflect a heretofore unappreciated difference in the rate of renewal of PC and PA by LPCAT and LPAAT, respectively, as fatty acid sources for continued PDAT activity.

Example 3

Synthesis of Plasmid pY306-N Comprising Variant YlLPCAT

The present example describes the construction of a *Yarrowia* autonomously replicating vector comprising a variant YlLPCAT sequence (plasmid pY306-N, SEQ ID NO:48). The variant YlLPCAT polynucleotide sequence, designated herein as YlLPCAT* (SEQ ID NOs:45), lacks two NcoI restriction enzyme sites that are present in the wild type YlLPCAT coding region. Removal of these internal NcoI sites facilitated subsequent cloning procedures.

As a control, the wild type YlLPCAT ORF (SEQ ID NO:3; Example 1) was cloned into a *Yarrowia* autonomously replicating vector to result in plasmid pY306 (SEQ ID NO:47), comprising a ColE1 plasmid origin of replication, an ampicillin-resistance gene, an f1 origin of replication and the *Y. lipolytica* Ura3 gene (Gen Bank Accession No. AJ306421).

The variant YlLPCAT sequence was synthesized by GenScript Corporation (Piscataway, N.J.). Two internal NcoI restriction sites were removed by creation of silent mutations, while NcoI and NotI sites were added, respectively, at the 5' and 3' ends of the YlLPCAT open reading frame to facilitate cloning. Specifically, an A12T mutation (i.e., a change from adenosine [A] in YlLPCAT (SEQ ID NO:3) at position 12 to thymine [T] in the YlLPCAT variant) and a T918C mutation (i.e., a change from thymine [T] in YlLPCAT (SEQ ID NO:3) at position 918 to cytosine [C] in the YlLPCAT variant) were introduced into the YlLPCAT coding sequence. These two nucleotide substitutions were silent with respect to the amino acids encoded by the variant sequence. The nucleotide sequence encoding the variant YlLPCAT lacking its internal NcoI sites (i.e., YlLPCAT*) is represented by SEQ ID NO:45, while the amino acid sequence encoded thereby is represented by SEQ ID NO:46, which is identical to SEQ ID NO:4 (wild type YlLPCAT).

YlLPCAT* was subsequently cloned into plasmid pY306, thereby producing pY306-N (SEQ ID NO:48; FIG. 4). Thus, construct pY306-N contained the following components:

TABLE 9

Components of Plasmid pY306-N (SEQ ID NO: 48)

| RE Sites and Nucleotides within SEQ ID NO: 48 | Description of Fragment and Chimeric Gene Components |
|---|---|
| BsiWI/BsiWI 1-2809 | YAT1::YlLPCAT*::Lip1 (complementary), comprising: YAT1: *Y. lipolytica* YAT1 promoter (U.S. Pat. Appl. Publ. No. 2010/0068789); YlLPCAT*: variant *Y. lipolytica* acyl-CoA:lysophosphatidylcholine acyltransferase, lacking two internal NcoI sites (SEQ ID NO: 45); Lip1: Lip1 terminator sequence from *Yarrowia* Lip1 gene (GenBank Accession No. Z50020) |
| BsiWI/EcoRI 2809-5605 | ColE1 plasmid origin of replication Ampicillin-resistance gene f1 origin of replication |
| EcoRI/PacI 5605-7021 | *Y. lipolytica* URA3 gene (GenBank Accession No. AJ306421) |

Plasmid pY306-N was used to prepare single- and double-mutants of YlLPCAT protein, as described below in Examples 4 and 6, respectively.

Example 4

Designing and Synthesizing Mutant YlLPCAT Enzymes with Modified Motifs

Based on the premise that conserved amino acid motifs within YlLPCAT are likely involved in catalysis, it was concluded that generation of mutants having variant motifs could result in the identification of an LPCAT enzyme having improved functional activity.

A series of single amino acid substitutions were designed within the conserved sequence spanning amino acid residues 132 to 148 of SEQ ID NO:4 (i.e., Motif I) and the conserved sequence spanning amino acid residues 376 to 390 of SEQ ID NO:4 (i.e., Motif II). Within Motif I, a total of 195 amino acid substitutions were designed, as shown in Table 10, by creating various substitutions at each of the 17 amino acid residues within the motif.

TABLE 10

| Single Amino Acid Substitutions within Motif I of YlLPCAT Protein | | |
|---|---|---|
| Wild type residue | Single Amino Acid Substitutions | SEQ ID NO |
| M132 | M132A, M132N, M132C, M132G, M132Q, M132H, M132I, M132L, M132F, M132P, M132S, M132T, M132W, M132Y and M132V | 49 |
| V133 | V133A, V133N, V133C, V133G, V133Q, V133H, V133L, V133M, V133F, V133P, V133S, V133T, V133W and V133Y | 50 |
| L134 | L134A, L134N, L134C, L134G, L134Q, L134H, L134M, L134F, L134P, L134S, L134T, L134W, L134Y and L134V | 51 |
| C135 | C135R, C135N, C135D, C135G, C135E, C135Q, C135H, C135I, C135L, C135K, C135M, C135F, C135P, C135S, C135W and C135Y | 52 |
| M136 | M136A, M136N, M136C, M136G, M136H, M136I, M136F, M136P, M136S, M136T, M136W, M136Y and M136V | 53 |
| K137 | K137A, K137R, K137N, K137G, K137H, K137P, K137S, K137T, K137Y | 54 |
| L138 | L138A, L138N, L138C, L138G, L138Q, L138H, L138I, L138M, L138F, L138P, L138S, L138T, L138W, L138Y | 55 |
| S139 | S139A, S139N, S139C, S139G, S139H, S139L, S139M, S139F, S139P, S139W, and S139V | 56 |
| S140 | S140N, S140C, S140H, S140I, S140L, S140F, S140P, S140W, S140Y and S140V | 57 |
| F141 | F141A, F141N, F141G, F141H, F141I, F141M, F141P, F141S, F141T, F141W, and F141V | 58 |
| G142 | G142N, G142H, G142I, G142L, G142M, G142F, G142P, G142T, G142W, G142Y and G142V | 59 |
| W143 | W143A, W143G, W143H, W143L, W143K, W143P, W143S, W143T and W143V | 60 |
| N144 | N144A, N144R, N144G, N144H, N144K, N144F, N144P, N144T and N144V | 61 |
| V145 | V145A, V145C, V145G, V145E, V145H, V145M, V145F, V145P, V145S, V145T, V145W | 62 |
| Y146 | Y146R, Y146N, Y146D, Y146G, Y146E, Y146Q, Y146I, Y146L, Y146M, Y146F, Y146P, Y146W and Y146V | 63 |
| D147 | D147A, D147N, D147G, D147E, D147Q, D147H, D147F, D147S, D147T | 64 |
| G148 | G148A, G148N, G148H, G148L, G148M, G148F, G148S, G148T and G148V | 65 |

Similarly, a total of 134 amino acid substitutions were designed within Motif II, as shown in Table 11, by creating various substitutions within 12 of the 15 amino acid residues within the motif. No substitutions were made at W379, H380 and G381, since the histidine of other LPCATs corresponding to H380 of YlLPCAT has been reported to be a likely active site residue (Lee et al., 2008, *Mol. Biol. Cell* 19:1174-1184).

TABLE 11

| Single Amino Acid Substitutions within Motif II of YlLPCAT Protein | | |
|---|---|---|
| Wild type residue | Single Amino Acid Substitutions | SEQ ID NO |
| S376 | S376A, S376G, S376H, S376L, S376F, S376P, S376T and S376V | 66 |
| A377 | A377N, A377G, A377H, A377L, A377F, A377P, A377S, A377T and A377V | 67 |
| F378 | F378A, F378N, F378C, F378G, F378H, F378L, F378P, F378S, F378T, F378W, F378Y | 68 |
| T382 | T382A, T382N, T382G, T382Q, T382H, T382I, T382M, T382P, T382S, T382W, T382Y | 69 |
| R383 | R383A, R383N, R383D, R383G, R383E, R383Q, R383H, R383I, R383L, R383K, R383M, R383F, R383P, R383T, R383W and R383V | 70 |
| P384 | P384A, P384R, P384G, P384H, P384I, P384L, P384K, P384M, P384F, P384S, P384T, P384W, P384Y and P384V | 71 |
| G385 | G385A, G385N, G385C, G385G, G385H, G385I, G385L, G385K, G385M, G385F, G385S, G385T, G385W, G385Y and G385V | 72 |

TABLE 11-continued

| Single Amino Acid Substitutions within Motif II of YlLPCAT Protein | | |
|---|---|---|
| Wild type residue | Single Amino Acid Substitutions | SEQ ID NO |
| Y386 | Y386A, Y386G, Y386H, Y386L, Y386F, Y386P, Y386S, Y386T and Y386V | 73 |
| Y387 | Y387A, Y387G, Y387H, Y387L, Y387F, Y387P, Y387S, Y387T, Y387W and Y387V | 74 |
| L388 | L388A, L388G, L388H, L388P, L388S, L388T, L388W, L388Y and L388V | 75 |
| T389 | T389A, T389C, T389G, T389H, T389I, T389L, T389M, T389F, T389P, T389S, T389W, T389Y and T389V | 76 |
| F390 | F390A, F390N, F390C, F390G, F390H, F390L, F390M, F390P, F390S, F390T and F390V | 77 |

Each of the 329 YlLPCAT mutants set forth above in Tables 10 and 11 were individually synthesized and cloned into NcoI/NotI-cut pY306-N vector by GenScript Corporation (Piscataway, N.J.).

Example 5

Identifying Single Amino Acid Substitutions in YlLPCAT Having Improved LPCAT Activity The present example describes the transformation of each of the 329 pY306-N vectors comprising a YlLPCAT mutant polynucleotide sequence (Example 4) into *Y. lipolytica* strain Y8406U2, followed by analysis of the lipid profiles of the transformants.

Improved LPCAT activity was indirectly evaluated, based on the observations set forth in U.S. Pat. Appl. Publ. No. 2010-0317882-A1 and summarized in Example 1 (above). Specifically, improved LPCAT activity within *Y. lipolytica* strain Y8406U2 transformants comprising a mutated YlLPCAT was concluded based on an increase in the concentration of EPA as a weight % of TFAs ["EPA % TFAs"] and/or an increase in the conversion efficiency of the delta-9 elongase, when either factor was compared to the EPA % TFAs or the conversion efficiency of the delta-9 elongase, respectively, in *Y. lipolytica* strain Y8406U2 expressing the parent wild type YlLPCAT protein.

Transformation of *Y. lipolytica* Strain Y8406U2

Strain Y8406U2 was transformed to individually express one of each of the pY306-N vectors containing a mutant YlLPCAT prepared in Example 4. Y8406U2 is a $Ura^-$ strain of Y8406. Details regarding the development of strains Y8406 and Y8406U2 are provided in U.S. Pat. Appl. Publ. No. 2010-0317882-A1, which is incorporated herein by reference. Following transformation, cells were placed onto MM plates and then three individual transformants of each transformation were streaked on fresh MM plates and kept in a 30° C. incubator for two days. Cells from streaked plates were cultivated in 24-well blocks with 3 mL MM, and incubated for 2 days at 30° C. with shaking at 250 rpm. The cells were then collected by centrifugation and resuspended in 3 mL High Glucose Media ["HGM"] (High Glucose Media comprises per liter: 80 g glucose, 2.58 g $KH_2PO_4$ and 5.36 g $K_2HPO_4$, pH 7.5 (do not need to adjust)). The cells were incubated another 5 days at 30° C. with shaking at 200 rpm. After 5 days growth in HGM, cells were collected by centrifugation, lipids were extracted, and FAMEs were prepared by transesterification of the lipid extract with sodium methoxide (Roughan, G., and Nishida I., *Arch. Biochem. Biophys.*, 276(1):38-46 (1990)) and subsequently analyzed by gas chromatography (GC).

Analysis of Lipid Profiles within *Yarrowia* Transformed for Expression of Single Mutants of YlLPCAT Tables 12 (Batch 1), 13 (Batch 2), 14 (Batch 3), 15 (Batch 4) and 16 (Batch 5) below show the fatty acid profiles and delta-9 elongase conversion efficiencies of individual Y8406U2 transformants comprising a plasmid for expressing a particular single-mutated YlLPCAT (single amino acid substitution in Motif I or Motif II). These measurements were also made for certain controls: transformants comprising an empty vector ["EV"] (i.e., a replicating plasmid with no LPCAT gene [Batch #1 only]) or pY306-N (wild type YlLPCAT protein expression ["WT"]).

More specifically, each table summarizes the number of replicates analyzed for each particular transformant ["#"], the average concentration of each fatty acid as a weight percent of TFAs ["% TFAs"], the standard deviation for EPA % TFAs ["EPA SD"], and the delta-9 elongase conversion efficiency ["% Conv"]. The % Conv. was calculated for each transformant according to the following formula: (EDA+HGLA+ARA+ERA+ETA+EPA)/(C18:2+C18:3+EDA+HGLA+ARA+ERA+ETA+EPA)*100.

The measured fatty acids were 16:0 (palmitate), 16:1 (palmitoleic acid), 18:0 (stearic acid), 18:1 (oleic acid), 18:2 (linoleic acid), ALA (alpha-linolenic acid), EDA (eicosadienoic acid), DGLA (dihomo-gamma-linolenic acid), ARA (arachidonic acid), ETrA (eicosatrienoic acid), ETA (eicosatetraenoic acid) and EPA (eicosapentaenoic acid).

Comparison of each mutant's performance relative to the wild type YlLPCAT control should only be made within the particular batch in which each mutant was analyzed (i.e., comparisons should not be made between Batch #1 and Batch #2, for example). Mutants shown in bold-face font and followed by a "+" were selected for further studies, as discussed below.

TABLE 12

Lipid Composition and Delta-9 Elongase Conversion Efficiency in Batch #1 Transformants Comprising a Vector Encoding YlLPCAT Having a Single Amino Acid Substitution

| | | % TFAs | | | | | | | | | | | | EPA | % |
|---|---|---|---|---|---|---|---|---|---|---|---|---|---|---|---|
| Mutant | # | 16:0 | 16:1 | 18:0 | 18:1 | LA | ALA | EDA | DGLA | ARA | ETrA | ETA | EPA | SD | Conv. |
| EV control | 6 | 2.8 | 0.5 | 2.6 | 4.6 | 19.2 | 1.8 | 2.8 | 2.6 | 0.6 | 1.4 | 2.6 | 48.7 | 0.2 | 74 |
| WT | 15 | 2.8 | 0.5 | 2.7 | 4.5 | 17.9 | 1.8 | 2.7 | 2.7 | 0.6 | 1.4 | 2.4 | 50.4 | 1.1 | 75 |
| M132A | 3 | 2.8 | 0.4 | 2.9 | 4.8 | 19.7 | 2.2 | 2.5 | 2.3 | 0.6 | 1.4 | 2.0 | 49.3 | 0.4 | 73 |
| M132I | 3 | 2.7 | 0.5 | 2.8 | 4.8 | 19.4 | 2.0 | 2.7 | 2.5 | 0.6 | 1.5 | 2.3 | 48.6 | 0.3 | 73 |
| V133M | 3 | 2.6 | 0.5 | 2.9 | 5.4 | 19.3 | 2.1 | 2.8 | 2.4 | 0.6 | 1.5 | 2.2 | 49.0 | 0.7 | 73 |
| C135I | 3 | 3.0 | 0.5 | 2.8 | 4.6 | 17.5 | 1.7 | 2.6 | 2.6 | 0.7 | 1.5 | 2.2 | 50.7 | 2.5 | 76 |
| C135M | 3 | 2.5 | 0.5 | 2.9 | 5.6 | 20.1 | 2.5 | 3.0 | 2.3 | 0.6 | 1.5 | 2.0 | 47.8 | 1.7 | 72 |
| M136A | 3 | 2.7 | 0.4 | 2.9 | 4.8 | 19.4 | 2.2 | 2.5 | 1.6 | 0.6 | 1.4 | 2.1 | 49.6 | 0.1 | 73 |
| L138A | 3 | 2.9 | 0.5 | 2.9 | 3.1 | 18.0 | 1.8 | 2.6 | 2.6 | 0.7 | 1.4 | 2.1 | 50.5 | 1.9 | 75 |
| L138C | 3 | 3.0 | 0.5 | 2.8 | 4.8 | 19.8 | 2.1 | 2.6 | 2.3 | 0.7 | 1.4 | 2.0 | 48.6 | 0.9 | 72 |
| L138M | 3 | 2.7 | 0.6 | 2.9 | 5.2 | 16.8 | 1.5 | 2.8 | 3.0 | 0.7 | 1.5 | 2.4 | 51.0 | 3.0 | 77 |
| S139A | 3 | 2.7 | 0.4 | 2.8 | 4.8 | 19.5 | 2.3 | 2.6 | 2.2 | 0.6 | 1.4 | 2.0 | 48.8 | 1.2 | 73 |
| S139C | 3 | 3.2 | 0.5 | 2.8 | 4.6 | 19.6 | 2.0 | 2.5 | 2.3 | 0.6 | 1.4 | 2.0 | 48.8 | 0.6 | 73 |
| S139L | 3 | 2.7 | 0.5 | 2.8 | 5.0 | 17.9 | 1.8 | 2.7 | 2.6 | 0.7 | 1.5 | 2.2 | 50.7 | 2.2 | 75 |
| S139M | 3 | 2.5 | 0.4 | 3.0 | 5.4 | 19.7 | 2.3 | 2.8 | 2.4 | 0.6 | 1.5 | 2.1 | 48.6 | 0.2 | 72 |
| S140I | 3 | 3.1 | 0.5 | 2.8 | 4.6 | 17.7 | 1.7 | 2.7 | 2.7 | 0.7 | 1.5 | 2.3 | 50.1 | 2.7 | 76 |
| F141M+ | 3 | 2.8 | 0.7 | 2.7 | 4.9 | 14.8 | 0.9 | 2.8 | 3.4 | 0.8 | 1.6 | 2.6 | 53.1 | 0.5 | 80 |
| G142I | 3 | 3.1 | 0.6 | 2.7 | 5.0 | 18.3 | 1.8 | 2.9 | 2.6 | 0.7 | 1.5 | 2.3 | 49.0 | 3.1 | 75 |
| G142L | 3 | 2.5 | 0.5 | 2.8 | 5.5 | 19.2 | 2.0 | 3.0 | 2.5 | 0.6 | 1.6 | 2.3 | 48.7 | 1.1 | 73 |
| W143L | 3 | 2.7 | 0.5 | 2.8 | 5.1 | 17.9 | 1.8 | 2.8 | 1.6 | 0.6 | 1.5 | 2.3 | 50.4 | 2.0 | 75 |
| N144H | 3 | 2.7 | 0.6 | 2.6 | 4.7 | 18.9 | 1.8 | 2.8 | 2.7 | 0.6 | 1.6 | 2.8 | 48.1 | 1.6 | 74 |
| N144K | 3 | 2.7 | 0.5 | 2.8 | 5.3 | 17.7 | 1.8 | 2.8 | 2.7 | 0.6 | 1.5 | 2.2 | 50.5 | 3.2 | 76 |
| V145C | 3 | 3.0 | 0.4 | 2.8 | 4.7 | 19.6 | 2.1 | 2.5 | 2.3 | 0.6 | 1.4 | 2.0 | 49.4 | 0.5 | 73 |
| V145M+ | 3 | 2.9 | 0.7 | 2.7 | 5.0 | 16.2 | 1.3 | 2.8 | 3.1 | 0.7 | 1.5 | 2.4 | 51.4 | 2.1 | 78 |
| Y146D | 3 | 3.0 | 0.5 | 2.8 | 3.3 | 19.6 | 2.0 | 2.5 | 2.4 | 0.7 | 1.4 | 2.1 | 49.0 | 0.6 | 73 |
| Y146E | 3 | 3.2 | 0.5 | 2.9 | 4.9 | 19.7 | 2.0 | 2.5 | 2.5 | 0.7 | 1.3 | 2.1 | 48.8 | 0.3 | 73 |

TABLE 12-continued

Lipid Composition and Delta-9 Elongase Conversion Efficiency in Batch #1 Transformants Comprising a Vector Encoding YlLPCAT Having a Single Amino Acid Substitution

| | | % TFAs | | | | | | | | | | | | EPA | % |
|---|---|---|---|---|---|---|---|---|---|---|---|---|---|---|---|
| Mutant | # | 16:0 | 16:1 | 18:0 | 18:1 | LA | ALA | EDA | DGLA | ARA | ETrA | ETA | EPA | SD | Conv. |
| Y146I | 3 | 3.0 | 0.5 | 2.8 | 5.4 | 20.0 | 2.3 | 2.8 | 2.3 | 0.6 | 1.5 | 2.1 | 47.6 | 2.3 | 72 |
| Y146L | 3 | 2.6 | 0.5 | 2.7 | 5.0 | 17.7 | 1.6 | 2.7 | 2.8 | 0.6 | 1.5 | 2.4 | 50.8 | 2.2 | 76 |
| Y146M | 3 | 2.6 | 0.5 | 2.7 | 5.2 | 18.1 | 1.9 | 2.7 | 2.7 | 0.7 | 1.5 | 2.1 | 50.7 | 1.8 | 75 |
| D147E | 3 | 3.2 | 0.5 | 2.8 | 4.7 | 18.3 | 1.7 | 2.7 | 2.7 | 0.7 | 1.5 | 2.2 | 49.5 | 0.2 | 75 |
| F378A | 3 | 2.6 | 0.4 | 2.9 | 4.8 | 19.5 | 2.3 | 2.5 | 2.2 | 0.6 | 1.4 | 2.0 | 49.9 | 0.3 | 73 |
| T382A | 3 | 2.7 | 0.5 | 2.8 | 5.1 | 19.8 | 2.2 | 2.8 | 2.4 | 0.6 | 1.4 | 2.2 | 48.3 | 1.7 | 72 |
| R383A | 3 | 2.9 | 0.6 | 2.8 | 3.6 | 17.8 | 1.5 | 2.9 | 2.8 | 0.7 | 1.4 | 2.3 | 50.2 | 1.5 | 76 |
| R383D | 3 | 3.3 | 0.5 | 2.9 | 5.0 | 19.6 | 2.0 | 2.5 | 2.4 | 0.7 | 1.4 | 2.1 | 48.7 | 0.8 | 73 |
| R383I | 3 | 3.1 | 0.5 | 2.8 | 4.6 | 18.6 | 1.7 | 2.6 | 2.6 | 0.7 | 1.5 | 2.3 | 49.2 | 0.5 | 74 |
| R383K | 3 | 2.5 | 0.5 | 2.7 | 5.4 | 20.1 | 2.4 | 3.1 | 2.3 | 0.6 | 1.5 | 2.1 | 47.7 | 2.6 | 72 |
| R383L | 3 | 2.5 | 0.4 | 2.8 | 5.0 | 19.6 | 2.1 | 2.7 | 2.4 | 0.6 | 1.5 | 2.1 | 49.4 | 0.4 | 73 |
| R383M+ | 3 | 3.0 | 0.6 | 2.8 | 5.0 | 16.5 | 1.5 | 2.7 | 3.0 | 0.7 | 1.5 | 2.2 | 52.2 | 2.8 | 78 |
| R383N | 3 | 3.0 | 0.5 | 2.8 | 4.8 | 19.3 | 2.0 | 2.5 | 2.4 | 0.6 | 1.4 | 2.1 | 49.2 | 0.5 | 73 |
| P384I | 3 | 2.8 | 0.5 | 2.9 | 4.8 | 19.3 | 2.1 | 2.6 | 2.3 | 0.6 | 1.4 | 2.1 | 49.3 | 0.4 | 73 |
| P384L | 3 | 2.5 | 0.5 | 2.8 | 5.2 | 18.8 | 1.9 | 2.8 | 2.6 | 0.6 | 1.5 | 2.3 | 49.6 | 0.6 | 74 |
| G385I | 3 | 2.4 | 0.4 | 2.9 | 5.2 | 19.4 | 2.1 | 2.7 | 2.4 | 0.6 | 1.5 | 2.1 | 49.2 | 0.3 | 73 |
| G385L | 3 | 2.5 | 0.5 | 3.0 | 5.5 | 19.7 | 2.3 | 2.9 | 2.3 | 0.6 | 1.5 | 2.1 | 48.4 | 0.1 | 72 |
| Y387A | 3 | 2.7 | 0.4 | 2.9 | 4.5 | 19.6 | 2.1 | 2.5 | 2.4 | 0.7 | 1.3 | 2.0 | 49.8 | 0.2 | 73 |
| L388A | 3 | 2.6 | 0.5 | 2.8 | 4.8 | 19.9 | 2.1 | 2.5 | 2.5 | 0.7 | 1.3 | 2.3 | 48.9 | 1.4 | 73 |
| T389I | 3 | 2.5 | 0.5 | 2.8 | 5.1 | 19.7 | 2.1 | 2.7 | 2.4 | 0.6 | 1.5 | 2.2 | 48.9 | 0.8 | 73 |
| T389L | 3 | 2.5 | 0.4 | 2.9 | 5.2 | 19.9 | 2.3 | 2.7 | 2.3 | 0.6 | 1.5 | 2.0 | 48.9 | 0.3 | 72 |
| F390L | 3 | 2.5 | 0.4 | 2.9 | 5.3 | 19.7 | 2.3 | 2.7 | 2.3 | 0.6 | 1.5 | 2.1 | 48.9 | 0.4 | 72 |
| Mutant AVG | | 2.8 | 0.5 | 2.8 | 4.9 | 18.9 | 2.0 | 2.7 | 2.5 | 0.6 | 1.5 | 2.2 | 49.5 | | 74 |
| Mutant SD | | 0.2 | 0.1 | 0.1 | 0.5 | 1.2 | 0.3 | 0.2 | 0.3 | 0.0 | 0.1 | 0.2 | 1.1 | | 56 |

TABLE 13

Lipid Composition and Delta-9 Elongase Conversion Efficiency in Batch #2 Transformants Comprising a Vector Encoding YlLPCAT Having a Single Amino Acid Substitution

| | | % TFAs | | | | | | | | | | | | EPA | % |
|---|---|---|---|---|---|---|---|---|---|---|---|---|---|---|---|
| Mutant | # | 16:0 | 16:1 | 18:0 | 18:1 | LA | ALA | EDA | DGLA | ARA | ETrA | ETA | EPA | SD | Conv. |
| WT | 5 | 3.0 | 0.6 | 2.9 | 4.9 | 15.0 | 1.2 | 2.8 | 3.2 | 0.7 | 1.5 | 2.5 | 52.9 | 1.1 | 79.7 |
| M132F | 3 | 2.6 | 0.6 | 2.8 | 5.6 | 19.2 | 1.9 | 2.8 | 2.7 | 0.6 | 1.5 | 2.5 | 48.7 | 1.3 | 73.6 |
| M132W | 3 | 2.6 | 0.6 | 2.7 | 5.5 | 18.5 | 1.7 | 2.9 | 2.7 | 0.5 | 1.6 | 2.7 | 48.6 | 0.4 | 74.4 |
| M132Y | 3 | 2.6 | 0.6 | 2.7 | 2.3 | 18.9 | 1.8 | 2.8 | 2.7 | 0.5 | 1.6 | 2.8 | 48.1 | 1.0 | 73.8 |
| V133F | 3 | 2.6 | 0.5 | 3.0 | 5.6 | 19.5 | 2.3 | 2.8 | 2.5 | 0.5 | 1.5 | 2.3 | 48.6 | 0.4 | 72.7 |
| V133W | 3 | 2.5 | 0.5 | 2.8 | 4.2 | 19.7 | 2.1 | 2.9 | 2.5 | 0.5 | 1.5 | 2.4 | 47.8 | 1.1 | 72.6 |
| L134F | 3 | 3.0 | 0.6 | 3.1 | 5.8 | 16.7 | 1.4 | 3.3 | 3.0 | 0.6 | 1.6 | 2.6 | 50.0 | 2.2 | 77.2 |
| L134V | 3 | 3.1 | 0.6 | 2.8 | 5.0 | 15.4 | 1.1 | 2.8 | 3.1 | 0.7 | 1.6 | 2.5 | 52.3 | 0.3 | 79.2 |
| L134W | 3 | 2.6 | 0.7 | 2.5 | 5.1 | 16.2 | 0.9 | 3.0 | 3.4 | 0.8 | 1.5 | 2.7 | 51.0 | 1.9 | 78.5 |
| L134Y | 3 | 2.9 | 0.6 | 2.8 | 2.1 | 16.8 | 1.3 | 2.7 | 1.9 | 0.6 | 1.7 | 2.6 | 50.8 | 0.2 | 76.9 |
| C135F | 3 | 3.0 | 0.7 | 2.7 | 5.2 | 15.1 | 1.0 | 2.8 | 3.3 | 0.7 | 1.5 | 2.6 | 52.5 | 0.5 | 79.7 |
| C135W | 3 | 2.5 | 0.5 | 2.8 | 5.1 | 18.1 | 1.5 | 2.8 | 2.7 | 0.6 | 1.5 | 2.6 | 49.9 | 0.2 | 75.4 |
| C135Y | 3 | 2.5 | 0.6 | 2.9 | 5.4 | 18.1 | 1.5 | 3.0 | 2.7 | 0.6 | 1.6 | 2.8 | 49.0 | 0.4 | 75.2 |
| M136F | 3 | 2.8 | 0.6 | 2.8 | 5.1 | 16.6 | 1.2 | 2.8 | 3.1 | 0.7 | 1.6 | 2.5 | 51.8 | 0.3 | 77.8 |
| M136S+ | 3 | 3.3 | 0.7 | 2.5 | 4.9 | 12.6 | 0.9 | 2.7 | 3.2 | 0.7 | 1.6 | 2.3 | 55.0 | 0.5 | 82.9 |
| M136T | 3 | 2.7 | 0.6 | 2.8 | 5.4 | 14.7 | 1.1 | 3.0 | 3.2 | 0.6 | 1.5 | 2.6 | 52.7 | 2.6 | 80.1 |
| M136V+ | 3 | 3.6 | 0.7 | 2.7 | 5.2 | 13.0 | 0.9 | 2.7 | 3.3 | 0.7 | 1.5 | 2.5 | 54.1 | 0.7 | 82.3 |
| M136W | 3 | 2.8 | 0.6 | 2.7 | 4.9 | 15.3 | 1.1 | 2.8 | 3.2 | 0.6 | 1.6 | 2.6 | 52.7 | 0.2 | 79.4 |
| L138F | 3 | 2.4 | 0.6 | 2.9 | 5.3 | 16.4 | 1.3 | 3.0 | 3.0 | 0.6 | 1.6 | 2.8 | 50.9 | 2.0 | 77.7 |
| L138W | 3 | 2.8 | 0.6 | 2.8 | 5.1 | 16.2 | 1.2 | 2.8 | 3.1 | 0.6 | 1.5 | 2.5 | 51.7 | 0.4 | 78.2 |
| L138Y | 3 | 2.6 | 0.6 | 2.6 | 3.5 | 16.9 | 1.5 | 2.7 | 1.8 | 0.6 | 1.5 | 2.6 | 51.2 | 1.9 | 76.7 |
| S139F | 3 | 3.1 | 0.7 | 2.7 | 3.8 | 16.0 | 1.3 | 2.8 | 3.1 | 0.7 | 1.6 | 2.6 | 50.9 | 2.7 | 78.1 |
| S139W | 3 | 2.9 | 0.6 | 2.8 | 4.9 | 14.8 | 1.1 | 2.8 | 3.2 | 0.7 | 1.5 | 2.5 | 53.2 | 0.3 | 80.1 |
| S140F | 3 | 2.8 | 0.6 | 2.7 | 5.1 | 15.6 | 1.3 | 2.8 | 3.1 | 0.6 | 1.5 | 2.5 | 52.2 | 2.3 | 78.7 |
| S140W+ | 3 | 3.2 | 0.6 | 2.7 | 5.3 | 12.8 | 0.9 | 2.7 | 3.3 | 0.7 | 1.6 | 2.4 | 54.6 | 0.4 | 82.7 |
| S140Y | 3 | 3.1 | 0.8 | 2.4 | 4.7 | 14.2 | 0.9 | 2.8 | 3.4 | 0.7 | 1.7 | 2.8 | 52.5 | 1.9 | 80.9 |
| F141V | 3 | 3.3 | 0.7 | 2.8 | 3.6 | 14.0 | 1.0 | 3.0 | 3.2 | 0.6 | 1.7 | 2.6 | 52.8 | 1.3 | 81.0 |
| F141W+ | 3 | 3.1 | 0.7 | 2.8 | 5.1 | 14.1 | 1.0 | 2.8 | 3.3 | 0.7 | 1.6 | 2.5 | 53.6 | 0.3 | 81.0 |
| G142F | 3 | 2.7 | 0.7 | 2.5 | 3.5 | 16.7 | 1.2 | 2.9 | 3.1 | 0.7 | 1.6 | 2.7 | 50.7 | 1.4 | 77.5 |
| G142V | 3 | 3.1 | 0.7 | 2.7 | 5.0 | 15.0 | 1.1 | 2.8 | 3.3 | 0.7 | 1.6 | 2.6 | 52.6 | 0.2 | 79.9 |
| G142W | 3 | 2.9 | 0.7 | 2.5 | 4.7 | 15.3 | 1.0 | 3.0 | 3.3 | 0.7 | 1.7 | 2.9 | 51.5 | 1.1 | 79.5 |
| G142Y | 3 | 2.9 | 0.6 | 2.6 | 4.9 | 17.5 | 1.5 | 2.8 | 2.9 | 0.6 | 1.6 | 2.6 | 50.1 | 1.6 | 76.1 |
| V145F | 3 | 2.9 | 0.6 | 2.6 | 5.0 | 14.9 | 1.0 | 2.8 | 3.3 | 0.7 | 1.5 | 2.6 | 52.9 | 0.1 | 80.0 |
| V145W+ | 3 | 3.0 | 1.0 | 3.0 | 5.0 | 15.0 | 1.0 | 3.0 | 3.0 | 1.0 | 2.0 | 3.0 | 53.1 | 0.1 | 80.1 |
| F378S | 3 | 2.8 | 0.6 | 2.6 | 4.9 | 16.2 | 1.2 | 2.8 | 3.0 | 0.6 | 1.5 | 2.5 | 52.2 | 0.2 | 78.3 |
| F378T | 3 | 2.7 | 0.7 | 2.6 | 4.9 | 15.8 | 1.2 | 3.0 | 3.0 | 0.6 | 1.6 | 2.8 | 51.6 | 0.1 | 78.7 |

TABLE 13-continued

Lipid Composition and Delta-9 Elongase Conversion Efficiency in Batch #2 Transformants Comprising a Vector Encoding YlLPCAT Having a Single Amino Acid Substitution

| | | % TFAs | | | | | | | | | | | | EPA | % |
|---|---|---|---|---|---|---|---|---|---|---|---|---|---|---|---|
| Mutant | # | 16:0 | 16:1 | 18:0 | 18:1 | LA | ALA | EDA | DGLA | ARA | ETrA | ETA | EPA | SD | Conv. |
| F378Y+ | 3 | 3.0 | 0.7 | 2.6 | 3.5 | 14.4 | 1.0 | 2.7 | 3.4 | 0.7 | 1.6 | 2.7 | 52.7 | 1.0 | 80.6 |
| T382P+ | 3 | 2.9 | 0.6 | 2.8 | 5.0 | 15.0 | 1.0 | 2.8 | 3.3 | 0.7 | 1.5 | 2.5 | 53.0 | 0.2 | 79.9 |
| T382S | 3 | 2.7 | 0.6 | 2.7 | 5.1 | 16.3 | 1.5 | 2.9 | 2.9 | 0.6 | 1.6 | 2.6 | 51.3 | 1.7 | 77.6 |
| T382W | 3 | 2.7 | 0.7 | 2.6 | 5.3 | 16.3 | 1.3 | 2.8 | 3.1 | 0.6 | 1.6 | 2.8 | 51.1 | 2.6 | 77.9 |
| T382Y+ | 2 | 3.1 | 0.7 | 2.7 | 5.0 | 14.6 | 1.0 | 2.7 | 3.3 | 0.7 | 1.6 | 2.7 | 52.8 | | 80.3 |
| R383F | 3 | 2.7 | 0.6 | 2.6 | 5.0 | 16.9 | 1.5 | 2.7 | 2.9 | 0.6 | 1.5 | 2.5 | 51.4 | 1.7 | 77.1 |
| R383P | 3 | 2.6 | 0.6 | 2.7 | 5.1 | 17.7 | 1.4 | 2.8 | 2.8 | 0.6 | 1.6 | 2.5 | 50.4 | 0.5 | 76.1 |
| R383T | 3 | 2.5 | 0.6 | 2.9 | 5.3 | 15.8 | 1.2 | 3.0 | 3.0 | 0.6 | 1.6 | 2.7 | 51.9 | 0.7 | 78.7 |
| R383V | 3 | 3.1 | 0.6 | 2.8 | 2.1 | 17.9 | 1.4 | 2.8 | 2.9 | 0.6 | 1.5 | 2.7 | 49.2 | 1.3 | 75.5 |
| R383W | 3 | 2.7 | 0.6 | 2.9 | 5.3 | 17.2 | 1.4 | 2.8 | 2.8 | 0.6 | 1.6 | 2.5 | 50.8 | 0.5 | 76.7 |
| P384F | 3 | 2.6 | 0.6 | 2.8 | 5.3 | 17.6 | 1.4 | 2.9 | 2.9 | 0.6 | 1.5 | 2.6 | 50.0 | 0.4 | 76.2 |
| P384M | 3 | 2.8 | 0.6 | 2.8 | 5.3 | 17.2 | 1.4 | 2.8 | 2.9 | 0.6 | 1.5 | 2.5 | 51.1 | 0.4 | 76.8 |
| P384T | 3 | 2.7 | 0.6 | 2.8 | 3.5 | 16.6 | 1.3 | 2.8 | 2.9 | 0.6 | 1.5 | 2.6 | 51.6 | 0.1 | 77.6 |
| P384W | 3 | 2.8 | 0.6 | 2.7 | 2.1 | 17.0 | 1.5 | 2.7 | 2.8 | 0.6 | 1.6 | 2.5 | 50.9 | 1.6 | 76.8 |
| P384Y | 3 | 2.8 | 0.7 | 2.6 | 3.7 | 17.6 | 1.4 | 2.9 | 3.0 | 0.6 | 1.7 | 2.8 | 49.2 | 0.7 | 76.1 |
| G385F | 3 | 2.5 | 0.5 | 3.0 | 5.5 | 18.5 | 1.8 | 2.8 | 2.6 | 0.6 | 1.5 | 2.5 | 48.9 | 0.1 | 74.3 |
| G385M | 3 | 2.7 | 0.5 | 3.2 | 5.8 | 19.2 | 2.1 | 2.9 | 2.5 | 0.6 | 1.6 | 2.3 | 48.1 | 0.2 | 73.1 |
| G385W | 3 | 2.9 | 0.6 | 2.8 | 5.1 | 18.9 | 2.0 | 2.8 | 2.4 | 0.5 | 1.7 | 2.4 | 47.9 | 0.4 | 73.5 |
| G385Y | 3 | 2.8 | 0.5 | 2.9 | 3.9 | 19.0 | 2.0 | 2.8 | 2.6 | 0.5 | 1.6 | 2.5 | 48.4 | 0.2 | 73.6 |
| Y387V | 3 | 2.9 | 0.5 | 2.9 | 5.1 | 17.8 | 1.5 | 2.7 | 2.7 | 0.6 | 1.6 | 2.4 | 49.9 | 0.2 | 75.6 |
| Y387W | 3 | 2.8 | 0.6 | 2.8 | 3.5 | 17.0 | 1.5 | 2.6 | 2.7 | 0.6 | 1.5 | 2.4 | 51.3 | 1.7 | 76.8 |
| L388V | 3 | 3.0 | 0.6 | 3.0 | 3.7 | 18.4 | 1.7 | 2.8 | 2.7 | 0.6 | 1.7 | 2.5 | 48.8 | 0.1 | 74.5 |
| L388W | 3 | 3.0 | 0.6 | 2.8 | 2.0 | 16.6 | 1.3 | 2.7 | 2.8 | 0.6 | 1.6 | 2.5 | 51.2 | 0.5 | 77.5 |
| L388Y+ | 3 | 2.8 | 0.7 | 2.5 | 4.8 | 15.3 | 1.0 | 2.7 | 3.3 | 0.7 | 1.5 | 2.6 | 52.9 | 1.5 | 79.7 |
| T389M | 3 | 3.1 | 0.6 | 2.9 | 5.2 | 15.6 | 1.1 | 2.9 | 3.2 | 0.7 | 1.5 | 2.5 | 52.0 | 0.3 | 78.9 |
| T389W | 3 | 2.6 | 0.7 | 2.6 | 2.3 | 19.2 | 1.9 | 2.8 | 2.6 | 0.5 | 1.6 | 2.8 | 47.3 | 0.7 | 73.2 |
| T389Y | 3 | 2.7 | 0.5 | 2.8 | 3.9 | 18.7 | 1.8 | 2.9 | 2.6 | 0.5 | 1.6 | 2.6 | 48.5 | 0.2 | 74.2 |
| Mutant AVG | | 2.8 | 0.6 | 2.7 | 4.6 | 16.5 | 1.3 | 2.8 | 2.9 | 0.6 | 1.6 | 2.6 | 51.0 | | 77.5 |
| Mutant SD | | 0.2 | 0.1 | 0.2 | 1.0 | 1.7 | 0.3 | 0.1 | 0.3 | 0.1 | 0.1 | 0.1 | 1.8 | | |

TABLE 14

Lipid Composition and Delta-9 Elongase Conversion Efficiency in Batch #3 Transformants Comprising a Vector Encoding YlLPCAT Having a Single Amino Acid Substitution

| | | % TFAs | | | | | | | | | | | | EPA | % |
|---|---|---|---|---|---|---|---|---|---|---|---|---|---|---|---|
| Mutant | # | 16:0 | 16:1 | 18:0 | 18:1 | LA | ALA | EDA | DGLA | ARA | ETrA | ETA | EPA | SD | Conv. |
| WT | 3 | 2.9 | 0.6 | 2.7 | 4.6 | 14.4 | 1.0 | 2.6 | 3.0 | 0.6 | 1.5 | 2.5 | 54.2 | 0.5 | 80.6 |
| M132C | 3 | 2.8 | 0.6 | 2.6 | 4.6 | 18.0 | 1.5 | 2.6 | 2.8 | 0.5 | 1.6 | 2.7 | 50.4 | 0.2 | 75.7 |
| M132L | 3 | 2.9 | 0.6 | 2.8 | 5.0 | 18.7 | 1.8 | 2.6 | 2.5 | 0.5 | 1.6 | 2.4 | 49.7 | 0.5 | 74.3 |
| M132Q | 3 | 2.9 | 0.4 | 2.8 | 4.7 | 19.4 | 2.2 | 2.4 | 2.4 | 0.5 | 1.3 | 2.1 | 50.1 | 0.0 | 73.1 |
| V133L | 3 | 2.9 | 0.5 | 2.7 | 5.3 | 20.4 | 2.8 | 2.8 | 2.0 | 0.4 | 1.5 | 2.1 | 48.1 | 2.2 | 71.1 |
| L134A+ | 3 | 3.1 | 0.7 | 2.5 | 4.6 | 14.2 | 1.0 | 2.6 | 3.2 | 0.6 | 1.5 | 2.5 | 54.4 | 0.7 | 81.1 |
| L134M | 3 | 3.2 | 0.6 | 2.7 | 4.6 | 15.9 | 1.5 | 2.4 | 2.8 | 0.6 | 1.4 | 2.3 | 53.3 | 2.9 | 78.3 |
| C135L | 3 | 3.3 | 0.6 | 3.0 | 4.9 | 15.9 | 1.5 | 2.4 | 2.7 | 0.6 | 1.5 | 2.2 | 52.6 | 4.4 | 78.0 |
| M136I | 3 | 3.1 | 0.6 | 2.7 | 4.7 | 16.2 | 1.7 | 2.5 | 2.6 | 0.5 | 1.5 | 2.2 | 52.4 | 3.2 | 77.5 |
| M136Y | 3 | 2.7 | 0.6 | 2.6 | 4.5 | 17.6 | 1.4 | 2.7 | 2.8 | 0.5 | 1.5 | 2.5 | 51.1 | 0.6 | 76.3 |
| K137N+ | 3 | 3.4 | 0.7 | 2.6 | 4.7 | 13.2 | 1.0 | 2.7 | 3.2 | 0.6 | 1.5 | 2.4 | 55.2 | 0.8 | 82.2 |
| K137R | 3 | 3.0 | 0.6 | 2.6 | 4.6 | 17.1 | 1.3 | 2.7 | 2.8 | 0.6 | 1.6 | 2.6 | 51.4 | 0.3 | 77.0 |
| L138Q | 3 | 3.0 | 0.5 | 2.8 | 4.6 | 18.2 | 1.8 | 2.4 | 2.6 | 0.6 | 1.4 | 2.3 | 51.0 | 1.6 | 75.0 |
| S139V | 3 | 3.1 | 0.7 | 2.6 | 4.7 | 15.8 | 1.1 | 2.6 | 3.0 | 0.6 | 1.5 | 2.4 | 53.1 | 0.5 | 78.9 |
| S140L | 3 | 3.3 | 0.6 | 2.7 | 4.8 | 15.1 | 1.5 | 2.4 | 2.8 | 0.5 | 1.5 | 2.3 | 53.8 | 3.8 | 79.2 |
| S140V | 3 | 3.2 | 0.6 | 2.8 | 4.8 | 15.8 | 1.4 | 2.5 | 2.8 | 0.6 | 1.4 | 2.3 | 53.2 | 2.9 | 78.4 |
| F141I | 3 | 3.1 | 0.6 | 2.7 | 4.8 | 16.0 | 1.6 | 2.5 | 2.7 | 0.6 | 1.5 | 2.2 | 53.0 | 3.3 | 78.0 |
| G142T | 3 | 3.2 | 0.6 | 2.7 | 5.0 | 15.9 | 1.4 | 2.5 | 2.7 | 0.6 | 1.5 | 2.3 | 52.7 | 2.3 | 78.3 |
| W143A | 3 | 3.0 | 0.5 | 2.7 | 5.3 | 19.3 | 2.4 | 2.7 | 2.1 | 0.5 | 1.5 | 2.2 | 48.8 | 3.8 | 72.7 |
| W143V | 3 | 3.2 | 0.6 | 2.7 | 4.4 | 16.4 | 1.5 | 2.5 | 2.8 | 0.6 | 1.5 | 2.4 | 52.5 | 2.2 | 77.6 |
| N144R | 3 | 3.0 | 0.6 | 2.6 | 4.6 | 15.2 | 1.2 | 2.8 | 2.9 | 0.6 | 1.5 | 2.4 | 53.5 | 0.1 | 79.5 |
| N144T+ | 3 | 3.3 | 0.7 | 2.6 | 4.7 | 13.6 | 0.9 | 2.6 | 3.2 | 0.6 | 1.5 | 2.4 | 55.2 | 0.1 | 81.9 |
| V145E | 3 | 3.1 | 0.7 | 2.6 | 4.6 | 14.3 | 1.0 | 2.5 | 3.2 | 0.6 | 1.5 | 2.5 | 54.2 | 0.7 | 80.8 |
| Y146F | 3 | 3.3 | 0.6 | 2.8 | 4.6 | 16.1 | 1.5 | 2.4 | 2.8 | 0.6 | 1.4 | 2.3 | 52.9 | 2.7 | 78.1 |
| Y146Q | 3 | 3.3 | 0.6 | 2.7 | 4.6 | 14.7 | 1.1 | 2.5 | 3.0 | 0.6 | 1.5 | 2.3 | 54.1 | 0.3 | 80.3 |
| Y146R | 3 | 3.2 | 0.5 | 2.7 | 4.6 | 16.4 | 1.6 | 2.4 | 2.6 | 0.5 | 1.5 | 2.2 | 53.0 | 3.2 | 77.6 |
| Y146V | 2 | 3.1 | 0.6 | 2.7 | 4.8 | 17.6 | 1.9 | 2.6 | 2.5 | 0.5 | 1.5 | 2.2 | 50.7 | | 75.5 |
| G148A+ | 3 | 3.2 | 0.7 | 2.6 | 4.6 | 13.4 | 0.9 | 2.5 | 3.2 | 0.6 | 1.6 | 2.5 | 54.9 | 0.3 | 82.0 |
| G148L | 3 | 3.0 | 0.6 | 2.7 | 4.8 | 16.8 | 1.7 | 2.5 | 2.6 | 0.5 | 1.5 | 2.3 | 52.2 | 2.5 | 77.0 |
| S376L | 3 | 2.7 | 0.5 | 2.8 | 4.9 | 19.2 | 2.1 | 2.6 | 2.4 | 0.5 | 1.6 | 2.3 | 49.2 | 0.3 | 73.4 |
| F378L | 3 | 3.0 | 0.5 | 2.8 | 4.5 | 16.9 | 1.3 | 2.5 | 2.7 | 0.6 | 1.5 | 2.3 | 52.3 | 0.1 | 77.2 |

TABLE 14-continued

Lipid Composition and Delta-9 Elongase Conversion Efficiency in Batch #3 Transformants Comprising a Vector Encoding YlLPCAT Having a Single Amino Acid Substitution

| | | % TFAs | | | | | | | | | | | | EPA | % |
|---|---|---|---|---|---|---|---|---|---|---|---|---|---|---|---|
| Mutant | # | 16:0 | 16:1 | 18:0 | 18:1 | LA | ALA | EDA | DGLA | ARA | ETrA | ETA | EPA | SD | Conv. |
| F378W | 3 | 3.0 | 0.7 | 2.5 | 4.9 | 14.9 | 1.0 | 3.0 | 3.4 | 0.6 | 1.5 | 2.7 | 53.0 | 1.0 | 80.2 |
| T382I+ | 3 | 3.3 | 0.7 | 2.6 | 4.7 | 12.9 | 0.9 | 2.4 | 3.2 | 0.6 | 1.4 | 2.4 | 55.8 | 0.5 | 82.6 |
| T382M | 3 | 2.9 | 0.5 | 2.7 | 4.5 | 16.9 | 1.7 | 2.6 | 2.6 | 0.5 | 1.5 | 2.3 | 51.9 | 2.8 | 76.8 |
| R383E | 3 | 3.1 | 0.4 | 2.9 | 4.7 | 19.7 | 2.4 | 2.3 | 2.2 | 0.5 | 1.3 | 2.1 | 49.5 | 0.5 | 72.4 |
| R383H | 3 | 2.9 | 0.6 | 2.6 | 4.8 | 16.5 | 1.2 | 2.7 | 2.9 | 0.6 | 1.6 | 2.5 | 52.1 | 0.4 | 77.8 |
| R383Q | 3 | 3.3 | 0.6 | 2.8 | 4.7 | 16.9 | 1.3 | 2.5 | 2.9 | 0.6 | 1.4 | 2.4 | 51.5 | 1.2 | 77.1 |
| P384A+ | 3 | 3.2 | 0.7 | 2.6 | 4.4 | 15.0 | 1.1 | 2.6 | 2.9 | 0.6 | 1.6 | 2.4 | 53.5 | 0.7 | 79.8 |
| P384S | 3 | 3.3 | 0.6 | 2.7 | 4.6 | 15.9 | 1.2 | 2.7 | 2.9 | 0.6 | 1.5 | 2.4 | 52.5 | 0.9 | 78.6 |
| P384T | 3 | 2.9 | 0.5 | 2.8 | 5.1 | 19.4 | 2.3 | 2.5 | 2.2 | 0.5 | 1.5 | 2.3 | 49.2 | 0.4 | 72.8 |
| P384V | 3 | 2.8 | 0.6 | 2.7 | 4.8 | 17.4 | 1.5 | 2.6 | 2.7 | 0.5 | 1.5 | 2.4 | 51.4 | 0.2 | 76.5 |
| G385A | 3 | 2.8 | 0.5 | 2.9 | 5.0 | 19.2 | 2.2 | 2.7 | 2.3 | 0.5 | 1.6 | 2.3 | 48.6 | 0.8 | 73.1 |
| G385C | 3 | 3.0 | 0.5 | 2.9 | 5.2 | 19.9 | 2.4 | 2.5 | 2.2 | 0.5 | 1.6 | 2.2 | 48.5 | 0.8 | 72.0 |
| G385V | 3 | 3.0 | 0.5 | 2.9 | 5.3 | 19.7 | 2.3 | 2.6 | 2.2 | 0.5 | 1.5 | 2.2 | 48.4 | 0.7 | 72.3 |
| Y387F | 3 | 3.1 | 0.5 | 2.8 | 4.8 | 18.3 | 1.8 | 2.4 | 2.4 | 0.5 | 1.5 | 2.2 | 50.8 | 1.5 | 74.8 |
| Y387L | 3 | 3.2 | 0.6 | 2.7 | 4.4 | 17.3 | 1.4 | 2.6 | 2.6 | 0.5 | 1.6 | 2.3 | 51.0 | 1.2 | 76.5 |
| T389A+ | 3 | 3.2 | 0.5 | 2.9 | 4.8 | 13.6 | 1.0 | 2.4 | 2.9 | 0.6 | 1.5 | 2.2 | 55.4 | 0.1 | 81.6 |
| T389C+ | 3 | 3.2 | 0.6 | 2.7 | 4.4 | 13.6 | 1.0 | 2.5 | 3.1 | 0.6 | 1.5 | 2.4 | 55.3 | 0.3 | 81.8 |
| T389S+ | 3 | 3.2 | 0.6 | 2.8 | 5.0 | 13.3 | 1.0 | 2.4 | 3.1 | 0.6 | 1.5 | 2.3 | 55.2 | 0.3 | 82.0 |
| T389V | 3 | 2.9 | 0.6 | 2.8 | 4.6 | 16.0 | 1.2 | 2.7 | 2.9 | 0.6 | 1.5 | 2.4 | 52.8 | 0.4 | 78.6 |
| Mutant AVG | | 3.1 | 0.6 | 2.7 | 4.7 | 16.3 | 1.5 | 2.6 | 2.7 | 0.6 | 1.5 | 2.3 | 52.3 | 1.3 | 77.7 |
| Mutant SD | | 0.2 | 0.1 | 0.1 | 0.2 | 1.9 | 0.4 | 0.1 | 0.3 | 0.0 | 0.1 | 0.1 | 2.0 | | 3.0 |

TABLE 15

Lipid Composition and Delta-9 Elongase Conversion Efficiency in Batch #4 Transformants Comprising a Vector Encoding YlLPCAT Having a Single Amino Acid Substitution

| | | % TFAs | | | | | | | | | | | | EPA | % |
|---|---|---|---|---|---|---|---|---|---|---|---|---|---|---|---|
| Mutant | # | 16:0 | 16:1 | 18:0 | 18:1 | LA | ALA | EDA | DGLA | ARA | ETrA | ETA | EPA | SD | Conv. |
| WT | 6 | 3.0 | 0.6 | 2.7 | 4.5 | 14.4 | 1.0 | 2.5 | 3.1 | 0.6 | 1.5 | 2.3 | 54.6 | 0.8 | 82.0 |
| M132G | 3 | 2.6 | 0.6 | 2.7 | 5.5 | 19.6 | 1.9 | 2.6 | 2.4 | 0.4 | 1.5 | 2.3 | 49.1 | 1.8 | 74.4 |
| M132H | 3 | 2.6 | 0.5 | 2.9 | 5.1 | 19.4 | 2.4 | 2.5 | 2.3 | 0.4 | 1.5 | 2.2 | 50.5 | 0.1 | 74.5 |
| M132N | 3 | 2.4 | 0.5 | 2.6 | 4.9 | 18.6 | 1.8 | 2.6 | 2.7 | 0.5 | 1.5 | 2.7 | 50.0 | 1.6 | 75.9 |
| V133A | 3 | 2.8 | 0.5 | 2.8 | 4.6 | 17.0 | 1.3 | 2.5 | 2.8 | 0.6 | 1.5 | 2.2 | 52.9 | 0.5 | 78.7 |
| V133C | 3 | 2.6 | 0.6 | 2.7 | 4.4 | 15.5 | 1.1 | 2.5 | 3.0 | 0.5 | 1.6 | 2.3 | 54.7 | 0.1 | 80.8 |
| V133G | 3 | 2.9 | 0.7 | 2.9 | 5.6 | 17.8 | 1.5 | 3.3 | 2.8 | 0.5 | 1.6 | 2.3 | 49.8 | 3.2 | 77.0 |
| V133H | 3 | 2.6 | 0.5 | 2.9 | 4.8 | 18.4 | 1.8 | 2.5 | 2.4 | 0.4 | 1.5 | 2.2 | 51.8 | 0.1 | 76.4 |
| V133N | 3 | 2.6 | 0.6 | 2.7 | 4.6 | 18.0 | 1.4 | 2.4 | 2.8 | 0.5 | 1.4 | 2.4 | 52.2 | 2.0 | 77.3 |
| V133Q | 3 | 2.7 | 0.5 | 2.9 | 4.9 | 19.2 | 2.1 | 2.4 | 2.3 | 0.4 | 1.5 | 2.0 | 51.0 | 7.9 | 75.0 |
| L134C | 3 | 2.7 | 0.7 | 2.5 | 4.6 | 13.7 | 0.9 | 2.6 | 3.4 | 0.6 | 1.6 | 2.6 | 55.0 | 1.5 | 83.2 |
| L134G+ | 3 | 3.0 | 0.7 | 2.7 | 4.4 | 14.1 | 1.0 | 2.5 | 3.0 | 0.5 | 1.7 | 2.1 | 55.3 | 0.6 | 82.6 |
| L134H | 3 | 2.5 | 0.6 | 2.6 | 4.5 | 16.7 | 1.3 | 2.5 | 2.8 | 0.5 | 1.6 | 2.6 | 53.6 | 0.3 | 79.2 |
| L134N | 3 | 2.8 | 0.5 | 2.7 | 4.6 | 16.6 | 1.4 | 2.4 | 2.7 | 0.5 | 1.5 | 2.2 | 53.5 | 2.8 | 79.0 |
| L134Q | 3 | 2.8 | 0.6 | 2.7 | 4.5 | 15.9 | 1.1 | 2.5 | 3.0 | 0.5 | 1.5 | 2.5 | 54.3 | 1.5 | 80.4 |
| C135D | 3 | 2.9 | 0.6 | 2.7 | 4.5 | 13.7 | 1.1 | 2.3 | 3.0 | 0.5 | 1.5 | 2.2 | 56.5 | 0.2 | 83.1 |
| C135E | 3 | 2.5 | 0.6 | 2.8 | 4.8 | 17.4 | 1.5 | 2.7 | 2.7 | 0.4 | 1.6 | 2.3 | 52.2 | 1.7 | 78.0 |
| C135G | 3 | 2.7 | 0.6 | 2.7 | 4.5 | 16.1 | 1.2 | 2.4 | 2.9 | 0.5 | 1.5 | 2.3 | 54.0 | 0.2 | 80.0 |
| C135H | 2 | 2.7 | 0.8 | 3.3 | 7.6 | 20.8 | 1.3 | 5.5 | 3.1 | 0.5 | 2.0 | 2.7 | 42.1 | 10.8 | 72.7 |
| C135K | 3 | 2.6 | 0.6 | 2.6 | 5.1 | 17.6 | 1.5 | 2.7 | 2.9 | 0.5 | 1.6 | 2.6 | 51.8 | 2.8 | 77.7 |
| C135N | 3 | 2.9 | 0.6 | 2.7 | 4.8 | 15.0 | 1.3 | 2.5 | 3.0 | 0.6 | 1.5 | 2.2 | 54.3 | 4.4 | 81.0 |
| C135Q | 3 | 2.8 | 0.6 | 2.8 | 4.5 | 16.2 | 1.2 | 2.5 | 2.8 | 0.5 | 1.6 | 2.3 | 54.2 | 0.5 | 79.9 |
| C135R | 3 | 2.5 | 0.5 | 2.7 | 5.1 | 19.2 | 2.0 | 2.6 | 2.6 | 0.5 | 1.5 | 2.3 | 49.9 | 0.2 | 75.0 |
| M136C | 3 | 3.0 | 0.7 | 2.6 | 4.8 | 14.6 | 1.0 | 2.9 | 3.3 | 0.6 | 1.5 | 2.3 | 54.2 | 1.3 | 81.9 |
| M136G | 2 | 3.1 | 0.6 | 2.7 | 4.5 | 12.5 | 0.9 | 2.4 | 3.1 | 0.6 | 1.5 | 2.3 | 57.0 | | 84.7 |
| M136H | 3 | 2.8 | 0.6 | 2.7 | 4.7 | 17.3 | 1.5 | 2.6 | 2.6 | 0.5 | 1.6 | 2.3 | 52.9 | 0.7 | 78.2 |
| M136N | 3 | 3.0 | 0.5 | 2.8 | 4.6 | 15.6 | 1.5 | 2.4 | 2.8 | 0.5 | 1.4 | 2.1 | 54.6 | 4.1 | 80.2 |
| K137A | 3 | 2.9 | 0.5 | 2.9 | 4.4 | 15.8 | 1.4 | 2.4 | 2.8 | 0.6 | 1.4 | 2.2 | 54.2 | 3.5 | 79.8 |
| K137G | 3 | 2.9 | 0.6 | 2.7 | 4.5 | 14.3 | 1.0 | 2.5 | 3.1 | 0.5 | 1.4 | 2.2 | 55.8 | 0.5 | 82.4 |
| K137H+ | 3 | 3.2 | 0.6 | 2.6 | 4.4 | 12.0 | 0.9 | 2.3 | 3.2 | 0.5 | 1.5 | 2.2 | 58.6 | 0.2 | 85.6 |
| L138G | 3 | 2.7 | 0.6 | 2.7 | 4.5 | 15.2 | 1.0 | 2.5 | 3.1 | 0.5 | 1.5 | 2.4 | 54.8 | 0.1 | 81.3 |
| L138H | 3 | 2.9 | 0.6 | 2.7 | 4.3 | 14.3 | 1.1 | 2.5 | 3.1 | 0.5 | 1.5 | 2.4 | 55.8 | 0.2 | 82.4 |
| L138I | 2 | 3.0 | 0.6 | 2.6 | 4.2 | 15.0 | 1.1 | 2.3 | 2.9 | 0.5 | 1.5 | 2.4 | 56.1 | | 81.7 |
| L138N | 3 | 2.9 | 0.6 | 2.6 | 4.4 | 15.3 | 1.1 | 2.4 | 3.0 | 0.6 | 1.5 | 2.3 | 54.6 | 0.9 | 81.1 |
| S139G | 3 | 2.7 | 0.6 | 2.7 | 4.5 | 15.0 | 1.0 | 2.6 | 3.1 | 0.5 | 1.5 | 2.4 | 54.8 | 1.6 | 81.4 |
| S139H | 3 | 2.8 | 0.6 | 2.6 | 4.7 | 15.5 | 1.4 | 2.5 | 2.9 | 0.5 | 1.5 | 2.4 | 54.4 | 3.9 | 80.5 |
| S139N | 3 | 2.9 | 0.6 | 2.7 | 4.4 | 15.4 | 1.1 | 2.4 | 3.0 | 0.6 | 1.5 | 2.3 | 54.7 | 0.1 | 81.0 |
| S140C | 3 | 2.9 | 0.6 | 2.8 | 4.9 | 14.9 | 1.3 | 2.6 | 3.0 | 0.5 | 1.5 | 2.1 | 54.4 | 4.3 | 81.1 |
| S140H+ | 3 | 3.1 | 0.6 | 2.6 | 4.3 | 12.1 | 0.9 | 2.4 | 3.2 | 0.5 | 1.5 | 2.3 | 58.6 | 0.5 | 85.5 |

TABLE 15-continued

Lipid Composition and Delta-9 Elongase Conversion Efficiency in Batch #4 Transformants Comprising a Vector Encoding YlLPCAT Having a Single Amino Acid Substitution

| | | % TFAs | | | | | | | | | | | | EPA | % |
|---|---|---|---|---|---|---|---|---|---|---|---|---|---|---|---|
| Mutant | # | 16:0 | 16:1 | 18:0 | 18:1 | LA | ALA | EDA | DGLA | ARA | ETrA | ETA | EPA | SD | Conv. |
| S140N | 3 | 3.0 | 0.6 | 2.7 | 4.3 | 13.5 | 0.9 | 2.3 | 3.1 | 0.6 | 1.5 | 2.2 | 56.6 | 0.1 | 83.5 |
| F141A | 3 | 3.0 | 0.6 | 2.8 | 4.2 | 14.3 | 1.0 | 2.4 | 3.1 | 0.6 | 1.4 | 2.2 | 55.9 | 0.2 | 82.5 |
| F141G | 3 | 2.7 | 0.5 | 2.6 | 4.7 | 16.9 | 1.3 | 2.6 | 2.8 | 0.5 | 1.5 | 2.2 | 53.3 | 0.9 | 78.8 |
| F141H | 3 | 2.4 | 0.5 | 2.6 | 4.8 | 18.0 | 1.7 | 2.6 | 2.6 | 0.4 | 1.5 | 2.5 | 52.3 | 2.2 | 77.2 |
| F141N | 3 | 2.8 | 0.6 | 2.6 | 4.8 | 16.7 | 1.4 | 2.6 | 2.7 | 0.5 | 1.6 | 2.2 | 53.2 | 0.9 | 78.9 |
| G142H | 2 | 2.8 | 0.7 | 2.6 | 4.2 | 14.3 | 0.9 | 2.4 | 3.2 | 0.5 | 1.5 | 2.7 | 55.9 | | 82.7 |
| G142N | 3 | 2.4 | 0.7 | 2.3 | 4.6 | 15.5 | 1.0 | 2.6 | 3.4 | 0.5 | 1.6 | 3.0 | 53.0 | 0.9 | 80.9 |
| W143G | 3 | 2.7 | 0.6 | 2.7 | 4.8 | 16.5 | 1.4 | 2.6 | 2.8 | 0.5 | 1.5 | 2.2 | 53.3 | 3.1 | 79.1 |
| W143H | 3 | 2.9 | 0.6 | 2.7 | 4.4 | 15.2 | 1.1 | 2.5 | 3.0 | 0.5 | 1.6 | 2.5 | 55.1 | 0.4 | 81.3 |
| W143K | 3 | 2.8 | 0.6 | 2.6 | 4.8 | 16.5 | 1.3 | 2.6 | 2.7 | 0.5 | 1.6 | 2.3 | 54.0 | 0.3 | 79.4 |
| N144A+ | 3 | 3.2 | 0.6 | 2.7 | 4.4 | 12.5 | 0.9 | 2.3 | 3.2 | 0.6 | 1.4 | 2.2 | 57.5 | 0.1 | 84.8 |
| N144G | 3 | 2.9 | 0.7 | 2.5 | 4.5 | 14.7 | 1.1 | 2.5 | 3.2 | 0.5 | 1.4 | 2.6 | 54.5 | 2.5 | 81.8 |
| V145A | 3 | 2.8 | 0.7 | 2.5 | 4.4 | 13.1 | 0.8 | 2.3 | 3.4 | 0.6 | 1.5 | 2.6 | 56.0 | 0.3 | 84.1 |
| V145G | 2 | 2.9 | 0.6 | 2.6 | 4.5 | 14.1 | 1.0 | 2.5 | 3.1 | 0.5 | 1.6 | 2.4 | 55.5 | | 82.7 |
| V145H | 3 | 3.1 | 0.6 | 2.7 | 4.6 | 15.5 | 1.2 | 2.5 | 2.9 | 0.5 | 1.6 | 2.4 | 54.5 | 1.2 | 80.7 |
| Y146G | 2 | 2.8 | 0.6 | 2.7 | 4.6 | 14.4 | 1.0 | 2.6 | 3.2 | 0.6 | 1.5 | 2.5 | 54.9 | | 82.2 |
| D147A | 3 | 2.8 | 0.6 | 2.6 | 4.6 | 15.6 | 1.4 | 2.5 | 2.9 | 0.5 | 1.6 | 2.3 | 53.9 | 4.0 | 80.2 |
| D147G | 3 | 2.4 | 0.6 | 3.2 | 6.5 | 20.5 | 1.9 | 4.2 | 2.7 | 0.4 | 1.8 | 2.4 | 45.2 | 7.2 | 72.9 |
| D147H+ | 3 | 3.4 | 0.6 | 2.6 | 4.2 | 13.3 | 1.0 | 2.4 | 3.0 | 0.5 | 1.5 | 2.2 | 57.5 | 0.9 | 83.9 |
| D147N | 3 | 2.9 | 0.6 | 2.7 | 4.4 | 14.5 | 1.0 | 2.5 | 3.1 | 0.6 | 1.6 | 2.3 | 55.1 | 3.2 | 82.1 |
| D147Q+ | 3 | 3.2 | 0.6 | 2.7 | 4.3 | 14.0 | 1.0 | 2.5 | 3.0 | 0.5 | 1.6 | 2.3 | 56.6 | 0.2 | 83.0 |
| G148H | 3 | 3.2 | 0.6 | 2.7 | 4.6 | 15.4 | 1.5 | 2.5 | 2.8 | 0.5 | 1.6 | 2.4 | 54.3 | 4.3 | 80.5 |
| G148N+ | 3 | 3.0 | 0.7 | 2.7 | 4.7 | 13.4 | 1.0 | 2.5 | 3.2 | 0.6 | 1.6 | 2.3 | 55.8 | 0.8 | 83.5 |
| S376A | 3 | 2.9 | 0.6 | 2.8 | 4.6 | 16.9 | 1.3 | 2.5 | 2.8 | 0.6 | 1.5 | 2.3 | 52.8 | 1.9 | 78.8 |
| S376G | 3 | 2.6 | 0.5 | 2.7 | 5.1 | 17.8 | 1.5 | 2.8 | 2.7 | 0.5 | 1.4 | 2.3 | 51.7 | 1.9 | 77.4 |
| S376H | 3 | 2.8 | 0.6 | 2.7 | 4.9 | 19.0 | 2.2 | 2.5 | 2.4 | 0.4 | 1.6 | 2.5 | 50.3 | 0.5 | 75.1 |
| A377G | 3 | 2.6 | 0.7 | 2.7 | 5.0 | 17.3 | 1.3 | 2.8 | 2.9 | 0.5 | 1.6 | 2.5 | 51.4 | 1.8 | 78.1 |
| A377H | 3 | 3.0 | 0.5 | 2.8 | 5.0 | 19.5 | 2.4 | 2.5 | 2.2 | 0.4 | 1.6 | 2.3 | 49.9 | 0.1 | 74.2 |
| A377L | 3 | 2.6 | 0.5 | 2.8 | 5.7 | 19.6 | 2.4 | 2.7 | 2.2 | 0.4 | 1.5 | 2.2 | 49.7 | 1.0 | 74.1 |
| A377N | 3 | 2.7 | 0.6 | 2.7 | 5.3 | 19.1 | 2.1 | 2.7 | 2.3 | 0.4 | 1.7 | 2.2 | 49.1 | 0.2 | 74.7 |
| F378C | 3 | 2.8 | 0.6 | 2.8 | 4.8 | 16.4 | 1.3 | 2.7 | 2.8 | 0.5 | 1.6 | 2.2 | 53.0 | 1.0 | 79.4 |
| F378G | 3 | 2.8 | 0.6 | 2.8 | 4.6 | 15.6 | 1.1 | 2.5 | 2.9 | 0.5 | 1.5 | 2.3 | 54.2 | 0.1 | 80.5 |
| F378H | 3 | 2.8 | 0.5 | 2.8 | 4.7 | 17.3 | 1.7 | 2.6 | 2.5 | 0.4 | 1.5 | 2.2 | 53.0 | 3.1 | 78.0 |
| F378N | 3 | 2.6 | 0.6 | 2.8 | 4.7 | 17.0 | 1.3 | 2.5 | 2.8 | 0.5 | 1.6 | 2.3 | 52.9 | 0.4 | 78.7 |
| T382G | 3 | 2.5 | 0.5 | 2.9 | 4.8 | 18.2 | 1.7 | 2.5 | 2.5 | 0.4 | 1.4 | 2.3 | 51.9 | 1.5 | 76.6 |
| T382H | 3 | 2.8 | 0.6 | 2.8 | 4.6 | 17.3 | 1.5 | 2.5 | 2.6 | 0.4 | 1.5 | 2.4 | 53.4 | 0.5 | 78.3 |
| T382N | 3 | 2.6 | 0.5 | 2.9 | 5.2 | 19.4 | 2.2 | 2.6 | 2.3 | 0.4 | 1.5 | 2.0 | 50.2 | 0.5 | 74.4 |
| T382Q | 2 | 2.9 | 0.7 | 3.1 | 5.7 | 16.8 | 1.0 | 3.9 | 3.2 | 0.5 | 1.8 | 2.7 | 50.0 | | 78.8 |
| R383G | 3 | 2.3 | 0.7 | 3.4 | 7.6 | 21.1 | 1.3 | 5.7 | 3.3 | 0.5 | 2.1 | 3.1 | 41.2 | 7.4 | 72.3 |
| P384G+ | 3 | 2.5 | 0.6 | 2.6 | 4.5 | 15.5 | 1.1 | 2.5 | 3.1 | 0.5 | 1.5 | 2.5 | 54.2 | 0.2 | 80.8 |
| P384H | 3 | 2.7 | 0.6 | 2.7 | 4.5 | 16.3 | 1.2 | 2.5 | 2.8 | 0.5 | 1.5 | 2.4 | 54.0 | 0.5 | 79.8 |
| P384K | 3 | 2.7 | 0.6 | 2.5 | 4.9 | 17.7 | 1.7 | 2.5 | 2.5 | 0.4 | 1.6 | 2.3 | 52.6 | 2.3 | 77.4 |
| P384R | 3 | 2.7 | 0.6 | 2.7 | 4.5 | 16.1 | 1.1 | 2.4 | 3.0 | 0.6 | 1.4 | 2.4 | 54.1 | 0.9 | 80.1 |
| G385G | 3 | 2.8 | 0.6 | 2.7 | 4.5 | 14.1 | 1.0 | 2.6 | 3.1 | 0.5 | 1.6 | 2.4 | 55.2 | 0.1 | 82.5 |
| G385H | 3 | 2.6 | 0.5 | 2.8 | 5.3 | 19.1 | 2.2 | 2.6 | 2.4 | 0.4 | 1.6 | 2.4 | 49.8 | 0.6 | 74.8 |
| G385K | 3 | 2.6 | 0.5 | 2.8 | 5.4 | 19.3 | 2.1 | 2.6 | 2.4 | 0.4 | 1.6 | 2.4 | 50.1 | 0.4 | 74.7 |
| G385N | 3 | 2.5 | 0.5 | 2.7 | 5.3 | 19.5 | 2.0 | 2.7 | 2.6 | 0.4 | 1.5 | 2.4 | 49.7 | 1.2 | 74.6 |
| Y386A | 3 | 2.7 | 0.5 | 2.9 | 4.9 | 19.2 | 2.0 | 2.5 | 2.5 | 0.5 | 1.5 | 2.2 | 50.1 | 0.3 | 74.9 |
| Y386G | 3 | 2.5 | 0.5 | 3.0 | 5.2 | 19.3 | 2.2 | 2.6 | 2.3 | 0.4 | 1.6 | 2.0 | 50.0 | 0.4 | 74.6 |
| Y386H | 3 | 2.8 | 0.5 | 2.9 | 5.2 | 19.3 | 2.2 | 2.5 | 2.3 | 0.4 | 1.6 | 2.4 | 50.0 | 0.5 | 74.6 |
| Y386L | 3 | 2.6 | 0.5 | 2.9 | 5.4 | 19.1 | 2.2 | 2.7 | 2.3 | 0.4 | 1.6 | 2.2 | 50.1 | 0.2 | 74.8 |
| Y387G | 3 | 2.5 | 0.6 | 2.6 | 5.1 | 17.9 | 1.5 | 2.8 | 2.8 | 0.5 | 1.6 | 2.5 | 51.0 | 2.1 | 77.2 |
| Y387H | 3 | 2.9 | 0.6 | 2.6 | 4.5 | 16.5 | 1.2 | 2.5 | 2.8 | 0.5 | 1.5 | 2.5 | 53.7 | 2.1 | 79.5 |
| L388G+ | 3 | 2.8 | 0.6 | 2.7 | 4.4 | 14.6 | 1.0 | 2.6 | 3.1 | 0.5 | 1.6 | 2.5 | 55.5 | 0.8 | 82.2 |
| L388H | 3 | 2.9 | 0.6 | 2.7 | 4.5 | 15.9 | 1.2 | 2.5 | 2.8 | 0.5 | 1.5 | 2.4 | 54.7 | 0.9 | 80.3 |
| T389G | 3 | 2.5 | 0.5 | 2.9 | 5.2 | 17.9 | 1.9 | 2.8 | 2.6 | 0.4 | 1.6 | 2.3 | 51.2 | 0.7 | 76.8 |
| T389H | 3 | 2.7 | 0.5 | 2.7 | 5.0 | 18.7 | 1.9 | 2.6 | 2.4 | 0.4 | 1.6 | 2.4 | 51.3 | 0.6 | 75.8 |
| F390A | 3 | 2.5 | 0.5 | 3.1 | 6.0 | 14.8 | 1.3 | 2.2 | 2.6 | 0.5 | 1.5 | 2.0 | 54.4 | 4.1 | 81.3 |
| F390C | 3 | 2.9 | 0.6 | 2.9 | 5.2 | 13.8 | 0.9 | 2.5 | 3.0 | 0.5 | 1.6 | 2.1 | 55.5 | 0.4 | 83.0 |
| F390G+ | 3 | 2.6 | 0.4 | 3.3 | 5.7 | 14.6 | 1.2 | 2.2 | 2.5 | 0.4 | 1.4 | 1.8 | 55.9 | 0.3 | 81.8 |
| F390H | 3 | 2.7 | 0.5 | 2.7 | 4.7 | 18.3 | 1.8 | 2.5 | 2.4 | 0.4 | 1.5 | 2.2 | 52.3 | 0.7 | 76.6 |
| F390N | 2 | 2.8 | 0.6 | 2.6 | 4.4 | 15.2 | 1.0 | 2.4 | 3.1 | 0.6 | 1.5 | 2.3 | 55.1 | 0.2 | 81.4 |
| Mutant AVG | | 2.8 | 0.6 | 2.7 | 4.8 | 16.4 | 1.4 | 2.6 | 2.8 | 0.5 | 1.5 | 2.3 | 53.1 | 1.5 | 79.3 |
| Mutant SD | | 0.2 | 0.1 | 0.2 | 0.6 | 2.1 | 0.4 | 0.5 | 0.3 | 0.1 | 0.1 | 0.2 | 2.9 | | 3.2 |

TABLE 16

Lipid Composition and Delta-9 Elongase Conversion Efficiency in Batch #5 Transformants Comprising a Vector Encoding YlLPCAT Having a Single Amino Acid Substitution

| | | % TFAs | | | | | | | | | | | | EPA | % |
|---|---|---|---|---|---|---|---|---|---|---|---|---|---|---|---|
| Mutant | # | 16:0 | 16:1 | 18:0 | 18:1 | LA | ALA | EDA | DGLA | ARA | ETrA | ETA | EPA | SD | Conv. |
| WT | 6 | 2.9 | 0.6 | 2.4 | 4.0 | 13.6 | 1.0 | 2.0 | 2.9 | 0.5 | 1.6 | 2.3 | 58.3 | 1.5 | 82.2 |
| M132P | 3 | 2.7 | 0.5 | 2.3 | 4.8 | 19.5 | 2.7 | 2.2 | 2.0 | 0.4 | 1.5 | 1.9 | 52.1 | 1.1 | 73.0 |
| M132S | 3 | 2.7 | 0.5 | 2.7 | 5.2 | 19.3 | 2.4 | 2.5 | 2.1 | 0.2 | 1.6 | 2.2 | 51.0 | 0.1 | 73.3 |
| M132T | 3 | 2.6 | 0.7 | 2.4 | 5.5 | 19.6 | 2.4 | 2.7 | 2.3 | 0.4 | 1.6 | 2.4 | 50.1 | 1.4 | 73.0 |
| V133P | 3 | 2.7 | 0.5 | 2.5 | 5.0 | 19.4 | 2.2 | 2.3 | 2.2 | 0.5 | 1.5 | 1.9 | 51.3 | 0.4 | 73.4 |
| V133S | 3 | 2.8 | 0.6 | 2.7 | 5.0 | 17.7 | 1.7 | 1.7 | 2.6 | 0.3 | 1.6 | 2.4 | 52.4 | 0.1 | 75.9 |
| V133T | 3 | 2.9 | 0.6 | 2.5 | 5.0 | 18.7 | 2.3 | 2.5 | 2.2 | 0.4 | 1.5 | 2.1 | 52.0 | 2.6 | 74.3 |
| V133Y | 3 | 2.5 | 0.5 | 2.5 | 4.8 | 19.0 | 2.3 | 2.2 | 2.2 | 0.4 | 1.4 | 2.2 | 52.5 | 0.2 | 74.0 |
| L134P | 3 | 2.5 | 0.5 | 2.3 | 4.4 | 18.9 | 2.4 | 2.0 | 2.1 | 0.4 | 1.5 | 2.1 | 53.2 | 0.4 | 74.2 |
| L134S | 3 | 2.8 | 0.6 | 2.7 | 5.6 | 19.9 | 2.6 | 2.6 | 2.2 | 0.2 | 1.6 | 2.1 | 49.6 | 6.0 | 72.1 |
| L134T | 3 | 2.8 | 0.5 | 2.6 | 5.3 | 20.0 | 2.8 | 2.5 | 1.9 | 0.3 | 1.5 | 1.9 | 50.6 | 0.5 | 72.0 |
| C135P | 3 | 2.5 | 0.5 | 2.3 | 4.2 | 18.2 | 2.0 | 1.9 | 2.3 | 0.4 | 1.5 | 2.3 | 54.1 | 0.6 | 75.5 |
| C135S | 3 | 3.0 | 0.6 | 2.6 | 4.6 | 15.4 | 1.3 | 2.5 | 2.8 | 0.5 | 1.6 | 2.4 | 55.0 | 0.7 | 79.5 |
| M136P | 3 | 3.0 | 0.6 | 2.2 | 3.7 | 12.6 | 0.9 | 1.8 | 2.8 | 0.5 | 1.5 | 2.3 | 60.2 | 0.7 | 83.6 |
| K137P | 3 | 2.6 | 0.5 | 2.4 | 4.3 | 17.8 | 2.1 | 2.1 | 2.3 | 0.4 | 1.4 | 2.1 | 54.5 | 3.5 | 76.0 |
| K137S | 3 | 3.0 | 0.7 | 2.5 | 4.4 | 14.0 | 1.1 | 2.5 | 3.1 | 0.5 | 1.7 | 2.5 | 56.6 | 0.5 | 81.6 |
| K137T | 3 | 2.9 | 0.6 | 2.4 | 4.7 | 18.0 | 2.3 | 2.3 | 2.2 | 0.4 | 1.6 | 2.1 | 53.1 | 4.4 | 75.3 |
| K137Y | 3 | 2.7 | 0.7 | 2.0 | 4.0 | 12.0 | 0.9 | 1.8 | 3.0 | 0.5 | 1.4 | 2.4 | 60.7 | 2.8 | 84.4 |
| L138P | 3 | 2.5 | 0.4 | 2.2 | 4.5 | 19.1 | 2.6 | 1.9 | 1.9 | 0.4 | 1.4 | 2.0 | 53.7 | 0.9 | 73.9 |
| L138S | 3 | 3.0 | 0.6 | 2.5 | 4.4 | 14.7 | 1.2 | 2.5 | 2.9 | 0.5 | 1.7 | 2.3 | 56.2 | 0.9 | 80.6 |
| L138T | 3 | 3.1 | 0.7 | 2.4 | 4.4 | 14.4 | 1.1 | 2.3 | 2.8 | 0.5 | 1.7 | 2.3 | 56.7 | 0.6 | 81.0 |
| S139P | 3 | 2.6 | 0.5 | 2.5 | 4.3 | 17.3 | 2.0 | 2.0 | 2.3 | 0.4 | 1.4 | 2.1 | 54.9 | 3.2 | 76.5 |
| S140P | 3 | 3.0 | 0.6 | 2.4 | 3.9 | 13.0 | 1.0 | 1.9 | 2.9 | 0.5 | 1.5 | 2.3 | 59.7 | 0.7 | 83.1 |
| F141P | 3 | 2.5 | 0.6 | 2.0 | 4.6 | 18.8 | 2.4 | 2.1 | 1.9 | 0.3 | 1.5 | 2.1 | 53.1 | 2.1 | 74.2 |
| F141S | 3 | 2.8 | 0.7 | 2.1 | 4.4 | 15.1 | 1.7 | 2.2 | 2.5 | 0.4 | 1.7 | 2.2 | 56.6 | 5.4 | 79.6 |
| F141T | 3 | 3.1 | 0.7 | 2.4 | 4.4 | 13.9 | 1.1 | 2.3 | 3.0 | 0.3 | 1.6 | 2.4 | 57.1 | 0.1 | 81.6 |
| G142M | 3 | 3.0 | 0.6 | 2.4 | 4.6 | 16.0 | 1.6 | 2.3 | 2.6 | 0.5 | 1.5 | 2.2 | 55.3 | 3.2 | 78.5 |
| G142P | 3 | 2.8 | 0.5 | 2.5 | 4.4 | 15.7 | 1.6 | 2.4 | 2.6 | 0.4 | 1.4 | 2.2 | 55.7 | 3.6 | 79.0 |
| W143P | 3 | 2.5 | 0.5 | 2.1 | 4.1 | 17.5 | 1.6 | 2.0 | 2.3 | 0.4 | 1.5 | 2.2 | 55.5 | 0.3 | 77.0 |
| W143S | 3 | 3.0 | 0.7 | 2.5 | 4.5 | 15.4 | 1.3 | 2.5 | 2.8 | 0.4 | 1.6 | 2.3 | 55.5 | 0.2 | 79.6 |
| W143T | 3 | 2.8 | 0.6 | 2.5 | 5.3 | 19.4 | 2.6 | 2.6 | 2.1 | 0.3 | 1.6 | 2.2 | 50.1 | 0.8 | 72.9 |
| N144F | 3 | 3.1 | 0.7 | 2.3 | 4.3 | 12.2 | 0.9 | 2.1 | 3.0 | 0.5 | 1.6 | 2.3 | 59.4 | 0.6 | 84.0 |
| N144P | 3 | 2.7 | 0.5 | 2.4 | 4.2 | 16.3 | 1.3 | 2.3 | 2.7 | 0.5 | 1.5 | 2.3 | 55.7 | 0.3 | 78.7 |
| N144V | 3 | 2.8 | 0.6 | 2.0 | 3.8 | 11.6 | 0.9 | 1.7 | 2.7 | 0.5 | 1.5 | 2.2 | 61.9 | 1.0 | 85.0 |
| V145P | 3 | 2.7 | 0.5 | 2.3 | 4.3 | 17.6 | 1.5 | 2.1 | 2.4 | 0.4 | 1.4 | 2.2 | 54.7 | 1.0 | 76.8 |
| V145S | 3 | 3.0 | 0.7 | 2.2 | 4.5 | 15.4 | 1.7 | 2.3 | 2.6 | 0.5 | 1.6 | 2.3 | 55.9 | 4.0 | 79.3 |
| V145T | 3 | 3.2 | 0.7 | 2.6 | 4.5 | 14.1 | 1.2 | 2.6 | 3.0 | 0.5 | 1.6 | 2.4 | 56.0 | 0.6 | 81.3 |
| Y146N | 3 | 2.7 | 0.6 | 2.1 | 4.0 | 15.4 | 1.5 | 1.8 | 2.4 | 0.4 | 1.4 | 2.2 | 57.8 | 3.6 | 79.6 |
| Y146P | 3 | 2.6 | 0.7 | 2.3 | 4.9 | 16.4 | 1.5 | 2.5 | 2.9 | 0.5 | 1.6 | 2.6 | 53.7 | 4.5 | 78.0 |
| D147F | 3 | 3.2 | 0.6 | 2.4 | 4.5 | 15.0 | 1.6 | 2.1 | 2.6 | 0.5 | 1.6 | 2.1 | 56.2 | 4.3 | 79.8 |
| D147S | 3 | 2.9 | 0.6 | 2.2 | 4.6 | 16.1 | 1.8 | 2.4 | 2.6 | 0.5 | 1.6 | 2.2 | 55.1 | 3.3 | 78.2 |
| D147T | 3 | 2.7 | 0.5 | 2.2 | 5.0 | 20.0 | 2.9 | 2.2 | 1.8 | 0.3 | 1.5 | 1.9 | 51.5 | 0.4 | 72.1 |
| G148F | 3 | 2.9 | 0.6 | 2.4 | 4.6 | 15.3 | 1.6 | 2.3 | 2.6 | 0.4 | 1.7 | 2.3 | 55.6 | 4.4 | 79.4 |
| G148M | 3 | 2.9 | 0.6 | 2.4 | 4.5 | 16.0 | 1.6 | 2.2 | 2.6 | 0.4 | 1.6 | 2.2 | 55.2 | 1.8 | 78.5 |
| G148S | 3 | 2.8 | 0.5 | 2.5 | 5.2 | 19.9 | 2.8 | 2.4 | 1.9 | 0.3 | 1.5 | 1.9 | 51.0 | 0.6 | 72.2 |
| G148T | 3 | 2.6 | 0.5 | 2.2 | 4.8 | 19.6 | 2.7 | 2.0 | 1.8 | 0.3 | 1.4 | 1.9 | 52.7 | 0.2 | 73.0 |
| G148V | 3 | 2.7 | 0.5 | 2.2 | 3.9 | 14.7 | 1.5 | 1.7 | 2.4 | 0.4 | 1.5 | 2.1 | 58.8 | 3.9 | 80.5 |
| S376F | 3 | 2.6 | 0.5 | 2.4 | 4.9 | 18.8 | 2.3 | 2.3 | 2.3 | 0.4 | 1.6 | 2.2 | 51.8 | 0.4 | 74.1 |
| S376P | 3 | 2.6 | 0.5 | 2.5 | 5.1 | 19.2 | 2.5 | 2.4 | 2.1 | 0.4 | 1.6 | 2.0 | 51.7 | 1.5 | 73.5 |
| S376V | 3 | 2.5 | 0.5 | 2.3 | 4.1 | 17.6 | 1.9 | 2.0 | 2.3 | 0.4 | 1.4 | 2.1 | 55.4 | 1.8 | 76.5 |
| A377F | 3 | 2.6 | 0.5 | 2.6 | 5.0 | 19.2 | 2.4 | 2.4 | 2.2 | 0.4 | 1.6 | 2.2 | 51.2 | 0.9 | 73.5 |
| A377P | 3 | 2.9 | 0.6 | 2.6 | 4.9 | 17.2 | 1.6 | 2.5 | 2.4 | 0.4 | 1.7 | 2.1 | 52.7 | 0.8 | 76.8 |
| A377S | 3 | 2.8 | 0.6 | 2.4 | 4.3 | 16.2 | 1.4 | 2.3 | 2.6 | 0.4 | 1.6 | 2.3 | 55.5 | 1.4 | 78.6 |
| A377T | 3 | 2.7 | 0.5 | 2.3 | 4.6 | 18.9 | 2.4 | 2.2 | 2.0 | 0.3 | 1.6 | 2.1 | 52.6 | 1.8 | 74.0 |
| A377V | 3 | 2.4 | 0.4 | 2.4 | 4.4 | 19.0 | 2.5 | 1.9 | 1.9 | 0.4 | 1.3 | 1.9 | 54.0 | 0.9 | 74.1 |
| F378P | 3 | 2.6 | 0.5 | 2.7 | 5.2 | 18.8 | 2.2 | 2.6 | 2.3 | 0.4 | 1.6 | 2.2 | 50.9 | 0.3 | 74.0 |
| G385S | 3 | 2.5 | 0.5 | 2.5 | 5.0 | 18.7 | 2.2 | 2.4 | 2.3 | 0.4 | 1.6 | 2.4 | 51.8 | 0.8 | 74.4 |
| G385T | 3 | 2.6 | 0.6 | 2.4 | 4.8 | 18.8 | 2.4 | 1.7 | 2.1 | 0.2 | 1.6 | 2.3 | 52.2 | 1.9 | 74.0 |
| Y386F | 3 | 2.9 | 0.9 | 2.1 | 4.7 | 16.5 | 1.3 | 2.3 | 2.6 | 0.4 | 1.6 | 2.4 | 54.0 | 2.7 | 78.1 |
| Y386P | 3 | 2.3 | 0.6 | 2.4 | 5.0 | 17.9 | 1.8 | 2.6 | 2.7 | 0.4 | 1.7 | 2.9 | 51.3 | 1.0 | 75.8 |
| Y386S | 3 | 2.7 | 0.6 | 2.6 | 5.3 | 19.2 | 2.3 | 2.5 | 2.2 | 0.4 | 1.6 | 2.2 | 51.0 | 0.2 | 73.5 |
| Y386T | 3 | 2.6 | 0.6 | 2.6 | 5.5 | 19.5 | 2.2 | 2.7 | 2.3 | 0.4 | 1.7 | 2.4 | 49.7 | 1.6 | 73.1 |
| Y386V | 3 | 2.4 | 0.4 | 2.5 | 4.5 | 18.9 | 2.4 | 2.1 | 2.0 | 0.3 | 1.4 | 2.0 | 53.3 | 1.3 | 74.1 |
| Y387P | 3 | 2.8 | 0.6 | 2.7 | 4.7 | 17.1 | 1.6 | 2.5 | 2.5 | 0.4 | 1.7 | 2.3 | 53.4 | 0.1 | 77.0 |
| Y387S | 3 | 2.6 | 0.7 | 2.5 | 4.9 | 17.1 | 1.6 | 2.6 | 2.6 | 0.4 | 1.6 | 2.4 | 53.4 | 1.9 | 77.2 |
| Y387T | 3 | 2.7 | 0.6 | 2.4 | 4.7 | 17.0 | 1.5 | 2.4 | 2.6 | 0.4 | 1.5 | 2.3 | 54.0 | 0.4 | 77.3 |
| L388P | 3 | 2.5 | 0.6 | 2.5 | 5.0 | 18.3 | 1.9 | 2.5 | 2.5 | 0.3 | 1.7 | 2.5 | 51.7 | 0.8 | 75.2 |
| L388S | 3 | 2.8 | 0.6 | 2.5 | 4.8 | 17.9 | 1.9 | 2.4 | 2.3 | 0.4 | 1.5 | 2.2 | 53.0 | 1.5 | 75.7 |
| L388T+ | 3 | 2.5 | 0.6 | 2.2 | 3.8 | 14.8 | 1.1 | 1.9 | 2.7 | 0.4 | 1.4 | 2.4 | 58.6 | 0.4 | 80.8 |
| T389F | 3 | 3.0 | 0.6 | 2.7 | 4.5 | 15.9 | 1.3 | 2.5 | 2.7 | 0.4 | 1.6 | 2.4 | 54.9 | 0.1 | 79.0 |
| T389P | 3 | 2.8 | 0.6 | 2.7 | 5.1 | 17.9 | 2.1 | 2.6 | 2.4 | 0.1 | 1.6 | 2.2 | 52.4 | 1.6 | 75.4 |
| F390M | 3 | 2.5 | 0.7 | 2.2 | 4.6 | 16.1 | 1.5 | 2.3 | 2.8 | 0.4 | 1.6 | 2.7 | 54.3 | 2.1 | 78.5 |
| F390P | 3 | 2.7 | 0.5 | 2.5 | 5.1 | 19.8 | 2.8 | 1.6 | 1.9 | 0.2 | 1.5 | 2.0 | 51.3 | 0.6 | 72.2 |

TABLE 16-continued

Lipid Composition and Delta-9 Elongase Conversion Efficiency in Batch #5 Transformants Comprising a Vector Encoding YlLPCAT Having a Single Amino Acid Substitution

| | | % TFAs | | | | | | | | | | | | EPA | % |
|---|---|---|---|---|---|---|---|---|---|---|---|---|---|---|---|
| Mutant | # | 16:0 | 16:1 | 18:0 | 18:1 | LA | ALA | EDA | DGLA | ARA | ETrA | ETA | EPA | SD | Conv. |
| F390S+ | 3 | 2.8 | 0.5 | 2.9 | 5.9 | 12.9 | 1.1 | 2.1 | 2.4 | 0.4 | 1.5 | 1.8 | 58.0 | 0.5 | 82.6 |
| F390T+ | 3 | 2.6 | 0.5 | 2.5 | 4.4 | 14.1 | 1.1 | 1.8 | 2.4 | 0.4 | 1.4 | 2.1 | 59.2 | 0.3 | 81.6 |
| F390V | 3 | 2.4 | 0.5 | 2.2 | 4.2 | 17.2 | 1.6 | 2.0 | 2.3 | 0.4 | 1.5 | 2.3 | 55.6 | 1.5 | 77.3 |
| Mutant AVG | | 2.7 | 0.6 | 2.4 | 4.6 | 17.0 | 1.8 | 2.2 | 2.4 | 0.4 | 1.5 | 2.2 | 54.3 | 1.5 | 77.0 |
| Mutant SD | | 0.2 | 0.1 | 0.2 | 0.5 | 2.3 | 0.6 | 0.3 | 0.3 | 0.1 | 0.1 | 0.2 | 2.8 | | 3.4 |

Based on the above data, it was clear that several of the YlLPCAT single-amino acid mutants functioned with approximately equal or improved activity when compared to the parent wild type YlLPCAT enzyme (SEQ ID NO:46). This conclusion was made based on measuring LPCAT activity as a function of EPA % TFAs and/or % Conv. In fact, all of the mutant YlLPCAT transformants had an EPA % TFAs of at least 75% of the EPA % TFAs measured in the control (transformants with wild type YlLPCAT). Also, all of the mutant YlLPCAT transformants had a % Conv. that was at least 87.6% of the % Conv. measured in the control.

Fifty-six (56) YlLPCAT mutants (comprising one of the following mutations with respect to SEQ ID NO:46: L134A, L134C, L134G, C135D, C135I, M136G, M136P, M1365, M136V, K137N, K137G, K137H, K137Y, L138A, L138H, L138M, S139L, S139W, S140N, S140H, S140P, 5140W, F141A, F141M, F141W, G142H, W143L, N144A, N144K, N144F, N144T, N144V, V145A, V145G, V145E, V145M, V145F, V145W, Y146G, Y146L, Y146M, D147N, D147Q, D147H, G148A, G148N, T382I, T382P, R383M, L388G, L388Y, T389A, T389C, T389S and F390C) were found to exhibit equivalent or improved EPA % TFAs and equivalent or improved % Conv. An additional 14 YlLPCAT mutants were determined to have equivalent or improved EPA % TFAs when compared to the control (but did not have an equivalent or improved % Conv.), including mutants V133C, M136N, L138G, L1381, L138N, S139G, S139N, W143H, G148V, L388H, L388T, F390G, F390N and F390T. An additional 12 YlLPCAT mutants were determined to have equivalent or improved % Conv. when compared to the control (but did not have an equivalent or improved EPA % TFAs), including mutants C135F, M136T, 5140Y, S1401, F141V, G142I, G142V, D147E, F378Y, T382Y, R383A and F390S.

A total of 26 YlLPCAT mutants, each comprising a single mutation within either Motif I or Motif II and having equivalent or improved EPA % TFAs and/or equivalent or improved % Conv. were selected for further evaluation (below, Example 6): L134A (100.4%, 100.6%), L134G (101.3%, 100.7%), M136S (104.0%, 104.0%), M136V (102.2%, 103.3%), K137H (107.3%, 104.4%), K137N (101.8%, 102.0%), S140H (107.3%, 104.3%), S140W (103.2%, 103.8%), F141M (105.4%, 106.7%), F141W (101.2%, 101.6%), N144A (105.3%, 103.4%), N144T (101.8%, 101.6%), V145M (102.0%, 104.0%), V145W (100.4%, 100.5%), D147H (105.3%, 102.3%), D147Q (103.6%, 101.2%), G148A (101.3%, 101.8%), G148N (102.2%, 101.8%), T382I (102.9%, 102.5%), T382P (100.2%, 100.2%), R383M (103.6%, 104.0%), L388G (101.6%, 100.2%), L388Y (100.0%, 99.9%), T389A (102.2%, 101.2%), T389C (102.1%, 101.5%), T389S (101.9%, 101.7%), where the first and second percentages in each parenthetical set correspond to the percentage ratio of EPA % TFAs and % Conv., respectively, in the mutant YlLPCAT transformants relative to the EPA TFAs and % Conv. in the wild type YlLPCAT control transformants. An additional 8 YlLPCAT mutants, each comprising a single mutation within either Motif I or Motif II, also were selected for further evaluation (below, Example 6): F378Y (99.6%, 101.1%), T382Y (99.8%, 100.8%), P384A (98.7%, 99.0%), P384G (99.2%, 98.6%), L388T (100.5%, 98.3%), F390G (102.4%, 99.8%), F390S (99.4%, 100.5%) and F390T (101.6%, 99.3%), where the parenthetical sets are as above.

Example 6

Identifying Double Amino Acid Substitutions in YlLPCAT Having Improved LPCAT Activity The present example describes the synthesis of double YlLPCAT mutants, wherein the double mutants comprise both a single mutation within Motif I and a single mutation within Motif II. These double mutants were transformed into *Y. lipolytica* strain Y8406U2, followed by analysis of the lipid profiles of the transformants. As in Example 5, improved LPCAT activity was indirectly evaluated based on EPA % TFAs and % Conv.

Generation of Double YlLPCAT Mutants

Preferred single mutations within Motif I (L134A, L134G, M136S, M136V, K137H, K137N, S140H, S140W, F141M, F141W, N144A, N144T, V145W, V145M, D147H, D147Q, G148A and G148N) were combined with preferred single mutations within Motif II (F378Y, T382I, T382P, T382Y, R383M, P384A, P384G, L388G, L388T, L388Y, T389A, T389C, T389S, F390G, F390S, F390T) to generate various combinations of double-mutant YlLPCAT sequences. Thus, for example, a YlLPCAT mutant comprising an S140W mutation within Motif I and a T382I mutation within Motif II is referred to herein as a YlLPCAT mutant S140W_T3821. These double mutants were individually synthesized and cloned into NcoI-NotI cut pY306-N vector by GenScript Corporation (Piscataway, N.J.); SEQ ID NO:42 represents the mutant YlLPCAT proteins encoded by the cloned sequences.

Transformation of *Y. lipolytica* Strain Y8406U2 and Analysis of Lipid Profiles within pY306-N Transformants The plasmids were transformed into *Y. lipolytica* strain Y8406U2 and transformants were subsequently grown and subjected to lipid analysis, as described in Example 5. Tables 17 (Batch 6), 18 (Batch 7), 19 (Batch 8) and 20 (Batch 10) show the fatty acid profiles and delta-9 elongase conversion efficiencies of individual transformants of Y8406U2. These measurements were also made for control transformants comprising pY306-N (wild type YlLPCAT protein expression ["WT"]). The Tables are formatted as described in Example 5.

Comparison of each mutant's performance relative to the wild type YILPCAT control should only be made within the particular batch in which each mutant was analyzed (i.e., comparisons should not be made between Batch #6 and Batch #7, for example). Mutants shown in bold-face font and followed by a "+" were selected for further studies including flask assays, as discussed below.

TABLE 17

Lipid Composition and Delta-9 Elongase Conversion Efficiency in Batch #6 Transformants Comprising a Vector Encoding YILPCAT Having Double Amino Acid Substitutions

| | | % TFAs | | | | | | | | | | | | EPA | % |
|---|---|---|---|---|---|---|---|---|---|---|---|---|---|---|---|
| Mutant | # | 16:0 | 16:1 | 18:0 | 18:1 | LA | ALA | EDA | DGLA | ARA | ETrA | ETA | EPA | SD | Conv. |
| WT | 6 | 2.7 | 0.7 | 2.3 | 5.6 | 14.4 | 0.9 | 3.0 | 3.1 | 0.7 | 1.5 | 2.7 | 52.9 | 0.2 | 80.6 |
| S140W_T382I | 3 | 2.9 | 0.8 | 2.2 | 5.8 | 13.0 | 0.8 | 2.9 | 3.2 | 0.7 | 1.5 | 2.7 | 53.7 | 1.2 | 82.4 |
| S140W_T382P+ | 3 | 2.9 | 0.8 | 2.2 | 5.7 | 12.6 | 0.8 | 2.9 | 3.3 | 0.7 | 1.5 | 2.8 | 54.3 | 0.6 | 83.0 |
| S140W_T382Y | 3 | 2.7 | 0.7 | 2.2 | 5.6 | 13.6 | 0.9 | 2.8 | 3.2 | 0.7 | 1.5 | 2.8 | 53.8 | 0.6 | 81.8 |
| S140W_R383M | 3 | 2.9 | 0.7 | 2.3 | 5.8 | 12.6 | 0.8 | 2.9 | 3.3 | 0.8 | 1.5 | 2.6 | 54.8 | 0.6 | 83.1 |
| S140W_P384A | 3 | 2.8 | 0.7 | 2.3 | 5.7 | 13.9 | 0.9 | 2.9 | 3.1 | 0.7 | 1.5 | 2.7 | 53.1 | 1.3 | 81.2 |
| S140W_L388Y | 3 | 2.5 | 0.9 | 2.1 | 6.5 | 12.7 | 0.8 | 3.0 | 3.2 | 0.6 | 1.6 | 3.2 | 52.9 | 1.9 | 82.7 |
| S140W_T389A+ | 3 | 2.4 | 0.7 | 2.2 | 6.5 | 11.6 | 0.7 | 2.5 | 3.1 | 0.7 | 1.5 | 2.6 | 55.8 | 0.4 | 84.3 |
| S140W_T389C | 3 | 2.7 | 0.7 | 2.3 | 6.0 | 12.6 | 0.8 | 2.8 | 3.4 | 0.8 | 1.5 | 2.7 | 54.1 | 0.4 | 83.0 |
| S140W_T389S | 3 | 2.6 | 0.6 | 2.5 | 6.3 | 14.6 | 1.3 | 2.7 | 2.7 | 0.7 | 1.5 | 2.2 | 53.3 | 4.1 | 79.9 |
| M136V_F378Y+ | 3 | 2.5 | 0.7 | 2.2 | 4.0 | 14.7 | 1.3 | 2.8 | 2.9 | 0.7 | 1.5 | 2.6 | 52.8 | 4.3 | 79.8 |
| M136V_T382I | 3 | 2.5 | 0.7 | 2.3 | 6.1 | 14.5 | 1.2 | 2.9 | 2.9 | 0.7 | 1.6 | 2.8 | 52.1 | 4.5 | 80.0 |
| M136V_T382P | 3 | 2.7 | 0.8 | 2.2 | 5.6 | 12.8 | 0.8 | 2.9 | 3.3 | 0.8 | 1.6 | 2.8 | 54.3 | 0.4 | 82.8 |
| M136V_T382Y | 3 | 2.6 | 0.8 | 2.2 | 5.5 | 13.1 | 0.8 | 2.8 | 3.3 | 0.7 | 1.5 | 3.0 | 54.3 | 0.3 | 82.5 |
| M136V_R383M | 3 | 2.6 | 0.8 | 2.1 | 5.9 | 13.8 | 1.0 | 2.8 | 3.2 | 0.7 | 1.6 | 3.1 | 52.3 | 2.3 | 81.2 |
| M136V_P384A | 3 | 2.8 | 0.8 | 2.2 | 5.7 | 13.3 | 0.8 | 3.1 | 3.3 | 0.7 | 1.4 | 2.8 | 53.2 | 1.1 | 82.0 |
| M136V_L388Y | 3 | 2.7 | 0.8 | 2.3 | 5.5 | 14.0 | 0.9 | 3.0 | 3.3 | 0.7 | 1.6 | 2.9 | 53.0 | 1.5 | 81.3 |
| M136V_T389A+ | 3 | 2.7 | 0.7 | 2.4 | 6.1 | 11.8 | 0.8 | 2.6 | 3.0 | 0.7 | 1.4 | 2.3 | 56.2 | 0.4 | 84.0 |
| M136V_T389S+ | 3 | 2.7 | 0.7 | 2.4 | 6.1 | 11.7 | 0.8 | 2.6 | 3.0 | 0.7 | 1.4 | 2.3 | 56.5 | 0.8 | 84.2 |
| K137N_F378Y | 3 | 2.8 | 0.8 | 2.2 | 5.5 | 13.6 | 0.9 | 2.9 | 3.3 | 0.7 | 1.5 | 2.8 | 53.4 | 1.1 | 81.7 |
| K137N_T382I | 3 | 2.4 | 0.8 | 2.2 | 6.0 | 15.0 | 1.3 | 2.8 | 3.0 | 0.6 | 1.6 | 2.9 | 51.6 | 4.7 | 79.3 |
| K137N_T382P | 3 | 2.4 | 0.9 | 2.0 | 3.6 | 13.1 | 0.8 | 2.8 | 3.4 | 0.7 | 1.5 | 3.4 | 53.5 | 1.7 | 82.5 |
| K137N_T382Y | 3 | 2.3 | 0.7 | 2.2 | 2.2 | 15.6 | 1.3 | 2.7 | 2.9 | 0.6 | 1.5 | 2.8 | 51.5 | 2.6 | 78.6 |
| K137N_L388Y | 3 | 2.2 | 0.8 | 2.1 | 3.7 | 14.9 | 1.1 | 2.9 | 3.0 | 0.6 | 1.6 | 3.1 | 51.4 | 3.0 | 79.6 |
| K137N_T389C+ | 3 | 2.6 | 0.8 | 2.1 | 5.4 | 12.5 | 0.8 | 2.7 | 3.5 | 0.8 | 1.5 | 2.8 | 55.1 | 0.9 | 83.4 |
| K137N_T389S+ | 3 | 2.5 | 0.7 | 2.3 | 6.0 | 11.8 | 0.7 | 2.6 | 3.2 | 0.7 | 1.5 | 2.5 | 56.0 | 0.2 | 84.2 |
| N144T_F378Y | 3 | 2.8 | 0.8 | 2.3 | 5.5 | 12.8 | 0.8 | 2.9 | 3.3 | 0.8 | 1.5 | 2.6 | 54.4 | 0.3 | 82.8 |
| N144T_T382I | 3 | 2.4 | 0.8 | 2.1 | 4.1 | 13.7 | 1.0 | 2.9 | 3.0 | 0.7 | 1.7 | 3.2 | 52.4 | 4.3 | 81.3 |
| N144T_T382Y | 3 | 2.5 | 0.8 | 2.3 | 3.7 | 13.8 | 0.9 | 2.9 | 3.2 | 0.7 | 1.5 | 2.8 | 53.7 | 0.2 | 81.6 |
| N144T_R383M | 3 | 2.5 | 0.8 | 2.1 | 5.2 | 12.7 | 0.8 | 2.7 | 3.3 | 0.7 | 1.5 | 2.8 | 54.2 | 0.1 | 82.9 |
| N144T_T389A | 2 | 2.4 | 0.7 | 2.4 | 5.8 | 12.5 | 0.8 | 2.7 | 3.3 | 0.7 | 1.6 | 2.7 | 54.5 | | 83.2 |
| N144T_T389C | 2 | 2.2 | 0.8 | 1.7 | 4.8 | 11.9 | 0.8 | 2.3 | 3.1 | 0.7 | 1.6 | 2.8 | 56.1 | | 84.0 |
| N144T_T389S | 3 | 2.5 | 0.6 | 2.3 | 5.9 | 12.0 | 0.7 | 2.7 | 3.2 | 0.7 | 1.7 | 2.5 | 54.7 | 0.7 | 83.7 |
| V145W_F378Y | 3 | 2.5 | 0.8 | 2.2 | 5.6 | 13.5 | 0.9 | 2.9 | 3.3 | 0.7 | 1.5 | 2.9 | 52.6 | 1.4 | 81.7 |
| V145W_T382P | 3 | 2.5 | 0.8 | 2.2 | 2.2 | 14.4 | 0.9 | 3.2 | 3.2 | 0.7 | 1.6 | 2.8 | 52.5 | 1.0 | 80.6 |
| V145W_L388Y | 2 | 2.7 | 0.8 | 2.3 | 3.3 | 16.1 | 1.3 | 3.0 | 2.7 | 0.6 | 1.6 | 2.6 | 49.6 | | 77.5 |
| V145W_T389A | 3 | 2.5 | 0.7 | 2.4 | 6.1 | 13.5 | 1.0 | 2.9 | 3.1 | 0.7 | 1.5 | 2.7 | 53.4 | 1.3 | 81.6 |
| V145W_T389C | 3 | 2.6 | 0.7 | 2.4 | 3.9 | 15.3 | 1.3 | 2.9 | 2.9 | 0.7 | 1.5 | 2.6 | 51.7 | 3.5 | 79.0 |
| V145W_T389S | 3 | 2.7 | 0.6 | 2.5 | 4.2 | 14.1 | 1.0 | 2.8 | 3.1 | 0.7 | 1.5 | 2.5 | 53.2 | 0.7 | 80.9 |
| Mutant AVG | | 2.6 | 0.7 | 2.2 | 5.2 | 13.4 | 0.9 | 2.8 | 3.2 | 0.7 | 1.5 | 2.8 | 53.6 | 1.6 | 81.8 |
| Mutant SD | | 0.2 | 0.1 | 0.1 | 1.1 | 1.1 | 0.2 | 0.2 | 0.2 | 0.0 | 0.1 | 0.2 | 1.5 | 1.4 | 1.7 |

TABLE 18

Lipid Composition and Delta-9 Elongase Conversion Efficiency in Batch #7 Transformants Comprising a Vector Encoding YILPCAT Having Double Amino Acid Substitutions

| | | % TFAs | | | | | | | | | | | | EPA | % |
|---|---|---|---|---|---|---|---|---|---|---|---|---|---|---|---|
| Mutant | # | 16:0 | 16:1 | 18:0 | 18:1 | LA | ALA | EDA | DGLA | ARA | ETrA | ETA | EPA | SD | Conv. |
| WT | 12 | 3.2 | 0.7 | 2.6 | 4.2 | 14.2 | 0.9 | 2.3 | 3.0 | 0.7 | 1.6 | 2.7 | 54.1 | 0.7 | 81.0 |
| M136S_F378Y | 3 | 3.4 | 0.7 | 2.6 | 4.7 | 12.0 | 0.8 | 2.1 | 3.0 | 0.7 | 1.6 | 2.5 | 56.4 | 1.3 | 84.0 |
| M136S_T382I | 3 | 3.4 | 0.8 | 2.6 | 5.2 | 11.2 | 0.8 | 2.2 | 2.9 | 0.6 | 1.6 | 2.6 | 56.3 | 1.2 | 85.0 |
| M136S_T382P | 3 | 2.9 | 0.8 | 2.3 | 4.5 | 11.5 | 0.7 | 2.1 | 3.3 | 0.6 | 1.5 | 3.1 | 56.2 | 1.6 | 85.0 |
| M136S_T382Y | 3 | 3.3 | 0.7 | 2.5 | 4.3 | 12.1 | 0.8 | 2.1 | 3.2 | 0.6 | 1.6 | 2.8 | 55.8 | 0.5 | 84.0 |
| M136S_R383M | 3 | 3.4 | 0.7 | 2.6 | 4.8 | 11.9 | 0.8 | 2.2 | 3.1 | 0.6 | 1.6 | 2.5 | 56.1 | 0.2 | 84.0 |
| M136S_P384A | 3 | 3.5 | 0.7 | 2.6 | 4.6 | 12.2 | 0.8 | 2.2 | 3.1 | 0.7 | 1.6 | 2.6 | 56.1 | 0.8 | 84.0 |
| M136S_L388Y | 3 | 3.3 | 0.7 | 2.5 | 4.3 | 12.2 | 0.8 | 2.3 | 3.2 | 0.6 | 1.6 | 2.6 | 56.1 | 1.5 | 84.0 |
| M136S_T389A+ | 3 | 3.2 | 0.6 | 2.6 | 4.6 | 11.0 | 0.8 | 2.0 | 2.7 | 0.6 | 1.6 | 2.1 | 57.9 | 0.6 | 85.0 |
| M136S_T389C+ | 3 | 3.3 | 0.6 | 2.7 | 4.8 | 11.2 | 0.8 | 2.1 | 3.0 | 0.7 | 1.6 | 2.3 | 57.3 | 0.2 | 85.0 |

TABLE 18-continued

Lipid Composition and Delta-9 Elongase Conversion Efficiency in Batch #7 Transformants Comprising a Vector Encoding YlLPCAT Having Double Amino Acid Substitutions

| | | % TFAs | | | | | | | | | | | | EPA | % |
|---|---|---|---|---|---|---|---|---|---|---|---|---|---|---|---|
| Mutant | # | 16:0 | 16:1 | 18:0 | 18:1 | LA | ALA | EDA | DGLA | ARA | ETrA | ETA | EPA | SD | Conv. |
| M136S_T389S+ | 3 | 2.8 | 0.6 | 2.7 | 5.3 | 11.2 | 0.7 | 2.0 | 2.9 | 0.6 | 1.6 | 2.2 | 57.7 | 0.8 | 85.0 |
| F141M_F378Y | 3 | 3.0 | 0.7 | 2.5 | 3.9 | 13.5 | 0.9 | 2.4 | 3.1 | 0.6 | 1.6 | 2.6 | 55.3 | 0.4 | 82.0 |
| F141M_T382I | 3 | 3.1 | 0.7 | 2.7 | 4.4 | 16.2 | 2.2 | 2.2 | 2.3 | 0.5 | 1.7 | 2.8 | 51.0 | 4.6 | 77.0 |
| F141M_T382P | 3 | 2.9 | 0.7 | 2.6 | 4.2 | 14.5 | 1.1 | 2.3 | 3.0 | 0.6 | 1.6 | 2.6 | 54.0 | 0.7 | 81.0 |
| F141M_T382Y | 3 | 3.0 | 0.7 | 2.5 | 4.1 | 14.1 | 0.9 | 2.3 | 3.0 | 0.7 | 1.6 | 2.7 | 54.2 | 0.3 | 81.0 |
| F141M_R383M | 3 | 3.1 | 0.7 | 2.5 | 3.9 | 13.4 | 0.9 | 2.3 | 3.1 | 0.7 | 1.5 | 2.6 | 55.3 | 0.1 | 82.0 |
| F141M_P384A | 3 | 3.1 | 0.7 | 2.5 | 3.8 | 14.3 | 0.9 | 2.3 | 3.2 | 0.6 | 1.6 | 2.8 | 54.5 | 1.0 | 81.0 |
| F141M_L388Y | 3 | 3.0 | 0.6 | 2.5 | 4.2 | 17.3 | 1.6 | 2.4 | 2.5 | 0.6 | 1.6 | 2.5 | 50.8 | 3.7 | 76.0 |
| F141M_T389A | 3 | 3.2 | 0.6 | 2.8 | 4.3 | 14.5 | 1.3 | 2.3 | 2.7 | 0.6 | 1.6 | 2.2 | 54.1 | 2.1 | 80.0 |
| F141M_T389C | 3 | 2.9 | 0.7 | 2.5 | 4.0 | 13.3 | 0.9 | 2.3 | 3.1 | 0.7 | 1.5 | 2.7 | 55.3 | 0.1 | 82.0 |
| F141M_T389S | 3 | 2.8 | 0.6 | 2.7 | 4.8 | 15.8 | 1.4 | 2.5 | 2.8 | 0.6 | 1.6 | 2.4 | 52.1 | 4.4 | 78.0 |
| F141W_F378Y | 3 | 3.2 | 0.7 | 2.6 | 4.7 | 12.8 | 0.9 | 2.3 | 3.1 | 0.6 | 1.6 | 2.5 | 55.5 | 1.2 | 83.0 |
| F141W_T382I+ | 3 | 3.0 | 0.7 | 2.5 | 4.6 | 11.7 | 0.8 | 2.1 | 3.2 | 0.7 | 1.5 | 2.5 | 57.1 | 0.5 | 84.0 |
| F141W_T382P | 3 | 3.3 | 0.8 | 2.6 | 4.2 | 13.5 | 0.9 | 2.3 | 3.2 | 0.7 | 1.5 | 2.7 | 54.8 | 1.6 | 82.0 |
| F141W_T382Y | 3 | 2.9 | 0.7 | 2.5 | 4.1 | 12.7 | 0.8 | 2.3 | 3.3 | 0.6 | 1.5 | 2.7 | 56.0 | 0.5 | 83.0 |
| F141W_R383M | 3 | 3.5 | 0.7 | 2.5 | 4.0 | 12.3 | 0.9 | 2.3 | 3.1 | 0.6 | 1.6 | 2.5 | 56.1 | 0.2 | 83.0 |
| F141W_P384A | 3 | 3.5 | 0.7 | 2.6 | 4.0 | 13.9 | 1.0 | 2.4 | 3.0 | 0.6 | 1.6 | 2.6 | 54.3 | 0.4 | 81.0 |
| F141W_L388Y | 3 | 3.2 | 0.7 | 2.7 | 4.3 | 14.2 | 1.0 | 2.4 | 3.0 | 0.6 | 1.5 | 2.6 | 53.9 | 0.8 | 81.0 |
| F141W_T389A | 3 | 3.3 | 0.6 | 2.8 | 4.6 | 12.3 | 0.9 | 2.1 | 2.9 | 0.6 | 1.6 | 2.2 | 56.3 | 0.4 | 83.0 |
| F141W_T389C | 3 | 3.3 | 0.7 | 2.8 | 4.4 | 12.5 | 1.0 | 2.4 | 3.0 | 0.6 | 1.4 | 2.4 | 55.7 | 0.8 | 83.0 |
| F141W_T389S | 3 | 3.1 | 0.6 | 2.7 | 4.4 | 12.5 | 0.9 | 2.2 | 3.0 | 0.6 | 1.5 | 2.4 | 56.0 | 1.2 | 83.0 |
| V145M_F378Y | 3 | 3.3 | 0.7 | 2.6 | 4.3 | 13.7 | 1.0 | 2.4 | 3.0 | 0.6 | 1.6 | 2.6 | 54.0 | 0.4 | 81.0 |
| V145M_T382I | 3 | 3.4 | 0.8 | 2.5 | 4.1 | 13.0 | 0.9 | 2.3 | 3.2 | 0.7 | 1.5 | 2.7 | 54.9 | 1.6 | 82.0 |
| V145M_T382P | 3 | 3.1 | 0.7 | 2.7 | 4.2 | 14.7 | 1.0 | 2.4 | 3.0 | 0.7 | 1.5 | 2.6 | 53.5 | 1.0 | 80.0 |
| V145M_T382Y | 3 | 3.6 | 0.7 | 2.7 | 4.3 | 14.4 | 1.0 | 2.3 | 3.0 | 0.6 | 1.6 | 2.6 | 53.6 | 2.7 | 81.0 |
| V145M_R383M | 3 | 3.4 | 0.7 | 2.5 | 4.0 | 13.3 | 0.9 | 2.3 | 2.9 | 0.6 | 1.6 | 2.4 | 54.9 | 0.6 | 82.0 |
| V145M_P384A | 3 | 3.2 | 0.8 | 2.4 | 3.9 | 15.4 | 1.0 | 2.4 | 2.8 | 0.6 | 1.7 | 2.8 | 51.4 | 3.6 | 79.0 |
| V145M_L388Y | 3 | 3.3 | 0.7 | 2.7 | 4.3 | 15.4 | 1.1 | 2.4 | 2.7 | 0.6 | 1.5 | 2.5 | 52.2 | 0.6 | 79.0 |
| V145M_T389A | 3 | 3.6 | 0.6 | 2.8 | 4.5 | 13.6 | 1.0 | 2.3 | 2.7 | 0.6 | 1.6 | 2.3 | 54.1 | 0.0 | 81.0 |
| V145M_T389C | 3 | 3.0 | 0.7 | 2.6 | 4.1 | 13.3 | 0.9 | 2.4 | 3.1 | 0.6 | 1.5 | 2.5 | 55.4 | 0.2 | 82.0 |
| V145M_T389S | 3 | 4.1 | 1.0 | 2.2 | 3.9 | 14.5 | 1.3 | 2.1 | 2.4 | 0.6 | 1.7 | 2.1 | 51.5 | 5.3 | 79.0 |
| G148A_F378Y | 3 | 3.3 | 0.7 | 2.6 | 4.3 | 12.5 | 0.9 | 2.3 | 3.1 | 0.6 | 1.5 | 2.5 | 55.9 | 0.3 | 83.0 |
| G148A_T382I | 3 | 3.3 | 0.7 | 2.6 | 4.7 | 11.8 | 0.8 | 2.3 | 3.1 | 0.6 | 1.6 | 2.5 | 56.4 | 0.5 | 84.0 |
| G148A_T382P | 3 | 2.9 | 0.6 | 2.6 | 4.4 | 15.1 | 1.2 | 2.4 | 2.9 | 0.6 | 1.6 | 2.7 | 53.0 | 3.7 | 79.0 |
| G148A_T382Y | 3 | 2.9 | 0.7 | 2.5 | 3.9 | 12.9 | 0.8 | 2.0 | 3.0 | 0.7 | 1.5 | 2.6 | 56.1 | 1.2 | 83.0 |
| G148A_R383M | 3 | 3.4 | 0.7 | 2.6 | 4.2 | 12.5 | 0.8 | 2.3 | 3.1 | 0.6 | 1.6 | 2.6 | 55.5 | 0.9 | 83.0 |
| G148A_P384A | 3 | 2.9 | 0.8 | 2.4 | 4.3 | 13.7 | 0.8 | 2.3 | 3.2 | 0.6 | 1.7 | 3.1 | 53.7 | 0.5 | 82.0 |
| G148A_L388Y | 3 | 2.7 | 0.8 | 2.3 | 4.0 | 13.8 | 0.9 | 2.4 | 3.2 | 0.6 | 1.6 | 3.0 | 54.2 | 0.5 | 82.0 |
| G148A_T389A | 3 | 3.0 | 0.6 | 2.7 | 4.8 | 12.5 | 0.8 | 2.2 | 3.0 | 0.6 | 1.5 | 2.4 | 56.1 | 0.2 | 83.0 |
| G148A_T389C | 3 | 3.5 | 0.7 | 2.6 | 4.2 | 12.6 | 0.9 | 2.3 | 3.0 | 0.6 | 1.5 | 2.4 | 55.8 | 0.1 | 83.0 |
| G148A_T389S | 3 | 3.3 | 0.6 | 2.8 | 4.7 | 14.8 | 1.3 | 2.4 | 2.7 | 0.6 | 1.6 | 2.3 | 52.9 | 5.0 | 80.0 |
| Mutant AVG | | 3.1 | 0.7 | 2.6 | 4.4 | 13.2 | 1.0 | 2.3 | 3.0 | 0.6 | 1.6 | 2.6 | 54.9 | 1.4 | 80.0 |
| Mutant SD | | 0.3 | 0.1 | 0.1 | 0.3 | 1.3 | 0.2 | 0.1 | 0.2 | 0.0 | 0.1 | 0.2 | 1.6 | | 2.0 |

TABLE 19

Lipid Composition and Delta-9 Elongase Conversion Efficiency in Batch #8 Transformants Comprising a Vector Encoding YlLPCAT Having Double Amino Acid Substitutions

| | | % TFAs | | | | | | | | | | | | EPA | % |
|---|---|---|---|---|---|---|---|---|---|---|---|---|---|---|---|
| Mutant | # | 16:0 | 16:1 | 18:0 | 18:1 | LA | ALA | EDA | DGLA | ARA | ETrA | ETA | EPA | SD | Conv. |
| WT | 3 | 2.6 | 0.7 | 2.6 | 4.3 | 14.4 | 1.0 | 2.6 | 3.2 | 0.6 | 1.7 | 2.8 | 53.8 | 0.8 | 81.0 |
| M136V_T389C+ | 3 | 2.8 | 0.6 | 2.6 | 4.8 | 12.1 | 0.9 | 2.3 | 3.3 | 0.6 | 1.5 | 2.6 | 56.6 | 0.5 | 84.0 |
| K137N_R383M | 3 | 2.8 | 0.7 | 2.5 | 4.4 | 12.9 | 0.9 | 2.4 | 3.3 | 0.6 | 1.5 | 2.8 | 55.8 | 0.4 | 83.0 |
| K137N_P384A | 3 | 2.6 | 0.6 | 2.7 | 4.9 | 17.7 | 1.9 | 2.8 | 2.6 | 0.6 | 1.6 | 2.5 | 49.8 | 4.2 | 75.0 |
| K137N_T389A+ | 3 | 2.6 | 0.5 | 2.7 | 4.9 | 12.4 | 0.9 | 2.2 | 3.1 | 0.7 | 1.6 | 2.3 | 56.8 | 0.6 | 83.0 |
| N144T_T382P | 3 | 2.7 | 0.6 | 2.6 | 4.3 | 14.1 | 1.0 | 2.6 | 3.3 | 0.7 | 1.6 | 2.7 | 54.4 | 0.6 | 81.0 |
| N144T_P384A | 3 | 2.6 | 0.6 | 2.5 | 4.2 | 14.4 | 1.0 | 2.5 | 3.2 | 0.7 | 1.6 | 2.7 | 54.3 | 0.6 | 81.0 |
| N144T_L388Y | 3 | 2.5 | 0.7 | 2.4 | 3.9 | 14.0 | 0.9 | 2.4 | 3.4 | 0.7 | 1.5 | 3.0 | 54.7 | 0.7 | 82.0 |
| V145W_T382I | 3 | 2.9 | 0.6 | 2.6 | 4.7 | 13.0 | 0.9 | 2.5 | 3.3 | 0.7 | 1.5 | 2.6 | 55.5 | 0.3 | 83.0 |
| V145W_T382Y | 3 | 2.6 | 0.6 | 2.6 | 4.4 | 16.5 | 1.6 | 2.5 | 2.8 | 0.6 | 1.5 | 2.6 | 52.1 | 3.3 | 77.0 |
| V145W_R383M | 3 | 2.8 | 0.6 | 2.6 | 4.7 | 16.1 | 1.5 | 2.6 | 2.8 | 0.6 | 1.6 | 2.4 | 52.3 | 3.9 | 78.0 |
| V145W_P384A | 3 | 2.6 | 0.6 | 2.6 | 4.2 | 15.6 | 1.1 | 2.7 | 3.1 | 0.7 | 1.6 | 2.7 | 52.7 | 0.3 | 79.0 |
| Mutant AVG | | 2.7 | 0.6 | 2.6 | 4.5 | 14.4 | 1.1 | 2.5 | 3.1 | 0.7 | 1.6 | 2.6 | 54.1 | 1.3 | 79.0 |
| Mutant SD | | 0.1 | 0.1 | 0.1 | 0.3 | 1.7 | 0.3 | 0.2 | 0.3 | 0.1 | 0.1 | 0.2 | 2.1 | | 2.8 |

TABLE 20

Lipid Composition and Delta-9 Elongase Conversion Efficiency in Batch #10 Transformants Comprising a Vector Encoding YlLPCAT Having Double Amino Acid Substitutions

| Mutant | # | % TFAs | | | | | | | | | | | | EPA | % |
|---|---|---|---|---|---|---|---|---|---|---|---|---|---|---|---|
| | | 16:0 | 16:1 | 18:0 | 18:1 | LA | ALA | EDA | DGLA | ARA | ETrA | ETA | EPA | SD | Conv. |
| WT | | 2.9 | 0.7 | 2.7 | 4.2 | 14.6 | 1.1 | 2.6 | 3.0 | 0.6 | 1.5 | 2.6 | 53.1 | 1.7 | 80.1 |
| L134A_T382I+ | | 3.0 | 0.7 | 2.6 | 4.6 | 12.5 | 0.9 | 2.2 | 3.1 | 0.6 | 1.5 | 2.5 | 55.9 | 0.6 | 83.0 |
| L134A_P384G | | 2.7 | 0.6 | 2.8 | 4.2 | 15.9 | 1.2 | 2.4 | 2.8 | 0.6 | 1.5 | 2.4 | 52.7 | 0.2 | 78.5 |
| L134A_L388G | | 2.8 | 0.6 | 2.7 | 4.4 | 14.6 | 1.1 | 2.4 | 2.9 | 0.6 | 1.5 | 2.5 | 53.9 | 0.3 | 80.3 |
| L134A_L388T | | 2.7 | 0.6 | 2.8 | 4.5 | 17.3 | 1.7 | 2.4 | 2.5 | 0.5 | 1.6 | 2.3 | 51.0 | 2.7 | 76.0 |
| L134A_F390G | | 2.7 | 0.4 | 3.4 | 5.4 | 14.7 | 1.2 | 2.1 | 2.4 | 0.5 | 1.5 | 2.0 | 53.6 | 0.3 | 79.6 |
| L134A_F390S | | 2.7 | 0.5 | 3.2 | 5.6 | 15.6 | 1.7 | 2.2 | 2.3 | 0.5 | 1.5 | 1.9 | 52.5 | 4.4 | 77.9 |
| L134A_F390T | | 2.7 | 0.5 | 3.0 | 4.7 | 14.4 | 1.1 | 2.3 | 2.8 | 0.5 | 1.5 | 2.4 | 54.2 | 0.5 | 80.5 |
| L134G_T382I | | 2.6 | 0.6 | 2.8 | 4.7 | 18.2 | 2.0 | 2.5 | 2.5 | 0.5 | 1.5 | 2.4 | 49.6 | 3.1 | 74.5 |
| L134G_P384G | | 2.6 | 0.6 | 2.7 | 4.2 | 16.3 | 1.3 | 2.4 | 2.7 | 0.6 | 1.5 | 2.5 | 52.4 | 0.7 | 78.0 |
| L134G_L388G | | 2.7 | 0.6 | 2.8 | 4.1 | 15.0 | 1.1 | 2.5 | 2.9 | 0.6 | 1.6 | 2.6 | 53.4 | 0.2 | 79.8 |
| L134G_L388T | | 2.7 | 0.7 | 2.6 | 4.1 | 15.5 | 1.2 | 2.5 | 2.8 | 0.6 | 1.6 | 2.6 | 52.4 | 0.5 | 78.9 |
| L134G_F390G | | 2.7 | 0.4 | 3.2 | 5.3 | 15.1 | 1.3 | 2.1 | 2.4 | 0.5 | 1.5 | 2.1 | 53.3 | 0.0 | 79.1 |
| L134G_F390S | | 2.8 | 0.5 | 3.1 | 5.4 | 15.7 | 1.7 | 2.4 | 2.3 | 0.5 | 1.6 | 2.2 | 52.0 | 3.6 | 77.8 |
| L134G_F390T | | 2.6 | 0.5 | 2.8 | 4.5 | 14.7 | 1.1 | 2.4 | 2.8 | 0.6 | 1.6 | 2.6 | 53.5 | 1.0 | 80.0 |
| K137N_P384G | | 2.9 | 0.6 | 2.7 | 4.1 | 14.4 | 1.0 | 2.4 | 3.0 | 0.6 | 1.5 | 2.6 | 54.2 | 0.3 | 80.7 |
| K137N_L388G | | 3.1 | 0.7 | 2.6 | 4.4 | 13.5 | 1.0 | 2.6 | 3.2 | 0.6 | 1.5 | 2.6 | 54.5 | 1.0 | 81.7 |
| K137N_L388T | | 3.1 | 0.6 | 2.7 | 4.2 | 13.9 | 1.0 | 2.3 | 3.0 | 0.6 | 1.5 | 2.5 | 54.8 | 0.4 | 81.3 |
| K137N_F390G+ | | 2.4 | 0.5 | 3.0 | 5.5 | 13.1 | 0.9 | 1.9 | 2.7 | 0.5 | 1.5 | 2.4 | 55.2 | 0.9 | 82.1 |
| K137N_F390S | | 2.8 | 0.5 | 3.2 | 5.5 | 13.9 | 1.1 | 2.1 | 2.6 | 0.5 | 1.5 | 2.1 | 54.5 | 1.2 | 80.9 |
| K137N_F390T | | 2.8 | 0.6 | 2.9 | 4.6 | 14.1 | 1.0 | 2.2 | 2.7 | 0.6 | 1.6 | 2.3 | 54.2 | 0.4 | 80.9 |
| K137H_T382I | | 3.1 | 0.6 | 2.8 | 4.7 | 14.8 | 1.5 | 2.2 | 2.7 | 0.5 | 1.5 | 2.3 | 53.7 | 4.7 | 79.4 |
| K137H_P384G | | 2.7 | 0.8 | 2.4 | 4.1 | 13.3 | 0.9 | 2.3 | 3.3 | 0.6 | 1.6 | 3.0 | 54.7 | 0.3 | 82.2 |
| K137H_L388G+ | | 3.2 | 0.7 | 2.5 | 4.3 | 12.5 | 0.9 | 2.2 | 3.1 | 0.6 | 1.5 | 2.5 | 56.2 | 0.6 | 83.1 |
| K137H_L388T+ | | 3.1 | 0.7 | 2.7 | 4.3 | 13.0 | 0.9 | 2.2 | 3.0 | 0.6 | 1.5 | 2.5 | 55.6 | 0.1 | 82.5 |
| K137H_F390G | | 2.8 | 0.5 | 3.3 | 5.7 | 14.6 | 1.2 | 2.0 | 2.5 | 0.5 | 1.5 | 2.1 | 53.6 | 1.2 | 79.7 |
| K137H_F390S | | 2.6 | 0.6 | 3.1 | 6.0 | 12.9 | 1.0 | 2.1 | 2.6 | 0.5 | 1.6 | 2.4 | 54.5 | 0.8 | 82.1 |
| K137H_F390T | | 2.8 | 0.5 | 2.9 | 4.9 | 14.0 | 1.0 | 2.2 | 2.8 | 0.5 | 1.5 | 2.5 | 54.4 | 0.6 | 81.0 |
| S140H_T382I+ | | 3.3 | 0.7 | 2.7 | 4.9 | 11.9 | 0.9 | 2.4 | 3.0 | 0.6 | 1.6 | 2.6 | 55.4 | 1.9 | 83.6 |
| S140H_P384G | | 3.0 | 0.7 | 2.7 | 3.8 | 14.1 | 1.0 | 2.2 | 3.0 | 0.6 | 1.6 | 2.7 | 54.5 | 0.7 | 81.1 |
| S140H_L388G+ | | 3.0 | 0.7 | 2.5 | 4.2 | 12.7 | 0.8 | 2.3 | 3.2 | 0.6 | 1.5 | 2.7 | 55.7 | 0.1 | 83.0 |
| S140H_L388T | | 3.2 | 0.7 | 2.5 | 4.1 | 13.2 | 0.9 | 2.4 | 3.0 | 0.6 | 1.7 | 2.6 | 54.7 | 0.4 | 82.1 |
| S140H_F390G | | 2.6 | 0.5 | 2.8 | 5.5 | 13.9 | 1.0 | 2.0 | 2.7 | 0.5 | 1.6 | 2.6 | 54.1 | 1.2 | 81.0 |
| S140H_F390S | | 2.8 | 0.5 | 3.1 | 5.2 | 14.1 | 1.1 | 2.2 | 2.6 | 0.5 | 1.5 | 2.2 | 54.1 | 0.4 | 80.6 |
| S140H_F390T | | 3.0 | 0.6 | 2.9 | 4.7 | 16.0 | 1.3 | 2.5 | 2.7 | 0.5 | 1.6 | 2.5 | 51.8 | 1.4 | 78.1 |
| N144A_T382I | | 3.1 | 0.6 | 2.7 | 4.8 | 14.5 | 1.5 | 2.2 | 2.7 | 0.5 | 1.6 | 2.4 | 53.8 | 5.3 | 79.8 |
| N144A_P384G | | 3.0 | 0.7 | 2.7 | 4.0 | 14.2 | 1.0 | 2.4 | 3.1 | 0.6 | 1.6 | 2.6 | 54.1 | 0.2 | 80.9 |
| N144A_L388G | | 3.4 | 0.8 | 2.7 | 4.2 | 13.2 | 1.0 | 2.2 | 3.1 | 0.6 | 1.6 | 2.5 | 54.7 | 0.2 | 82.1 |
| N144A_L388T | | 3.2 | 0.7 | 2.8 | 4.2 | 13.6 | 1.0 | 2.3 | 3.0 | 0.6 | 1.6 | 2.5 | 54.6 | 0.4 | 81.5 |
| N144A_F390G | | 2.8 | 0.5 | 3.4 | 5.9 | 13.5 | 1.1 | 1.9 | 2.4 | 0.5 | 1.5 | 1.9 | 54.6 | 0.4 | 81.2 |
| N144A_F390S+ | | 2.7 | 0.5 | 3.2 | 6.0 | 12.8 | 1.0 | 1.9 | 2.5 | 0.6 | 1.5 | 2.0 | 55.6 | 1.2 | 82.3 |
| N144A_F390T | | 2.8 | 0.6 | 2.9 | 4.7 | 13.9 | 1.0 | 2.2 | 2.8 | 0.6 | 1.5 | 2.5 | 54.5 | 1.1 | 81.1 |
| D147Q_T382I | | 3.2 | 0.7 | 2.6 | 4.4 | 12.7 | 0.9 | 2.2 | 3.1 | 0.6 | 1.6 | 2.5 | 55.6 | 0.4 | 82.7 |
| D147Q_P384G | | 2.9 | 0.6 | 2.7 | 4.1 | 16.4 | 1.3 | 2.5 | 2.7 | 0.6 | 1.7 | 2.5 | 52.0 | 0.2 | 77.8 |
| D147Q_L388G | | 3.1 | 0.7 | 2.6 | 4.0 | 15.0 | 1.1 | 2.5 | 2.9 | 0.6 | 1.7 | 2.5 | 53.4 | 0.4 | 79.8 |
| D147Q_L388T | | 2.7 | 0.7 | 2.6 | 4.0 | 15.1 | 1.1 | 2.3 | 2.9 | 0.6 | 1.6 | 2.7 | 53.1 | 0.1 | 79.7 |
| D147Q_F390G | | 2.8 | 0.5 | 3.1 | 5.2 | 16.1 | 1.5 | 2.3 | 2.4 | 0.5 | 1.7 | 2.2 | 51.7 | 1.6 | 77.7 |
| D147Q_F390S | | 2.7 | 0.5 | 3.1 | 5.1 | 14.0 | 1.1 | 2.2 | 2.5 | 0.6 | 1.5 | 2.1 | 54.7 | 0.7 | 80.9 |
| D147Q_F390T | | 2.8 | 0.5 | 2.9 | 4.5 | 15.5 | 1.2 | 2.4 | 2.7 | 0.6 | 1.6 | 2.4 | 52.8 | 0.5 | 79.0 |
| D147H_T382I+ | | 3.2 | 0.7 | 2.6 | 4.6 | 12.4 | 0.9 | 2.3 | 3.1 | 0.6 | 1.6 | 2.4 | 55.8 | 0.1 | 83.2 |
| D147H_P384G | | 2.7 | 0.7 | 2.5 | 3.9 | 15.0 | 1.0 | 2.4 | 3.1 | 0.6 | 1.8 | 2.8 | 52.9 | 0.5 | 79.9 |
| D147H_L388G | | 2.9 | 0.7 | 2.6 | 4.3 | 14.1 | 1.0 | 2.4 | 3.0 | 0.6 | 1.6 | 2.6 | 54.3 | 0.3 | 81.1 |
| D147H_L388T | | 2.8 | 0.6 | 2.6 | 4.2 | 14.4 | 1.0 | 2.4 | 3.0 | 0.6 | 1.6 | 2.6 | 54.0 | 0.2 | 80.7 |
| D147H_F390G | | 2.8 | 0.5 | 3.1 | 5.4 | 15.4 | 1.3 | 2.2 | 2.5 | 0.5 | 1.5 | 2.2 | 52.4 | 2.2 | 78.6 |
| D147H_F390S | | 2.8 | 0.5 | 3.1 | 5.6 | 13.7 | 1.1 | 2.1 | 2.6 | 0.5 | 1.5 | 2.1 | 54.5 | 0.5 | 81.1 |
| D147H_F390T | | 2.8 | 0.5 | 2.9 | 4.6 | 14.8 | 1.1 | 2.4 | 2.8 | 0.5 | 1.6 | 2.5 | 53.5 | 0.4 | 79.9 |
| G148A_P384G | | 2.7 | 0.8 | 2.5 | 4.1 | 14.6 | 0.9 | 2.4 | 3.3 | 0.6 | 1.7 | 3.1 | 53.1 | 0.4 | 80.6 |
| G148A_L388G | | 3.1 | 0.7 | 2.7 | 4.1 | 14.1 | 1.1 | 2.5 | 3.0 | 0.6 | 1.6 | 2.6 | 54.3 | 0.4 | 81.0 |
| G148A_L388T+ | | 3.2 | 0.7 | 2.9 | 4.7 | 16.7 | 1.9 | 2.8 | 2.4 | 0.5 | 1.7 | 2.5 | 50.2 | 3.4 | 76.3 |
| G148A_F390G | | 2.9 | 0.5 | 3.2 | 5.3 | 16.4 | 1.8 | 2.2 | 2.2 | 0.4 | 1.5 | 2.0 | 51.7 | 4.4 | 76.8 |
| G148A_F390S+ | | 2.6 | 0.5 | 3.3 | 5.8 | 12.3 | 1.0 | 2.1 | 2.6 | 0.5 | 1.5 | 2.0 | 56.1 | 0.3 | 82.9 |
| G148A_F390T | | 3.0 | 0.5 | 3.0 | 4.6 | 14.0 | 1.1 | 2.2 | 2.6 | 0.5 | 1.6 | 2.3 | 54.7 | 0.2 | 80.9 |
| G148N_T382I+ | | 3.6 | 0.7 | 2.7 | 4.3 | 10.6 | 0.7 | 2.2 | 3.2 | 0.6 | 1.4 | 2.5 | 58.5 | 3.2 | 85.8 |
| G148N_P384G | | 2.7 | 0.6 | 2.7 | 4.0 | 15.0 | 1.1 | 2.5 | 2.9 | 0.6 | 1.5 | 2.6 | 53.5 | 0.3 | 79.8 |
| G148N_L388G | | 2.9 | 0.7 | 2.6 | 4.5 | 15.0 | 1.1 | 2.7 | 3.2 | 0.6 | 1.6 | 2.9 | 52.2 | 3.3 | 79.7 |
| G148N_L388T | | 2.8 | 0.6 | 2.7 | 4.1 | 14.4 | 1.1 | 2.5 | 3.0 | 0.6 | 1.6 | 2.7 | 54.0 | 0.7 | 80.6 |
| G148N_F390G | | 2.5 | 0.4 | 3.2 | 5.7 | 13.6 | 1.1 | 2.0 | 2.5 | 0.5 | 1.4 | 2.0 | 55.3 | 0.3 | 81.3 |
| G148N_F390S+ | | 2.5 | 0.4 | 3.2 | 6.0 | 12.4 | 1.0 | 2.0 | 2.6 | 0.5 | 1.4 | 2.0 | 56.2 | 0.2 | 82.8 |
| G148N_F390T | | 2.7 | 0.5 | 3.0 | 4.8 | 16.2 | 1.7 | 2.4 | 2.6 | 0.5 | 1.5 | 2.5 | 52.0 | 3.8 | 77.4 |
| Mutant AVG | | 2.9 | 0.6 | 2.8 | 4.7 | 14.3 | 1.1 | 2.3 | 2.8 | 0.6 | 1.6 | 2.4 | 53.9 | 1.1 | 80.4 |

Based on the data set forth above, it is clear that most of the 167 YILPCAT double mutants analyzed above functioned with approximately equal or improved activity when compared to the parent wild type enzyme (SEQ ID NO:46). This conclusion was made based on measuring LPCAT activity as a function of EPA % TFAs and/or % Conv.

More specifically, 106 YILPCAT mutants comprising a single amino acid mutation within Motif I and a single amino acid mutation within Motif II were found to exhibit equivalent or improved EPA % TFAs and equivalent or improved % Conv. These mutants were L134A_T382I, L134A_L388G, L134A_F390T M136S_F378Y, M136S_T382I, M136S_T382P, M136S_T382Y, M136S_R383M, M136S_P384A, M136S_L388Y, M136S_T389A, M136S_T389C, M136S_T389S, M136V_T382P, M136V_T382Y, M136V_P384A, M136V_L388Y, M136V_T389A, M136V_T389C, M136V_T389S, K137H_P384G, K137H_L388G, K137H_L388T, K137H_F390S, K137H_F390T, K137N_T382P, K137N_R383M, K137N P384G, K137N_F378Y, K137N_L388G, K137N_L388T, K137N_T389A, K137N_T389C, K137N_T389S, K137N_F390G, K137N_F390S, K137N_F390T, S140H_T382I, S140H_P384G, S140H_L388G, S140H_L388T, S140H_F390G, S140H_F390S, S140W_T382I, S140W_T382P, S140W_T382Y, S140W_R383M, S140W_P384A, S140W_L388Y, S140W_T389A, S140W_T389C, F141M_F378Y, F141M_T382Y, F141M_R383M, F141M_P384A, F141M_T389C, F141W_F378Y, F141W_T382I, F141W_T382P, F141W_T382Y, F141W_R383M, F141W_P384A, F141W_T389A, F141W_T389C, F141W_T389S, N144A_P384G, N144A_L388G, N144A_L388T, N144A_F390G, N144A_F390S, N144A_F390T, N144T_F378Y, N144T_T382P, N144T_T382Y, N144T R383M, N144T P384A, N144T_L388Y, N144T_T389A, N144T_T389C, N144T_T389S, V145M_T382I, V145M_R383M, V145M_T389A, V145M_T389C, V145W_T382I, D147H_T382I, D147H_L388G, D147H_L388T, D147H_F390S, D147Q_T382I, D147Q_F390S, G148A_F378Y, G148A_T3821, G148A_T382Y, G148A R383M, G148A_P384G, G148A_L388G, G148A_L388Y, G148A_T389A, G148A_T389C, G148A_F390S, G148A_F390T, G148N_T3821, G148N_L388T, G148N_F390G and G148N_F390S).

An additional 15 YILPCAT double mutants (of the 167 analyzed) had equivalent or improved EPA % TFAs when compared to the control, while an additional 6 YILPCAT double mutants (of the 167 analyzed) were determined to have equivalent or improved % Conv. when compared to the control.

Confirmation of Improved LPCAT Activity by Flask Assay

A total of 23 YILPCAT double mutants, each comprising a single amino acid mutation within Motif I and a single amino acid mutation within Motif II, and having equivalent or improved EPA % TFAs and/or equivalent or improved % Conv., were selected for further evaluation (these mutants are noted in bold and with a "+" in Tables 17-20). These mutants were: S140W_T382P, S140W_T389A, M136V_T389A, M136V_T389C, M136V_T389S, K137N_T389A, K137N_T389C, K137N_T389S, M136S_T389A, M136S_T389C, M136S_T389S, F141W_T3821, L134A_T3821, K137N_F390G, K137H_L388G, K137H_L388T, S140H_T3821, S140H_L388G, N144A_F390S, D147H_T3821, G148A_F390S, G148N_T3821 and G148N_F390S. Additionally, mutants M136VF378Y and G148A_L388T, each having slightly diminished EPA % TFAs and slightly diminished % Conv. in comparison to the control, were selected for further evaluation.

Transformants expressing these double mutant YILPCAT proteins were subjected to flask assays for a detailed analysis of the total lipid content and composition. Specifically, the double mutant strains were individually inoculated into 3 mL FM in 15-mL Falcon™ tubes and grown overnight at 30° C. and 250 rpm. The $OD_{600nm}$ was measured and an aliquot of the cells was added to a final $OD_{600nm}$ of 0.3 in 25 mL FM medium in a 125-mL flask. After 2 days in a Multitron shaking incubator at 250 rpm and at 30° C., 6 mL of the culture was harvested by centrifugation and resuspended in 25 mL HGM in the original 125-mL flask. After 5 days in a shaking incubator at 250 rpm and at 30° C., water was added to flasks to bring the total volume back to 25 mL (thereby accounting for evaporation). An aliquot was used for fatty acid analysis (above) and 10 mL of the culture was dried for dry cell weight determination.

For DCW determination, 10 mL culture was harvested by centrifugation for 5 min at 4000 rpm in a Beckman GH-3.8 rotor in a Beckman GS-6R centrifuge. The pellet was resuspended in 25 mL of water and re-harvested as above. The washed pellet was re-suspended in 20 mL of water and transferred to a pre-weighed aluminum pan. The cell suspension was dried overnight in a vacuum oven at 80° C. The weight of the cells was determined.

The flask assay results are shown below in Tables 21 (Group I) and 22 (Group II). The Tables summarize the number of replicates analyzed for each particular transformant ["#"], the average total dry cell weight of the cells ["DCW"], the average total lipid content of the cells ["TFAs % DCW"], the average concentration of each fatty acid as a weight percent of TFAs ["% TFAs"], the delta-9 elongase conversion efficiency ["% Conv."] and the average EPA content as a percent of the dry cell weight ["EPA % DCW"].

TABLE 21

Total Lipid Content, Composition and Delta-9 Elongase Conversion Efficiency in Selected Transformants Comprising a Vector Encoding YILPCAT Having Double Amino Acid Substitutions, by Flask Assay (Group I)

| | | DCW | TFAs % | % TFAs | | | | | | | | | | | | % | EPA % |
|---|---|---|---|---|---|---|---|---|---|---|---|---|---|---|---|---|---|
| Mutant | # | (g/L) | DCW | 16:0 | 16:1 | 18:0 | 18:1 | LA | ALA | EDA | DGLA | ARA | ETrA | ETA | EPA | Conv | DCW |
| WT | 2 | 3.7 | 26.0 | 2.7 | 0.7 | 2.6 | 4.8 | 13.7 | 1.1 | 2.5 | 3.5 | 1.0 | 0.7 | 2.9 | 53.9 | 81.3 | 14.0 |
| S140W_T382P | 2 | 3.9 | 28.6 | 2.7 | 0.7 | 2.5 | 5.2 | 11.8 | 0.9 | 2.6 | 4.0 | 1.1 | 0.9 | 3.3 | 54.2 | 83.8 | 15.5 |
| S140W_T389A | 2 | 4.0 | 28.2 | 2.7 | 0.6 | 2.8 | 6.1 | 11.7 | 0.9 | 2.4 | 3.4 | 0.9 | 0.6 | 2.5 | 55.5 | 83.7 | 15.7 |
| M136V_F378Y | 2 | 4.0 | 27.7 | 2.9 | 0.7 | 2.5 | 5.4 | 12.0 | 0.9 | 2.7 | 3.7 | 1.0 | 0.7 | 3.0 | 54.2 | 83.4 | 15.0 |
| M136V_T389A | 2 | 4.1 | 27.1 | 2.8 | 0.6 | 2.8 | 5.9 | 12.0 | 1.0 | 2.5 | 3.3 | 1.0 | 0.7 | 2.6 | 54.6 | 83.3 | 14.8 |
| M136V_T389C+ | 2 | 4.0 | 27.3 | 3.0 | 0.5 | 2.7 | 5.0 | 11.6 | 1.0 | 2.6 | 3.3 | 1.0 | 0.6 | 2.6 | 56.2 | 84.0 | 15.4 |

TABLE 21-continued

Total Lipid Content, Composition and Delta-9 Elongase Conversion Efficiency in Selected Transformants Comprising a Vector Encoding YILPCAT Having Double Amino Acid Substitutions, by Flask Assay (Group I)

| Mutant | # | DCW (g/L) | TFAs % DCW | % TFAs 16:0 | 16:1 | 18:0 | 18:1 | LA | ALA | EDA | DGLA | ARA | ETrA | ETA | EPA | % Conv | EPA % DCW |
|---|---|---|---|---|---|---|---|---|---|---|---|---|---|---|---|---|---|
| M136V_T389S | 2 | 4.0 | 28.2 | 2.8 | 0.6 | 2.8 | 5.8 | 11.7 | 1.0 | 2.5 | 3.3 | 1.0 | 0.7 | 2.6 | 54.8 | 83.7 | 15.5 |
| K137N_T389A | 2 | 3.8 | 25.8 | 3.0 | 0.5 | 3.0 | 5.6 | 12.1 | 1.1 | 2.4 | 3.1 | 0.9 | 0.6 | 2.3 | 55.8 | 83.2 | 14.4 |
| K137N_T389C | 2 | 4.0 | 27.4 | 2.8 | 0.8 | 2.5 | 5.4 | 13.2 | 1.0 | 2.8 | 3.8 | 1.0 | 0.6 | 3.1 | 53.2 | 81.9 | 14.6 |
| K137N_T389S | 2 | 3.9 | 27.2 | 2.7 | 0.7 | 2.7 | 6.0 | 12.3 | 1.0 | 2.6 | 3.5 | 0.9 | 0.6 | 2.6 | 54.8 | 83.0 | 14.9 |
| M136S_T389A+ | 2 | 3.9 | 27.7 | 2.7 | 0.6 | 2.8 | 5.9 | 11.7 | 1.0 | 2.5 | 3.3 | 0.9 | 0.6 | 2.5 | 55.8 | 83.9 | 15.5 |
| M136S_T389C+ | 2 | 3.9 | 26.9 | 3.0 | 0.5 | 2.8 | 5.3 | 11.7 | 1.0 | 2.5 | 3.3 | 0.9 | 0.7 | 2.6 | 56.0 | 83.9 | 15.1 |
| M136S_T389S+ | 2 | 3.7 | 27.7 | 2.8 | 0.6 | 2.9 | 5.8 | 11.4 | 1.0 | 2.3 | 3.1 | 1.0 | 0.7 | 2.4 | 55.8 | 84.1 | 15.5 |
| F141W_T382I | 2 | 3.8 | 28.7 | 2.5 | 0.8 | 2.5 | 5.7 | 11.9 | 0.8 | 2.6 | 4.2 | 1.0 | 0.7 | 3.4 | 53.4 | 83.7 | 15.3 |

TABLE 22

Total Lipid Content, Composition and Delta-9 Elongase Conversion Efficiency in Selected Transformants Comprising a Vector Encoding YILPCAT Having Double Amino Acid Substitutions, by Flask Assay (Group II)

| Mutant | # | DCW (g/L) | TFAs % DCW | % TFAs 16:0 | 16:1 | 18:0 | 18:1 | LA | ALA | EDA | DGLA | ARA | ETrA | ETA | EPA | % Conv. | EPA % DCW |
|---|---|---|---|---|---|---|---|---|---|---|---|---|---|---|---|---|---|
| WT | | 2.0 | 26.0 | 3.0 | 0.7 | 2.5 | 4.2 | 13.7 | 0.9 | 2.4 | 3.4 | 0.7 | 0.5 | 3.5 | 54.7 | 82 | 14.2 |
| L134A_T382I | | 2.0 | 24.0 | 3.3 | 0.7 | 2.6 | 4.4 | 12.6 | 0.9 | 2.2 | 3.5 | 0.8 | 0.6 | 3.5 | 53.3 | 83 | 12.9 |
| K137N_F390G | | 2.1 | 27.3 | 2.1 | 0.4 | 2.5 | 6.2 | 12.4 | 0.9 | 1.9 | 3.7 | 0.8 | 0.8 | 3.8 | 54.1 | 83 | 14.8 |
| K137H_L388G | | 2.0 | 28.1 | 3.2 | 0.7 | 2.4 | 4.3 | 12.6 | 0.9 | 2.4 | 3.5 | 0.8 | 0.6 | 3.5 | 54.6 | 83 | 15.4 |
| K137H_L388T | | 2.0 | 27.4 | 2.9 | 0.7 | 2.4 | 4.4 | 13.2 | 0.9 | 2.4 | 3.6 | 0.7 | 0.6 | 3.5 | 54.8 | 82 | 15.0 |
| S140H_T382I | | 2.1 | 21.3 | 3.4 | 0.9 | 2.6 | 4.8 | 12.6 | 0.9 | 2.4 | 3.7 | 0.7 | 0.5 | 3.6 | 52.7 | 82 | 11.3 |
| S140H_L388G | | 2.0 | 26.1 | 2.7 | 0.8 | 2.2 | 4.4 | 13.0 | 0.9 | 2.5 | 3.9 | 0.7 | 0.6 | 4.0 | 54.3 | 83 | 14.2 |
| N144A_F390S+ | | 2.1 | 26.2 | 2.6 | 0.4 | 2.8 | 6.7 | 12.0 | 0.8 | 1.9 | 3.2 | 0.7 | 0.5 | 3.1 | 55.9 | 84 | 14.7 |
| D147H_T382I | | 2.1 | 26.6 | 3.0 | 0.7 | 2.3 | 4.6 | 12.4 | 0.9 | 2.4 | 3.6 | 0.8 | 0.5 | 3.7 | 54.3 | 83 | 14.4 |
| G148A_F390S+ | | 2.1 | 27.0 | 2.8 | 0.4 | 3.0 | 6.5 | 12.0 | 0.8 | 2.1 | 2.9 | 0.8 | 0.7 | 3.0 | 55.1 | 83 | 14.9 |
| G148N_T382I+ | | 1.9 | 26.5 | 3.3 | 0.7 | 2.3 | 4.7 | 12.2 | 0.8 | 2.3 | 3.5 | 0.8 | 0.6 | 3.5 | 56.7 | 84 | 15.0 |
| G148N_F390S+ | | 2.1 | 26.7 | 2.8 | 0.4 | 2.9 | 6.5 | 12.0 | 0.8 | 2.0 | 3.0 | 0.7 | 0.6 | 2.9 | 55.9 | 84 | 14.9 |
| G148A_L388T | | 2.0 | 24.7 | 2.5 | 0.6 | 2.2 | 5.4 | 11.7 | 0.9 | 2.2 | 3.6 | 0.8 | 0.5 | 3.7 | 55.1 | 84 | 13.6 |

Of the 25 YILPCAT double mutants analyzed, each comprising a single amino acid mutation within Motif I and a single amino acid mutation within Motif II, 17 were observed to have both equivalent or improved EPA TFAs and equivalent or improved % Conv., while the remaining 8 had equivalent or improved % Conv.

Based on the data set forth above, 22 of the 25 YILPCAT double mutants analyzed above functioned with improved activity when compared to the parent wild type enzyme (SEQ ID NO:46).

Also, the over-expression of certain double-mutant LPCAT polypeptides resulted in increased total lipid content (TFAs % DCW) in the recombinant *Yarrowia*. For example, over-expression of mutant LPCAT polypeptides comprising the S140W_T382P, S140W_T389A, M136V_T389S and F141W_T382I, or K137H_L388G mutation pairs resulted in total lipid contents that were 8% or more increased relative to the total lipid content of the control (Tables 21 and 22). Interestingly, certain transformants had both increased total lipid content and EPA % TFAs. For example, transformants that over-expressed LPCATs with S140W_T389A, M136V_T389C, M136S_T389A, or M136S_T389S mutation pairs had at least a 5% increase in total lipid content and at least a ~3% increase in EPA % TFAs with respect to control (Tables 21 and 22). This is a significant observation since it had previously been difficult to induce a simultaneous increase in both total lipid content and EPA % TFAs. Usually, an increase in total lipid content had corresponded with a decrease in EPA % TFAs, and vice versa.

The double mutant YILPCAT polypeptides listed in bold and with a "+" in Tables 21 and 22, i.e., M136S_T389A, M136S_T389C, M136S_T389S, M136V_T389C, N144A_F390S, G148A_F390S, G148N_T382I and G148N_F390S, are disclosed herein as SEQ ID NOs:79, 81, 83, 85, 87, 89, 91 and 93, respectively.

Example 7

Over-Expression of *Yarrowia lipolytica* PDAT Along with Over-Expression of a Mutant *Yarrowia lipolytica* LPCAT for EPA Production The present Example describes over-expression of a *Y. lipolytica* PDAT in a *Y. lipolytica* strain engineered to produce high levels of lipids containing eicosapentaenoic acid ["EPA"], wherein the strain also over-expresses a mutant *Y. lipolytica* LPCAT comprising a single mutation within Motif I and/or a single mutation within Motif II.

More specifically, any of the preferred mutant YILPCAT polynucleotides described in Example 6 would be cloned into expression plasmid pY301 (SEQ ID NO:44, Example 2), to replace the polynucleotide encoding wild type YILPCAT with a polynucleotide encoding a mutant YILPCAT. This modified plasmid would then be used to transform any preferred strain of *Y. lipolytica* that had been engineered to produce a PUFA, e.g., EPA. The transformed *Yarrowia* would be grown and analyzed for lipid content and PUFA production as in Example 2.

What is claimed is:

1. A recombinant microbial cell for the production of at least one long-chain polyunsaturated fatty acid, said recombinant microbial cell comprising:

(a) at least one polypeptide having acyl CoA:lysophosphatidylcholine acyltransferase (LPCAT) activity, wherein the polypeptide having LPCAT activity has at least 95% amino acid sequence identity with the polypeptide of SEQ ID NO: 4 (YlLPCAT), based on the Clustal W method of alignment, and wherein the polypeptide having LPCAT activity is a polypeptide comprising at least one mutant membrane-bound O-acyltransferase protein family motif comprising the amino acid sequence set forth in SEQ ID NO: 39, wherein the amino acid residue at position 2 of SEQ ID NO: 39 is C, the amino acid residue at position 3 of SEQ ID NO: 39 is selected from the group consisting of A, C and G, the amino acid residue at position 6 of SEQ ID NO: 39 is selected from the group consisting of H, G, N, and Y, the amino acid residue at position 7 of SEQ ID NO: 39 is selected from the group consisting of A, N, G, H and M, the amino acid residue at position 16 of SEQ ID NO: 39 is selected from the group consisting of Q, N, and H, and the amino acid residue at position 17 of SEQ ID NO: 39 is selected from the group consisting of A, V and N;

(b) at least one polypeptide having phospholipid:diacylglycerol acyltransferase (PDAT) activity, wherein the polypeptide having PDAT activity has at least 95% amino acid sequence identity with the polypeptide of SEQ ID NO: 32 (YlPDAT), based on the Clustal W method of alignment; and (c) a polyunsaturated fatty acid biosynthetic pathway capable of producing at least one long chain polyunsaturated fatty acid;

wherein said polypeptides of (a) and (b) are expressed, and wherein the recombinant microbial cell comprises an increased amount of a polyunsaturated fatty acid measured as a weight percent of total fatty acids, when compared to a control cell, wherein the control cell is the recombinant microbial cell wherein said polypeptides of (a) and (b) are not expressed.

2. The recombinant microbial cell of claim 1, wherein the recombinant microbial cell further comprises at least one of the following, when compared to the control cell:

(i) an increased $C_{18}$ to $C_{20}$ elongation conversion efficiency, or (ii) an increased amount of total fatty acids measured as a weight percent of dry cell weight.

3. The recombinant microbial cell of claim 2, wherein the increased $C_{18}$ to $C_{20}$ elongation conversion efficiency is an effect of increased delta-9 elongase conversion efficiency or increased delta-6 elongase conversion efficiency.

4. The recombinant microbial cell of claim 1, wherein the long-chain polyunsaturated fatty acid is selected from the group consisting of: eicosadienoic acid, dihomo-gamma-linolenic acid, arachidonic acid, docosatetraenoic acid, omega-6 docosapentaenoic acid, eicosatrienoic acid, eicosatetraenoic acid, eicosapentaenoic acid, omega-3 docosapentaenoic acid and docosahexaenoic acid.

5. The recombinant microbial cell of claim 1, wherein the microbial cell is selected from the group consisting of: algae, yeast, euglenoids, stramenopiles, oomycetes and fungi.

6. The recombinant microbial cell of claim 5, wherein the cell is an oleaginous yeast.

7. The recombinant microbial cell of claim 6, wherein the oleaginous yeast is of the genus *Yarrowia*.

8. The recombinant microbial cell of claim 1, wherein the polypeptide having LPCAT activity comprises an amino acid sequence that (i) is at least 97% identical to SEQ ID NO: 4, and (ii) comprises substitutions at residues corresponding to residues 136 and 389 of SEQ ID NO: 4.

9. The recombinant microbial cell of claim 8, wherein said residue corresponding to residue 136 is substituted with a serine or valine, and said residue corresponding to residue 389 is substituted with an alanine, cysteine, or serine.

10. A method for producing at least one polyunsaturated fatty acid comprising:

(a) growing the recombinant microbial cell of claim 1 in the presence of a fermentable carbon source; and (b) optionally recovering the long-chain polyunsaturated fatty acid.

11. The method of claim 10, wherein the recombinant microbial cell is an oleaginous yeast and the long-chain polyunsaturated fatty acid is selected from the group consisting of: eicosadienoic acid, dihomo-gamma-linolenic acid, arachidonic acid, docosatetraenoic acid, omega-6 docosapentaenoic acid, eicosatrienoic acid, eicosatetraenoic acid, eicosapentaenoic acid, omega-3 docosapentaenoic acid and docosahexaenoic acid.

12. The method of claim 11, wherein the oleaginous yeast is of the genus *Yarrowia*.

* * * * *

SEQUENCE LISTING

<160> NUMBER OF SEQ ID NOS: 93

<210> SEQ ID NO 1
<211> LENGTH: 1860
<212> TYPE: DNA
<213> ORGANISM: Saccharomyces cerevisiae
<220> FEATURE:
<221> NAME/KEY: CDS
<222> LOCATION: (1)..(1860)
<223> OTHER INFORMATION: GenBank Accession No. NP_014818; "YOR175C"
<300> PUBLICATION INFORMATION:
<302> TITLE: Genes encoding a novel type of lysophophatidylcholine acyltransferases and their use to increase triacylglycerol production and/or modify fatty acid composition
<310> PATENT DOCUMENT NUMBER: US-2008-0145867-A1
<311> PATENT FILING DATE: 2007-06-15
<312> PUBLICATION DATE: 2008-06-19
<313> RELEVANT RESIDUES IN SEQ ID NO: (1)..(1860)
<300> PUBLICATION INFORMATION:
<302> TITLE: Genes encoding a novel type of lysophophatidylcholine acyltransferases and their use to increase triacylglycerol production and/or modify fatty acid composition
<310> PATENT DOCUMENT NUMBER: WO 2008/076377
<311> PATENT FILING DATE: 2007-12-13
<312> PUBLICATION DATE: 2008-06-26
<313> RELEVANT RESIDUES IN SEQ ID NO: (1)..(1860)
<300> PUBLICATION INFORMATION:
<302> TITLE: USE OF A CLASS OF GENES ENCODING LYSOPHOSPHOLIPID ACYL TRANSFERASES FOR APPLICATION IN AGRICULTURE, BIOTECHNOLOGY AND MEDICINE
<310> PATENT DOCUMENT NUMBER: WO 2009/001315
<311> PATENT FILING DATE: 2008-06-25
<312> PUBLICATION DATE: 2008-12-31
<313> RELEVANT RESIDUES IN SEQ ID NO: (1)..(1860)

<400> SEQUENCE: 1 atg tac aat cct gtg gac gct gtt tta aca aag ata att acc aac tat 48
Met Tyr Asn Pro Val Asp Ala Val Leu Thr Lys Ile Ile Thr Asn Tyr
1 5 10 15 ggg att gat agt ttt aca ctg cga tat gct atc tgc tta ttg gga tcg 96
Gly Ile Asp Ser Phe Thr Leu Arg Tyr Ala Ile Cys Leu Leu Gly Ser
20 25 30 ttc cca ctg aat gct att ttg aag aga att ccc gag aag cgt ata ggt 144
Phe Pro Leu Asn Ala Ile Leu Lys Arg Ile Pro Glu Lys Arg Ile Gly
35 40 45 tta aaa tgt tgt ttt atc att tct atg tcg atg ttt tac tta ttc ggt 192
Leu Lys Cys Cys Phe Ile Ile Ser Met Ser Met Phe Tyr Leu Phe Gly
50 55 60 gtg ctg aat cta gta agt gga ttc agg acc ctg ttt att agt acc atg 240
Val Leu Asn Leu Val Ser Gly Phe Arg Thr Leu Phe Ile Ser Thr Met
65 70 75 80 ttt act tac ttg atc tca aga ttt tac cgt tcc aag ttt atg cca cac 288
Phe Thr Tyr Leu Ile Ser Arg Phe Tyr Arg Ser Lys Phe Met Pro His
85 90 95 ttg aat ttc atg ttt gtt atg ggt cat ttg gca ata aat cat ata cac 336
Leu Asn Phe Met Phe Val Met Gly His Leu Ala Ile Asn His Ile His
100 105 110 gcc caa ttc ctt aac gaa cag act caa act acc gtt gac att aca agt 384
Ala Gln Phe Leu Asn Glu Gln Thr Gln Thr Thr Val Asp Ile Thr Ser
115 120 125 tca caa atg gtt tta gcc atg aaa cta act tct ttt gca tgg tcg tac 432
Ser Gln Met Val Leu Ala Met Lys Leu Thr Ser Phe Ala Trp Ser Tyr
130 135 140 tat gat ggt tca tgc act agc gaa agc gat ttc aaa gat ttg act gag 480
Tyr Asp Gly Ser Cys Thr Ser Glu Ser Asp Phe Lys Asp Leu Thr Glu
145 150 155 160 cat caa aaa tct cgt gct gtc aga ggt cat cca ccc tta tta aag ttc 528

-continued

```
His Gln Lys Ser Arg Ala Val Arg Gly His Pro Pro Leu Leu Lys Phe
                165                 170                 175

ctg gca tat gca ttt ttc tat tca acg ttg cta act ggc cca agt ttc      576
Leu Ala Tyr Ala Phe Phe Tyr Ser Thr Leu Leu Thr Gly Pro Ser Phe
            180                 185                 190

gat tat gcc gat ttt gac agc tgg ttg aat tgt gag atg ttc cgt gac      624
Asp Tyr Ala Asp Phe Asp Ser Trp Leu Asn Cys Glu Met Phe Arg Asp
        195                 200                 205

ttg cct gaa agc aaa aag cct atg aga aga cac cac cct ggt gaa aga      672
Leu Pro Glu Ser Lys Lys Pro Met Arg Arg His His Pro Gly Glu Arg
    210                 215                 220

aga cag att cca aag aat ggt aaa ctt gca tta tgg aaa gtt gtt caa      720
Arg Gln Ile Pro Lys Asn Gly Lys Leu Ala Leu Trp Lys Val Val Gln
225                 230                 235                 240

ggt ctt gct tgg atg att tta agt aca cta gga atg aag cac ttc ccc      768
Gly Leu Ala Trp Met Ile Leu Ser Thr Leu Gly Met Lys His Phe Pro
                245                 250                 255

gta aaa tac gtt ttg gac aaa gat ggc ttc cca acg aga tct ttt ata      816
Val Lys Tyr Val Leu Asp Lys Asp Gly Phe Pro Thr Arg Ser Phe Ile
            260                 265                 270

ttc aga atc cat tac tta ttc ttg ctt ggt ttc atc cat aga ttc aag      864
Phe Arg Ile His Tyr Leu Phe Leu Leu Gly Phe Ile His Arg Phe Lys
        275                 280                 285

tac tac gct gcc tgg act att tcg gaa gga tct tgt att ttg tgc ggt      912
Tyr Tyr Ala Ala Trp Thr Ile Ser Glu Gly Ser Cys Ile Leu Cys Gly
    290                 295                 300

ttg ggt tat aat ggt tat gat tca aag aca caa aag atc aga tgg gat      960
Leu Gly Tyr Asn Gly Tyr Asp Ser Lys Thr Gln Lys Ile Arg Trp Asp
305                 310                 315                 320

cgt gtc aga aat att gac att tgg acc gta gaa acg gcg cag aat acg     1008
Arg Val Arg Asn Ile Asp Ile Trp Thr Val Glu Thr Ala Gln Asn Thr
                325                 330                 335

cgt gaa atg ttg gaa gca tgg aat atg aat act aac aag tgg cta aaa     1056
Arg Glu Met Leu Glu Ala Trp Asn Met Asn Thr Asn Lys Trp Leu Lys
            340                 345                 350

tac tct gtt tat tta cgt gtc aca aag aag ggc aaa aaa cct ggt ttc     1104
Tyr Ser Val Tyr Leu Arg Val Thr Lys Lys Gly Lys Lys Pro Gly Phe
        355                 360                 365

cgc tca act ttg ttt act ttc cta act tcc gca ttt tgg cat ggt acc     1152
Arg Ser Thr Leu Phe Thr Phe Leu Thr Ser Ala Phe Trp His Gly Thr
    370                 375                 380

aga cct ggg tac tat ctg act ttt gcg aca ggg gct ttg tac caa aca     1200
Arg Pro Gly Tyr Tyr Leu Thr Phe Ala Thr Gly Ala Leu Tyr Gln Thr
385                 390                 395                 400

tgt ggt aaa atc tac aga cgc aat ttt aga cca att ttc ttg cga gaa     1248
Cys Gly Lys Ile Tyr Arg Arg Asn Phe Arg Pro Ile Phe Leu Arg Glu
                405                 410                 415

gat ggt gtc act cct ttg cct tct aaa aaa atc tac gat tta gtt ggc     1296
Asp Gly Val Thr Pro Leu Pro Ser Lys Lys Ile Tyr Asp Leu Val Gly
            420                 425                 430

ata tat gca att aaa cta gca ttt ggt tac atg gtg caa cca ttt att     1344
Ile Tyr Ala Ile Lys Leu Ala Phe Gly Tyr Met Val Gln Pro Phe Ile
        435                 440                 445

atc ctt gat ttg aag cca tct tta atg gta tgg ggc tct gtt tat ttc     1392
Ile Leu Asp Leu Lys Pro Ser Leu Met Val Trp Gly Ser Val Tyr Phe
    450                 455                 460

tat gtt cat att att gtt gct ttc tca ttt ttc cta ttc aga gga cca     1440
Tyr Val His Ile Ile Val Ala Phe Ser Phe Phe Leu Phe Arg Gly Pro
465                 470                 475                 480
```

-continued

```
tat gct aaa caa gtt act gaa ttt ttt aaa tcc aaa caa cct aaa gaa     1488
Tyr Ala Lys Gln Val Thr Glu Phe Phe Lys Ser Lys Gln Pro Lys Glu
                485                 490                 495

ata ttc att aga aaa caa aag aag ttg gaa aaa gat att tct gca agc     1536
Ile Phe Ile Arg Lys Gln Lys Lys Leu Glu Lys Asp Ile Ser Ala Ser
            500                 505                 510

tct cca aac ttg ggt ggt ata ttg aag gca aag att gaa cat gaa aag     1584
Ser Pro Asn Leu Gly Gly Ile Leu Lys Ala Lys Ile Glu His Glu Lys
        515                 520                 525

gga aag aca gca gaa gaa gaa gaa atg aac tta ggt att cca cca att     1632
Gly Lys Thr Ala Glu Glu Glu Glu Met Asn Leu Gly Ile Pro Pro Ile
    530                 535                 540

gag tta gaa aag tgg gac aat gct aag gaa gat tgg gaa gat ttc tgc     1680
Glu Leu Glu Lys Trp Asp Asn Ala Lys Glu Asp Trp Glu Asp Phe Cys
545                 550                 555                 560

aaa gat tac aaa gaa tgg aga aat aaa aat ggt ctt gaa ata gaa gag     1728
Lys Asp Tyr Lys Glu Trp Arg Asn Lys Asn Gly Leu Glu Ile Glu Glu
                565                 570                 575

gaa aac ctt tct aaa gct ttt gaa aga ttc aag cag gaa ttt tct aac     1776
Glu Asn Leu Ser Lys Ala Phe Glu Arg Phe Lys Gln Glu Phe Ser Asn
            580                 585                 590

gct gca agt gga tca ggt gaa cgt gtg aga aaa atg agt ttt agt ggt     1824
Ala Ala Ser Gly Ser Gly Glu Arg Val Arg Lys Met Ser Phe Ser Gly
        595                 600                 605

tac tca cca aag cct att tca aaa aag gaa gag tag                     1860
Tyr Ser Pro Lys Pro Ile Ser Lys Lys Glu Glu
    610                 615


<210> SEQ ID NO 2
<211> LENGTH: 619
<212> TYPE: PRT
<213> ORGANISM: Saccharomyces cerevisiae

<400> SEQUENCE: 2

Met Tyr Asn Pro Val Asp Ala Val Leu Thr Lys Ile Ile Thr Asn Tyr
1               5                   10                  15

Gly Ile Asp Ser Phe Thr Leu Arg Tyr Ala Ile Cys Leu Leu Gly Ser
            20                  25                  30

Phe Pro Leu Asn Ala Ile Leu Lys Arg Ile Pro Glu Lys Arg Ile Gly
        35                  40                  45

Leu Lys Cys Cys Phe Ile Ile Ser Met Ser Met Phe Tyr Leu Phe Gly
    50                  55                  60

Val Leu Asn Leu Val Ser Gly Phe Arg Thr Leu Phe Ile Ser Thr Met
65                  70                  75                  80

Phe Thr Tyr Leu Ile Ser Arg Phe Tyr Arg Ser Lys Phe Met Pro His
                85                  90                  95

Leu Asn Phe Met Phe Val Met Gly His Leu Ala Ile Asn His Ile His
            100                 105                 110

Ala Gln Phe Leu Asn Glu Gln Thr Gln Thr Thr Val Asp Ile Thr Ser
        115                 120                 125

Ser Gln Met Val Leu Ala Met Lys Leu Thr Ser Phe Ala Trp Ser Tyr
    130                 135                 140

Tyr Asp Gly Ser Cys Thr Ser Glu Ser Asp Phe Lys Asp Leu Thr Glu
145                 150                 155                 160

His Gln Lys Ser Arg Ala Val Arg Gly His Pro Pro Leu Leu Lys Phe
                165                 170                 175

Leu Ala Tyr Ala Phe Phe Tyr Ser Thr Leu Leu Thr Gly Pro Ser Phe
            180                 185                 190
```

-continued

```
Asp Tyr Ala Asp Phe Asp Ser Trp Leu Asn Cys Glu Met Phe Arg Asp
        195                 200                 205

Leu Pro Glu Ser Lys Lys Pro Met Arg Arg His His Pro Gly Glu Arg
    210                 215                 220

Arg Gln Ile Pro Lys Asn Gly Lys Leu Ala Leu Trp Lys Val Val Gln
225                 230                 235                 240

Gly Leu Ala Trp Met Ile Leu Ser Thr Leu Gly Met Lys His Phe Pro
                245                 250                 255

Val Lys Tyr Val Leu Asp Lys Asp Gly Phe Pro Thr Arg Ser Phe Ile
            260                 265                 270

Phe Arg Ile His Tyr Leu Phe Leu Leu Gly Phe Ile His Arg Phe Lys
        275                 280                 285

Tyr Tyr Ala Ala Trp Thr Ile Ser Glu Gly Ser Cys Ile Leu Cys Gly
    290                 295                 300

Leu Gly Tyr Asn Gly Tyr Asp Ser Lys Thr Gln Lys Ile Arg Trp Asp
305                 310                 315                 320

Arg Val Arg Asn Ile Asp Ile Trp Thr Val Glu Thr Ala Gln Asn Thr
                325                 330                 335

Arg Glu Met Leu Glu Ala Trp Asn Met Asn Thr Asn Lys Trp Leu Lys
            340                 345                 350

Tyr Ser Val Tyr Leu Arg Val Thr Lys Lys Gly Lys Lys Pro Gly Phe
        355                 360                 365

Arg Ser Thr Leu Phe Thr Phe Leu Thr Ser Ala Phe Trp His Gly Thr
    370                 375                 380

Arg Pro Gly Tyr Tyr Leu Thr Phe Ala Thr Gly Ala Leu Tyr Gln Thr
385                 390                 395                 400

Cys Gly Lys Ile Tyr Arg Arg Asn Phe Arg Pro Ile Phe Leu Arg Glu
                405                 410                 415

Asp Gly Val Thr Pro Leu Pro Ser Lys Lys Ile Tyr Asp Leu Val Gly
            420                 425                 430

Ile Tyr Ala Ile Lys Leu Ala Phe Gly Tyr Met Val Gln Pro Phe Ile
        435                 440                 445

Ile Leu Asp Leu Lys Pro Ser Leu Met Val Trp Gly Ser Val Tyr Phe
    450                 455                 460

Tyr Val His Ile Ile Val Ala Phe Ser Phe Phe Leu Phe Arg Gly Pro
465                 470                 475                 480

Tyr Ala Lys Gln Val Thr Glu Phe Phe Lys Ser Lys Gln Pro Lys Glu
                485                 490                 495

Ile Phe Ile Arg Lys Gln Lys Lys Leu Glu Lys Asp Ile Ser Ala Ser
            500                 505                 510

Ser Pro Asn Leu Gly Gly Ile Leu Lys Ala Lys Ile Glu His Glu Lys
        515                 520                 525

Gly Lys Thr Ala Glu Glu Glu Glu Met Asn Leu Gly Ile Pro Pro Ile
    530                 535                 540

Glu Leu Glu Lys Trp Asp Asn Ala Lys Glu Asp Trp Glu Asp Phe Cys
545                 550                 555                 560

Lys Asp Tyr Lys Glu Trp Arg Asn Lys Asn Gly Leu Glu Ile Glu Glu
                565                 570                 575

Glu Asn Leu Ser Lys Ala Phe Glu Arg Phe Lys Gln Glu Phe Ser Asn
            580                 585                 590

Ala Ala Ser Gly Ser Gly Glu Arg Val Arg Lys Met Ser Phe Ser Gly
        595                 600                 605
```

```
Tyr Ser Pro Lys Pro Ile Ser Lys Lys Glu Glu
    610                 615


<210> SEQ ID NO 3
<211> LENGTH: 1539
<212> TYPE: DNA
<213> ORGANISM: Yarrowia lipolytica
<220> FEATURE:
<221> NAME/KEY: CDS
<222> LOCATION: (1)..(1539)
<223> OTHER INFORMATION: GenBank Accession No. XP_505624; "YALI0F19514p"

<400> SEQUENCE: 3

atg gcc ttt cca tgg gca gat aag tgg gca gcc gat gcg tct gca tct       48
Met Ala Phe Pro Trp Ala Asp Lys Trp Ala Ala Asp Ala Ser Ala Ser
1               5                   10                  15

aca ggg ctg cct ccg gac ctc ctc aag att gca ttc act ctg gtc atg       96
Thr Gly Leu Pro Pro Asp Leu Leu Lys Ile Ala Phe Thr Leu Val Met
            20                  25                  30

tct tat ccg ctg agt tct ctc atg aaa cgg ctg cca gat gac gcc aaa      144
Ser Tyr Pro Leu Ser Ser Leu Met Lys Arg Leu Pro Asp Asp Ala Lys
        35                  40                  45

aac ctc aag atc atc tat atc atc tcc gtg tcc atc ttc tac atg gtg      192
Asn Leu Lys Ile Ile Tyr Ile Ile Ser Val Ser Ile Phe Tyr Met Val
    50                  55                  60

ggt gtc ttc tcc ctc tat ggc gga gct gcc act ctg ctc ttc tcc tca      240
Gly Val Phe Ser Leu Tyr Gly Gly Ala Ala Thr Leu Leu Phe Ser Ser
65                  70                  75                  80

atg ggt acc ttc ttc atc acc caa tgg aag agc cct tac atg ccc tgg      288
Met Gly Thr Phe Phe Ile Thr Gln Trp Lys Ser Pro Tyr Met Pro Trp
                85                  90                  95

gtc aat ttt ggt ttt gtc atg acc cat ctc ttc gtc aat cac ctg cgt      336
Val Asn Phe Gly Phe Val Met Thr His Leu Phe Val Asn His Leu Arg
            100                 105                 110

tcg cag ttt ttc ccc gaa aca tac gac ccc aat gtc att gac atc acc      384
Ser Gln Phe Phe Pro Glu Thr Tyr Asp Pro Asn Val Ile Asp Ile Thr
        115                 120                 125

gga gca cag atg gtt ctg tgt atg aag cta tcg tct ttt gga tgg aac      432
Gly Ala Gln Met Val Leu Cys Met Lys Leu Ser Ser Phe Gly Trp Asn
    130                 135                 140

gtc tac gat gga tgg cag att gag aag ggt gag cag ctc agc gag ttc      480
Val Tyr Asp Gly Trp Gln Ile Glu Lys Gly Glu Gln Leu Ser Glu Phe
145                 150                 155                 160

cag act aaa agg gct gtt ctc aag cac ccc agt ctt atg gac ttc cta      528
Gln Thr Lys Arg Ala Val Leu Lys His Pro Ser Leu Met Asp Phe Leu
                165                 170                 175

gct ttt gtg ttc tac ttc cct tcc att ctg aca ggt cct tct tac gac      576
Ala Phe Val Phe Tyr Phe Pro Ser Ile Leu Thr Gly Pro Ser Tyr Asp
            180                 185                 190

tat atg gag ttc cat aac tgg ctc gat ctc agc ctg ttc aag gag ctg      624
Tyr Met Glu Phe His Asn Trp Leu Asp Leu Ser Leu Phe Lys Glu Leu
        195                 200                 205

gag aaa gat aag gac ccc aag cga gct gct cga cga aag cga cac aag      672
Glu Lys Asp Lys Asp Pro Lys Arg Ala Ala Arg Arg Lys Arg His Lys
    210                 215                 220

atc ccc cga tct gga atc gct gct tcc aag aaa ctc gcc gct ggt atc      720
Ile Pro Arg Ser Gly Ile Ala Ala Ser Lys Lys Leu Ala Ala Gly Ile
225                 230                 235                 240

ttc tgg atc gtt ctg tgg acc cag gtg gac tct cga atc tcc acc gcc      768
Phe Trp Ile Val Leu Trp Thr Gln Val Asp Ser Arg Ile Ser Thr Ala
                245                 250                 255
```

-continued

```
tac gct tac tca gac gca ttc acc aag gag cac aac atc ttt gga cga      816
Tyr Ala Tyr Ser Asp Ala Phe Thr Lys Glu His Asn Ile Phe Gly Arg
            260                 265                 270

att gtg tac ctc tac atg ctc ggt ttc atg tac cga ctc aag tac tac      864
Ile Val Tyr Leu Tyr Met Leu Gly Phe Met Tyr Arg Leu Lys Tyr Tyr
        275                 280                 285

gga gcc tgg tcc att tcc gag gga gcc tgc atc ttg tct ggc ctc gga      912
Gly Ala Trp Ser Ile Ser Glu Gly Ala Cys Ile Leu Ser Gly Leu Gly
    290                 295                 300

ttc cat ggc gtg gac ccc aaa act ggc aag tac aag tgg gac cgt gtc      960
Phe His Gly Val Asp Pro Lys Thr Gly Lys Tyr Lys Trp Asp Arg Val
305                 310                 315                 320

cag aac gtg gac ccg tgg gga ttc gaa act ggt caa aac aca aag gct     1008
Gln Asn Val Asp Pro Trp Gly Phe Glu Thr Gly Gln Asn Thr Lys Ala
                325                 330                 335

ctg ctg gag gcc tgg aac cag aac act aac aag tgg cta cga aac tat     1056
Leu Leu Glu Ala Trp Asn Gln Asn Thr Asn Lys Trp Leu Arg Asn Tyr
            340                 345                 350

gtg tac ctc cga gtg gtg ccc aaa ggc caa aag cct gga ttc cga gcc     1104
Val Tyr Leu Arg Val Val Pro Lys Gly Gln Lys Pro Gly Phe Arg Ala
        355                 360                 365

act atc ttc aca ttt gtg gtt tcc gcc ttc tgg cat gga act cga cct     1152
Thr Ile Phe Thr Phe Val Val Ser Ala Phe Trp His Gly Thr Arg Pro
    370                 375                 380

ggc tac tat ctc acc ttt gtg acc gct gcc atg tac cag tct gtt ggt     1200
Gly Tyr Tyr Leu Thr Phe Val Thr Ala Ala Met Tyr Gln Ser Val Gly
385                 390                 395                 400

aag ttc ttc cga cga tac ctg cga ccc ttc ttc atg gag tct gat gga     1248
Lys Phe Phe Arg Arg Tyr Leu Arg Pro Phe Phe Met Glu Ser Asp Gly
                405                 410                 415

aag act gcc ggt ccc tat aag atc tac tac gac att gtg tgt tgg atc     1296
Lys Thr Ala Gly Pro Tyr Lys Ile Tyr Tyr Asp Ile Val Cys Trp Ile
            420                 425                 430

gtt gtc caa acc gca ttt gga tac gct acc cag tcc ttt atg att cta     1344
Val Val Gln Thr Ala Phe Gly Tyr Ala Thr Gln Ser Phe Met Ile Leu
        435                 440                 445

gac ttc tgg ctg tcg ctc aag tgt tgg aag aac tcc tgg ttc ctg tac     1392
Asp Phe Trp Leu Ser Leu Lys Cys Trp Lys Asn Ser Trp Phe Leu Tyr
    450                 455                 460

cac att gct ctg ggc gcc atc ttt gca att tct agc ccc tac aag gca     1440
His Ile Ala Leu Gly Ala Ile Phe Ala Ile Ser Ser Pro Tyr Lys Ala
465                 470                 475                 480

tgg gcg att ccc aag atc aag aaa aag cag gct gga gcc gtc act gac     1488
Trp Ala Ile Pro Lys Ile Lys Lys Lys Gln Ala Gly Ala Val Thr Asp
                485                 490                 495

aag aag gac gcc aag gag gag gtg aag aag gac acc atc aag acc aag     1536
Lys Lys Asp Ala Lys Glu Glu Val Lys Lys Asp Thr Ile Lys Thr Lys
            500                 505                 510

taa                                                                 1539
```

<210> SEQ ID NO 4
<211> LENGTH: 512
<212> TYPE: PRT
<213> ORGANISM: Yarrowia lipolytica

<400> SEQUENCE: 4

```
Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30
```

-continued

```
Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Met Lys Leu Ser Ser Phe Gly Trp Asn
    130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Pro
    370                 375                 380

Gly Tyr Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445
```

-continued

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510

<210> SEQ ID NO 5
<211> LENGTH: 12
<212> TYPE: PRT
<213> ORGANISM: Artificial Sequence
<220> FEATURE:
<223> OTHER INFORMATION: membrane bound O-acyltransferase motif
<220> FEATURE:
<221> NAME/KEY: misc_feature
<222> LOCATION: (4)..(6)
<223> OTHER INFORMATION: Xaa can be any naturally occurring amino acid
<220> FEATURE:
<221> NAME/KEY: misc_feature
<222> LOCATION: (9)..(11)
<223> OTHER INFORMATION: Xaa can be any naturally occurring amino acid
<300> PUBLICATION INFORMATION:
<301> AUTHORS: Hideo Shindou, Miki Etoa, Ryo Morimotoa and Takao
      Shimizua
<302> TITLE: Identification of membrane O-acyltransferase family motifs
<303> JOURNAL: Biochemical and Biophysical Research Communications
<304> VOLUME: 383
<305> ISSUE: 3
<306> PAGES: 320-325
<307> DATE: 2009-04-08
<313> RELEVANT RESIDUES IN SEQ ID NO: (1)..(12)

<400> SEQUENCE: 5

Trp His Gly Xaa Xaa Xaa Gly Tyr Xaa Xaa Xaa Phe
1               5                   10

<210> SEQ ID NO 6
<211> LENGTH: 6
<212> TYPE: PRT
<213> ORGANISM: Artificial Sequence
<220> FEATURE:
<223> OTHER INFORMATION: membrane bound O-acyltransferase motif
<220> FEATURE:
<221> NAME/KEY: misc_feature
<222> LOCATION: (2)..(5)
<223> OTHER INFORMATION: Xaa can be any naturally occurring amino acid
<300> PUBLICATION INFORMATION:
<301> AUTHORS: Hideo Shindou, Miki Etoa, Ryo Morimotoa and Takao
      Shimizua
<302> TITLE: Identification of membrane O-acyltransferase family motifs
<303> JOURNAL: Biochemical and Biophysical Research Communications
<304> VOLUME: 383
<305> ISSUE: 3
<306> PAGES: 320-325
<307> DATE: 2009-04-08
<313> RELEVANT RESIDUES IN SEQ ID NO: (1)..(6)

<400> SEQUENCE: 6

Tyr Xaa Xaa Xaa Xaa Phe
1               5

<210> SEQ ID NO 7
<211> LENGTH: 9
<212> TYPE: PRT
<213> ORGANISM: Artificial Sequence
<220> FEATURE:
<223> OTHER INFORMATION: membrane bound O-acyltransferase motif
<220> FEATURE:
<221> NAME/KEY: misc_feature

```
<222> LOCATION: (2)..(4)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid
<300> PUBLICATION INFORMATION:
<301> AUTHORS: Hideo Shindou, Miki Etoa, Ryo Morimotoa and Takao
      Shimizua
<302> TITLE: Identification of membrane O-acyltransferase family motifs
<303> JOURNAL: Biochemical and Biophysical Research Communications
<304> VOLUME: 383
<305> ISSUE: 3
<306> PAGES: 320-325
<307> DATE: 2009-04-08
<313> RELEVANT RESIDUES IN SEQ ID NO: (1)..(9)

<400> SEQUENCE: 7

Tyr Xaa Xaa Xaa Tyr Phe Xaa Xaa His
1               5


<210> SEQ ID NO 8
<211> LENGTH: 17
<212> TYPE: PRT
<213> ORGANISM: Artificial Sequence
<220> FEATURE:
<223> OTHER INFORMATION: membrane bound O-acyltransferase motif
<220> FEATURE:
<221> NAME/KEY: MISC_FEATURE
<222> LOCATION: (2)..(2)
<223> OTHER INFORMATION: Xaa = Val [V] or Ile [I]
<220> FEATURE:
<221> NAME/KEY: MISC_FEATURE
<222> LOCATION: (3)..(3)
<223> OTHER INFORMATION: Xaa = Leu [L] or Ile [I]
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa = Leu [L] or Ile [I] or Val [V]
<220> FEATURE:
<221> NAME/KEY: misc_feature
<222> LOCATION: (8)..(15)
<223> OTHER INFORMATION: Xaa can be any naturally occurring amino acid
<300> PUBLICATION INFORMATION:
<302> TITLE: GENES ENCODING A NOVEL TYPE OF LYSOPHOPHATIDYLCHOLINE
      ACYLTRANSFERASES AND THEIR USE TO INCREASE TRIACYLGLYCEROL
      PRODUCTION AND/OR MODIFY FATTY ACID COMPOSITION
<310> PATENT DOCUMENT NUMBER: U.S. Patent Publication No.
      2008-0145867-A1
<311> PATENT FILING DATE: 2007-06-15
<312> PUBLICATION DATE: 2008-06-19
<313> RELEVANT RESIDUES IN SEQ ID NO: (1)..(15)

<400> SEQUENCE: 8

Met Xaa Xaa Xaa Xaa Lys Xaa Xaa Xaa Xaa Xaa Xaa Xaa Xaa Xaa Asp
1               5                   10                  15

Gly


<210> SEQ ID NO 9
<211> LENGTH: 24
<212> TYPE: PRT
<213> ORGANISM: Artificial Sequence
<220> FEATURE:
<223> OTHER INFORMATION: membrane bound O-acyltransferase motif
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
```

<222> LOCATION: (6)..(7)
<223> OTHER INFORMATION: Xaa can be any naturally occurring amino acid
<220> FEATURE:
<221> NAME/KEY: misc_feature
<222> LOCATION: (9)..(11)
<223> OTHER INFORMATION: Xaa can be any naturally occurring amino acid
<220> FEATURE:
<221> NAME/KEY: MISC_FEATURE
<222> LOCATION: (12)..(12)
<223> OTHER INFORMATION: Xaa = Glu [E] or Asp [D]
<220> FEATURE:
<221> NAME/KEY: MISC_FEATURE
<222> LOCATION: (13)..(13)
<223> OTHER INFORMATION: Xaa = Ala [A] or Gly [G]
<220> FEATURE:
<221> NAME/KEY: misc_feature
<222> LOCATION: (14)..(18)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: MISC_FEATURE
<222> LOCATION: (22)..(22)
<223> OTHER INFORMATION: Xaa = Phe [F] or Tyr [Y]
<220> FEATURE:
<221> NAME/KEY: misc_feature
<222> LOCATION: (23)..(23)
<223> OTHER INFORMATION: Xaa can be any naturally occurring amino acid
<300> PUBLICATION INFORMATION:
<302> TITLE: GENES ENCODING A NOVEL TYPE OF LYSOPHOPHATIDYLCHOLINE
      ACYLTRANSFERASES AND THEIR USE TO INCREASE TRIACYLGLYCEROL
      PRODUCTION AND/OR MODIFY FATTY ACID COMPOSITION
<310> PATENT DOCUMENT NUMBER: U.S. Patent Publication No.
      2008-0145867-A1
<311> PATENT FILING DATE: 2007-06-15
<312> PUBLICATION DATE: 2008-06-19
<313> RELEVANT RESIDUES IN SEQ ID NO: (1)..(15)

<400> SEQUENCE: 9

```
Arg Xaa Lys Tyr Tyr Xaa Xaa Trp Xaa Xaa Xaa Xaa Xaa Xaa Xaa Xaa
1               5                   10                  15

Xaa Xaa Gly Xaa Gly Xaa Xaa Gly
            20
```

<210> SEQ ID NO 10
<211> LENGTH: 20
<212> TYPE: PRT
<213> ORGANISM: Artificial Sequence
<220> FEATURE:
<223> OTHER INFORMATION: membrane bound O-acyltransferase motif
<220> FEATURE:
<221> NAME/KEY: misc_feature
<222> LOCATION: (2)..(12)
<223> OTHER INFORMATION: Xaa can be any naturally occurring amino acid
<220> FEATURE:
<221> NAME/KEY: misc_feature
<222> LOCATION: (15)..(16)
<223> OTHER INFORMATION: Xaa can be any naturally occurring amino acid
<220> FEATURE:
<221> NAME/KEY: MISC_FEATURE
<222> LOCATION: (17)..(17)
<223> OTHER INFORMATION: Xaa = Thr [T] or Val [V]
<220> FEATURE:
<221> NAME/KEY: misc_feature
<222> LOCATION: (18)..(19)
<223> OTHER INFORMATION: Xaa can be any naturally occurring amino acid
<300> PUBLICATION INFORMATION:
<302> TITLE: GENES ENCODING A NOVEL TYPE OF LYSOPHOPHATIDYLCHOLINE
      ACYLTRANSFERASES AND THEIR USE TO INCREASE TRIACYLGLYCEROL
      PRODUCTION AND/OR MODIFY FATTY ACID COMPOSITION
<310> PATENT DOCUMENT NUMBER: U.S. Patent Publication No.
      2008-0145867-A1
<311> PATENT FILING DATE: 2007-06-15
<312> PUBLICATION DATE: 2008-06-19

<313> RELEVANT RESIDUES IN SEQ ID NO: (1)..(15)

<400> SEQUENCE: 10

```
Glu Xaa Xaa Xaa Xaa Xaa Xaa Xaa Xaa Xaa Xaa Xaa Trp Asn Xaa Xaa
1               5                   10                  15

Xaa Xaa Xaa Trp
            20
```

<210> SEQ ID NO 11
<211> LENGTH: 15
<212> TYPE: PRT
<213> ORGANISM: Artificial Sequence
<220> FEATURE:
<223> OTHER INFORMATION: membrane bound O-acyltransferase motif
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (12)..(13)
<223> OTHER INFORMATION: Xaa can be any naturally occurring amino acid
<220> FEATURE:
<221> NAME/KEY: MISC_FEATURE
<222> LOCATION: (14)..(14)
<223> OTHER INFORMATION: Xaa = Thr [T] or Phe [F]
<300> PUBLICATION INFORMATION:
<302> TITLE: GENES ENCODING A NOVEL TYPE OF LYSOPHOPHATIDYLCHOLINE ACYLTRANSFERASES AND THEIR USE TO INCREASE TRIACYLGLYCEROL PRODUCTION AND/OR MODIFY FATTY ACID COMPOSITION
<310> PATENT DOCUMENT NUMBER: U.S. Patent Publication No. 2008-0145867-A1
<311> PATENT FILING DATE: 2007-06-15
<312> PUBLICATION DATE: 2008-06-19
<313> RELEVANT RESIDUES IN SEQ ID NO: (1)..(15)

<400> SEQUENCE: 11

```
Ser Ala Xaa Trp His Gly Xaa Xaa Pro Gly Tyr Xaa Xaa Xaa Phe
1               5                   10                  15
```

<210> SEQ ID NO 12
<211> LENGTH: 17
<212> TYPE: PRT
<213> ORGANISM: Artificial Sequence
<220> FEATURE:
<223> OTHER INFORMATION: membrane bound O-acyltransferase motif
<220> FEATURE:
<221> NAME/KEY: MISC_FEATURE
<222> LOCATION: (2)..(2)
<223> OTHER INFORMATION: Xaa = Val [V] or Ile [I]
<220> FEATURE:
<221> NAME/KEY: MISC_FEATURE
<222> LOCATION: (3)..(3)
<223> OTHER INFORMATION: Xaa = Leu [L] or Ile [I] or Val [V]
<220> FEATURE:
<221> NAME/KEY: misc_feature
<222> LOCATION: (4)..(4)
<223> OTHER INFORMATION: Xaa = Ala [A] or Cys [C] or Thr [T] or Val [V]
<220> FEATURE:
<221> NAME/KEY: misc_feature
<222> LOCATION: (5)..(5)
<223> OTHER INFORMATION: Xaa = Gln [Q] or Leu [L] or Met [M]
<220> FEATURE:
<221> NAME/KEY: MISC_FEATURE
<222> LOCATION: (7)..(7)
<223> OTHER INFORMATION: Xaa = Leu [L] or Ile [I] or Met [M] or Val [V]
<220> FEATURE:
<221> NAME/KEY: misc_feature
<222> LOCATION: (8)..(8)
<223> OTHER INFORMATION: Xaa = Ile [I] or Ser [S] or Thr [T] or Tyr [Y]

```
<220> FEATURE:
<221> NAME/KEY: misc_feature
<222> LOCATION: (9)..(9)
<223> OTHER INFORMATION: Xaa = Ala [A] or Gly [G] or Met [M] or Ser [S]
      or Thr [T]
<220> FEATURE:
<221> NAME/KEY: misc_feature
<222> LOCATION: (10)..(10)
<223> OTHER INFORMATION: Xaa = Cys [C] or Leu [L] or Phe [F] or Tyr [Y]
<220> FEATURE:
<221> NAME/KEY: misc_feature
<222> LOCATION: (11)..(11)
<223> OTHER INFORMATION: Xaa = Ala [A] or Cys [C] or Gly [G] or Ser [S]
<220> FEATURE:
<221> NAME/KEY: misc_feature
<222> LOCATION: (12)..(12)
<223> OTHER INFORMATION: Xaa = Cys [C] or Ile [I] or Met [M] or Phe [F]
      or Trp [W] or Tyr [Y]
<220> FEATURE:
<221> NAME/KEY: misc_feature
<222> LOCATION: (13)..(13)
<223> OTHER INFORMATION: Xaa =  Asn [N] or Asp [D] or Glu [E] or Gln [Q]
      or Ser [S]
<220> FEATURE:
<221> NAME/KEY: misc_feature
<222> LOCATION: (14)..(14)
<223> OTHER INFORMATION: Xaa =  Ile [I] or Leu [L] or Tyr [Y] or Val [V]
<220> FEATURE:
<221> NAME/KEY: misc_feature
<222> LOCATION: (15)..(15)
<223> OTHER INFORMATION: Xaa = Ala [A] or Asn [N] or His [H] or Ser [S]
      or Thr [T] or Tyr [Y]
<300> PUBLICATION INFORMATION:
<302> TITLE: GENES ENCODING A NOVEL TYPE OF LYSOPHOPHATIDYLCHOLINE
      ACYLTRANSFERASES AND THEIR USE TO INCREASE TRIACYLGLYCEROL
      PRODUCTION AND/OR MODIFY FATTY ACID COMPOSITION
<310> PATENT DOCUMENT NUMBER: U.S. Patent 7,732,155
<311> PATENT FILING DATE: 2007-06-15
<312> PUBLICATION DATE: 2010-06-08
<313> RELEVANT RESIDUES IN SEQ ID NO: (1)..(17)

<400> SEQUENCE: 12

Met Xaa Xaa Xaa Xaa Lys Xaa Xaa Xaa Xaa Xaa Xaa Xaa Xaa Xaa Asp
1               5                   10                  15

Gly


<210> SEQ ID NO 13
<211> LENGTH: 24
<212> TYPE: PRT
<213> ORGANISM: Artificial Sequence
<220> FEATURE:
<223> OTHER INFORMATION: membrane bound O-acyltransferase motif
<220> FEATURE:
<221> NAME/KEY: misc_feature
<222> LOCATION: (2)..(2)
<223> OTHER INFORMATION: Xaa = Leu [L] or Met [M] or Phe [F] or Pro [P]
      or Trp [W] or Tyr [Y]
<220> FEATURE:
<221> NAME/KEY: misc_feature
<222> LOCATION: (6)..(6)
<223> OTHER INFORMATION: Xaa = Ala [A] or Gly [G] or His [H] or Phe [F]
      or Ser [S]
<220> FEATURE:
<221> NAME/KEY: misc_feature
<222> LOCATION: (7)..(7)
<223> OTHER INFORMATION: Xaa = Ala [A] or Cys [C] or Ile [I] or Val [V]
<220> FEATURE:
<221> NAME/KEY: misc_feature
<222> LOCATION: (9)..(9)
<223> OTHER INFORMATION: Xaa = Glu [E] or Leu [L] or Met [M] or Ser [S]
      or Thr [T] or Tyr [Y]
<220> FEATURE:
<221> NAME/KEY: misc_feature
<222> LOCATION: (10)..(10)
<223> OTHER INFORMATION: Xaa = Asn [N] or Ile [I] or Leu [L]
<220> FEATURE:
```

```
<221> NAME/KEY: misc_feature
<222> LOCATION: (11)..(11)
<223> OTHER INFORMATION: Xaa = Ala [A] or Ser [S] or Thr [T]
<220> FEATURE:
<221> NAME/KEY: MISC_FEATURE
<222> LOCATION: (12)..(12)
<223> OTHER INFORMATION: Xaa = Glu [E] or Asp [D]
<220> FEATURE:
<221> NAME/KEY: MISC_FEATURE
<222> LOCATION: (13)..(13)
<223> OTHER INFORMATION: Xaa = Ala [A] or Gly [G]
<220> FEATURE:
<221> NAME/KEY: misc_feature
<222> LOCATION: (14)..(14)
<223> OTHER INFORMATION: Xaa = Ala [A] or Ile [I] or Ser [S] or Val [V]
<220> FEATURE:
<221> NAME/KEY: misc_feature
<222> LOCATION: (15)..(15)
<223> OTHER INFORMATION: Xaa = Asn [N] or Cys [C] or His [H] or Ile [I]
      or Leu [L] or Ser [S]
<220> FEATURE:
<221> NAME/KEY: misc_feature
<222> LOCATION: (16)..(16)
<223> OTHER INFORMATION: Xaa = Asn [N] or Ile [I] or Val [V]
<220> FEATURE:
<221> NAME/KEY: misc_feature
<222> LOCATION: (17)..(17)
<223> OTHER INFORMATION: Xaa = Ala [A] or Asn [N] or Cys [C] or Ile [I]
      or Leu [L]
<220> FEATURE:
<221> NAME/KEY: misc_feature
<222> LOCATION: (18)..(18)
<223> OTHER INFORMATION: Xaa = Ala [A] or Cys [C] or Ile [I] or Ser [S]
      or Trp [W]
<220> FEATURE:
<221> NAME/KEY: misc_feature
<222> LOCATION: (20)..(20)
<223> OTHER INFORMATION: Xaa = Ala [A] or Ile [I] or Leu [L] or Met [M]
      or Phe [F]
<220> FEATURE:
<221> NAME/KEY: MISC_FEATURE
<222> LOCATION: (22)..(22)
<223> OTHER INFORMATION: Xaa = Phe [F] or Tyr [Y]
<220> FEATURE:
<221> NAME/KEY: misc_feature
<222> LOCATION: (23)..(23)
<223> OTHER INFORMATION: Xaa = Arg [R] or Asn [N] or Glu [E] or Lys [K]
      or Ser [S] or Thr [T]
<300> PUBLICATION INFORMATION:
<302> TITLE: GENES ENCODING A NOVEL TYPE OF LYSOPHOPHATIDYLCHOLINE
      ACYLTRANSFERASES AND THEIR USE TO INCREASE TRIACYLGLYCEROL
      PRODUCTION AND/OR MODIFY FATTY ACID COMPOSITION
<310> PATENT DOCUMENT NUMBER: U.S. Patent 7,732,155
<311> PATENT FILING DATE: 2007-06-15
<312> PUBLICATION DATE: 2010-06-08
<313> RELEVANT RESIDUES IN SEQ ID NO: (1)..(15)

<400> SEQUENCE: 13

Arg Xaa Lys Tyr Tyr Xaa Xaa Trp Xaa Xaa Xaa Xaa Xaa Xaa Xaa Xaa
1               5                   10                  15

Xaa Xaa Gly Xaa Gly Xaa Xaa Gly
            20


<210> SEQ ID NO 14
<211> LENGTH: 20
<212> TYPE: PRT
<213> ORGANISM: Artificial Sequence
<220> FEATURE:
<223> OTHER INFORMATION: membrane bound O-acyltransferase motif
<220> FEATURE:
<221> NAME/KEY: misc_feature
<222> LOCATION: (2)..(2)
<223> OTHER INFORMATION: Xaa = Leu [L] or Met [M] or Phe [F] or Thr [T]
<220> FEATURE:
<221> NAME/KEY: misc_feature
<222> LOCATION: (3)..(3)
```

```
<223> OTHER INFORMATION: Xaa = Ala [A] or Ser [S]
<220> FEATURE:
<221> NAME/KEY: misc_feature
<222> LOCATION: (4)..(4)
<223> OTHER INFORMATION: Xaa = Asp [D] or Gln [Q] or Lys [K] or Pro [P]
      or Thr [T]
<220> FEATURE:
<221> NAME/KEY: misc_feature
<222> LOCATION: (5)..(5)
<223> OTHER INFORMATION: Xaa = Asn [N] or Ser [S]
<220> FEATURE:
<221> NAME/KEY: misc_feature
<222> LOCATION: (6)..(6)
<223> OTHER INFORMATION: Xaa = Ala [A] or Ile [I] or Leu [L] or Met [M]
      or Phe [F] or Ser [S] or Thr [T]
<220> FEATURE:
<221> NAME/KEY: misc_feature
<222> LOCATION: (7)..(7)
<223> OTHER INFORMATION: Xaa = Arg [R] or His [H] or Lys [K] or Val [V]
<220> FEATURE:
<221> NAME/KEY: misc_feature
<222> LOCATION: (8)..(8)
<223> OTHER INFORMATION: Xaa = Asp [D] or Cys [C] or Gly [G] or Glu [E]
      or Gln [Q] or Met [M] or Thr [T]
<220> FEATURE:
<221> NAME/KEY: misc_feature
<222> LOCATION: (9)..(9)
<223> OTHER INFORMATION: Xaa = Ala [A] or Ile [I] or Leu [L] or Met [M]
      or Phe [F] or Tyr [Y]
<220> FEATURE:
<221> NAME/KEY: misc_feature
<222> LOCATION: (10)..(10)
<223> OTHER INFORMATION: Xaa = Ile [I] or Leu [L] or Pro [P] or Ser [S]
<220> FEATURE:
<221> NAME/KEY: misc_feature
<222> LOCATION: (11)..(11)
<223> OTHER INFORMATION: Xaa = Ala [A] or Asn [N] or Asp [D] or Gly [G]
      or Glu [E] or Leu [L]
<220> FEATURE:
<221> NAME/KEY: misc_feature
<222> LOCATION: (12)..(12)
<223> OTHER INFORMATION: Xaa = Ala [A] or Asn [N] or Met [M] or Phe [F]
      or Ser [S] or Val [V]
<220> FEATURE:
<221> NAME/KEY: misc_feature
<222> LOCATION: (15)..(15)
<223> OTHER INFORMATION: Xaa = Cys [C] or Ile [I] or Lys [K] or Met [M]
<220> FEATURE:
<221> NAME/KEY: misc_feature
<222> LOCATION: (16)..(16)
<223> OTHER INFORMATION: Xaa = Asn [N] or Gly [G] or Gln [Q] or Lys [K]
<220> FEATURE:
<221> NAME/KEY: MISC_FEATURE
<222> LOCATION: (17)..(17)
<223> OTHER INFORMATION: Xaa = Thr [T] or Val [V]
<220> FEATURE:
<221> NAME/KEY: misc_feature
<222> LOCATION: (18)..(18)
<223> OTHER INFORMATION: Xaa = Ala [A] or Asn [N] or Ser [S]
<220> FEATURE:
<221> NAME/KEY: misc_feature
<222> LOCATION: (19)..(19)
<223> OTHER INFORMATION: Xaa = Arg [R] or Asn [N] or His [H] or Leu [L]
      or Lys [K] or Thr [T]
<300> PUBLICATION INFORMATION:
<302> TITLE: GENES ENCODING A NOVEL TYPE OF LYSOPHOPHATIDYLCHOLINE
      ACYLTRANSFERASES AND THEIR USE TO INCREASE TRIACYLGLYCEROL
      PRODUCTION AND/OR MODIFY FATTY ACID COMPOSITION
<310> PATENT DOCUMENT NUMBER: U.S. Patent 7,732,155
<311> PATENT FILING DATE: 2007-06-15
<312> PUBLICATION DATE: 2010-06-08
<313> RELEVANT RESIDUES IN SEQ ID NO: (1)..(15)

<400> SEQUENCE: 14

Glu Xaa Xaa Xaa Xaa Xaa Xaa Xaa Xaa Xaa Xaa Xaa Trp Asn Xaa Xaa
1               5                   10                  15

Xaa Xaa Xaa Trp
```

```
            20


<210> SEQ ID NO 15
<211> LENGTH: 15
<212> TYPE: PRT
<213> ORGANISM: Artificial Sequence
<220> FEATURE:
<223> OTHER INFORMATION: membrane bound O-acyltransferase motif
<220> FEATURE:
<221> NAME/KEY: misc_feature
<222> LOCATION: (3)..(3)
<223> OTHER INFORMATION: Xaa = Ile [I] or Met [M] or Phe [F] or Val [V]
<220> FEATURE:
<221> NAME/KEY: misc_feature
<222> LOCATION: (7)..(7)
<223> OTHER INFORMATION: Xaa = Leu [L] or Phe [F] or Thr [T] or Val [V]
<220> FEATURE:
<221> NAME/KEY: misc_feature
<222> LOCATION: (8)..(8)
<223> OTHER INFORMATION: Xaa = Arg [R] or Ser [S] or Tyr [Y]
<220> FEATURE:
<221> NAME/KEY: misc_feature
<222> LOCATION: (12)..(12)
<223> OTHER INFORMATION: Xaa = Ile [I] or Met [M] or Tyr [Y]
<220> FEATURE:
<221> NAME/KEY: misc_feature
<222> LOCATION: (13)..(13)
<223> OTHER INFORMATION: Xaa =  Ile [I] or Leu [L] or Met [M] or Phe [F]
<220> FEATURE:
<221> NAME/KEY: MISC_FEATURE
<222> LOCATION: (14)..(14)
<223> OTHER INFORMATION: Xaa = Thr [T] or Phe [F]
<300> PUBLICATION INFORMATION:
<302> TITLE: GENES ENCODING A NOVEL TYPE OF LYSOPHOPHATIDYLCHOLINE
      ACYLTRANSFERASES AND THEIR USE TO INCREASE TRIACYLGLYCEROL
      PRODUCTION AND/OR MODIFY FATTY ACID COMPOSITION
<310> PATENT DOCUMENT NUMBER: U.S. Patent 7,732,155
<311> PATENT FILING DATE: 2007-06-15
<312> PUBLICATION DATE: 2010-06-08
<313> RELEVANT RESIDUES IN SEQ ID NO: (1)..(15)

<400> SEQUENCE: 15

Ser Ala Xaa Trp His Gly Xaa Xaa Pro Gly Tyr Xaa Xaa Xaa Phe
1               5                   10                  15


<210> SEQ ID NO 16
<211> LENGTH: 7
<212> TYPE: PRT
<213> ORGANISM: Artificial Sequence
<220> FEATURE:
<223> OTHER INFORMATION: membrane bound O-acyltransferase motif
<220> FEATURE:
<221> NAME/KEY: MISC_FEATURE
<222> LOCATION: (2)..(2)
<223> OTHER INFORMATION: Xaa = Val [V] or Ile [I]
<220> FEATURE:
<221> NAME/KEY: misc_feature
<222> LOCATION: (4)..(5)
<223> OTHER INFORMATION: Xaa can be any naturally occurring amino acid
<300> PUBLICATION INFORMATION:
<302> TITLE: IMPROVEMENT OF LONG CHAIN OMEGA-3 AND OMEGA-6
      POLYUNSATURATED FATTY ACID BIOSYNTHESIS BY EXPRESSION OF ACYL-CoA
      LYSOPHOSPHOLIPID ACYLTRANSFERASES
<310> PATENT DOCUMENT NUMBER: U.S. Pat. Pub. No. 2010-0317882-A1
<311> PATENT FILING DATE: 2010-06-14
<312> PUBLICATION DATE: 2010-12-16
<313> RELEVANT RESIDUES IN SEQ ID NO: (1)..(7)

<400> SEQUENCE: 16

Met Xaa Leu Xaa Xaa Lys Leu
1               5


<210> SEQ ID NO 17
<211> LENGTH: 8
```

<212> TYPE: PRT
<213> ORGANISM: Artificial Sequence
<220> FEATURE:
<223> OTHER INFORMATION: membrane bound O-acyltransferase motif
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid
<300> PUBLICATION INFORMATION:
<302> TITLE: IMPROVEMENT OF LONG CHAIN OMEGA-3 AND OMEGA-6
POLYUNSATURATED FATTY ACID BIOSYNTHESIS BY EXPRESSION OF ACYL-CoA
LYSOPHOSPHOLIPID ACYLTRANSFERASES
<310> PATENT DOCUMENT NUMBER: U.S. Pat. Pub. No. 2010-0317882-A1
<311> PATENT FILING DATE: 2010-06-14
<312> PUBLICATION DATE: 2010-12-16
<313> RELEVANT RESIDUES IN SEQ ID NO: (1)..(8)

<400> SEQUENCE: 17

Arg Xaa Lys Tyr Tyr Xaa Xaa Trp
1 5

<210> SEQ ID NO 18
<211> LENGTH: 6
<212> TYPE: PRT
<213> ORGANISM: Artificial Sequence
<220> FEATURE:
<223> OTHER INFORMATION: membrane bound O-acyltransferase motif
<220> FEATURE:
<221> NAME/KEY: misc_feature
<222> LOCATION: (3)..(3)
<223> OTHER INFORMATION: Xaa can be any naturally occurring amino acid
<300> PUBLICATION INFORMATION:
<302> TITLE: IMPROVEMENT OF LONG CHAIN OMEGA-3 AND OMEGA-6
POLYUNSATURATED FATTY ACID BIOSYNTHESIS BY EXPRESSION OF ACYL-CoA
LYSOPHOSPHOLIPID ACYLTRANSFERASES
<310> PATENT DOCUMENT NUMBER: U.S. Pat. Pub. No. 2010-0317882-A1
<311> PATENT FILING DATE: 2010-06-14
<312> PUBLICATION DATE: 2010-12-16
<313> RELEVANT RESIDUES IN SEQ ID NO: (1)..(6)

<400> SEQUENCE: 18

Ser Ala Xaa Trp His Gly
1 5

<210> SEQ ID NO 19
<211> LENGTH: 512
<212> TYPE: PRT
<213> ORGANISM: Yarrowia lipolytica
<220> FEATURE:
<221> NAME/KEY: misc_feature
<222> LOCATION: (133)..(148)
<223> OTHER INFORMATION: Xaa can be any naturally occurring amino acid
<220> FEATURE:
<221> NAME/KEY: misc_feature
<222> LOCATION: (378)..(378)
<223> OTHER INFORMATION: Xaa can be any naturally occurring amino acid
<220> FEATURE:
<221> NAME/KEY: misc_feature
<222> LOCATION: (382)..(383)
<223> OTHER INFORMATION: Xaa can be any naturally occurring amino acid
<220> FEATURE:
<221> NAME/KEY: misc_feature
<222> LOCATION: (385)..(385)
<223> OTHER INFORMATION: Xaa can be any naturally occurring amino acid
<220> FEATURE:
<221> NAME/KEY: misc_feature
<222> LOCATION: (388)..(390)
<223> OTHER INFORMATION: Xaa can be any naturally occurring amino acid

<400> SEQUENCE: 19

-continued

```
Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Xaa Xaa Xaa Xaa Xaa Xaa Xaa Xaa Xaa Xaa Xaa Xaa
    130                 135                 140

Xaa Xaa Xaa Xaa Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Xaa Trp His Gly Xaa Xaa Pro
    370                 375                 380

Xaa Tyr Tyr Xaa Xaa Xaa Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
```

```
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510


<210> SEQ ID NO 20
<211> LENGTH: 945
<212> TYPE: DNA
<213> ORGANISM: Mortierella alpina
<220> FEATURE:
<221> NAME/KEY: CDS
<222> LOCATION: (1)..(945)
<223> OTHER INFORMATION: LPAAT1
<300> PUBLICATION INFORMATION:
<302> TITLE: High eicosapentaenoic acid producing strains of Yarrowia
      lipolytica
<310> PATENT DOCUMENT NUMBER: U.S. 7,879,591
<311> PATENT FILING DATE: 2009-06-19
<312> PUBLICATION DATE: 2011-02-01
<313> RELEVANT RESIDUES IN SEQ ID NO: (1)..(945)
<300> PUBLICATION INFORMATION:
<302> TITLE: High eicosapentaenoic acid producing strains of Yarrowia
      lipolytica
<310> PATENT DOCUMENT NUMBER: WO 2006/052870
<311> PATENT FILING DATE: 2005-11-03
<312> PUBLICATION DATE: 2006-05-18
<313> RELEVANT RESIDUES IN SEQ ID NO: (1)..(945)

<400> SEQUENCE: 20

atg tcc ata ggt tct tcc aat cct gtc ctg ctg gca gcg atc ccc ttc       48
Met Ser Ile Gly Ser Ser Asn Pro Val Leu Leu Ala Ala Ile Pro Phe
1               5                   10                  15

gtc tac ctc ttc gtc ctc cct cgt gtc ctc gcc ttc ctc cct caa aag       96
Val Tyr Leu Phe Val Leu Pro Arg Val Leu Ala Phe Leu Pro Gln Lys
            20                  25                  30

gcc cag ttc ctc gca aaa tgc atc gtg gtc ttg atc gcc acc ctt atc      144
Ala Gln Phe Leu Ala Lys Cys Ile Val Val Leu Ile Ala Thr Leu Ile
        35                  40                  45

atg tcc gtc gca ggc tgc ttc att tcc atc gtc tgt gcg ctc ctc gat      192
Met Ser Val Ala Gly Cys Phe Ile Ser Ile Val Cys Ala Leu Leu Asp
    50                  55                  60

aaa cgc tat gtg atc aac tac gtc gtc tca aga ctc ttc tca ttc ctc      240
Lys Arg Tyr Val Ile Asn Tyr Val Val Ser Arg Leu Phe Ser Phe Leu
65                  70                  75                  80

gct gca aga ccc tgc ggt gtc acc tac aag atc gtc ggc gag gaa cat      288
Ala Ala Arg Pro Cys Gly Val Thr Tyr Lys Ile Val Gly Glu Glu His
                85                  90                  95

ctg gac aag tac ccc gcc att gtc gtc tgc aac cac cag agc tcc atg      336
Leu Asp Lys Tyr Pro Ala Ile Val Val Cys Asn His Gln Ser Ser Met
            100                 105                 110

gac atg atg gtc ctg gga cgc gtc ttc cca aag cac tgt gtc gtc atg      384
Asp Met Met Val Leu Gly Arg Val Phe Pro Lys His Cys Val Val Met
        115                 120                 125

gca aag aag gaa ctt ctt tac ttt ccg ttc ctg ggc atg ttt atg aag      432
Ala Lys Lys Glu Leu Leu Tyr Phe Pro Phe Leu Gly Met Phe Met Lys
    130                 135                 140
```

```
ctg agt aac gcc atc ttc att gac cgc aag aac cac aag aag gcg atc      480
Leu Ser Asn Ala Ile Phe Ile Asp Arg Lys Asn His Lys Lys Ala Ile
145                 150                 155                 160

gag tcc acc acc caa gct gtc gcc gac atg aag aag cac aac tct gga      528
Glu Ser Thr Thr Gln Ala Val Ala Asp Met Lys Lys His Asn Ser Gly
                165                 170                 175

atc tgg att ttc ccc gaa gga aca cgt tcc cgc ttg gac aag gcc gat      576
Ile Trp Ile Phe Pro Glu Gly Thr Arg Ser Arg Leu Asp Lys Ala Asp
            180                 185                 190

ctc ttg ccc ttc aag aag gga gcc ttc cac ctc gcc att caa gcc caa      624
Leu Leu Pro Phe Lys Lys Gly Ala Phe His Leu Ala Ile Gln Ala Gln
        195                 200                 205

ctc ccg atc ctc ccc atc atc tcg caa gga tac tca cac atc tac gat      672
Leu Pro Ile Leu Pro Ile Ile Ser Gln Gly Tyr Ser His Ile Tyr Asp
    210                 215                 220

tcg tca aaa cgc tac ttc ccc ggt gga gag ctc gag atc aga gtc ctg      720
Ser Ser Lys Arg Tyr Phe Pro Gly Gly Glu Leu Glu Ile Arg Val Leu
225                 230                 235                 240

gaa cct atc ccc acc acg gga ttg acc aca gac gat gtg aac gac ctg      768
Glu Pro Ile Pro Thr Thr Gly Leu Thr Thr Asp Asp Val Asn Asp Leu
                245                 250                 255

atg gac aag act cgc aac ctg atg ctg aag cac ctc aag gag atg gat      816
Met Asp Lys Thr Arg Asn Leu Met Leu Lys His Leu Lys Glu Met Asp
            260                 265                 270

tct caa tac tcc tcc tcc acc gct gaa aac gga tcg acc cat att gac      864
Ser Gln Tyr Ser Ser Ser Thr Ala Glu Asn Gly Ser Thr His Ile Asp
        275                 280                 285

gcc gat atc gca aag tca act gcc aca tcg atc gga aac acg gac gat      912
Ala Asp Ile Ala Lys Ser Thr Ala Thr Ser Ile Gly Asn Thr Asp Asp
    290                 295                 300

gct atc aca aag agg agg aca cca aaa gag tag                          945
Ala Ile Thr Lys Arg Arg Thr Pro Lys Glu
305                 310
```

<210> SEQ ID NO 21
<211> LENGTH: 314
<212> TYPE: PRT
<213> ORGANISM: Mortierella alpina

<400> SEQUENCE: 21

```
Met Ser Ile Gly Ser Ser Asn Pro Val Leu Leu Ala Ala Ile Pro Phe
1               5                   10                  15

Val Tyr Leu Phe Val Leu Pro Arg Val Leu Ala Phe Leu Pro Gln Lys
            20                  25                  30

Ala Gln Phe Leu Ala Lys Cys Ile Val Val Leu Ile Ala Thr Leu Ile
        35                  40                  45

Met Ser Val Ala Gly Cys Phe Ile Ser Ile Val Cys Ala Leu Leu Asp
    50                  55                  60

Lys Arg Tyr Val Ile Asn Tyr Val Val Ser Arg Leu Phe Ser Phe Leu
65                  70                  75                  80

Ala Ala Arg Pro Cys Gly Val Thr Tyr Lys Ile Val Gly Glu Glu His
                85                  90                  95

Leu Asp Lys Tyr Pro Ala Ile Val Val Cys Asn His Gln Ser Ser Met
            100                 105                 110

Asp Met Met Val Leu Gly Arg Val Phe Pro Lys His Cys Val Val Met
        115                 120                 125

Ala Lys Lys Glu Leu Leu Tyr Phe Pro Phe Leu Gly Met Phe Met Lys
    130                 135                 140
```

-continued

```
Leu Ser Asn Ala Ile Phe Ile Asp Arg Lys Asn His Lys Lys Ala Ile
145                 150                 155                 160

Glu Ser Thr Thr Gln Ala Val Ala Asp Met Lys Lys His Asn Ser Gly
                165                 170                 175

Ile Trp Ile Phe Pro Glu Gly Thr Arg Ser Arg Leu Asp Lys Ala Asp
            180                 185                 190

Leu Leu Pro Phe Lys Lys Gly Ala Phe His Leu Ala Ile Gln Ala Gln
        195                 200                 205

Leu Pro Ile Leu Pro Ile Ile Ser Gln Gly Tyr Ser His Ile Tyr Asp
    210                 215                 220

Ser Ser Lys Arg Tyr Phe Pro Gly Gly Glu Leu Glu Ile Arg Val Leu
225                 230                 235                 240

Glu Pro Ile Pro Thr Thr Gly Leu Thr Thr Asp Asp Val Asn Asp Leu
                245                 250                 255

Met Asp Lys Thr Arg Asn Leu Met Leu Lys His Leu Lys Glu Met Asp
            260                 265                 270

Ser Gln Tyr Ser Ser Ser Thr Ala Glu Asn Gly Ser Thr His Ile Asp
        275                 280                 285

Ala Asp Ile Ala Lys Ser Thr Ala Thr Ser Ile Gly Asn Thr Asp Asp
    290                 295                 300

Ala Ile Thr Lys Arg Arg Thr Pro Lys Glu
305                 310


<210> SEQ ID NO 22
<211> LENGTH: 1549
<212> TYPE: DNA
<213> ORGANISM: Yarrowia lipolytica
<220> FEATURE:
<221> NAME/KEY: CDS
<222> LOCATION: (501)..(1349)
<223> OTHER INFORMATION: LPAAT1
<300> PUBLICATION INFORMATION:
<302> TITLE: High eicosapentaenoic acid producing strains of Yarrowia
      lipolytica
<310> PATENT DOCUMENT NUMBER: U.S. 7,932,077
<311> PATENT FILING DATE: 2005-11-02
<312> PUBLICATION DATE: 2011-04-26
<313> RELEVANT RESIDUES IN SEQ ID NO: (1)..(1549)
<300> PUBLICATION INFORMATION:
<302> TITLE: High eicosapentaenoic acid producing strains of Yarrowia
      lipolytica
<310> PATENT DOCUMENT NUMBER: WO 2006/052870
<311> PATENT FILING DATE: 2005-11-03
<312> PUBLICATION DATE: 2006-05-18
<313> RELEVANT RESIDUES IN SEQ ID NO: (1)..(1549)

<400> SEQUENCE: 22

cacagcataa taccacggca tgaccccgct gactccaacc ttcatttcgg cacatgtagg      60

tgcacaaggg acttcaagag gggccaattt catgcggaca catggcgcaa aaaacgcccg     120

actttgatta cacagacacg taataacgac gaagccgaga tgagcacacg tggccaagtc     180

tgccaatggc cccctggacc cccctgacaa agtttcccaa caagcccagc cgtgcatggt     240

gtgtttttgt gcggagacac acgccaatta ggctcatttg agggtatgca gcgaaaaaaa     300

attagtgtgg gtagtttgtt tgcaggaatc aagtgggtgg ttgaaaaaca agaaagagcg     360

acgacaagag agagagaaaa agagagagag actccataaa gcgtgcatca aaattaaggt     420

gtgtgactat ccgaaaacca aacatgaaca gttggatata tgtcgctgtg attgcagttg     480

ctgccgttct cattgcccga atg tcc gtt gca tcc aag ctc gtc ttc tac gtc     533
                      Met Ser Val Ala Ser Lys Leu Val Phe Tyr Val
                      1               5                   10
```

-continued

```
cgc gcc gcc atc gcc gtg gtc atc ttt gcc gcc tgt gcc acc tac ggc      581
Arg Ala Ala Ile Ala Val Val Ile Phe Ala Ala Cys Ala Thr Tyr Gly
            15                  20                  25

gtg ctg gcg tcc acc att ctc acc gcc atc ggc aag cag ggc ctg gcc      629
Val Leu Ala Ser Thr Ile Leu Thr Ala Ile Gly Lys Gln Gly Leu Ala
        30                  35                  40

caa tgg acc gtt gcc aga gcc ttc tac tac tcg gtg cgc atc ttc ctg      677
Gln Trp Thr Val Ala Arg Ala Phe Tyr Tyr Ser Val Arg Ile Phe Leu
    45                  50                  55

ggt atc agc atc aag ctg cgt agc cgg cag gtg acc gga acc gcc ggt      725
Gly Ile Ser Ile Lys Leu Arg Ser Arg Gln Val Thr Gly Thr Ala Gly
60                  65                  70                  75

ctg gat gcc tcc aag atc cag gtc gcc aac acc acc aag ccc att gac      773
Leu Asp Ala Ser Lys Ile Gln Val Ala Asn Thr Thr Lys Pro Ile Asp
                80                  85                  90

gac atc acc aaa cac ctg ccc cga cca tgc att ctg att tcc aac cac      821
Asp Ile Thr Lys His Leu Pro Arg Pro Cys Ile Leu Ile Ser Asn His
            95                  100                 105

cag aac gaa atg gac att ctg gtg ctc ggt cgc atc ttc ccc cag tac      869
Gln Asn Glu Met Asp Ile Leu Val Leu Gly Arg Ile Phe Pro Gln Tyr
        110                 115                 120

tgc tcc gtc acc gcc aaa aag gcc ctc aag tgg tac cct ctg ctg ggc      917
Cys Ser Val Thr Ala Lys Lys Ala Leu Lys Trp Tyr Pro Leu Leu Gly
    125                 130                 135

cag ttc atg gcg ctg tcc ggc acc atc ttc ctg gac cga aag gac cga      965
Gln Phe Met Ala Leu Ser Gly Thr Ile Phe Leu Asp Arg Lys Asp Arg
140                 145                 150                 155

acc aag tcc gtg cag acc ctc ggc ggc gcc gtc aag acc atc cag agc     1013
Thr Lys Ser Val Gln Thr Leu Gly Gly Ala Val Lys Thr Ile Gln Ser
                160                 165                 170

ggc aac gga ggc aag ggc cag agc gtc ttc atg ttc ccc gag gga acc     1061
Gly Asn Gly Gly Lys Gly Gln Ser Val Phe Met Phe Pro Glu Gly Thr
            175                 180                 185

cga tcc tac tcc aag gac gtc ggc atc atg ccc ttc aag aag ggc tgt     1109
Arg Ser Tyr Ser Lys Asp Val Gly Ile Met Pro Phe Lys Lys Gly Cys
        190                 195                 200

ttc cac ctg gcg gtc cag tcg ggc gct ccc att gtc ccc gtg gtg gtc     1157
Phe His Leu Ala Val Gln Ser Gly Ala Pro Ile Val Pro Val Val Val
    205                 210                 215

cag aac acc tcc cga atg ttt tct ttc ggc cga ggc aag ctg gac gcc     1205
Gln Asn Thr Ser Arg Met Phe Ser Phe Gly Arg Gly Lys Leu Asp Ala
220                 225                 230                 235

gga gag atc ctt gtc gac gtc ctg agc ccc att gag acc aag ggt ctg     1253
Gly Glu Ile Leu Val Asp Val Leu Ser Pro Ile Glu Thr Lys Gly Leu
                240                 245                 250

gac gcc agc aac gtc gac gct ctc atg gcc acc act tat aag gcc atg     1301
Asp Ala Ser Asn Val Asp Ala Leu Met Ala Thr Thr Tyr Lys Ala Met
            255                 260                 265

tgc gag act gcc gac cag att ggc tac gct ggc cag aag act cag tag     1349
Cys Glu Thr Ala Asp Gln Ile Gly Tyr Ala Gly Gln Lys Thr Gln
        270                 275                 280

agactgcagc acaagaagtg cttgtagcta ctttaggaga gagataggta atatgaaaca   1409

tttttcagat cgacacccac ggcgaaccat tggctgtgga gctatgggtg aatggattaa   1469

tatagcaacg aaatctacct cgattaccaa cgcaaaacga gcccactttc tctgtactgt   1529

gctatatcgt gtatacccca                                                1549
```

<210> SEQ ID NO 23
<211> LENGTH: 282

<212> TYPE: PRT
<213> ORGANISM: Yarrowia lipolytica

<400> SEQUENCE: 23

```
Met Ser Val Ala Ser Lys Leu Val Phe Tyr Val Arg Ala Ala Ile Ala
1               5                   10                  15

Val Val Ile Phe Ala Ala Cys Ala Thr Tyr Gly Val Leu Ala Ser Thr
            20                  25                  30

Ile Leu Thr Ala Ile Gly Lys Gln Gly Leu Ala Gln Trp Thr Val Ala
        35                  40                  45

Arg Ala Phe Tyr Tyr Ser Val Arg Ile Phe Leu Gly Ile Ser Ile Lys
    50                  55                  60

Leu Arg Ser Arg Gln Val Thr Gly Thr Ala Gly Leu Asp Ala Ser Lys
65                  70                  75                  80

Ile Gln Val Ala Asn Thr Thr Lys Pro Ile Asp Asp Ile Thr Lys His
                85                  90                  95

Leu Pro Arg Pro Cys Ile Leu Ile Ser Asn His Gln Asn Glu Met Asp
            100                 105                 110

Ile Leu Val Leu Gly Arg Ile Phe Pro Gln Tyr Cys Ser Val Thr Ala
        115                 120                 125

Lys Lys Ala Leu Lys Trp Tyr Pro Leu Leu Gly Gln Phe Met Ala Leu
    130                 135                 140

Ser Gly Thr Ile Phe Leu Asp Arg Lys Asp Arg Thr Lys Ser Val Gln
145                 150                 155                 160

Thr Leu Gly Gly Ala Val Lys Thr Ile Gln Ser Gly Asn Gly Gly Lys
                165                 170                 175

Gly Gln Ser Val Phe Met Phe Pro Glu Gly Thr Arg Ser Tyr Ser Lys
            180                 185                 190

Asp Val Gly Ile Met Pro Phe Lys Lys Gly Cys Phe His Leu Ala Val
        195                 200                 205

Gln Ser Gly Ala Pro Ile Val Pro Val Val Val Gln Asn Thr Ser Arg
    210                 215                 220

Met Phe Ser Phe Gly Arg Gly Lys Leu Asp Ala Gly Glu Ile Leu Val
225                 230                 235                 240

Asp Val Leu Ser Pro Ile Glu Thr Lys Gly Leu Asp Ala Ser Asn Val
                245                 250                 255

Asp Ala Leu Met Ala Thr Thr Tyr Lys Ala Met Cys Glu Thr Ala Asp
            260                 265                 270

Gln Ile Gly Tyr Ala Gly Gln Lys Thr Gln
        275                 280
```

<210> SEQ ID NO 24
<211> LENGTH: 303
<212> TYPE: PRT
<213> ORGANISM: Saccharomyces cerevisiae
<220> FEATURE:
<221> NAME/KEY: MISC_FEATURE
<222> LOCATION: (1)..(303)
<223> OTHER INFORMATION: Slc1p; GenBank Accession No. NP_010231

<400> SEQUENCE: 24

```
Met Ser Val Ile Gly Arg Phe Leu Tyr Tyr Leu Arg Ser Val Leu Val
1               5                   10                  15

Val Leu Ala Leu Ala Gly Cys Gly Phe Tyr Gly Val Ile Ala Ser Ile
            20                  25                  30

Leu Cys Thr Leu Ile Gly Lys Gln His Leu Ala Gln Trp Ile Thr Ala
        35                  40                  45
```

```
Arg Cys Phe Tyr His Val Met Lys Leu Met Leu Gly Leu Asp Val Lys
    50                  55                  60

Val Val Gly Glu Glu Asn Leu Ala Lys Lys Pro Tyr Ile Met Ile Ala
65                  70                  75                  80

Asn His Gln Ser Thr Leu Asp Ile Phe Met Leu Gly Arg Ile Phe Pro
                85                  90                  95

Pro Gly Cys Thr Val Thr Ala Lys Lys Ser Leu Lys Tyr Val Pro Phe
            100                 105                 110

Leu Gly Trp Phe Met Ala Leu Ser Gly Thr Tyr Phe Leu Asp Arg Ser
        115                 120                 125

Lys Arg Gln Glu Ala Ile Asp Thr Leu Asn Lys Gly Leu Glu Asn Val
    130                 135                 140

Lys Lys Asn Lys Arg Ala Leu Trp Val Phe Pro Glu Gly Thr Arg Ser
145                 150                 155                 160

Tyr Thr Ser Glu Leu Thr Met Leu Pro Phe Lys Lys Gly Ala Phe His
                165                 170                 175

Leu Ala Gln Gln Gly Lys Ile Pro Ile Val Pro Val Val Val Ser Asn
            180                 185                 190

Thr Ser Thr Leu Val Ser Pro Lys Tyr Gly Val Phe Asn Arg Gly Cys
        195                 200                 205

Met Ile Val Arg Ile Leu Lys Pro Ile Ser Thr Glu Asn Leu Thr Lys
    210                 215                 220

Asp Lys Ile Gly Glu Phe Ala Glu Lys Val Arg Asp Gln Met Val Asp
225                 230                 235                 240

Thr Leu Lys Glu Ile Gly Tyr Ser Pro Ala Ile Asn Asp Thr Thr Leu
                245                 250                 255

Pro Pro Gln Ala Ile Glu Tyr Ala Ala Leu Gln His Asp Lys Lys Val
            260                 265                 270

Asn Lys Lys Ile Lys Asn Glu Pro Val Pro Ser Val Ser Ile Ser Asn
        275                 280                 285

Asp Val Asn Thr His Asn Glu Gly Ser Ser Val Lys Lys Met His
    290                 295                 300


<210> SEQ ID NO 25
<211> LENGTH: 7
<212> TYPE: PRT
<213> ORGANISM: Artificial Sequence
<220> FEATURE:
<223> OTHER INFORMATION: 1-acyl-sn-glycerol-3-phosphate acyltransferase
      motif
<220> FEATURE:
<221> NAME/KEY: misc_feature
<222> LOCATION: (3)..(6)
<223> OTHER INFORMATION: Xaa can be any naturally occurring amino acid

<400> SEQUENCE: 25

Asn His Xaa Xaa Xaa Xaa Asp
1               5


<210> SEQ ID NO 26
<211> LENGTH: 4
<212> TYPE: PRT
<213> ORGANISM: Artificial Sequence
<220> FEATURE:
<223> OTHER INFORMATION: 1-acyl-sn-glycerol-3-phosphate acyltransferase
      motif

<400> SEQUENCE: 26

Glu Gly Thr Arg
```

1

<210> SEQ ID NO 27
<211> LENGTH: 7
<212> TYPE: PRT
<213> ORGANISM: Artificial Sequence
<220> FEATURE:
<223> OTHER INFORMATION: 1-acyl-sn-glycerol-3-phosphate acyltransferase
motif
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa = Asp [D] or Arg [R]
<300> PUBLICATION INFORMATION:
<301> AUTHORS: Tal M. Lewin, Ping Wang, and Rosalind A. Coleman
<302> TITLE: Analysis of Amino Acid Motifs Diagnostic for the
sn-Glycerol-3-phosphate Acyltransferase Reaction
<303> JOURNAL: Biochemistry
<304> VOLUME: 38
<305> ISSUE: 18
<306> PAGES: 57645771
<307> DATE: 1999-04-15
<313> RELEVANT RESIDUES IN SEQ ID NO: (1)..(7)
<300> PUBLICATION INFORMATION:
<301> AUTHORS: Atsushi Yamashita, Hiroki Nakanishia, Hiroshi Suzukia,
Ryo Kamataa, Ken Tanakaa, Keizo Wakua and Takayuki Sugiura
<302> TITLE: Topology of acyltransferase motifs and substrate
specificity and accessibility in 1-acyl-sn-glycero-3-phosphate
acyltransferase 1
<303> JOURNAL: Biochimica et Biophysica Acta
<304> VOLUME: 1771
<305> ISSUE: 9
<306> PAGES: 1202-1215
<307> DATE: 2007-07-17
<313> RELEVANT RESIDUES IN SEQ ID NO: (1)..(7)

<400> SEQUENCE: 27

Gly Xaa Xaa Phe Ile Xaa Arg
1               5

<210> SEQ ID NO 28
<211> LENGTH: 6
<212> TYPE: PRT
<213> ORGANISM: Artificial Sequence
<220> FEATURE:
<223> OTHER INFORMATION: 1-acyl-sn-glycerol-3-phosphate acyltransferase
motif
<220> FEATURE:
<221> NAME/KEY: MISC_FEATURE
<222> LOCATION: (1)..(1)
<223> OTHER INFORMATION: Xaa = Val [V] or Ile [I]
<220> FEATURE:
<221> NAME/KEY: MISC_FEATURE
<222> LOCATION: (2)..(2)
<223> OTHER INFORMATION: Xaa = Pro [P] or Xaa
<220> FEATURE:
<221> NAME/KEY: MISC_FEATURE
<222> LOCATION: (3)..(3)
<223> OTHER INFORMATION: Xaa = Ile [I] or Val [V] or Leu [L]
<220> FEATURE:
<221> NAME/KEY: MISC_FEATURE
<222> LOCATION: (4)..(4)
<223> OTHER INFORMATION: Xaa = Ile [I] or Val [V]
<220> FEATURE:
<221> NAME/KEY: MISC_FEATURE
<222> LOCATION: (6)..(6)
<223> OTHER INFORMATION: Xaa =  Val [V] or Ile [I]
<300> PUBLICATION INFORMATION:
<301> AUTHORS: Atsushi Yamashita, Hiroki Nakanishia, Hiroshi Suzukia,
Ryo Kamataa, Ken Tanakaa, Keizo Wakua and Takayuki Sugiura
<302> TITLE: Topology of acyltransferase motifs and substrate
specificity and accessibility in 1-acyl-sn-glycero-3-phosphate acyltransferase 1
<303> JOURNAL: Biochimica et Biophysica Acta
<304> VOLUME: 1771
<305> ISSUE: 9
<306> PAGES: 1202-1215
<307> DATE: 2007-07-17
<313> RELEVANT RESIDUES IN SEQ ID NO: (1)..(6)

<400> SEQUENCE: 28

Xaa Xaa Xaa Xaa Pro Xaa
1 5

<210> SEQ ID NO 29
<211> LENGTH: 6
<212> TYPE: PRT
<213> ORGANISM: Artificial Sequence
<220> FEATURE:
<223> OTHER INFORMATION: 1-acyl-sn-glycerol-3-phosphate acyltransferase motif
<300> PUBLICATION INFORMATION:
<301> AUTHORS: Atsushi Yamashita, Hiroki Nakanishia, Hiroshi Suzukia, Ryo Kamataa, Ken Tanakaa, Keizo Wakua and Takayuki Sugiura
<302> TITLE: Topology of acyltransferase motifs and substrate specificity and accessibility in 1-acyl-sn-glycero-3-phosphate acyltransferase 1
<303> JOURNAL: Biochimica et Biophysica Acta
<304> VOLUME: 1771
<305> ISSUE: 9
<306> PAGES: 1202-1215
<307> DATE: 2007-07-17
<313> RELEVANT RESIDUES IN SEQ ID NO: (1)..(6)

<400> SEQUENCE: 29

Ile Val Pro Ile Val Met
1 5

<210> SEQ ID NO 30
<211> LENGTH: 661
<212> TYPE: PRT
<213> ORGANISM: Saccharomyces cerevisiae
<220> FEATURE:
<221> NAME/KEY: MISC_FEATURE
<222> LOCATION: (1)..(661)
<223> OTHER INFORMATION: GenBank Accession No. P40345

<400> SEQUENCE: 30

Met Gly Thr Leu Phe Arg Arg Asn Val Gln Asn Gln Lys Ser Asp Ser
1 5 10 15

Asp Glu Asn Asn Lys Gly Gly Ser Val His Asn Lys Arg Glu Ser Arg
20 25 30

Asn His Ile His His Gln Gln Gly Leu Gly His Lys Arg Arg Arg Gly
35 40 45

Ile Ser Gly Ser Ala Lys Arg Asn Glu Arg Gly Lys Asp Phe Asp Arg
50 55 60

Lys Arg Asp Gly Asn Gly Arg Lys Arg Trp Arg Asp Ser Arg Arg Leu
65 70 75 80

Ile Phe Ile Leu Gly Ala Phe Leu Gly Val Leu Leu Pro Phe Ser Phe
85 90 95

Gly Ala Tyr His Val His Asn Ser Asp Ser Asp Leu Phe Asp Asn Phe
100 105 110

Val Asn Phe Asp Ser Leu Lys Val Tyr Leu Asp Asp Trp Lys Asp Val
115 120 125

Leu Pro Gln Gly Ile Ser Ser Phe Ile Asp Asp Ile Gln Ala Gly Asn
130 135 140

-continued

```
Tyr Ser Thr Ser Ser Leu Asp Asp Leu Ser Glu Asn Phe Ala Val Gly
145                 150                 155                 160

Lys Gln Leu Leu Arg Asp Tyr Asn Ile Glu Ala Lys His Pro Val Val
                165                 170                 175

Met Val Pro Gly Val Ile Ser Thr Gly Ile Glu Ser Trp Gly Val Ile
            180                 185                 190

Gly Asp Asp Glu Cys Asp Ser Ser Ala His Phe Arg Lys Arg Leu Trp
        195                 200                 205

Gly Ser Phe Tyr Met Leu Arg Thr Met Val Met Asp Lys Val Cys Trp
    210                 215                 220

Leu Lys His Val Met Leu Asp Pro Glu Thr Gly Leu Asp Pro Pro Asn
225                 230                 235                 240

Phe Thr Leu Arg Ala Ala Gln Gly Phe Glu Ser Thr Asp Tyr Phe Ile
                245                 250                 255

Ala Gly Tyr Trp Ile Trp Asn Lys Val Phe Gln Asn Leu Gly Val Ile
            260                 265                 270

Gly Tyr Glu Pro Asn Lys Met Thr Ser Ala Ala Tyr Asp Trp Arg Leu
        275                 280                 285

Ala Tyr Leu Asp Leu Glu Arg Arg Asp Arg Tyr Phe Thr Lys Leu Lys
    290                 295                 300

Glu Gln Ile Glu Leu Phe His Gln Leu Ser Gly Glu Lys Val Cys Leu
305                 310                 315                 320

Ile Gly His Ser Met Gly Ser Gln Ile Ile Phe Tyr Phe Met Lys Trp
                325                 330                 335

Val Glu Ala Glu Gly Pro Leu Tyr Gly Asn Gly Gly Arg Gly Trp Val
            340                 345                 350

Asn Glu His Ile Asp Ser Phe Ile Asn Ala Ala Gly Thr Leu Leu Gly
        355                 360                 365

Ala Pro Lys Ala Val Pro Ala Leu Ile Ser Gly Glu Met Lys Asp Thr
    370                 375                 380

Ile Gln Leu Asn Thr Leu Ala Met Tyr Gly Leu Glu Lys Phe Phe Ser
385                 390                 395                 400

Arg Ile Glu Arg Val Lys Met Leu Gln Thr Trp Gly Gly Ile Pro Ser
                405                 410                 415

Met Leu Pro Lys Gly Glu Glu Val Ile Trp Gly Asp Met Lys Ser Ser
            420                 425                 430

Ser Glu Asp Ala Leu Asn Asn Asn Thr Asp Thr Tyr Gly Asn Phe Ile
        435                 440                 445

Arg Phe Glu Arg Asn Thr Ser Asp Ala Phe Asn Lys Asn Leu Thr Met
    450                 455                 460

Lys Asp Ala Ile Asn Met Thr Leu Ser Ile Ser Pro Glu Trp Leu Gln
465                 470                 475                 480

Arg Arg Val His Glu Gln Tyr Ser Phe Gly Tyr Ser Lys Asn Glu Glu
                485                 490                 495

Glu Leu Arg Lys Asn Glu Leu His His Lys His Trp Ser Asn Pro Met
            500                 505                 510

Glu Val Pro Leu Pro Glu Ala Pro His Met Lys Ile Tyr Cys Ile Tyr
        515                 520                 525

Gly Val Asn Asn Pro Thr Glu Arg Ala Tyr Val Tyr Lys Glu Glu Asp
    530                 535                 540

Asp Ser Ser Ala Leu Asn Leu Thr Ile Asp Tyr Glu Ser Lys Gln Pro
545                 550                 555                 560

Val Phe Leu Thr Glu Gly Asp Gly Thr Val Pro Leu Val Ala His Ser
```

```
                565                 570                 575

Met Cys His Lys Trp Ala Gln Gly Ala Ser Pro Tyr Asn Pro Ala Gly
            580                 585                 590

Ile Asn Val Thr Ile Val Glu Met Lys His Gln Pro Asp Arg Phe Asp
        595                 600                 605

Ile Arg Gly Gly Ala Lys Ser Ala Glu His Val Asp Ile Leu Gly Ser
    610                 615                 620

Ala Glu Leu Asn Asp Tyr Ile Leu Lys Ile Ala Ser Gly Asn Gly Asp
625                 630                 635                 640

Leu Val Glu Pro Arg Gln Leu Ser Asn Leu Ser Gln Trp Val Ser Gln
                645                 650                 655

Met Pro Phe Pro Met
            660


<210> SEQ ID NO 31
<211> LENGTH: 1947
<212> TYPE: DNA
<213> ORGANISM: Yarrowia lipolytica
<220> FEATURE:
<221> NAME/KEY: CDS
<222> LOCATION: (1)..(1947)
<223> OTHER INFORMATION: phospholipid:diacylglycerol acyltransferase
<300> PUBLICATION INFORMATION:
<302> TITLE: ACYLTRANSFERASES FOR ALTERATION OF POLYUNSATURATED FATTY
      ACIDS AND OIL CONTENT IN OLEAGINOUS YEASTS
<310> PATENT DOCUMENT NUMBER: US 7,901,928
<311> PATENT FILING DATE: 2009-03-11
<312> PUBLICATION DATE: 2011-03-08
<313> RELEVANT RESIDUES IN SEQ ID NO: (1)..(1947)

<400> SEQUENCE: 31

atg aca caa cct gtg aat cgg aag gcg act gtc gag cgg gtc gag cca       48
Met Thr Gln Pro Val Asn Arg Lys Ala Thr Val Glu Arg Val Glu Pro
1               5                   10                  15

gca gtg gag gtg gct gac tcc gag tcc gag gcc aag acc gac gtc cac       96
Ala Val Glu Val Ala Asp Ser Glu Ser Glu Ala Lys Thr Asp Val His
            20                  25                  30

gtt cac cac cat cat cac cac cac aag cga aaa tcc gtc aag ggc aag      144
Val His His His His His His His Lys Arg Lys Ser Val Lys Gly Lys
        35                  40                  45

att ctc aac ttc ttc acc cga agt cga cgt atc acc ttc gtc ctc ggc      192
Ile Leu Asn Phe Phe Thr Arg Ser Arg Arg Ile Thr Phe Val Leu Gly
    50                  55                  60

gcc gtg gtc ggt gtg ata gcc gcg gga tac tac gct gcg cca ccg gag      240
Ala Val Val Gly Val Ile Ala Ala Gly Tyr Tyr Ala Ala Pro Pro Glu
65                  70                  75                  80

ctc agc att gat atc gat gct ctt ctc ggc gac ttg ccc tcg ttc gac      288
Leu Ser Ile Asp Ile Asp Ala Leu Leu Gly Asp Leu Pro Ser Phe Asp
                85                  90                  95

ttt gac gct cta tct ctc gac aac ttg tcc atg gac agt gtg tcg gac      336
Phe Asp Ala Leu Ser Leu Asp Asn Leu Ser Met Asp Ser Val Ser Asp
            100                 105                 110

ttt gta caa gac atg aaa tcg cgg ttt ccg acc aag att ctg cag gag      384
Phe Val Gln Asp Met Lys Ser Arg Phe Pro Thr Lys Ile Leu Gln Glu
        115                 120                 125

gcg gcc aag atc gag aag cac cag aaa agc gaa cag aag gct gcc cct      432
Ala Ala Lys Ile Glu Lys His Gln Lys Ser Glu Gln Lys Ala Ala Pro
    130                 135                 140

ttt gct gtg ggc aag gct atg aag agc gag gga ctc aac gcc aag tac      480
Phe Ala Val Gly Lys Ala Met Lys Ser Glu Gly Leu Asn Ala Lys Tyr
145                 150                 155                 160
```

```
ccg gtg gtg ctg gtg ccc ggc gtc atc tcc acg gga ctg gag agc tgg      528
Pro Val Val Leu Val Pro Gly Val Ile Ser Thr Gly Leu Glu Ser Trp
            165                 170                 175

tcc ctg gag gga acc gag gag tgt ccc acc gag tcg cac ttc aga aag      576
Ser Leu Glu Gly Thr Glu Glu Cys Pro Thr Glu Ser His Phe Arg Lys
            180                 185                 190

cga atg tgg ggc tcc tgg tac atg atc cga gtc atg ctg ctg gac aag      624
Arg Met Trp Gly Ser Trp Tyr Met Ile Arg Val Met Leu Leu Asp Lys
            195                 200                 205

tac tgc tgg ctg cag aac ctg atg ctg gac aca gag acc ggt cta gac      672
Tyr Cys Trp Leu Gln Asn Leu Met Leu Asp Thr Glu Thr Gly Leu Asp
            210                 215                 220

cct ccc cat ttc aag ctg cga gcc gcc cag gga ttt gcc tcc gcc gac      720
Pro Pro His Phe Lys Leu Arg Ala Ala Gln Gly Phe Ala Ser Ala Asp
225                 230                 235                 240

ttc ttt atg gca ggc tac tgg ctg tgg aac aag ctg ctc gag aac ctg      768
Phe Phe Met Ala Gly Tyr Trp Leu Trp Asn Lys Leu Leu Glu Asn Leu
                245                 250                 255

gct gtt att gga tac gat acg gat aca atg tct gct gcg gcg tac gac      816
Ala Val Ile Gly Tyr Asp Thr Asp Thr Met Ser Ala Ala Ala Tyr Asp
                260                 265                 270

tgg aga ctg tcc tac cct gat ttg gag cac cga gac gga tac ttc tcc      864
Trp Arg Leu Ser Tyr Pro Asp Leu Glu His Arg Asp Gly Tyr Phe Ser
            275                 280                 285

aag ctc aaa gct tca atc gaa gag act aag cgt atg aca ggt gag aag      912
Lys Leu Lys Ala Ser Ile Glu Glu Thr Lys Arg Met Thr Gly Glu Lys
            290                 295                 300

aca gtt ctg acg ggc cat tcc atg ggc tcc cag gtc atc ttc tac ttc      960
Thr Val Leu Thr Gly His Ser Met Gly Ser Gln Val Ile Phe Tyr Phe
305                 310                 315                 320

atg aag tgg gct gag gcc gag gga tat gga gga gga ggt ccc aac tgg     1008
Met Lys Trp Ala Glu Ala Glu Gly Tyr Gly Gly Gly Gly Pro Asn Trp
                325                 330                 335

gtc aat gac cat att gaa tcc ttt gtc gac att tcc ggc tcc atg ctg     1056
Val Asn Asp His Ile Glu Ser Phe Val Asp Ile Ser Gly Ser Met Leu
                340                 345                 350

ggt act ccc aag acc ctg gtt gct ctt ctg tct gga gaa atg aag gat     1104
Gly Thr Pro Lys Thr Leu Val Ala Leu Leu Ser Gly Glu Met Lys Asp
            355                 360                 365

acc gtg cag ctg aac gcg atg gct gtg tat gga ctg gag cag ttc ttc     1152
Thr Val Gln Leu Asn Ala Met Ala Val Tyr Gly Leu Glu Gln Phe Phe
            370                 375                 380

tct cga cga gag cga gcc gat ctg ctg cga aca tgg gga gga att gct     1200
Ser Arg Arg Glu Arg Ala Asp Leu Leu Arg Thr Trp Gly Gly Ile Ala
385                 390                 395                 400

tcc atg att ccc aag ggt ggt aag gct atc tgg ggt gat cat tct gga     1248
Ser Met Ile Pro Lys Gly Gly Lys Ala Ile Trp Gly Asp His Ser Gly
                405                 410                 415

gcc cct gat gac gag ccc ggc cag aat gtc acc ttt ggc aac ttc atc     1296
Ala Pro Asp Asp Glu Pro Gly Gln Asn Val Thr Phe Gly Asn Phe Ile
                420                 425                 430

aag ttc aag gag tcc ttg acc gag tac tct gct aag aac ctc acc atg     1344
Lys Phe Lys Glu Ser Leu Thr Glu Tyr Ser Ala Lys Asn Leu Thr Met
            435                 440                 445

gat gaa acc gtt gac ttc ctg tat tct cag tct ccc gag tgg ttt gtg     1392
Asp Glu Thr Val Asp Phe Leu Tyr Ser Gln Ser Pro Glu Trp Phe Val
            450                 455                 460

aac cga acc gag ggt gct tac tcc ttt gga att gcc aag act cga aag     1440
Asn Arg Thr Glu Gly Ala Tyr Ser Phe Gly Ile Ala Lys Thr Arg Lys
465                 470                 475                 480
```

-continued

```
cag gtt gag cag aat gag aag cga cct tct acc tgg agc aac cct ctg      1488
Gln Val Glu Gln Asn Glu Lys Arg Pro Ser Thr Trp Ser Asn Pro Leu
                485                 490                 495

gaa gct gct ctc ccc aat gcc ccc gat ctc aag atc tac tgc ttc tat      1536
Glu Ala Ala Leu Pro Asn Ala Pro Asp Leu Lys Ile Tyr Cys Phe Tyr
            500                 505                 510

gga gtc ggt aag gat acc gag cga gcc tac tac tac cag gat gag ccc      1584
Gly Val Gly Lys Asp Thr Glu Arg Ala Tyr Tyr Tyr Gln Asp Glu Pro
        515                 520                 525

aat ccc gag cag acc aac ttg aac gtc agt atc gct gga aac gac cct      1632
Asn Pro Glu Gln Thr Asn Leu Asn Val Ser Ile Ala Gly Asn Asp Pro
    530                 535                 540

gat ggt gtg ctt atg ggt cag ggc gat gga acc gtc tcc ctt gtg acc      1680
Asp Gly Val Leu Met Gly Gln Gly Asp Gly Thr Val Ser Leu Val Thr
545                 550                 555                 560

cat acc atg tgt cac cga tgg aag gac gag aat tcc aag ttc aac cct      1728
His Thr Met Cys His Arg Trp Lys Asp Glu Asn Ser Lys Phe Asn Pro
                565                 570                 575

ggt aac gcc cag gtc aag gtt gtg gag atg ttg cac cag cct gat cga      1776
Gly Asn Ala Gln Val Lys Val Val Glu Met Leu His Gln Pro Asp Arg
            580                 585                 590

ctt gat att cga ggc ggt gct cag act gcc gag cat gtg gac att ctg      1824
Leu Asp Ile Arg Gly Gly Ala Gln Thr Ala Glu His Val Asp Ile Leu
        595                 600                 605

ggg cgt tct gag ttg aac gag atg gtt ctg aag gtg gct agt gga aag      1872
Gly Arg Ser Glu Leu Asn Glu Met Val Leu Lys Val Ala Ser Gly Lys
    610                 615                 620

gga aat gag att gaa gag aga gtc atc tcc aac att gat gag tgg gtg      1920
Gly Asn Glu Ile Glu Glu Arg Val Ile Ser Asn Ile Asp Glu Trp Val
625                 630                 635                 640

tgg aag att gat ctc ggc agc aat tag                                  1947
Trp Lys Ile Asp Leu Gly Ser Asn
                645


<210> SEQ ID NO 32
<211> LENGTH: 648
<212> TYPE: PRT
<213> ORGANISM: Yarrowia lipolytica

<400> SEQUENCE: 32

Met Thr Gln Pro Val Asn Arg Lys Ala Thr Val Glu Arg Val Glu Pro
1               5                   10                  15

Ala Val Glu Val Ala Asp Ser Glu Ser Glu Ala Lys Thr Asp Val His
            20                  25                  30

Val His His His His His His His Lys Arg Lys Ser Val Lys Gly Lys
        35                  40                  45

Ile Leu Asn Phe Phe Thr Arg Ser Arg Arg Ile Thr Phe Val Leu Gly
    50                  55                  60

Ala Val Val Gly Val Ile Ala Ala Gly Tyr Tyr Ala Ala Pro Pro Glu
65                  70                  75                  80

Leu Ser Ile Asp Ile Asp Ala Leu Leu Gly Asp Leu Pro Ser Phe Asp
                85                  90                  95

Phe Asp Ala Leu Ser Leu Asp Asn Leu Ser Met Asp Ser Val Ser Asp
            100                 105                 110

Phe Val Gln Asp Met Lys Ser Arg Phe Pro Thr Lys Ile Leu Gln Glu
        115                 120                 125

Ala Ala Lys Ile Glu Lys His Gln Lys Ser Glu Gln Lys Ala Ala Pro
    130                 135                 140
```

```
Phe Ala Val Gly Lys Ala Met Lys Ser Glu Gly Leu Asn Ala Lys Tyr
145                 150                 155                 160

Pro Val Val Leu Val Pro Gly Val Ile Ser Thr Gly Leu Glu Ser Trp
                165                 170                 175

Ser Leu Glu Gly Thr Glu Glu Cys Pro Thr Glu Ser His Phe Arg Lys
            180                 185                 190

Arg Met Trp Gly Ser Trp Tyr Met Ile Arg Val Met Leu Leu Asp Lys
        195                 200                 205

Tyr Cys Trp Leu Gln Asn Leu Met Leu Asp Thr Glu Thr Gly Leu Asp
    210                 215                 220

Pro Pro His Phe Lys Leu Arg Ala Ala Gln Gly Phe Ala Ser Ala Asp
225                 230                 235                 240

Phe Phe Met Ala Gly Tyr Trp Leu Trp Asn Lys Leu Leu Glu Asn Leu
                245                 250                 255

Ala Val Ile Gly Tyr Asp Thr Asp Thr Met Ser Ala Ala Ala Tyr Asp
            260                 265                 270

Trp Arg Leu Ser Tyr Pro Asp Leu Glu His Arg Asp Gly Tyr Phe Ser
        275                 280                 285

Lys Leu Lys Ala Ser Ile Glu Glu Thr Lys Arg Met Thr Gly Glu Lys
    290                 295                 300

Thr Val Leu Thr Gly His Ser Met Gly Ser Gln Val Ile Phe Tyr Phe
305                 310                 315                 320

Met Lys Trp Ala Glu Ala Glu Gly Tyr Gly Gly Gly Gly Pro Asn Trp
                325                 330                 335

Val Asn Asp His Ile Glu Ser Phe Val Asp Ile Ser Gly Ser Met Leu
            340                 345                 350

Gly Thr Pro Lys Thr Leu Val Ala Leu Leu Ser Gly Glu Met Lys Asp
        355                 360                 365

Thr Val Gln Leu Asn Ala Met Ala Val Tyr Gly Leu Glu Gln Phe Phe
    370                 375                 380

Ser Arg Arg Glu Arg Ala Asp Leu Leu Arg Thr Trp Gly Gly Ile Ala
385                 390                 395                 400

Ser Met Ile Pro Lys Gly Gly Lys Ala Ile Trp Gly Asp His Ser Gly
                405                 410                 415

Ala Pro Asp Asp Glu Pro Gly Gln Asn Val Thr Phe Gly Asn Phe Ile
            420                 425                 430

Lys Phe Lys Glu Ser Leu Thr Glu Tyr Ser Ala Lys Asn Leu Thr Met
        435                 440                 445

Asp Glu Thr Val Asp Phe Leu Tyr Ser Gln Ser Pro Glu Trp Phe Val
    450                 455                 460

Asn Arg Thr Glu Gly Ala Tyr Ser Phe Gly Ile Ala Lys Thr Arg Lys
465                 470                 475                 480

Gln Val Glu Gln Asn Glu Lys Arg Pro Ser Thr Trp Ser Asn Pro Leu
                485                 490                 495

Glu Ala Ala Leu Pro Asn Ala Pro Asp Leu Lys Ile Tyr Cys Phe Tyr
            500                 505                 510

Gly Val Gly Lys Asp Thr Glu Arg Ala Tyr Tyr Tyr Gln Asp Glu Pro
        515                 520                 525

Asn Pro Glu Gln Thr Asn Leu Asn Val Ser Ile Ala Gly Asn Asp Pro
    530                 535                 540

Asp Gly Val Leu Met Gly Gln Gly Asp Gly Thr Val Ser Leu Val Thr
545                 550                 555                 560
```

```
His Thr Met Cys His Arg Trp Lys Asp Glu Asn Ser Lys Phe Asn Pro
                565                 570                 575

Gly Asn Ala Gln Val Lys Val Val Glu Met Leu His Gln Pro Asp Arg
            580                 585                 590

Leu Asp Ile Arg Gly Gly Ala Gln Thr Ala Glu His Val Asp Ile Leu
        595                 600                 605

Gly Arg Ser Glu Leu Asn Glu Met Val Leu Lys Val Ala Ser Gly Lys
    610                 615                 620

Gly Asn Glu Ile Glu Glu Arg Val Ile Ser Asn Ile Asp Glu Trp Val
625                 630                 635                 640

Trp Lys Ile Asp Leu Gly Ser Asn
                645


<210> SEQ ID NO 33
<211> LENGTH: 7
<212> TYPE: PRT
<213> ORGANISM: Artificial Sequence
<220> FEATURE:
<223> OTHER INFORMATION: membrane bound O-acyltransferase motif
<220> FEATURE:
<221> NAME/KEY: MISC_FEATURE
<222> LOCATION: (1)..(1)
<223> OTHER INFORMATION: Xaa = Met [M] or Ala [A] or Asn [N] or Cys [C]
      or Gly [G] or Gln [Q] or His [H] or Ile [I] or Leu [L] or Phe [F]
      or Pro [P] or Ser [S] or Thr [T] or Trp [W] or Tyr [Y] or Val [V]
<220> FEATURE:
<221> NAME/KEY: MISC_FEATURE
<222> LOCATION: (2)..(2)
<223> OTHER INFORMATION: Xaa = Val [V] or Ala [A] or Asn [N] or Cys [C]
      or Gly [G] or Gln [Q] or His [H] or Leu [L] or Met [M] or Phe [F]
      or Pro [P] or Ser [S] or Thr [T] or Trp [W] or Tyr [Y] or Ile [I]
<220> FEATURE:
<221> NAME/KEY: MISC_FEATURE
<222> LOCATION: (3)..(3)
<223> OTHER INFORMATION: Xaa = Leu [L] or Ala [A] or Asn [N] or Cys [C]
      or Gly [G] or Gln [Q] or His [H] or Met [M] or  Phe [F] or Pro [P]
      or Ser [S] or Thr [T] or Trp [W] or Tyr [Y] or Val [V]
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa = Lys [K] or Ala [A] or Arg [R] or Asn [N]
      or Gly [G] or His [H] or Pro [P] or Ser [S] or Thr [T] or Tyr [Y]
<220> FEATURE:
<221> NAME/KEY: MISC_FEATURE
<222> LOCATION: (7)..(7)
<223> OTHER INFORMATION: Xaa = Leu [L] or Ala [A] or Asn [N] or Cys [C]
      or Gly [G] or Gln [Q] or His [H] or Ile [I] or Met [M] or Phe [F]
      or Pro [P] or Ser [S] or Thr [T] or Trp [W] or Tyr [Y]

<400> SEQUENCE: 33

Xaa Xaa Xaa Xaa Xaa Xaa Xaa
1               5


<210> SEQ ID NO 34
<211> LENGTH: 17
<212> TYPE: PRT
<213> ORGANISM: Artificial Sequence
<220> FEATURE:
<223> OTHER INFORMATION: membrane bound O-acyltransferase motif
<220> FEATURE:
<221> NAME/KEY: MISC_FEATURE
<222> LOCATION: (1)..(1)
<223> OTHER INFORMATION: Xaa = Met [M] or Ala [A] or Asn [N] or Cys [C]
      or Gly [G] or Gln [Q] or His [H] or Ile [I] or Leu [L] or Phe [F]
      or Pro [P] or Ser [S] or Thr [T] or Trp [W] or Tyr [Y] or Val [V]
<220> FEATURE:
<221> NAME/KEY: MISC_FEATURE
```

<222> LOCATION: (2)..(2)
<223> OTHER INFORMATION: Xaa = Val [V] or Ala [A] or Asn [N] or Cys [C]
      or Gly [G] or Gln [Q] or His [H] or Leu [L] or Met [M] or Phe [F]
      or Pro [P] or Ser [S] or Thr [T] or Trp [W] or Tyr [Y] or Ile [I]
<220> FEATURE:
<221> NAME/KEY: MISC_FEATURE
<222> LOCATION: (3)..(3)
<223> OTHER INFORMATION: Xaa = Leu [L] or Ala [A] or Asn [N] or Cys [C]
      or Gly [G] or Gln [Q] or His [H] or Met [M] or  Phe [F] or Pro [P]
      or Ser [S] or Thr [T] or Trp [W] or Tyr [Y] or Val [V] or Ile [I]
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa = Lys [K] or Ala [A] or Arg [R] or Asn [N]
      or Gly [G] or His [H] or Pro [P] or Ser [S] or Thr [T] or Tyr [Y]
<220> FEATURE:
<221> NAME/KEY: MISC_FEATURE
<222> LOCATION: (7)..(7)
<223> OTHER INFORMATION: Xaa = Leu [L] or Ala [A] or Asn [N] or Cys [C]
      or Gly [G] or Gln [Q] or His [H] or Ile [I] or Met [M] or Phe [F]
      or Pro [P] or Ser [S] or Thr [T] or Trp [W] or Tyr [Y] or Val [V]
<220> FEATURE:
<221> NAME/KEY: misc_feature
<222> LOCATION: (8)..(13)
<223> OTHER INFORMATION: Xaa can be any naturally occurring amino acid
<220> FEATURE:
<221> NAME/KEY: misc_feature
<222> LOCATION: (14)..(15)
<223> OTHER INFORMATION: Xaa can be any naturally occurring amino acid
<220> FEATURE:
<221> NAME/KEY: MISC_FEATURE
<222> LOCATION: (16)..(16)
<223> OTHER INFORMATION: Xaa =  Asp [D] or Ala [A] or Asn [N] or Gly [G]
      or Glu [E] or Gln [Q] or His [H] or Phe [F] or Ser [S] or Thr [T]
<220> FEATURE:
<221> NAME/KEY: MISC_FEATURE
<222> LOCATION: (17)..(17)
<223> OTHER INFORMATION: Xaa = Gly [G] or Ala [A] or Asn [N] or His [H]
      or Leu [L] or Met [M] or Phe [F] or Ser [S] or Thr [T] or Val [V]

<400> SEQUENCE: 34

Met Xaa Xaa Xaa Xaa Xaa Xaa Xaa Xaa Xaa Xaa Xaa Xaa Xaa Xaa Xaa
1               5                   10                  15

Xaa

<210> SEQ ID NO 35
<211> LENGTH: 12
<212> TYPE: PRT
<213> ORGANISM: Artificial Sequence
<220> FEATURE:
<223> OTHER INFORMATION: membrane bound O-acyltransferase motif
<220> FEATURE:
<221> NAME/KEY: misc_feature
<222> LOCATION: (4)..(6)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa = Gly [G] or Ala [A] or Asn [N] or Cys [C]
      or His [H] or Ile [I] or Leu [L] or Lys [K] or Met [M] or Phe [F]
      or Ser [S] or Thr [T] or Trp [W] or Tyr [Y] or Val [V]
<220> FEATURE:
<221> NAME/KEY: misc_feature
<222> LOCATION: (8)..(8)
<223> OTHER INFORMATION: Xaa = Tyr [Y] or Ala [A] or Gly [G] or  His [H]
      or Leu [L] or Phe [F] or Pro [P] or Ser [S] or Thr [T] or Val [V]
<220> FEATURE:
<221> NAME/KEY: misc_feature
<222> LOCATION: (9)..(11)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa = Phe [F] or Ala [A] or Asn [N] or Cys [C]
or Gly [G] or His [H] or Leu [L] or Met [M] or Pro [P] or Ser [S]
or Thr [T] or Val [V]

<400> SEQUENCE: 35

Trp His Gly Xaa Xaa Xaa Xaa Xaa Xaa Xaa Xaa Xaa
1 5 10

<210> SEQ ID NO 36
<211> LENGTH: 15
<212> TYPE: PRT
<213> ORGANISM: Artificial Sequence
<220> FEATURE:
<223> OTHER INFORMATION: membrane bound O-acyltransferase motif
<220> FEATURE:
<221> NAME/KEY: MISC_FEATURE
<222> LOCATION: (1)..(1)
<223> OTHER INFORMATION: Xaa = Ser [S] or Ala [A] or Gly [G] or His [H]
or Leu [L] or Phe [F] or Thr [T] or Val [V]
<220> FEATURE:
<221> NAME/KEY: MISC_FEATURE
<222> LOCATION: (2)..(2)
<223> OTHER INFORMATION: Xaa = Ala [A] or Asn [N] or Gly [G] or His [H]
or Leu [L] or Phe [F] or Pro [P] or Ser [S] or Thr [T] or Val [V]
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: Xaa = Pro [P] or Ala [A] or Arg [R] or Gly [G]
or His [H] or Ile [I] or Leu [L] or Lys [K] or Met [M] or Phe [F]
or Pro [P] or Ser [S] or Thr [T] or Trp [W] or Tyr [Y] or Val [V]
<220> FEATURE:
<221> NAME/KEY: MISC_FEATURE
<222> LOCATION: (10)..(10)
<223> OTHER INFORMATION: Xaa = Gly [G] or Ala [A] or Asn [N] or Cys [C]
or His [H] or Ile [I] or Leu [L] or Lys [K] or Met [M] or Phe [F]
or Ser [S] or Thr [T] or Trp [W] or Tyr [Y] or Val [V]
<220> FEATURE:
<221> NAME/KEY: MISC_FEATURE
<222> LOCATION: (11)..(11)
<223> OTHER INFORMATION: Xaa = Tyr [Y] or Ala [A] or Gly [G] or His [H]
or Leu [L] or Phe [F] or Pro [P] or Ser [S] or Thr [T] or Val [V]
<220> FEATURE:
<221> NAME/KEY: misc_feature
<222> LOCATION: (12)..(13)
<223> OTHER INFORMATION: Xaa can be any naturally occurring amino acid
<220> FEATURE:
<221> NAME/KEY: MISC_FEATURE
<222> LOCATION: (14)..(14)
<223> OTHER INFORMATION: Xaa = Thr [T] or Phe [F] or Ala [A] or Cys [C]
or Gly [G] or His [H[ or Ile [I] or Leu [L] or Met [M] or Pro [P]
or Ser [S] or Trp [W] or Tyr [Y] or Val [V]
<220> FEATURE:
<221> NAME/KEY: MISC_FEATURE
<222> LOCATION: (15)..(15)
<223> OTHER INFORMATION: Xaa = Phe [F] or Ala [A] or Asn [N] or Cys [C]
or Gly [G] or His [H] or Leu [L] or Met [M] or Pro [P] or Ser [S]
or Thr [T] or Val [V]

<400> SEQUENCE: 36

Xaa Xaa Xaa Trp His Gly Xaa Xaa Xaa Xaa Xaa Xaa Xaa Xaa Xaa
1 5 10 15

<210> SEQ ID NO 37
<211> LENGTH: 512
<212> TYPE: PRT
<213> ORGANISM: Yarrowia lipolytica
<220> FEATURE:
<221> NAME/KEY: MISC_FEATURE
<222> LOCATION: (133)..(133)
<223> OTHER INFORMATION: Xaa = Val [V] or Cys [C]
<220> FEATURE:
<221> NAME/KEY: MISC_FEATURE
<222> LOCATION: (134)..(134)
<223> OTHER INFORMATION: Xaa = Leu [L] or Ala [A] or Cys [C] or Gly [G]
<220> FEATURE:
<221> NAME/KEY: MISC_FEATURE
<222> LOCATION: (135)..(135)
<223> OTHER INFORMATION: Xaa = Cys [C] or Asp [D] or Ile [I] or Phe [F]
<220> FEATURE:
<221> NAME/KEY: MISC_FEATURE
<222> LOCATION: (136)..(136)
<223> OTHER INFORMATION: Xaa = Met [M] or Gly [G] or Pro [P] or Ser [S] or Val [V] or Asn [N] or Thr [T]
<220> FEATURE:
<221> NAME/KEY: MISC_FEATURE
<222> LOCATION: (137)..(137)
<223> OTHER INFORMATION: Xaa = Lys [K] or Asn [N] or Gly [G] or His [H] or Tyr [Y]
<220> FEATURE:
<221> NAME/KEY: MISC_FEATURE
<222> LOCATION: (138)..(138)
<223> OTHER INFORMATION: Xaa = Leu [L] or Ala [A] or His [H] or Met [M] or Gly [G] or Ile [I] or Asn [N]
<220> FEATURE:
<221> NAME/KEY: MISC_FEATURE
<222> LOCATION: (139)..(139)
<223> OTHER INFORMATION: Xaa = Ser [S] or Leu [L] or Trp [W] or Gly [G] or Asn [N]
<220> FEATURE:
<221> NAME/KEY: MISC_FEATURE
<222> LOCATION: (140)..(140)
<223> OTHER INFORMATION: Xaa = Ser [S] or Asn [N] or His [H] or Pro [P] or Trp [W] or Tyr [Y] or Ile [I]
<220> FEATURE:
<221> NAME/KEY: MISC_FEATURE
<222> LOCATION: (141)..(141)
<223> OTHER INFORMATION: Xaa = Phe [F] or Ala [A] or Met [M] or Trp [W] or Val [V]
<220> FEATURE:
<221> NAME/KEY: MISC_FEATURE
<222> LOCATION: (142)..(142)
<223> OTHER INFORMATION: Xaa = Gly [G] or His [H] or Ile [I] or Val [V]
<220> FEATURE:
<221> NAME/KEY: MISC_FEATURE
<222> LOCATION: (143)..(143)
<223> OTHER INFORMATION: Xaa = Trp [W] or Leu [L] or His [H]
<220> FEATURE:
<221> NAME/KEY: MISC_FEATURE
<222> LOCATION: (144)..(144)
<223> OTHER INFORMATION: Xaa = Asn [N] or Ala [A] or Lys [K] or Phe [F] or Thr [T] or Val [V]
<220> FEATURE:
<221> NAME/KEY: MISC_FEATURE
<222> LOCATION: (145)..(145)
<223> OTHER INFORMATION: Xaa = Val [V] or Ala [A] or Gly [G] or Glu [E] or Met [M] or Phe [F] or Trp [W]
<220> FEATURE:
<221> NAME/KEY: MISC_FEATURE
<222> LOCATION: (146)..(146)
<223> OTHER INFORMATION: Xaa = Tyr [Y] or Gly [G] or Leu [L] or Met [M]
<220> FEATURE:
<221> NAME/KEY: MISC_FEATURE
<222> LOCATION: (147)..(147)
<223> OTHER INFORMATION: Xaa = Asp [D] or Asn [N] or Gln [Q] or His [H] or Glu [E]
<220> FEATURE:
<221> NAME/KEY: MISC_FEATURE
<222> LOCATION: (148)..(148)
<223> OTHER INFORMATION: Xaa = Gly [G] or Ala [A] or Asn [N] or Val [V]
<220> FEATURE:
<221> NAME/KEY: MISC_FEATURE
<222> LOCATION: (378)..(378)
<223> OTHER INFORMATION: Xaa = Phe [F] or Tyr [Y]
<220> FEATURE:
<221> NAME/KEY: MISC_FEATURE
<222> LOCATION: (382)..(382)
<223> OTHER INFORMATION: Xaa = Thr [T] or Ile [I] or Pro [P] or Tyr [Y]
<220> FEATURE:
<221> NAME/KEY: MISC_FEATURE
<222> LOCATION: (383)..(383)
<223> OTHER INFORMATION: Xaa = Arg [R] or Ala [A] or Met [M]
<220> FEATURE:
<221> NAME/KEY: MISC_FEATURE
<222> LOCATION: (388)..(388)
<223> OTHER INFORMATION: Xaa = Leu [L] or Gly [G] or Tyr [Y] or His [H]
or Thr [T]
<220> FEATURE:
<221> NAME/KEY: MISC_FEATURE
<222> LOCATION: (389)..(389)
<223> OTHER INFORMATION: Xaa = Thr [T] or Ala [A] or Cys [C] or Ser [S]
<220> FEATURE:
<221> NAME/KEY: MISC_FEATURE
<222> LOCATION: (390)..(390)
<223> OTHER INFORMATION: Xaa = Phe [F] or Cys [C] or Gly [G] or Asn [N]
or Ser [S] or Thr [T]

<400> SEQUENCE: 37

```
Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Xaa Xaa Xaa Xaa Xaa Xaa Xaa Xaa Xaa Xaa Xaa Xaa
    130                 135                 140

Xaa Xaa Xaa Xaa Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300
```

```
Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Xaa Trp His Gly Xaa Xaa Pro
    370                 375                 380

Gly Tyr Tyr Xaa Xaa Xaa Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510


<210> SEQ ID NO 38
<211> LENGTH: 7
<212> TYPE: PRT
<213> ORGANISM: Artificial Sequence
<220> FEATURE:
<223> OTHER INFORMATION: membrane bound O-acyltransferase motif
<220> FEATURE:
<221> NAME/KEY: MISC_FEATURE
<222> LOCATION: (2)..(2)
<223> OTHER INFORMATION: Xaa = Val [V] or Ile [I] or Cys [C]
<220> FEATURE:
<221> NAME/KEY: MISC_FEATURE
<222> LOCATION: (3)..(3)
<223> OTHER INFORMATION: Xaa = Leu [L] or Ala [A] or Cys [C] or Gly [G]
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa = Lys [K] or His [H] or Gly [G] or Asn [N]
      or Tyr [Y]
<220> FEATURE:
<221> NAME/KEY: MISC_FEATURE
<222> LOCATION: (7)..(7)
<223> OTHER INFORMATION: Xaa = Leu [L] or Ala [A] or Asn [N] or Gly [G]
      or His [H] or Ile [I] or Met [M]

<400> SEQUENCE: 38

Met Xaa Xaa Xaa Xaa Xaa Xaa
1               5


<210> SEQ ID NO 39
<211> LENGTH: 17
<212> TYPE: PRT
```

<213> ORGANISM: Artificial Sequence
<220> FEATURE:
<223> OTHER INFORMATION: membrane bound O-acyltransferase motif
<220> FEATURE:
<221> NAME/KEY: MISC_FEATURE
<222> LOCATION: (2)..(2)
<223> OTHER INFORMATION: Xaa = Val [V] or Ile [I] or Cys [C]
<220> FEATURE:
<221> NAME/KEY: MISC_FEATURE
<222> LOCATION: (3)..(3)
<223> OTHER INFORMATION: Xaa = Leu [L] or Ile [I] or Ala [A] or Cys [C]
or Gly [G]
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa = Lys [K] or His [H] or Gly [G] or Asn [N]
or Tyr [Y]
<220> FEATURE:
<221> NAME/KEY: MISC_FEATURE
<222> LOCATION: (7)..(7)
<223> OTHER INFORMATION: Xaa = Leu [L] or Ala [A] or Asn [N] or Gly [G]
or His [H] or Ile [I] or Met [M] or Val [V]
<220> FEATURE:
<221> NAME/KEY: misc_feature
<222> LOCATION: (8)..(13)
<223> OTHER INFORMATION: Xaa can be any naturally occurring amino acid
<220> FEATURE:
<221> NAME/KEY: misc_feature
<222> LOCATION: (14)..(15)
<223> OTHER INFORMATION: Xaa can be any naturally occurring amino acid
<220> FEATURE:
<221> NAME/KEY: MISC_FEATURE
<222> LOCATION: (16)..(16)
<223> OTHER INFORMATION: Xaa = Asp [D] or Gln [Q] or Asn [N] or His [H]
<220> FEATURE:
<221> NAME/KEY: MISC_FEATURE
<222> LOCATION: (17)..(17)
<223> OTHER INFORMATION: Xaa = Gly [G] or Ala [A] or Val [V] or Asn [N]

<400> SEQUENCE: 39

```
Met Xaa Xaa Xaa Xaa Xaa Xaa Xaa Xaa Xaa Xaa Xaa Xaa Xaa Xaa Xaa
1               5                   10                  15

Xaa
```

<210> SEQ ID NO 40
<211> LENGTH: 12
<212> TYPE: PRT
<213> ORGANISM: Artificial Sequence
<220> FEATURE:
<223> OTHER INFORMATION: membrane bound O-acyltransferase motif
<220> FEATURE:
<221> NAME/KEY: misc_feature
<222> LOCATION: (4)..(6)
<223> OTHER INFORMATION: Xaa can be any naturally occurring amino acid
<220> FEATURE:
<221> NAME/KEY: misc_feature
<222> LOCATION: (9)..(11)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa = Phe [F] or Asn [N] or Cys [C] or Gly [G]
or Thr [T]

<400> SEQUENCE: 40

```
Trp His Gly Xaa Xaa Xaa Gly Tyr Xaa Xaa Xaa Xaa
1               5                   10
```

<210> SEQ ID NO 41
<211> LENGTH: 15

<212> TYPE: PRT
<213> ORGANISM: Artificial Sequence
<220> FEATURE:
<223> OTHER INFORMATION: membrane bound O-acyltransferase motif
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (12)..(13)
<223> OTHER INFORMATION: Xaa can be any naturally occurring amino acid
<220> FEATURE:
<221> NAME/KEY: MISC_FEATURE
<222> LOCATION: (14)..(14)
<223> OTHER INFORMATION: Xaa = Thr [T] or Phe [F] or Ala [A] or Cys [C] or Ser [S]
<220> FEATURE:
<221> NAME/KEY: MISC_FEATURE
<222> LOCATION: (15)..(15)
<223> OTHER INFORMATION: Xaa = Phe [F] or Asn [N] or Cys [C] or Gly [G] or Thr [T]

<400> SEQUENCE: 41

Ser Ala Xaa Trp His Gly Xaa Xaa Pro Gly Tyr Xaa Xaa Xaa Xaa
1 5 10 15

<210> SEQ ID NO 42
<211> LENGTH: 512
<212> TYPE: PRT
<213> ORGANISM: Yarrowia lipolytica
<220> FEATURE:
<221> NAME/KEY: MISC_FEATURE
<222> LOCATION: (134)..(134)
<223> OTHER INFORMATION: Xaa = Leu [L] or Ala [A] or Gly [G]
<220> FEATURE:
<221> NAME/KEY: MISC_FEATURE
<222> LOCATION: (136)..(136)
<223> OTHER INFORMATION: Xaa = Met [M] or Ser [S] or Val [V]
<220> FEATURE:
<221> NAME/KEY: MISC_FEATURE
<222> LOCATION: (137)..(137)
<223> OTHER INFORMATION: Xaa = Lys [K] or Asn [N] or His [H]
<220> FEATURE:
<221> NAME/KEY: MISC_FEATURE
<222> LOCATION: (140)..(140)
<223> OTHER INFORMATION: Xaa = Ser [S] or His [H] or Trp [W]
<220> FEATURE:
<221> NAME/KEY: MISC_FEATURE
<222> LOCATION: (141)..(141)
<223> OTHER INFORMATION: Xaa = Phe [F] or Met [M] or Trp [W]
<220> FEATURE:
<221> NAME/KEY: MISC_FEATURE
<222> LOCATION: (144)..(144)
<223> OTHER INFORMATION: Xaa = Asn [N] or Ala [A] or Thr [T]
<220> FEATURE:
<221> NAME/KEY: MISC_FEATURE
<222> LOCATION: (145)..(145)
<223> OTHER INFORMATION: Xaa = Val [V] or Met [M] or Trp [W]
<220> FEATURE:
<221> NAME/KEY: MISC_FEATURE
<222> LOCATION: (147)..(147)
<223> OTHER INFORMATION: Xaa = Asp [D] or Gln [Q] or His [H]
<220> FEATURE:
<221> NAME/KEY: MISC_FEATURE
<222> LOCATION: (148)..(148)
<223> OTHER INFORMATION: Xaa = Gly [G] or Ala [A] or Asn [N]
<220> FEATURE:
<221> NAME/KEY: MISC_FEATURE
<222> LOCATION: (378)..(378)
<223> OTHER INFORMATION: Xaa = Phe [F] or Tyr [Y]
<220> FEATURE:
<221> NAME/KEY: MISC_FEATURE
<222> LOCATION: (382)..(382)
<223> OTHER INFORMATION: Xaa = Thr [T] or Ile [I] or Pro [P] or Tyr [Y]
<220> FEATURE:
<221> NAME/KEY: MISC_FEATURE
<222> LOCATION: (383)..(383)
<223> OTHER INFORMATION: Xaa = Arg [R] or Met [M]
<220> FEATURE:
<221> NAME/KEY: MISC_FEATURE
<222> LOCATION: (384)..(384)
<223> OTHER INFORMATION: Xaa = Pro [P] or Ala [A] or Gly [G]
<220> FEATURE:
<221> NAME/KEY: MISC_FEATURE
<222> LOCATION: (388)..(388)
<223> OTHER INFORMATION: Xaa = Leu [L] or Gly [G] or Tyr [Y] or Thr [T]
<220> FEATURE:
<221> NAME/KEY: MISC_FEATURE
<222> LOCATION: (389)..(389)
<223> OTHER INFORMATION: Xaa = Thr [T] or Ala [A] or Cys [C] or Ser [S]
<220> FEATURE:
<221> NAME/KEY: MISC_FEATURE
<222> LOCATION: (390)..(390)
<223> OTHER INFORMATION: Xaa = Phe [F] or Gly [G] or Ser [S] or Thr [T]

<400> SEQUENCE: 42

```
Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Xaa Cys Xaa Xaa Leu Ser Xaa Xaa Gly Trp Xaa
    130                 135                 140

Xaa Tyr Xaa Xaa Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285
```

-continued

```
Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Xaa Trp His Gly Xaa Xaa Xaa
    370                 375                 380

Gly Tyr Tyr Xaa Xaa Xaa Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510
```

<210> SEQ ID NO 43
<211> LENGTH: 11017
<212> TYPE: DNA
<213> ORGANISM: Artificial Sequence
<220> FEATURE:
<223> OTHER INFORMATION: Plasmid pY196

<400> SEQUENCE: 43

```
cggatcgggc aagctcaatg gtctgcttgg agtactcgcc agtggccaga gagcccttgc      60

aagacagctc ggccagcatg agcagacctc tggccagctt ctcgttggga gaggggacta     120

ggaactcctt gtactgggag ttctcgtagt cagagacgtc ctccttcttc tgttcagaga     180

cagtttcctc ggcaccagct cgcaggccag caatgattcc ggttccgggt acaccgtggg     240

cgttggtgat atcggaccac tcggcgattc ggtgacaccg gtactggtgc ttgacagtgt     300

tgccaatatc tgcgaacttt ctgtcctcga acaggaagaa accgtgctta agagcaagtt     360

ccttgagggg gagcacagtg ccggcgtagg tgaagtcgtc aatgatgtcg atatgggttt     420

tgatcatgca cacataaggt ccgaccttat cggcaagctc aatgagctcc ttggtggtgg     480

taacatccag agaagcacac aggttggttt tcttggctgc cacgagcttg agcactcgag     540

cggcaaaggc ggacttgtgg acgttagctc gagcttcgta ggagggcatt ttggtggtga     600

agaggagact gaaataaatt tagtctgcag aactttttat cggaacctta tctggggcag     660

tgaagtatat gttatggtaa tagttacgag ttagttgaac ttatagatag actggactat     720

acggctatcg gtccaaatta gaaagaacgt caatggctct ctgggcgtcg cctttgccga     780

caaaaatgtg atcatgatga aagccagcaa tgacgttgca gctgatattg ttgtcggcca     840
```

```
accgcgccga aaacgcagct gtcagaccca cagcctagga aatgtaacga aactgaaatt    900
tgaccagata ttgtgtccgc ggtggagctc cagcttttgt tccctttagt gagggttaat    960
ttcgagcttg gcgtaatcat ggtcatagct gtttcctgtg tgaaattgtt atccgctcac   1020
aagcttccac acaacgtacg agccggaagc ataaagtgta aagcctgggg tgcctaatga   1080
gtgagctaac tcacattaat tgcgttgcgc tcactgcccg ctttccagtc gggaaacctg   1140
tcgtgccagc tgcattaatg aatcggccaa cgcgcgggga gaggcggttt gcgtattggg   1200
cgctcttccg cttcctcgct cactgactcg ctgcgctcgg tcgttcggct gcggcgagcg   1260
gtatcagctc actcaaaggc ggtaatacgg ttatccacag aatcagggga taacgcagga   1320
aagaacatgt gagcaaaagg ccagcaaaag gccaggaacc gtaaaaaggc cgcgttgctg   1380
gcgtttttcc ataggctccg cccccctgac gagcatcaca aaaatcgacg ctcaagtcag   1440
aggtggcgaa acccgacagg actataaaga taccaggcgt ttccccctgg aagctccctc   1500
gtgcgctctc ctgttccgac cctgccgctt accggatacc tgtccgcctt tctcccttcg   1560
ggaagcgtgg cgctttctca tagctcacgc tgtaggtatc tcagttcggt gtaggtcgtt   1620
cgctccaagc tgggctgtgt gcacgaaccc cccgttcagc ccgaccgctg cgccttatcc   1680
ggtaactatc gtcttgagtc caacccggta agacacgact tatcgccact ggcagcagcc   1740
actggtaaca ggattagcag agcgaggtat gtaggcggtg ctacagagtt cttgaagtgg   1800
tggcctaact acggctacac tagaaggaca gtatttggta tctgcgctct gctgaagcca   1860
gttaccttcg gaaaaagagt tggtagctct tgatccggca aacaaaccac cgctggtagc   1920
ggtggttttt ttgtttgcaa gcagcagatt acgcgcagaa aaaaaggatc tcaagaagat   1980
cctttgatct tttctacggg gtctgacgct cagtggaacg aaaactcacg ttaagggatt   2040
ttggtcatga gattatcaaa aaggatcttc acctagatcc ttttaaatta aaaatgaagt   2100
tttaaatcaa tctaaagtat atatgagtaa acttggtctg acagttacca atgcttaatc   2160
agtgaggcac ctatctcagc gatctgtcta tttcgttcat ccatagttgc ctgactcccc   2220
gtcgtgtaga taactacgat acgggagggc ttaccatctg gccccagtgc tgcaatgata   2280
ccgcgagacc cacgctcacc ggctccagat ttatcagcaa taaaccagcc agccggaagg   2340
gccgagcgca gaagtggtcc tgcaacttta tccgcctcca tccagtctat taattgttgc   2400
cgggaagcta gagtaagtag ttcgccagtt aatagtttgc gcaacgttgt tgccattgct   2460
acaggcatcg tggtgtcacg ctcgtcgttt ggtatggctt cattcagctc cggttcccaa   2520
cgatcaaggc gagttacatg atcccccatg ttgtgcaaaa aagcggttag ctccttcggt   2580
cctccgatcg ttgtcagaag taagttggcc gcagtgttat cactcatggt tatggcagca   2640
ctgcataatt ctcttactgt catgccatcc gtaagatgct tttctgtgac tggtgagtac   2700
tcaaccaagt cattctgaga atagtgtatg cggcgaccga gttgctcttg cccggcgtca   2760
atacgggata ataccgcgcc acatagcaga actttaaaag tgctcatcat tggaaaacgt   2820
tcttcggggc gaaaactctc aaggatctta ccgctgttga gatccagttc gatgtaaccc   2880
actcgtgcac ccaactgatc ttcagcatct tttactttca ccagcgtttc tgggtgagca   2940
aaaacaggaa ggcaaaatgc cgcaaaaaag ggaataaggg cgacacggaa atgttgaata   3000
ctcatactct tcctttttca atattgggat ctgttcggaa atcaacggat gctcaatcga   3060
tttcgacagt aattaattaa gtcatacaca agtcagcttt cttcgagcct catataagta   3120
taagtagttc aacgtattag cactgtaccc agcatctccg tatcgagaaa cacaacaaca   3180
```

-continued

```
tgccccattg gacagatcat gcggatacac aggttgtgca gtatcataca tactcgatca   3240
gacaggtcgt ctgaccatca tacaagctga acaagcgctc catacttgca cgctctctat   3300
atacacagtt aaattacata tccatagtct aacctctaac agttaatctt ctggtaagcc   3360
tcccagccag ccttctggta tcgcttggcc tcctcaatag gatctcggtt ctggccgtac   3420
agacctcggc cgacaattat gatatccgtt ccggtagaca tgacatcctc aacagttcgg   3480
tactgctgtc cgagagcgtc tcccttgtcg tcaagaccca ccccgggggt cagaataagc   3540
cagtcctcag agtcgccctt aggtcggttc tgggcaatga agccaaccac aaactcgggg   3600
tcggatcggg caagctcaat ggtctgcttg gagtactcgc cagtggccag agagcccttg   3660
caagacagct cggccagcat gagcagacct ctggccagct tctcgttggg agaggggact   3720
aggaactcct tgtactggga gttctcgtag tcagagacgt cctccttctt ctgttcagag   3780
acagtttcct cggcaccagc tcgcaggcca gcaatgattc cggttccggg tacaccgtgg   3840
gcgttggtga tatcggacca ctcggcgatt cggtgacacc ggtactggtg cttgacagtg   3900
ttgccaatat ctgcgaactt tctgtcctcg aacaggaaga aaccgtgctt aagagcaagt   3960
tccttgaggg ggagcacagt gccggcgtag gtgaagtcgt caatgatgtc gatatgggtt   4020
ttgatcatgc acacataagg tccgacctta tcggcaagct caatgagctc cttggtggtg   4080
gtaacatcca gagaagcaca caggttggtt ttcttggctg ccacgagctt gagcactcga   4140
gcggcaaagg cggacttgtg gacgttagct cgagcttcgt aggagggcat tttggtggtg   4200
aagaggagac tgaaataaat ttagtctgca gaacttttta tcggaacctt atctggggca   4260
gtgaagtata tgttatggta atagttacga gttagttgaa cttatagata gactggacta   4320
tacggctatc ggtccaaatt agaaagaacg tcaatggctc tctgggcgtc gcctttgccg   4380
acaaaaatgt gatcatgatg aaagccagca atgacgttgc agctgatatt gttgtcggcc   4440
aaccgcgccg aaaacgcagc tgtcagaccc acagcctcca acgaagaatg tatcgtcaaa   4500
gtgatccaag cacactcata gttggagtcg tactccaaag gcggcaatga cgagtcagac   4560
agatactcgt cgaccgtacg atagttagta gacaacaatc gatagttgga gcaagggaga   4620
aatgtagagt gtgaaagact cactatggtc cgggcttatc tcgaccaata gccaaagtct   4680
ggagtttctg agagaaaaag gcaagatacg tatgtaacaa agcgacgcat ggtacaataa   4740
taccggaggc atgtatcata gagagttagt ggttcgatga tggcactggt gcctggtatg   4800
actttatacg gctgactaca tatttgtcct cagacataca attacagtca agcacttacc   4860
cttggacatc tgtaggtacc ccccggccaa gacgatctca gcgtgtcgta tgtcggattg   4920
gcgtagctcc ctcgctcgtc aattggctcc catctacttt cttctgcttg gctacaccca   4980
gcatgtctgc tatggctcgt tttcgtgcct tatctatcct cccagtatta ccaactctaa   5040
atgacatgat gtgattgggt ctacactttc atatcagaga taaggagtag cacagttgca   5100
taaaaagccc aactctaatc agcttcttcc tttcttgtaa ttagtacaaa ggtgattagc   5160
gaaatctgga agcttagttg gccctaaaaa aatcaaaaaa agcaaaaaac gaaaaacgaa   5220
aaaccacagt tttgagaaca gggaggtaac gaaggatcgt atatatatat atatatatat   5280
atacccacgg atcccgagac cggcctttga ttcttcccta caaccaacca ttctcaccac   5340
cctaattcac aaccatggcc acacaacctg tgaatcggaa ggcgactgtc gagcgggtcg   5400
agccagcagt ggaggtggct gactccgagt ccgaggccaa gaccgacgtc cacgttcacc   5460
accatcatca ccaccacaag cgaaaatccg tcaagggcaa gattctcaac ttcttcaccc   5520
gaagtcgacg tatcaccttc gtcctcggcg ccgtggtcgg tgtgatagcc gcgggatact   5580
```

-continued

```
acgctgcgcc accggagctc agcattgata tcgacgctct tctcggcgac ttgccctcgt   5640
tcgactttga cgctctatct ctcgacaact tgtcgatgga cagtgtgtcg gactttgtac   5700
aagacatgaa atcgcggttt ccgaccaaga ttctgcagga ggcggccaag atcgagaagc   5760
accagaaaag cgaacagaag gctgcccctt ttgctgtggg caaggctatg aagagcgagg   5820
gactcaacgc caagtacccg gtggtgctgg tgcccggcgt catctccacg ggactggaga   5880
gctggtccct ggagggaacc gaggagtgtc ccaccgagtc gcacttcaga aagcgaatgt   5940
ggggctcctg gtacatgatc cgagtcatgc tgctggacaa gtactgctgg ctgcagaacc   6000
tgatgctgga cacagagacc ggtctagacc ctccccattt caagctgcga gccgcccagg   6060
gatttgcctc cgccgacttc tttatggcag gctactggct gtggaacaag ctgctcgaga   6120
acctggctgt tattggatac gatacggata caatgtctgc tgcggcctac gactggagac   6180
tgtcctaccc tgatttggag caccgagacg gatacttctc caagctcaaa gcttcaatcg   6240
aagagactaa gcgtatgaca ggtgagaaga cagttctgac gggccattcg atgggctccc   6300
aggtcatctt ctacttcatg aagtgggctg aggccgaggg atatggagga ggaggtccca   6360
actgggtcaa tgaccatatt gaatcctttg tcgacatttc cggctccatg ctgggtactc   6420
ccaagaccct ggttgctctt ctgtctggag aaatgaagga taccgtgcag ctgaacgcga   6480
tggctgtgta tggactggag cagttcttct ctcgacgaga gcgagccgat ctgctgcgaa   6540
catggggagg aattgcttcc atgattccca agggtggtaa ggctatctgg ggtgatcatt   6600
ctggagcccc tgatgacgag cccggccaga atgtcacctt tggcaacttc atcaagttca   6660
aggagtcctt gaccgagtac tctgctaaga acctcactat ggatgaaacc gttgacttcc   6720
tgtattctca gtctcccgag tggtttgtga accgaaccga gggtgcttac tcctttggaa   6780
ttgccaagac tcgaaagcag gttgagcaga atgagaagcg accttctacc tggagcaacc   6840
ctctggaagc tgctctcccc aatgcccccg atctcaagat ctactgcttc tatggagtcg   6900
gtaaggatac cgagcgagcc tactactacc aggatgagcc caatcccgag cagaccaact   6960
tgaacgtcag tatcgctgga aacgaccctg atggtgtgct tatgggtcag ggcgatggaa   7020
ccgtctccct tgtgacccat accatgtgtc accgatggaa ggacgagaac tccaagttca   7080
accctggtaa cgcccaggtc aaggttgtgg agatgttgca ccagcctgat cgacttgata   7140
ttcgaggcgg tgctcagact gccgagcatg tggacattct ggggcgttct gagttgaacg   7200
agatggttct gaaggtggct agtggaaagg gaaatgagat tgaagagaga gtcatctcca   7260
acattgatga gtgggtgtgg aagattgatc tcggcagcaa ttaggcggcc gcattgatga   7320
ttggaaacac acacatgggt tatatctagg tgagagttag ttggacagtt atatattaaa   7380
tcagctatgc caacggtaac ttcattcatg tcaacgagga accagtgact gcaagtaata   7440
tagaatttga ccaccttgcc attctcttgc actcctttac tatatctcat ttatttctta   7500
tatacaaatc acttcttctt cccagcatcg agctcggaaa cctcatgagc aataacatcg   7560
tggatctcgt caatagaggg ctttttggac tccttgctgt tggccacctt gtccttgctg   7620
tttaaacagt gtacgcagat ctactataga ggaacatttc tttcgcattt cgccctatat   7680
ctagttcttt ggtgcccaaa gaagggcacc cctgcggggt tcccccacgc cttcggcgcg   7740
gctccccctc cggcaaaaag tggcccctcc ggggcttgtt gatcgactgc gcggccttcg   7800
gccttgccca aggtggcgct gcccccttgg aacccccgca ctcgccgccg tgaggctcgg   7860
gacctgcagg gggggggggg aaagccacgt tgtgtctcaa aatctctgat gttacattgc   7920
```

-continued

```
acaagataaa aatatatcat catgaacaat aaaactgtct gcttacataa acagtaatac   7980
aaggggtgtt atgagccata ttcaacggga aacgtcttgc tcgaggccgc gattaaattc   8040
caacatggat gctgatttat atgggtataa atgggctcgc gataatgtcg ggcaatcagg   8100
tgcgacaatc tatcgattgt atgggaagcc cgatgcgcca gagttgtttc tgaaacatgg   8160
caaaggtagc gttgccaatg atgttacaga tgagatggtc agactaaact ggctgacgga   8220
atttatgcct cttccgacca tcaagcattt tatccgtact cctgatgatg catggttact   8280
caccactgcg atccccggga aaacagcatt ccaggtatta gaagaatatc ctgattcagg   8340
tgaaaatatt gttgatgcgc tggcagtgtt cctgcgccgg ttgcattcga ttcctgtttg   8400
taattgtcct tttaacagcg atcgcgtatt tcgtctcgct caggcgcaat cacgaatgaa   8460
taacggtttg gttgatgcga gtgattttga tgacgagcgt aatggctggc ctgttgaaca   8520
agtctggaaa gaaatgcata agcttttgcc attctcaccg gattcagtcg tcactcatgg   8580
tgatttctca cttgataacc ttatttttga cgaggggaaa ttaataggtt gtattgatgt   8640
tggacgagtc ggaatcgcag accgatacca ggatcttgcc atcctatgga actgcctcgg   8700
tgagttttct ccttcattac agaaacggct ttttcaaaaa tatggtattg ataatcctga   8760
tatgaataaa ttgcagtttc atttgatgct cgatgagttt ttctaatcag aattggttaa   8820
ttggttgtaa cactggcaga gcattacgct gacttgacgg gacggcggct ttgttgaata   8880
aatcgaactt ttgctgagtt gaaggatcag atcaatttaa atgggccctc cttcacttca   8940
agttcattct tcatctgctt ctgttttact ttgacaggca aatgaagaca tggtacgact   9000
tgatggaggc caagaacgcc atttcacccc gagacaccga agtgcctgaa atcctggctg   9060
cccccattga taacatcgga aactacggta ttccggaaag tgtatataga acctttcccc   9120
agcttgtgtc tgtggatatg gatggtgtaa tcccctttga gtactcgtct tggcttctct   9180
ccgagcagta tgaggctctc taatctagcg catttaatat ctcaatgtat ttatatattt   9240
atcttctcat gcggccgcct actgagtctt ctggccagcg tagccaatct ggtcggcagt   9300
ctcgcacatg gccttataag tggtggccat gagagcgtcg acgttgctgg cgtccagacc   9360
cttggtctca atggggctca ggacgtcgac aaggatctct ccggcgtcca gcttgcctcg   9420
gccgaaagaa aacattcggg aggtgttctg gaccaccacg gggacaatgg gagcgcccga   9480
ctggaccgcc aggtggaaac agcccttctt gaagggcatg atgccgacgt ccttggagta   9540
ggatcgggtt ccctcgggga acatgaagac gctctggccc ttgcctccgt tgccgctctg   9600
gatggtcttg acggcgccgc cgagggtctg cacggacttg gttcggtcct ttcggtccag   9660
gaagatggtg ccggacagcg ccatgaactg gcccagcaga gggtaccact tgagggcctt   9720
tttggcggtg acggagcagt actgggggaa gatgcgaccg agcaccagaa tgtccatttc   9780
gttctggtgg ttggaaatca gaatgcatgg tcggggcagg tgtttggtga tgtcgtcaat   9840
gggcttggtg gtgttggcga cctggatctt ggaggcatcc agaccggcgg ttccggtcac   9900
ctgccggcta cgcagcttga tgctgatacc caggaagatg cgcaccgagt agtagaaggc   9960
tctggcaacg gtccattggg ccaggccctg cttgccgatg gcggtgagaa tggtggacgc  10020
cagcacgccg taggtggcac aggcggcaaa gatgaccacg gcgatggcgg cgcggacgta  10080
gaagacgagc ttggatgcaa cggacatgag ctgggttagt ttgtgtagag agtgtgtgtt  10140
gctagcgact ttcggattgt gtcattacac aaaacgcgtc gtctcgacac tgatcttgtc  10200
gtggatactc acggctcgga attctgtgat gtgtagttta gatttcgaat ctgtggggaa  10260
agaaaggaaa aaagagactg gcaaccgatt gggagagcca ctgtttatat ataccctaga  10320
```

```
caagcccccc gcttgtaaga tgttggtcaa tgtaaaccag tattaaggtt ggcaagtgca  10380

ggagaagcaa ggtgtgggta ccgagcaatg gaaatgtgcg gaaggcaaaa aaatgaggcc  10440

acggcctatt gtcggggcta tatccagggg gcgattgaag tacactaaca tgacatgtgt  10500

ccacagaccc tcaatctggc ctgatgagcc aaatccatac gcgctttcgc agctctaaag  10560

gctataacaa gtcacaccac cctgctcgac ctcagcgccc tcactttttg ttaagacaaa  10620

ctgtacacgc tgttccagcg ttttctgcct gcacctggtg ggacatttgg tgcaacctaa  10680

agtgctcgga acctctgtgg tgtccagatc agcgcagcag ttccgaggta gttttgaggc  10740

ccttagatga tgcaatggtg tcagtcgctg gatcacgagt cttaatggca gtattcgttc  10800

ttatttgtgc cattgagccc cgttatcctc gtatcttcta ccccccatcc catccctttg  10860

ttggtgcaac cctacccatt tattgttggg tgcagcccaa ccgacgtgga gagcttggct  10920

tggccatata aaaaggcccc cccctagtgg caatggcaga aagtcagctg tgagttgttg  10980

aatttgtcat ctaggcggcc tggccgtctt ctgcatg                           11017
```

<210> SEQ ID NO 44
<211> LENGTH: 10575
<212> TYPE: DNA
<213> ORGANISM: Artificial Sequence
<220> FEATURE:
<223> OTHER INFORMATION: Plasmid pY301

<400> SEQUENCE: 44

```
ggccgcattg atgattggaa acacacacat gggttatatc taggtgagag ttagttggac     60

agttatatat taaatcagct atgccaacgg taacttcatt catgtcaacg aggaaccagt    120

gactgcaagt aatatagaat ttgaccacct tgccattctc ttgcactcct ttactatatc    180

tcatttattt cttatataca aatcacttct tcttcccagc atcgagctcg gaaacctcat    240

gagcaataac atcgtggatc tcgtcaatag agggcttttt ggactccttg ctgttggcca    300

ccttgtcctt gctgtttaaa cagtgtacgc agatctacta tagaggaaca tttctttcgc    360

atttcgccct atatctagtt ctttggtgcc caaagaaggg caccccctgcg gggttccccc    420

acgccttcgg cgcggctccc cctccggcaa aaagtggccc ctccggggct tgttgatcga    480

ctgcgcggcc ttcggccttg cccaaggtgg cgctgccccc ttggaacccc cgcactcgcc    540

gccgtgaggc tcgggacctg caggggggggg ggggaaagcc acgttgtgtc tcaaaatctc    600

tgatgttaca ttgcacaaga taaaaatata tcatcatgaa caataaaact gtctgcttac    660

ataaacagta atacaagggg tgttatgagc catattcaac gggaaacgtc ttgctcgagg    720

ccgcgattaa attccaacat ggatgctgat ttatatgggt ataaatgggc tcgcgataat    780

gtcgggcaat caggtgcgac aatctatcga ttgtatggga agcccgatgc gccagagttg    840

tttctgaaac atggcaaagg tagcgttgcc aatgatgtta cagatgagat ggtcagacta    900

aactggctga cggaatttat gcctcttccg accatcaagc attttatccg tactcctgat    960

gatgcatggt tactcaccac tgcgatcccc gggaaaacag cattccaggt attagaagaa   1020

tatcctgatt caggtgaaaa tattgttgat gcgctggcag tgttcctgcg ccggttgcat   1080

tcgattcctg tttgtaattg tccttttaac agcgatcgcg tatttcgtct cgctcaggcg   1140

caatcacgaa tgaataacgg tttggttgat gcgagtgatt ttgatgacga gcgtaatggc   1200

tggcctgttg aacaagtctg gaaagaaatg cataagcttt tgccattctc accggattca   1260

gtcgtcactc atggtgattt ctcacttgat aaccttattt ttgacgaggg gaaattaata   1320
```

-continued

```
ggttgtattg atgttggacg agtcggaatc gcagaccgat accaggatct tgccatccta   1380
tggaactgcc tcggtgagtt ttctccttca ttacagaaac ggctttttca aaaatatggt   1440
attgataatc ctgatatgaa taaattgcag tttcatttga tgctcgatga gtttttctaa   1500
tcagaattgg ttaattggtt gtaacactgg cagagcatta cgctgacttg acgggacggc   1560
ggctttgttg aataaatcga acttttgctg agttgaagga tcagatcaat ttaaattcct   1620
tcacttcaag ttcattcttc atctgcttct gttttacttt gacaggcaaa tgaagacatg   1680
gtacgacttg atggaggcca agaacgccat ttcaccccga gacaccgaag tgcctgaaat   1740
cctggctgcc cccattgata acatcggaaa ctacggtatt ccggaaagtg tatatagaac   1800
ctttccccag cttgtgtctg tggatatgga tggtgtaatc ccctttgagt actcgtcttg   1860
gcttctctcc gagcagtatg aggctctcta atctagcgca tttaatatct caatgtattt   1920
atatatttat cttctcatgc ggccgcttac ttggtcttga tggtgtcctt cttcacctcc   1980
tccttggcgt ccttcttgtc agtgacggct ccagcctgct tttcttgat cttgggaatc    2040
gcccatgcct tgtaggggct agaaattgca aagatggcgc ccagagcaat gtggtacagg   2100
aaccaggagt tcttccaaca cttgagcgac agccagaagt ctagaatcat aaaggactgg   2160
gtagcgtatc caaatgcggt ttggacaacg atccaacaca caatgtcgta gtagatctta   2220
tagggaccgg cagtctttcc atcagactcc atgaagaagg gtcgcaggta tcgtcggaag   2280
aacttaccaa cagactggta catggcagcg gtcacaaagg tgagatagta gccaggtcga   2340
gttccatgcc agaaggcgga aaccacaaat gtgaagatag tggctcggaa tccaggcttt   2400
tggcctttgg gcaccactcg gaggtacaca tagtttcgta gccacttgtt agtgttctgg   2460
ttccaggcct ccagcagagc ctttgtgttt tgaccagttt cgaatcccca cgggtccacg   2520
ttctggacac ggtcccactt gtacttgcca gttttggggt ccacgccatg gaatccgagg   2580
ccagacaaga tgcaggctcc ctcggaaatg gaccaggctc cgtagtactt gagtcggtac   2640
atgaaaccga gcatgtagag gtacacaatt cgtccaaaga tgttgtgctc cttggtgaat   2700
gcgtctgagt aagcgtaggc ggtggagatt cgagagtcca cctgggtcca cagaacgatc   2760
cagaagatac cagcggcgag tttcttggaa gcagcgattc cagatcgggg gatcttgtgt   2820
cgctttcgtc gagcagctcg cttggggtcc ttatctttct ccagctcctt gaacaggctg   2880
agatcgagcc agttatggaa ctccatatag tcgtaagaag gacctgtcag aatggaaggg   2940
aagtagaaca caaaagctag gaagtccata agactggggt gcttgagaac agccctttta   3000
gtctggaact cgctgagctg ctcaccccttc tcaatctgcc atccatcgta gacgttccat  3060
ccaaaagacg atagcttcat acacagaacc atctgtgctc cggtgatgtc aatgacattg   3120
gggtcgtatg tttcggggaa aaactgcgaa cgcaggtgat tgacgaagag atgggtcatg   3180
acaaaaccaa aattgaccca gggcatgtaa gggctcttcc attgggtgat gaagaaggta   3240
cccattgagg agaagagcag agtggcagct ccgccataga gggagaagac acccaccatg   3300
tagaagatgg acacggagat gatatagatg atcttgaggt ttttggcgtc atctggcagc   3360
cgtttcatga gagaactcag cggataagac atgaccagag tgaatgcaat cttgaggagg   3420
tccggaggca gccctgtaga tgcagacgca tcggctgccc acttatctgc ccatggaaag   3480
gccatggttg tgaattaggg tggtgagaat ggttggttgt agggaagaat caaaggccgg   3540
tctcgggatc cgtgggtata tatatatata tatatatata cgatccttcg ttacctccct   3600
gttctcaaaa ctgtggtttt tcgtttttcg ttttttgctt tttttgattt ttttagggcc   3660
aactaagctt ccagatttcg ctaatcacct ttgtactaat tacaagaaag gaagaagctg   3720
```

attagagttg ggctttttat gcaactgtgc tactccttat ctctgatatg aaagtgtaga 3780
cccaatcaca tcatgtcatt tagagttggt aatactggga ggatagataa ggcacgaaaa 3840
cgagccatag cagacatgct gggtgtagcc aagcagaaga aagtagatgg gagccaattg 3900
acgagcgagg gagctacgcc aatccgacat acgacacgct gagatcgtct tggccggggg 3960
gtacctacag atgtccaagg gtaagtgctt gactgtaatt gtatgtctga ggacaaatat 4020
gtagtcagcc gtataaagtc ataccaggca ccagtgccat catcgaacca ctaactctct 4080
atgatacatg cctccggtat tattgtacca tgcgtcgctt tgttacatac gtatcttgcc 4140
tttttctctc agaaactcca gactttggct attggtcgag ataagcccgg accatagtga 4200
gtctttcaca ctctacattt ctcccttgct ccaactatcg attgttgtct actaactatc 4260
gtagcatgcg gatcgggcaa gctcaatggt ctgcttggag tactcgccag tggccagaga 4320
gcccttgcaa gacagctcgg ccagcatgag cagacctctg gccagcttct cgttgggaga 4380
ggggactagg aactccttgt actgggagtt ctcgtagtca gagacgtcct ccttcttctg 4440
ttcagagaca gtttcctcgg caccagctcg caggccagca atgattccgg ttccgggtac 4500
accgtgggcg ttggtgatat cggaccactc ggcgattcgg tgacaccggt actggtgctt 4560
gacagtgttg ccaatatctg cgaactttct gtcctcgaac aggaagaaac cgtgcttaag 4620
agcaagttcc ttgaggggga gcacagtgcc ggcgtaggtg aagtcgtcaa tgatgtcgat 4680
atgggttttg atcatgcaca cataaggtcc gaccttatcg gcaagctcaa tgagctcctt 4740
ggtggtggta acatccagag aagcacacag gttggttttc ttggctgcca cgagcttgag 4800
cactcgagcg gcaaaggcgg acttgtggac gttagctcga gcttcgtagg agggcatttt 4860
ggtggtgaag aggagactga aataaattta gtctgcagaa ctttttatcg gaaccttatc 4920
tggggcagtg aagtatatgt tatggtaata gttacgagtt agttgaactt atagatagac 4980
tggactatac ggctatcggt ccaaattaga aagaacgtca atggctctct gggcgtcgcc 5040
tttgccgaca aaaatgtgat catgatgaaa gccagcaatg acgttgcagc tgatattgtt 5100
gtcggccaac cgcgccgaaa acgcagctgt cagacccaca gcctaggacg aaactgaaat 5160
ttgaccagat attgtgtccg cggtggagct ccagcttttg ttccctttag tgagggttaa 5220
tttcgagctt ggcgtaatca tggtcatagc tgtttcctgt gtgaaattgt tatccgctca 5280
caagcttcca cacaacgtac gagccggaag cataaagtgt aaagcctggg gtgcctaatg 5340
agtgagctaa ctcacattaa ttgcgttgcg ctcactgccc gctttccagt cgggaaacct 5400
gtcgtgccag ctgcattaat gaatcggcca acgcgcgggg agaggcggtt tgcgtattgg 5460
gcgctcttcc gcttcctcgc tcactgactc gctgcgctcg gtcgttcggc tgcggcgagc 5520
ggtatcagct cactcaaagg cggtaatacg gttatccaca gaatcagggg ataacgcagg 5580
aaagaacatg tgagcaaaag gccagcaaaa ggccaggaac cgtaaaaagg ccgcgttgct 5640
ggcgtttttc cataggctcc gcccccctga cgagcatcac aaaaatcgac gctcaagtca 5700
gaggtggcga aacccgacag gactataaag ataccaggcg tttccccctg gaagctccct 5760
cgtgcgctct cctgttccga ccctgccgct taccggatac ctgtccgcct ttctcccttc 5820
gggaagcgtg gcgctttctc atagctcacg ctgtaggtat ctcagttcgg tgtaggtcgt 5880
tcgctccaag ctgggctgtg tgcacgaacc ccccgttcag cccgaccgct gcgccttatc 5940
cggtaactat cgtcttgagt ccaacccggt aagacacgac ttatcgccac tggcagcagc 6000
cactggtaac aggattagca gagcgaggta tgtaggcggt gctacagagt tcttgaagtg 6060
gtggcctaac tacggctaca ctagaaggac agtatttggt atctgcgctc tgctgaagcc 6120
agttaccttc ggaaaaagag ttggtagctc ttgatccggc aaacaaacca ccgctggtag 6180
cggtggtttt tttgtttgca agcagcagat tacgcgcaga aaaaaaggat ctcaagaaga 6240
tcctttgatc ttttctacgg ggtctgacgc tcagtggaac gaaaactcac gttaagggat 6300
tttggtcatg agattatcaa aaaggatctt cacctagatc cttaattaag tcatacacaa 6360
gtcagctttc ttcgagcctc atataagtat aagtagttca acgtattagc actgtaccca 6420
gcatctccgt atcgagaaac acaacaacat gccccattgg acagatcatg cggatacaca 6480
ggttgtgcag tatcatacat actcgatcag acaggtcgtc tgaccatcat acaagctgaa 6540
caagcgctcc atacttgcac gctctctata tacacagtta aattacatat ccatagtcta 6600
acctctaaca gttaatcttc tggtaagcct cccagccagc cttctggtat cgcttggcct 6660
cctcaatagg atctcggttc tggccgtaca gacctcggcc gacaattatg atatccgttc 6720
cggtagacat gacatcctca acagttcggt actgctgtcc gagagcgtct cccttgtcgt 6780
caagacccac cccgggggtc agaataagcc agtcctcaga gtcgccctta ggtcggttct 6840
gggcaatgaa gccaaccaca aactcggggt cggatcgggc aagctcaatg gtctgcttgg 6900
agtactcgcc agtggccaga gagcccttgc aagacagctc ggccagcatg agcagacctc 6960
tggccagctt ctcgttggga gaggggacta ggaactcctt gtactgggag ttctcgtagt 7020
cagagacgtc ctccttcttc tgttcagaga cagtttcctc ggcaccagct cgcaggccag 7080
caatgattcc ggttccgggt acaccgtggg cgttggtgat atcggaccac tcggcgattc 7140
ggtgacaccg gtactggtgc ttgacagtgt tgccaatatc tgcgaacttt ctgtcctcga 7200
acaggaagaa accgtgctta agagcaagtt ccttgagggg gagcacagtg ccggcgtagg 7260
tgaagtcgtc aatgatgtcg atatgggttt tgatcatgca cacataaggt ccgaccttat 7320
cggcaagctc aatgagctcc ttggtggtgg taacatccag agaagcacac aggttggttt 7380
tcttggctgc cacgagcttg agcactcgag cggcaaaggc ggacttgtgg acgttagctc 7440
gagcttcgta ggagggcatt ttggtggtga agaggagact gaaataaatt tagtctgcag 7500
aactttttat cggaacctta tctggggcag tgaagtatat gttatggtaa tagttacgag 7560
ttagttgaac ttatagatag actggactat acggctatcg gtccaaatta gaaagaacgt 7620
caatggctct ctgggcgtcg cctttgccga caaaaatgtg atcatgatga aagccagcaa 7680
tgacgttgca gctgatattg ttgtcggcca accgcgccga aaacgcagct gtcagaccca 7740
cagcctccaa cgaagaatgt atcgtcaaag tgatccaagc acactcatag ttggagtcgt 7800
actccaaagg cggcaatgac gagtcagaca gatactcgtc gaccgtacga tagttagtag 7860
acaacaatcg atagttggag caagggagaa atgtagagtg tgaaagactc actatggtcc 7920
gggcttatct cgaccaatag ccaaagtctg gagtttctga gagaaaaagg caagatacgt 7980
atgtaacaaa gcgacgcatg gtacaataat accggaggca tgtatcatag agagttagtg 8040
gttcgatgat ggcactggtg cctggtatga ctttatacgg ctgactacat atttgtcctc 8100
agacatacaa ttacagtcaa gcacttaccc ttggacatct gtaggtaccc cccggccaag 8160
acgatctcag cgtgtcgtat gtcggattgg cgtagctccc tcgctcgtca attggctccc 8220
atctactttc ttctgcttgg ctacacccag catgtctgct atggctcgtt ttcgtgcctt 8280
atctatcctc ccagtattac caactctaaa tgacatgatg tgattgggtc tacactttca 8340
tatcagagat aaggagtagc acagttgcat aaaaagccca actctaatca gcttcttcct 8400
ttcttgtaat tagtacaaag gtgattagcg aaatctggaa gcttagttgg ccctaaaaaa 8460

-continued

```
atcaaaaaaa gcaaaaaacg aaaaacgaaa aaccacagtt ttgagaacag ggaggtaacg   8520

aaggatcgta tatatatata tatatatata tacccacgga tcccgagacc ggcctttgat   8580

tcttccctac aaccaaccat tctcaccacc ctaattcaca accatggcca cacaacctgt   8640

gaatcggaag gcgactgtcg agcgggtcga gccagcagtg gaggtggctg actccgagtc   8700

cgaggccaag accgacgtcc acgttcacca ccatcatcac caccacaagc gaaaatccgt   8760

caagggcaag attctcaact tcttcacccg aagtcgacgt atcaccttcg tcctcggcgc   8820

cgtggtcggt gtgatagccg cgggatacta cgctgcgcca ccggagctca gcattgatat   8880

cgacgctctt ctcggcgact tgccctcgtt cgactttgac gctctatctc tcgacaactt   8940

gtcgatggac agtgtgtcgg actttgtaca agacatgaaa tcgcggtttc cgaccaagat   9000

tctgcaggag gcggccaaga tcgagaagca ccagaaaagc gaacagaagg ctgccccttt   9060

tgctgtgggc aaggctatga agagcgaggg actcaacgcc aagtacccgg tggtgctggt   9120

gcccggcgtc atctccacgg gactggagag ctggtccctg gagggaaccg aggagtgtcc   9180

caccgagtcg cacttcagaa agcgaatgtg ggctcctgg tacatgatcc gagtcatgct   9240

gctggacaag tactgctggc tgcagaacct gatgctggac acagagaccg gtctagaccc   9300

tccccatttc aagctgcgag ccgcccaggg atttgcctcc gccgacttct ttatggcagg   9360

ctactggctg tggaacaagc tgctcgagaa cctggctgtt attggatacg atacggatac   9420

aatgtctgct gcggcctacg actggagact gtcctaccct gatttggagc accgagacgg   9480

atacttctcc aagctcaaag cttcaatcga agagactaag cgtatgacag gtgagaagac   9540

agttctgacg ggccattcga tggctccca ggtcatcttc tacttcatga agtgggctga   9600

ggccgaggga tatggaggag gaggtcccaa ctgggtcaat gaccatattg aatcctttgt   9660

cgacatttcc ggctccatgc tgggtactcc caagaccctg gttgctcttc tgtctggaga   9720

aatgaaggat accgtgcagc tgaacgcgat ggctgtgtat ggactggagc agttcttctc   9780

tcgacgagag cgagccgatc tgctgcgaac atggggagga attgcttcca tgattcccaa   9840

gggtggtaag gctatctggg gtgatcattc tggagcccct gatgacgagc ccggccagaa   9900

tgtcaccttt ggcaacttca tcaagttcaa ggagtccttg accgagtact ctgctaagaa   9960

cctcactatg gatgaaaccg ttgacttcct gtattctcag tctcccgagt ggtttgtgaa  10020

ccgaaccgag ggtgcttact cctttggaat tgccaagact cgaaagcagg ttgagcagaa  10080

tgagaagcga ccttctacct ggagcaaccc tctggaagct gctctcccca atgcccccga  10140

tctcaagatc tactgcttct atggagtcgg taaggatacc gagcgagcct actactacca  10200

ggatgagccc aatcccgagc agaccaactt gaacgtcagt atcgctggaa acgaccctga  10260

tggtgtgctt atgggtcagg gcgatggaac cgtctccctt gtgacccata ccatgtgtca  10320

ccgatggaag gacgagaact ccaagttcaa ccctggtaac gcccaggtca aggttgtgga  10380

gatgttgcac cagcctgatc gacttgatat tcgaggcggt gctcagactg ccgagcatgt  10440

ggacattctg gggcgttctg agttgaacga gatggttctg aaggtggcta gtggaaaggg  10500

aaatgagatt gaagagagag tcatctccaa cattgatgag tgggtgtgga agattgatct  10560

cggcagcaat taggc                                                   10575
```

<210> SEQ ID NO 45
<211> LENGTH: 1539
<212> TYPE: DNA
<213> ORGANISM: Yarrowia lipolytica
<220> FEATURE:

```
<221> NAME/KEY: CDS
<222> LOCATION: (1)..(1539)

<400> SEQUENCE: 45

atg gcc ttt cct tgg gca gat aag tgg gca gcc gat gcg tct gca tct       48
Met Ala Phe Pro Trp Ala Asp Lys Trp Ala Ala Asp Ala Ser Ala Ser
1               5                   10                  15

aca ggg ctg cct ccg gac ctc ctc aag att gca ttc act ctg gtc atg       96
Thr Gly Leu Pro Pro Asp Leu Leu Lys Ile Ala Phe Thr Leu Val Met
            20                  25                  30

tct tat ccg ctg agt tct ctc atg aaa cgg ctg cca gat gac gcc aaa      144
Ser Tyr Pro Leu Ser Ser Leu Met Lys Arg Leu Pro Asp Asp Ala Lys
        35                  40                  45

aac ctc aag atc atc tat atc atc tcc gtg tcc atc ttc tac atg gtg      192
Asn Leu Lys Ile Ile Tyr Ile Ile Ser Val Ser Ile Phe Tyr Met Val
    50                  55                  60

ggt gtc ttc tcc ctc tat ggc gga gct gcc act ctg ctc ttc tcc tca      240
Gly Val Phe Ser Leu Tyr Gly Gly Ala Ala Thr Leu Leu Phe Ser Ser
65                  70                  75                  80

atg ggt acc ttc ttc atc acc caa tgg aag agc cct tac atg ccc tgg      288
Met Gly Thr Phe Phe Ile Thr Gln Trp Lys Ser Pro Tyr Met Pro Trp
                85                  90                  95

gtc aat ttt ggt ttt gtc atg acc cat ctc ttc gtc aat cac ctg cgt      336
Val Asn Phe Gly Phe Val Met Thr His Leu Phe Val Asn His Leu Arg
            100                 105                 110

tcg cag ttt ttc ccc gaa aca tac gac ccc aat gtc att gac atc acc      384
Ser Gln Phe Phe Pro Glu Thr Tyr Asp Pro Asn Val Ile Asp Ile Thr
        115                 120                 125

gga gca cag atg gtt ctg tgt atg aag cta tcg tct ttt gga tgg aac      432
Gly Ala Gln Met Val Leu Cys Met Lys Leu Ser Ser Phe Gly Trp Asn
    130                 135                 140

gtc tac gat gga tgg cag att gag aag ggt gag cag ctc agc gag ttc      480
Val Tyr Asp Gly Trp Gln Ile Glu Lys Gly Glu Gln Leu Ser Glu Phe
145                 150                 155                 160

cag act aaa agg gct gtt ctc aag cac ccc agt ctt atg gac ttc cta      528
Gln Thr Lys Arg Ala Val Leu Lys His Pro Ser Leu Met Asp Phe Leu
                165                 170                 175

gct ttt gtg ttc tac ttc cct tcc att ctg aca ggt cct tct tac gac      576
Ala Phe Val Phe Tyr Phe Pro Ser Ile Leu Thr Gly Pro Ser Tyr Asp
            180                 185                 190

tat atg gag ttc cat aac tgg ctc gat ctc agc ctg ttc aag gag ctg      624
Tyr Met Glu Phe His Asn Trp Leu Asp Leu Ser Leu Phe Lys Glu Leu
        195                 200                 205

gag aaa gat aag gac ccc aag cga gct gct cga cga aag cga cac aag      672
Glu Lys Asp Lys Asp Pro Lys Arg Ala Ala Arg Arg Lys Arg His Lys
    210                 215                 220

atc ccc cga tct gga atc gct gct tcc aag aaa ctc gcc gct ggt atc      720
Ile Pro Arg Ser Gly Ile Ala Ala Ser Lys Lys Leu Ala Ala Gly Ile
225                 230                 235                 240

ttc tgg atc gtt ctg tgg acc cag gtg gac tct cga atc tcc acc gcc      768
Phe Trp Ile Val Leu Trp Thr Gln Val Asp Ser Arg Ile Ser Thr Ala
                245                 250                 255

tac gct tac tca gac gca ttc acc aag gag cac aac atc ttt gga cga      816
Tyr Ala Tyr Ser Asp Ala Phe Thr Lys Glu His Asn Ile Phe Gly Arg
            260                 265                 270

att gtg tac ctc tac atg ctc ggt ttc atg tac cga ctc aag tac tac      864
Ile Val Tyr Leu Tyr Met Leu Gly Phe Met Tyr Arg Leu Lys Tyr Tyr
        275                 280                 285

gga gcc tgg tcc att tcc gag gga gcc tgc atc ttg tct ggc ctc gga      912
Gly Ala Trp Ser Ile Ser Glu Gly Ala Cys Ile Leu Ser Gly Leu Gly
```

```
    290                 295                 300

ttc cac ggc gtg gac ccc aaa act ggc aag tac aag tgg gac cgt gtc      960
Phe His Gly Val Asp Pro Lys Thr Gly Lys Tyr Lys Trp Asp Arg Val
305                 310                 315                 320

cag aac gtg gac ccg tgg gga ttc gaa act ggt caa aac aca aag gct     1008
Gln Asn Val Asp Pro Trp Gly Phe Glu Thr Gly Gln Asn Thr Lys Ala
                325                 330                 335

ctg ctg gag gcc tgg aac cag aac act aac aag tgg cta cga aac tat     1056
Leu Leu Glu Ala Trp Asn Gln Asn Thr Asn Lys Trp Leu Arg Asn Tyr
            340                 345                 350

gtg tac ctc cga gtg gtg ccc aaa ggc caa aag cct gga ttc cga gcc     1104
Val Tyr Leu Arg Val Val Pro Lys Gly Gln Lys Pro Gly Phe Arg Ala
        355                 360                 365

act atc ttc aca ttt gtg gtt tcc gcc ttc tgg cat gga act cga cct     1152
Thr Ile Phe Thr Phe Val Val Ser Ala Phe Trp His Gly Thr Arg Pro
    370                 375                 380

ggc tac tat ctc acc ttt gtg acc gct gcc atg tac cag tct gtt ggt     1200
Gly Tyr Tyr Leu Thr Phe Val Thr Ala Ala Met Tyr Gln Ser Val Gly
385                 390                 395                 400

aag ttc ttc cga cga tac ctg cga ccc ttc ttc atg gag tct gat gga     1248
Lys Phe Phe Arg Arg Tyr Leu Arg Pro Phe Phe Met Glu Ser Asp Gly
                405                 410                 415

aag act gcc ggt ccc tat aag atc tac tac gac att gtg tgt tgg atc     1296
Lys Thr Ala Gly Pro Tyr Lys Ile Tyr Tyr Asp Ile Val Cys Trp Ile
            420                 425                 430

gtt gtc caa acc gca ttt gga tac gct acc cag tcc ttt atg att cta     1344
Val Val Gln Thr Ala Phe Gly Tyr Ala Thr Gln Ser Phe Met Ile Leu
        435                 440                 445

gac ttc tgg ctg tcg ctc aag tgt tgg aag aac tcc tgg ttc ctg tac     1392
Asp Phe Trp Leu Ser Leu Lys Cys Trp Lys Asn Ser Trp Phe Leu Tyr
    450                 455                 460

cac att gct ctg ggc gcc atc ttt gca att tct agc ccc tac aag gca     1440
His Ile Ala Leu Gly Ala Ile Phe Ala Ile Ser Ser Pro Tyr Lys Ala
465                 470                 475                 480

tgg gcg att ccc aag atc aag aaa aag cag gct gga gcc gtc act gac     1488
Trp Ala Ile Pro Lys Ile Lys Lys Lys Gln Ala Gly Ala Val Thr Asp
                485                 490                 495

aag aag gac gcc aag gag gag gtg aag aag gac acc atc aag acc aag     1536
Lys Lys Asp Ala Lys Glu Glu Val Lys Lys Asp Thr Ile Lys Thr Lys
            500                 505                 510

taa                                                                 1539


<210> SEQ ID NO 46
<211> LENGTH: 512
<212> TYPE: PRT
<213> ORGANISM: Yarrowia lipolytica

<400> SEQUENCE: 46

Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80
```

-continued

```
Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Met Lys Leu Ser Ser Phe Gly Trp Asn
    130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Pro
    370                 375                 380

Gly Tyr Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
```

500 505 510

<210> SEQ ID NO 47
<211> LENGTH: 8518
<212> TYPE: DNA
<213> ORGANISM: Artificial Sequence
<220> FEATURE:
<223> OTHER INFORMATION: Plasmid pY306

<400> SEQUENCE: 47
ggccgcatga gaagataaat atataaatac attgagatat taaatgcgct agattagaga 60
gcctcatact gctcggagag aagccaagac gagtactcaa aggggattac accatccata 120
tccacagaca caagctgggg aaaggttcta tatacacttt ccggaatacc gtagtttccg 180
atgttatcaa tgggggcagc caggatttca ggcacttcgg tgtctcgggg tgaaatggcg 240
ttcttggcct ccatcaagtc gtaccatgtc ttcatttgcc tgtcaaagta aaacagaagc 300
agatgaagaa tgaacttgaa gtgaaggaat ttaaatgtaa cgaaactgaa atttgaccag 360
atattgtgtc cgcggtggag ctccagcttt tgttcccttt agtgagggtt aatttcgagc 420
ttggcgtaat catggtcata gctgtttcct gtgtgaaatt gttatccgct cacaagcttc 480
cacacaacgt acgagccgga agcataaagt gtaaagcctg gggtgcctaa tgagtgagct 540
aactcacatt aattgcgttg cgctcactgc ccgctttcca gtcgggaaac ctgtcgtgcc 600
agctgcatta atgaatcggc caacgcgcgg ggagaggcgg tttgcgtatt gggcgctctt 660
ccgcttcctc gctcactgac tcgctgcgct cggtcgttcg gctgcggcga gcggtatcag 720
ctcactcaaa ggcggtaata cggttatcca cagaatcagg ggataacgca ggaaagaaca 780
tgtgagcaaa aggccagcaa aaggccagga accgtaaaaa ggccgcgttg ctggcgtttt 840
tccataggct ccgcccccct gacgagcatc acaaaaatcg acgctcaagt cagaggtggc 900
gaaacccgac aggactataa agataccagg cgtttccccc tggaagctcc ctcgtgcgct 960
ctcctgttcc gaccctgccg cttaccggat acctgtccgc ctttctccct tcgggaagcg 1020
tggcgctttc tcatagctca cgctgtaggt atctcagttc ggtgtaggtc gttcgctcca 1080
agctgggctg tgtgcacgaa ccccccgttc agcccgaccg ctgcgcctta tccggtaact 1140
atcgtcttga gtccaacccg gtaagacacg acttatcgcc actggcagca gccactggta 1200
acaggattag cagagcgagg tatgtaggcg gtgctacaga gttcttgaag tggtggccta 1260
actacggcta cactagaagg acagtatttg gtatctgcgc tctgctgaag ccagttacct 1320
tcggaaaaag agttggtagc tcttgatccg gcaaacaaac caccgctggt agcggtggtt 1380
tttttgtttg caagcagcag attacgcgca gaaaaaaagg atctcaagaa gatcctttga 1440
tcttttctac ggggtctgac gctcagtgga acgaaaactc acgttaaggg attttggtca 1500
tgagattatc aaaaaggatc ttcacctaga tccttttaaa ttaaaaatga agttttaaat 1560
caatctaaag tatatatgag taaacttggt ctgacagtta ccaatgctta atcagtgagg 1620
cacctatctc agcgatctgt ctatttcgtt catccatagt tgcctgactc cccgtcgtgt 1680
agataactac gatacgggag ggcttaccat ctggccccag tgctgcaatg ataccgcgag 1740
acccacgctc accggctcca gatttatcag caataaacca gccagccgga agggccgagc 1800
gcagaagtgg tcctgcaact ttatccgcct ccatccagtc tattaattgt tgccgggaag 1860
ctagagtaag tagttcgcca gttaatagtt tgcgcaacgt tgttgccatt gctacaggca 1920
tcgtggtgtc acgctcgtcg tttggtatgg cttcattcag ctccggttcc caacgatcaa 1980
ggcgagttac atgatccccc atgttgtgca aaaaagcggt tagctccttc ggtcctccga 2040

-continued

```
tcgttgtcag aagtaagttg gccgcagtgt tatcactcat ggttatggca gcactgcata   2100

attctcttac tgtcatgcca tccgtaagat gcttttctgt gactggtgag tactcaacca   2160

agtcattctg agaatagtgt atgcggcgac cgagttgctc ttgcccggcg tcaatacggg   2220

ataataccgc gccacatagc agaactttaa aagtgctcat cattggaaaa cgttcttcgg   2280

ggcgaaaact ctcaaggatc ttaccgctgt tgagatccag ttcgatgtaa cccactcgtg   2340

cacccaactg atcttcagca tcttttactt tcaccagcgt ttctgggtga gcaaaaacag   2400

gaaggcaaaa tgccgcaaaa aagggaataa gggcgacacg gaaatgttga atactcatac   2460

tcttcctttt tcaatattat tgaagcattt atcagggtta ttgtctcatg agcggataca   2520

tatttgaatg tatttagaaa aataaacaaa taggggttcc gcgcacattt ccccgaaaag   2580

tgccacctga cgcgccctgt agcggcgcat taagcgcggc gggtgtggtg gttacgcgca   2640

gcgtgaccgc tacacttgcc agcgccctag cgcccgctcc tttcgctttc ttcccttcct   2700

ttctcgccac gttcgccggc tttccccgtc aagctctaaa tcgggggctc cctttagggt   2760

tccgatttag tgctttacgg cacctcgacc ccaaaaaact tgattagggt gatggttcac   2820

gtagtgggcc atcgccctga tagacggttt ttcgcccttt gacgttggag tccacgttct   2880

ttaatagtgg actcttgttc caaactggaa caacactcaa ccctatctcg gtctattctt   2940

ttgatttata agggattttg ccgatttcgg cctattggtt aaaaaatgag ctgatttaac   3000

aaaaatttaa cgcgaatttt aacaaaatat taacgcttac aatttccatt cgccattcag   3060

gctgcgcaac tgttgggaag ggcgatcggt gcgggcctct tcgctattac gccagctggc   3120

gaaaggggga tgtgctgcaa ggcgattaag ttgggtaacg ccagggtttt cccagtcacg   3180

acgttgtaaa acgacggcca gtgaattgta atacgactca ctatagggcg aattgggtac   3240

cgggcccccc ctcgaggtcg atggtgtcga taagcttgat atcgaattca tgtcacacaa   3300

accgatcttc gcctcaagga aacctaattc tacatccgag agactgccga gatccagtct   3360

acactgatta attttcgggc caataattta aaaaaatcgt gttatataat attatatgta   3420

ttatatatat acatcatgat gatactgaca gtcatgtccc attgctaaat agacagactc   3480

catctgccgc ctccaactga tgttctcaat atttaagggg tcatctcgca ttgtttaata   3540

ataaacagac tccatctacc gcctccaaat gatgttctca aaatatattg tatgaactta   3600

tttttattac ttagtattat tagacaactt acttgcttta tgaaaaacac ttcctattta   3660

ggaaacaatt tataatggca gttcgttcat ttaacaattt atgtagaata aatgttataa   3720

atgcgtatgg gaaatcttaa atatggatag cataaatgat atctgcattg cctaattcga   3780

aatcaacagc aacgaaaaaa atcccttgta caacataaat agtcatcgag aaatatcaac   3840

tatcaaagaa cagctattca cacgttacta ttgagattat tattggacga gaatcacaca   3900

ctcaactgtc tttctctctt ctagaaatac aggtacaagt atgtactatt ctcattgttc   3960

atacttctag tcatttcatc ccacatattc cttggatttc tctccaatga atgacattct   4020

atcttgcaaa ttcaacaatt ataataagat ataccaaagt agcggtatag tggcaatcaa   4080

aaagcttctc tggtgtgctt ctcgtattta tttttattct aatgatccat taaaggtata   4140

tatttatttc ttgttatata atccttttgt ttattacatg ggctggatac ataaaggtat   4200

tttgatttaa ttttttgctt aaattcaatc ccccctcgtt cagtgtcaac tgtaatggta   4260

ggaaattacc atacttttga agaagcaaaa aaaatgaaag aaaaaaaaaa tcgtatttcc   4320

aggttagacg ttccgcagaa tctagaatgc ggtatgcggt acattgttct tcgaacgtaa   4380
```

```
aagttgcgct ccctgagata ttgtacattt ttgcttttac aagtacaagt acatcgtaca   4440
actatgtact actgttgatg catccacaac agtttgtttt gttttttttt gttttttttt   4500
tttctaatga ttcattaccg ctatgtatac ctacttgtac ttgtagtaag ccgggttatt   4560
ggcgttcaat taatcataga cttatgaatc tgcacggtgt gcgctgcgag ttacttttag   4620
cttatgcatg ctacttgggt gtaatattgg gatctgttcg gaaatcaacg gatgctcaat   4680
cgatttcgac agtaattaat taagtcatac acaagtcagc tttcttcgag cctcatataa   4740
gtataagtag ttcaacgtat tagcactgta cccagcatct ccgtatcgag aaacacaaca   4800
acatgcccca ttggacagat catgcggata cacaggttgt gcagtatcat acatactcga   4860
tcagacaggt cgtctgacca tcatacaagc tgaacaagcg ctccatactt gcacgctctc   4920
tatatacaca gttaaattac atatccatag tctaacctct aacagttaat cttctggtaa   4980
gcctcccagc cagccttctg gtatcgcttg gcctcctcaa taggatctcg gttctggccg   5040
tacagacctc ggccgacaat tatgatatcc gttccggtag acatgacatc ctcaacagtt   5100
cggtactgct gtccgagagc gtctcccttg tcgtcaagac ccaccccggg ggtcagaata   5160
agccagtcct cagagtcgcc cttaggtcgg ttctgggcaa tgaagccaac cacaaactcg   5220
gggtcggatc gggcaagctc aatggtctgc ttggagtact cgccagtggc cagagagccc   5280
ttgcaagaca gctcggccag catgagcaga cctctggcca gcttctcgtt gggagagggg   5340
actaggaact ccttgtactg ggagttctcg tagtcagaga cgtcctcctt cttctgttca   5400
gagacagttt cctcggcacc agctcgcagg ccagcaatga ttccggttcc gggtacaccg   5460
tgggcgttgg tgatatcgga ccactcggcg attcggtgac accggtactg gtgcttgaca   5520
gtgttgccaa tatctgcgaa ctttctgtcc tcgaacagga agaaaccgtg cttaagagca   5580
agttccttga gggggagcac agtgccggcg taggtgaagt cgtcaatgat gtcgatatgg   5640
gttttgatca tgcacacata aggtccgacc ttatcggcaa gctcaatgag ctccttggtg   5700
gtggtaacat ccagagaagc acacaggttg gttttcttgg ctgccacgag cttgagcact   5760
cgagcggcaa aggcggactt gtggacgtta gctcgagctt cgtaggaggg cattttggtg   5820
gtgaagagga gactgaaata aatttagtct gcagaacttt ttatcggaac cttatctggg   5880
gcagtgaagt atatgttatg gtaatagtta cgagttagtt gaacttatag atagactgga   5940
ctatacggct atcggtccaa attagaaaga acgtcaatgg ctctctgggc gtcgcctttg   6000
ccgacaaaaa tgtgatcatg atgaaagcca gcaatgacgt tgcagctgat attgttgtcg   6060
gccaaccgcg ccgaaaacgc agctgtcaga cccacagcct ccaacgaaga atgtatcgtc   6120
aaagtgatcc aagcacactc atagttggag tcgtactcca aaggcggcaa tgacgagtca   6180
gacagatact cgtcgaccgt acgatagtta gtagacaaca atcgatagtt ggagcaaggg   6240
agaaatgtag agtgtgaaag actcactatg gtccgggctt atctcgacca atagccaaag   6300
tctggagttt ctgagagaaa aaggcaagat acgtatgtaa caaagcgacg catggtacaa   6360
taataccgga ggcatgtatc atagagagtt agtggttcga tgatggcact ggtgcctggt   6420
atgactttat acggctgact acatatttgt cctcagacat acaattacag tcaagcactt   6480
acccttggac atctgtaggt accccccggc caagacgatc tcagcgtgtc gtatgtcgga   6540
ttggcgtagc tccctcgctc gtcaattggc tcccatctac tttcttctgc ttggctacac   6600
ccagcatgtc tgctatggct cgttttcgtg ccttatctat cctcccagta ttaccaactc   6660
taaatgacat gatgtgattg ggtctacact ttcatatcag agataaggag tagcacagtt   6720
gcataaaaag cccaactcta atcagcttct tcctttcttg taattagtac aaaggtgatt   6780
```

```
agcgaaatct ggaagcttag ttggccctaa aaaaatcaaa aaaagcaaaa aacgaaaaac   6840

gaaaaaccac agttttgaga acagggaggt aacgaaggat cgtatatata tatatatata   6900

tatataccca cggatcccga gaccggcctt tgattcttcc ctacaaccaa ccattctcac   6960

caccctaatt cacaaccatg gcctttccat gggcagataa gtgggcagcc gatgcgtctg   7020

catctacagg gctgcctccg gacctcctca agattgcatt cactctggtc atgtcttatc   7080

cgctgagttc tctcatgaaa cggctgccag atgacgccaa aaacctcaag atcatctata   7140

tcatctccgt gtccatcttc tacatggtgg gtgtcttctc cctctatggc ggagctgcca   7200

ctctgctctt ctcctcaatg ggtaccttct tcatcaccca atggaagagc ccttacatgc   7260

cctgggtcaa ttttggtttt gtcatgaccc atctcttcgt caatcacctg cgttcgcagt   7320

ttttccccga aacatacgac cccaatgtca ttgacatcac cggagcacag atggttctgt   7380

gtatgaagct atcgtctttt ggatggaacg tctacgatgg atggcagatt gagaagggtg   7440

agcagctcag cgagttccag actaaaaggg ctgttctcaa gcaccccagt cttatggact   7500

tcctagcttt tgtgttctac ttcccttcca ttctgacagg tccttcttac gactatatgg   7560

agttccataa ctggctcgat ctcagcctgt tcaaggagct ggagaaagat aaggacccca   7620

agcgagctgc tcgacgaaag cgacacaaga tcccccgatc tggaatcgct gcttccaaga   7680

aactcgccgc tggtatcttc tggatcgttc tgtggaccca ggtggactct cgaatctcca   7740

ccgcctacgc ttactcagac gcattcacca aggagcacaa catctttgga cgaattgtgt   7800

acctctacat gctcggtttc atgtaccgac tcaagtacta cggagcctgg tccatttccg   7860

agggagcctg catcttgtct ggcctcggat tccatggcgt ggaccccaaa actggcaagt   7920

acaagtggga ccgtgtccag aacgtggacc cgtggggatt cgaaactggt caaaacacaa   7980

aggctctgct ggaggcctgg aaccagaaca ctaacaagtg gctacgaaac tatgtgtacc   8040

tccgagtggt gcccaaaggc caaaagcctg gattccgagc cactatcttc acatttgtgg   8100

tttccgcctt ctggcatgga actcgacctg gctactatct cacctttgtg accgctgcca   8160

tgtaccagtc tgttggtaag ttcttccgac gatacctgcg acccttcttc atggagtctg   8220

atggaaagac tgccggtccc tataagatct actacgacat tgtgtgttgg atcgttgtcc   8280

aaaccgcatt tggatacgct acccagtcct ttatgattct agacttctgg ctgtcgctca   8340

agtgttggaa gaactcctgg ttcctgtacc acattgctct gggcgccatc tttgcaattt   8400

ctagccccta caaggcatgg gcgattccca agatcaagaa aaagcaggct ggagccgtca   8460

ctgacaagaa ggacgccaag gaggaggtga agaaggacac catcaagacc aagtaagc     8518
```

<210> SEQ ID NO 48
<211> LENGTH: 8518
<212> TYPE: DNA
<213> ORGANISM: Artificial Sequence
<220> FEATURE:
<223> OTHER INFORMATION: Plasmid pY306-N

<400> SEQUENCE: 48

```
catggccttt ccttgggcag ataagtgggc agccgatgcg tctgcatcta cagggctgcc     60

tccggacctc ctcaagattg cattcactct ggtcatgtct tatccgctga gttctctcat    120

gaaacggctg ccagatgacg ccaaaaacct caagatcatc tatatcatct ccgtgtccat    180

cttctacatg gtgggtgtct tctccctcta tggcggagct gccactctgc tcttctcctc    240

aatgggtacc ttcttcatca cccaatggaa gagcccttac atgccctggg tcaattttgg    300
```

-continued

```
ttttgtcatg acccatctct tcgtcaatca cctgcgttcg cagtttttcc ccgaaacata    360
cgaccccaat gtcattgaca tcaccggagc acagatggtt ctgtgtatga agctatcgtc    420
ttttggatgg aacgtctacg atggatggca gattgagaag ggtgagcagc tcagcgagtt    480
ccagactaaa agggctgttc tcaagcaccc cagtcttatg gacttcctag cttttgtgtt    540
ctacttccct tccattctga caggtccttc ttacgactat atggagttcc ataactggct    600
cgatctcagc ctgttcaagg agctggagaa agataaggac cccaagcgag ctgctcgacg    660
aaagcgacac aagatccccc gatctggaat cgctgcttcc aagaaactcg ccgctggtat    720
cttctggatc gttctgtgga cccaggtgga ctctcgaatc tccaccgcct acgcttactc    780
agacgcattc accaaggagc acaacatctt tggacgaatt gtgtacctct acatgctcgg    840
tttcatgtac cgactcaagt actacggagc ctggtccatt tccgagggag cctgcatctt    900
gtctggcctc ggattccacg gcgtggaccc caaaactggc aagtacaagt gggaccgtgt    960
ccagaacgtg gacccgtggg gattcgaaac tggtcaaaac acaaaggctc tgctggaggc   1020
ctggaaccag aacactaaca agtggctacg aaactatgtg tacctccgag tggtgcccaa   1080
aggccaaaag cctggattcc gagccactat cttcacattt gtggtttccg ccttctggca   1140
tggaactcga cctggctact atctcacctt tgtgaccgct gccatgtacc agtctgttgg   1200
taagttcttc cgacgatacc tgcgaccctt cttcatggag tctgatggaa agactgccgg   1260
tccctataag atctactacg acattgtgtg ttggatcgtt gtccaaaccg catttggata   1320
cgctacccag tcctttatga ttctagactt ctggctgtcg ctcaagtgtt ggaagaactc   1380
ctggttcctg taccacattg ctctgggcgc catctttgca atttctagcc cctacaaggc   1440
atgggcgatt cccaagatca agaaaaagca ggctggagcc gtcactgaca agaaggacgc   1500
caaggaggag gtgaagaagg acaccatcaa gaccaagtaa gcggccgcat gagaagataa   1560
atatataaat acattgagat attaaatgcg ctagattaga gagcctcata ctgctcggag   1620
agaagccaag acgagtactc aaaggggatt acaccatcca tatccacaga cacaagctgg   1680
ggaaaggttc tatatacact ttccggaata ccgtagtttc cgatgttatc aatgggggca   1740
gccaggattt caggcacttc ggtgtctcgg ggtgaaatgg cgttcttggc ctccatcaag   1800
tcgtaccatg tcttcatttg cctgtcaaag taaaacagaa gcagatgaag aatgaacttg   1860
aagtgaagga atttaaatgt aacgaaactg aaatttgacc agatattgtg tccgcggtgg   1920
agctccagct tttgttccct ttagtgaggg ttaatttcga gcttggcgta atcatggtca   1980
tagctgtttc ctgtgtgaaa ttgttatccg ctcacaagct tccacacaac gtacgagccg   2040
gaagcataaa gtgtaaagcc tggggtgcct aatgagtgag ctaactcaca ttaattgcgt   2100
tgcgctcact gcccgctttc cagtcgggaa acctgtcgtg ccagctgcat taatgaatcg   2160
gccaacgcgc ggggagaggc ggtttgcgta ttgggcgctc ttccgcttcc tcgctcactg   2220
actcgctgcg ctcggtcgtt cggctgcggc gagcggtatc agctcactca aaggcggtaa   2280
tacggttatc cacagaatca ggggataacg caggaaagaa catgtgagca aaaggccagc   2340
aaaaggccag gaaccgtaaa aaggccgcgt tgctggcgtt tttccatagg ctccgccccc   2400
ctgacgagca tcacaaaaat cgacgctcaa gtcagaggtg gcgaaacccg acaggactat   2460
aaagatacca ggcgtttccc cctggaagct ccctcgtgcg ctctcctgtt ccgaccctgc   2520
cgcttaccgg atacctgtcc gcctttctcc cttcgggaag cgtggcgctt tctcatagct   2580
cacgctgtag gtatctcagt tcggtgtagg tcgttcgctc caagctgggc tgtgtgcacg   2640
aaccccccgt tcagcccgac cgctgcgcct tatccggtaa ctatcgtctt gagtccaacc   2700
```

cggtaagaca cgacttatcg ccactggcag cagccactgg taacaggatt agcagagcga 2760
ggtatgtagg cggtgctaca gagttcttga agtggtggcc taactacggc tacactagaa 2820
ggacagtatt tggtatctgc gctctgctga agccagttac cttcggaaaa agagttggta 2880
gctcttgatc cggcaaacaa accaccgctg gtagcggtgg tttttttgtt tgcaagcagc 2940
agattacgcg cagaaaaaaa ggatctcaag aagatccttt gatcttttct acggggtctg 3000
acgctcagtg gaacgaaaac tcacgttaag ggattttggt catgagatta tcaaaaagga 3060
tcttcaccta gatcctttta aattaaaaat gaagttttaa atcaatctaa agtatatatg 3120
agtaaacttg gtctgacagt taccaatgct taatcagtga ggcacctatc tcagcgatct 3180
gtctatttcg ttcatccata gttgcctgac tccccgtcgt gtagataact acgatacggg 3240
agggcttacc atctggcccc agtgctgcaa tgataccgcg agacccacgc tcaccggctc 3300
cagatttatc agcaataaac cagccagccg gaagggccga gcgcagaagt ggtcctgcaa 3360
ctttatccgc ctccatccag tctattaatt gttgccggga agctagagta agtagttcgc 3420
cagttaatag tttgcgcaac gttgttgcca ttgctacagg catcgtggtg tcacgctcgt 3480
cgtttggtat ggcttcattc agctccggtt cccaacgatc aaggcgagtt acatgatccc 3540
ccatgttgtg caaaaaagcg gttagctcct tcggtcctcc gatcgttgtc agaagtaagt 3600
tggccgcagt gttatcactc atggttatgg cagcactgca taattctctt actgtcatgc 3660
catccgtaag atgcttttct gtgactggtg agtactcaac caagtcattc tgagaatagt 3720
gtatgcggcg accgagttgc tcttgcccgg cgtcaatacg ggataatacc gcgccacata 3780
gcagaacttt aaaagtgctc atcattggaa aacgttcttc ggggcgaaaa ctctcaagga 3840
tcttaccgct gttgagatcc agttcgatgt aacccactcg tgcacccaac tgatcttcag 3900
catcttttac tttcaccagc gtttctgggt gagcaaaaac aggaaggcaa aatgccgcaa 3960
aaaagggaat aagggcgaca cggaaatgtt gaatactcat actcttcctt tttcaatatt 4020
attgaagcat ttatcagggt tattgtctca tgagcggata catatttgaa tgtatttaga 4080
aaaataaaca aataggggtt ccgcgcacat ttccccgaaa agtgccacct gacgcgccct 4140
gtagcggcgc attaagcgcg gcgggtgtgg tggttacgcg cagcgtgacc gctacacttg 4200
ccagcgccct agcgcccgct cctttcgctt tcttcccttc ctttctcgcc acgttcgccg 4260
gctttccccg tcaagctcta aatcgggggc tccctttagg gttccgattt agtgctttac 4320
ggcacctcga ccccaaaaaa cttgattagg gtgatggttc acgtagtggg ccatcgccct 4380
gatagacggt ttttcgccct ttgacgttgg agtccacgtt ctttaatagt ggactcttgt 4440
tccaaactgg aacaacactc aaccctatct cggtctattc ttttgattta taagggattt 4500
tgccgatttc ggcctattgg ttaaaaaatg agctgattta acaaaaattt aacgcgaatt 4560
ttaacaaaat attaacgctt acaatttcca ttcgccattc aggctgcgca actgttggga 4620
agggcgatcg gtgcgggcct cttcgctatt acgccagctg gcgaaagggg gatgtgctgc 4680
aaggcgatta agttgggtaa cgccagggtt ttcccagtca cgacgttgta aaacgacggc 4740
cagtgaattg taatacgact cactataggg cgaattgggt accgggcccc ccctcgaggt 4800
cgatggtgtc gataagcttg atatcgaatt catgtcacac aaaccgatct tcgcctcaag 4860
gaaacctaat tctacatccg agagactgcc gagatccagt ctacactgat taattttcgg 4920
gccaataatt taaaaaaatc gtgttatata atattatatg tattatatat atacatcatg 4980
atgatactga cagtcatgtc ccattgctaa atagacagac tccatctgcc gcctccaact 5040

```
gatgttctca atatttaagg ggtcatctcg cattgtttaa taataaacag actccatcta   5100

ccgcctccaa atgatgttct caaaatatat tgtatgaact tatttttatt acttagtatt   5160

attagacaac ttacttgctt tatgaaaaac acttcctatt taggaaacaa tttataatgg   5220

cagttcgttc atttaacaat ttatgtagaa taaatgttat aaatgcgtat gggaaatctt   5280

aaatatggat agcataaatg atatctgcat tgcctaattc gaaatcaaca gcaacgaaaa   5340

aaatcccttg tacaacataa atagtcatcg agaaatatca actatcaaag aacagctatt   5400

cacacgttac tattgagatt attattggac gagaatcaca cactcaactg tctttctctc   5460

ttctagaaat acaggtacaa gtatgtacta ttctcattgt tcatacttct agtcatttca   5520

tcccacatat tccttggatt tctctccaat gaatgacatt ctatcttgca aattcaacaa   5580

ttataataag atataccaaa gtagcggtat agtggcaatc aaaaagcttc tctggtgtgc   5640

ttctcgtatt tatttttatt ctaatgatcc attaaaggta tatatttatt tcttgttata   5700

taatcctttt gtttattaca tgggctggat acataaaggt attttgattt aatttttttgc   5760

ttaaattcaa tcccccctcg ttcagtgtca actgtaatgg taggaaatta ccatactttt   5820

gaagaagcaa aaaaaatgaa agaaaaaaaa aatcgtattt ccaggttaga cgttccgcag   5880

aatctagaat gcggtatgcg gtacattgtt cttcgaacgt aaaagttgcg ctccctgaga   5940

tattgtacat ttttgctttt acaagtacaa gtacatcgta caactatgta ctactgttga   6000

tgcatccaca acagtttgtt ttgttttttt ttgttttttt tttttctaat gattcattac   6060

cgctatgtat acctacttgt acttgtagta agccgggtta ttggcgttca attaatcata   6120

gacttatgaa tctgcacggt gtgcgctgcg agttactttt agcttatgca tgctacttgg   6180

gtgtaatatt gggatctgtt cggaaatcaa cggatgctca atcgatttcg acagtaatta   6240

attaagtcat acacaagtca gctttcttcg agcctcatat aagtataagt agttcaacgt   6300

attagcactg tacccagcat ctccgtatcg agaaacacaa caacatgccc cattggacag   6360

atcatgcgga tacacaggtt gtgcagtatc atacatactc gatcagacag gtcgtctgac   6420

catcatacaa gctgaacaag cgctccatac ttgcacgctc tctatataca cagttaaatt   6480

acatatccat agtctaacct ctaacagtta atcttctggt aagcctccca gccagccttc   6540

tggtatcgct tggcctcctc aataggatct cggttctggc cgtacagacc tcggccgaca   6600

attatgatat ccgttccggt agacatgaca tcctcaacag ttcggtactg ctgtccgaga   6660

gcgtctccct tgtcgtcaag acccaccccg ggggtcagaa taagccagtc ctcagagtcg   6720

cccttaggtc ggttctgggc aatgaagcca accacaaact cggggtcgga tcgggcaagc   6780

tcaatggtct gcttggagta ctcgccagtg gccagagagc ccttgcaaga cagctcggcc   6840

agcatgagca gacctctggc cagcttctcg ttgggagagg ggactaggaa ctccttgtac   6900

tgggagttct cgtagtcaga gacgtcctcc ttcttctgtt cagagacagt ttcctcggca   6960

ccagctcgca ggccagcaat gattccggtt ccgggtacac cgtgggcgtt ggtgatatcg   7020

gaccactcgg cgattcggtg acaccggtac tggtgcttga cagtgttgcc aatatctgcg   7080

aactttctgt cctcgaacag gaagaaaccg tgcttaagag caagttcctt gagggggagc   7140

acagtgccgg cgtaggtgaa gtcgtcaatg atgtcgatat gggttttgat catgcacaca   7200

taaggtccga ccttatcggc aagctcaatg agctccttgg tggtggtaac atccagagaa   7260

gcacacaggt tggttttctt ggctgccacg agcttgagca ctcgagcggc aaaggcggac   7320

ttgtggacgt tagctcgagc ttcgtaggag ggcattttgg tggtgaagag gagactgaaa   7380

taaatttagt ctgcagaact ttttatcgga accttatctg gggcagtgaa gtatatgtta   7440
```

```
tggtaatagt tacgagttag ttgaacttat agatagactg gactatacgg ctatcggtcc   7500
aaattagaaa gaacgtcaat ggctctctgg gcgtcgcctt tgccgacaaa aatgtgatca   7560
tgatgaaagc cagcaatgac gttgcagctg atattgttgt cggccaaccg cgccgaaaac   7620
gcagctgtca gacccacagc ctccaacgaa gaatgtatcg tcaaagtgat ccaagcacac   7680
tcatagttgg agtcgtactc caaaggcggc aatgacgagt cagacagata ctcgtcgacc   7740
gtacgatagt tagtagacaa caatcgatag ttggagcaag ggagaaatgt agagtgtgaa   7800
agactcacta tggtccgggc ttatctcgac caatagccaa agtctggagt ttctgagaga   7860
aaaaggcaag atacgtatgt aacaaagcga cgcatggtac aataataccg gaggcatgta   7920
tcatagagag ttagtggttc gatgatggca ctggtgcctg gtatgacttt atacggctga   7980
ctacatattt gtcctcagac atacaattac agtcaagcac ttacccttgg acatctgtag   8040
gtacccccg gccaagacga tctcagcgtg tcgtatgtcg gattggcgta gctccctcgc   8100
tcgtcaattg gctcccatct actttcttct gcttggctac acccagcatg tctgctatgg   8160
ctcgttttcg tgccttatct atcctcccag tattaccaac tctaaatgac atgatgtgat   8220
tgggtctaca ctttcatatc agagataagg agtagcacag ttgcataaaa agcccaactc   8280
taatcagctt cttcctttct tgtaattagt acaaaggtga ttagcgaaat ctggaagctt   8340
agttggccct aaaaaaatca aaaaaagcaa aaaacgaaaa acgaaaaacc acagttttga   8400
gaacagggag gtaacgaagg atcgtatata tatatatata tatatatacc cacggatccc   8460
gagaccggcc tttgattctt ccctacaacc aaccattctc accaccctaa ttcacaac     8518
```

```
<210> SEQ ID NO 49
<211> LENGTH: 512
<212> TYPE: PRT
<213> ORGANISM: Yarrowia lipolytica
<220> FEATURE:
<221> NAME/KEY: MISC_FEATURE
<222> LOCATION: (132)..(132)
<223> OTHER INFORMATION: Xaa = Ala [A], Asn [N], Cys [C], Gly [G], Glu
      [Q], His [H], Ile [I], Leu [L], Phe [F], Pro [P], Ser [S], Thr
      [T], Trp [W], Tyr [Y] or Val [V]

<400> SEQUENCE: 49

Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Xaa Val Leu Cys Met Lys Leu Ser Ser Phe Gly Trp Asn
    130                 135                 140

Val Tyr Asp Gly Trp Gln Ile Glu Lys Gly Glu Gln Leu Ser Glu Phe
```

-continued

```
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Pro
    370                 375                 380

Gly Tyr Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510
```

<210> SEQ ID NO 50
<211> LENGTH: 512
<212> TYPE: PRT
<213> ORGANISM: Yarrowia lipolytica
<220> FEATURE:
<221> NAME/KEY: MISC_FEATURE
<222> LOCATION: (133)..(133)
<223> OTHER INFORMATION: Xaa = Ala [A], Asn [N], Cys [C], Gly [G],
Glu [Q], His [H], Leu [L], Met [M], Phe [F], Pro [P], Ser [S],
Thr [T], Trp [W] or Tyr [Y]

<400> SEQUENCE: 50

```
Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Xaa Leu Cys Met Lys Leu Ser Ser Phe Gly Trp Asn
    130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Pro
    370                 375                 380

Gly Tyr Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
```

```
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510


<210> SEQ ID NO 51
<211> LENGTH: 512
<212> TYPE: PRT
<213> ORGANISM: Yarrowia lipolytica
<220> FEATURE:
<221> NAME/KEY: MISC_FEATURE
<222> LOCATION: (134)..(134)
<223> OTHER INFORMATION: Xaa = Ala [A], Asn [N], Cys [C], Gly [G],
      Glu [Q], His [H], Met [M], Phe [F], Pro [P], Ser [S], Thr [T],
      Trp [W], Tyr [Y] or Val [V]

<400> SEQUENCE: 51

Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Xaa Cys Met Lys Leu Ser Ser Phe Gly Trp Asn
    130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240
```

-continued

Phe Trp Ile Val Leu Trp Thr Gln Val Asp Ser Arg Ile Ser Thr Ala
245 250 255

Tyr Ala Tyr Ser Asp Ala Phe Thr Lys Glu His Asn Ile Phe Gly Arg
260 265 270

Ile Val Tyr Leu Tyr Met Leu Gly Phe Met Tyr Arg Leu Lys Tyr Tyr
275 280 285

Gly Ala Trp Ser Ile Ser Glu Gly Ala Cys Ile Leu Ser Gly Leu Gly
290 295 300

Phe His Gly Val Asp Pro Lys Thr Gly Lys Tyr Lys Trp Asp Arg Val
305 310 315 320

Gln Asn Val Asp Pro Trp Gly Phe Glu Thr Gly Gln Asn Thr Lys Ala
325 330 335

Leu Leu Glu Ala Trp Asn Gln Asn Thr Asn Lys Trp Leu Arg Asn Tyr
340 345 350

Val Tyr Leu Arg Val Val Pro Lys Gly Gln Lys Pro Gly Phe Arg Ala
355 360 365

Thr Ile Phe Thr Phe Val Val Ser Ala Phe Trp His Gly Thr Arg Pro
370 375 380

Gly Tyr Tyr Leu Thr Phe Val Thr Ala Ala Met Tyr Gln Ser Val Gly
385 390 395 400

Lys Phe Phe Arg Arg Tyr Leu Arg Pro Phe Phe Met Glu Ser Asp Gly
405 410 415

Lys Thr Ala Gly Pro Tyr Lys Ile Tyr Tyr Asp Ile Val Cys Trp Ile
420 425 430

Val Val Gln Thr Ala Phe Gly Tyr Ala Thr Gln Ser Phe Met Ile Leu
435 440 445

Asp Phe Trp Leu Ser Leu Lys Cys Trp Lys Asn Ser Trp Phe Leu Tyr
450 455 460

His Ile Ala Leu Gly Ala Ile Phe Ala Ile Ser Ser Pro Tyr Lys Ala
465 470 475 480

Trp Ala Ile Pro Lys Ile Lys Lys Lys Gln Ala Gly Ala Val Thr Asp
485 490 495

Lys Lys Asp Ala Lys Glu Glu Val Lys Lys Asp Thr Ile Lys Thr Lys
500 505 510

<210> SEQ ID NO 52
<211> LENGTH: 512
<212> TYPE: PRT
<213> ORGANISM: Yarrowia lipolytica
<220> FEATURE:
<221> NAME/KEY: MISC_FEATURE
<222> LOCATION: (135)..(135)
<223> OTHER INFORMATION: Xaa = Arg [R], Asn [N], Asp [D], Gln [E], Gly [G], Glu [Q], His [H], Ile [I], Leu [L], Lys [K], Met [M], Phe [F], Pro [P], Ser [S], Trp [W] or Tyr [Y]

<400> SEQUENCE: 52

Met Ala Phe Pro Trp Ala Asp Lys Trp Ala Ala Asp Ala Ser Ala Ser
1 5 10 15

Thr Gly Leu Pro Pro Asp Leu Leu Lys Ile Ala Phe Thr Leu Val Met
20 25 30

Ser Tyr Pro Leu Ser Ser Leu Met Lys Arg Leu Pro Asp Asp Ala Lys
35 40 45

Asn Leu Lys Ile Ile Tyr Ile Ile Ser Val Ser Ile Phe Tyr Met Val
50 55 60

Gly Val Phe Ser Leu Tyr Gly Gly Ala Ala Thr Leu Leu Phe Ser Ser
65 70 75 80

-continued

```
Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Xaa Met Lys Leu Ser Ser Phe Gly Trp Asn
    130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Pro
    370                 375                 380

Gly Tyr Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495
```

```
Lys Lys Asp Ala Lys Glu Glu Val Lys Lys Asp Thr Ile Lys Thr Lys
            500                 505                 510


<210> SEQ ID NO 53
<211> LENGTH: 512
<212> TYPE: PRT
<213> ORGANISM: Yarrowia lipolytica
<220> FEATURE:
<221> NAME/KEY: MISC_FEATURE
<222> LOCATION: (136)..(136)
<223> OTHER INFORMATION: Xaa = Ala [A], Asn [N], Cys [C], Gly [G],
      His [H], Ile [I], Phe [F], Pro [P], Ser [S], Thr [T], Trp [W],
      Tyr [Y] or Val [V]

<400> SEQUENCE: 53

Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Xaa Lys Leu Ser Ser Phe Gly Trp Asn
    130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335
```

```
Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Pro
    370                 375                 380

Gly Tyr Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510


<210> SEQ ID NO 54
<211> LENGTH: 512
<212> TYPE: PRT
<213> ORGANISM: Yarrowia lipolytica
<220> FEATURE:
<221> NAME/KEY: MISC_FEATURE
<222> LOCATION: (137)..(137)
<223> OTHER INFORMATION: Xaa = Ala [A], Arg [R], Asn [N], Gly [G],
      His [H], Pro [P], Ser [S], Thr [T] or Tyr [Y]

<400> SEQUENCE: 54

Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Met Xaa Leu Ser Ser Phe Gly Trp Asn
    130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175
```

```
Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Pro
    370                 375                 380

Gly Tyr Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510
```

<210> SEQ ID NO 55
<211> LENGTH: 512
<212> TYPE: PRT
<213> ORGANISM: Yarrowia lipolytica
<220> FEATURE:
<221> NAME/KEY: MISC_FEATURE
<222> LOCATION: (138)..(138)
<223> OTHER INFORMATION: Xaa = Ala [A], Asn [N], Cys [C], Gly [G], Glu [Q], His [H], Ile [I], Met [M], Phe [F], Pro [P], Ser [S], Thr [T], Trp [W] or Tyr [Y]

<400> SEQUENCE: 55

```
Met Ala Phe Pro Trp Ala Asp Lys Trp Ala Ala Asp Ala Ser Ala Ser
```

-continued

```
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Met Lys Xaa Ser Ser Phe Gly Trp Asn
    130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Pro
    370                 375                 380

Gly Tyr Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430
```

```
Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510


<210> SEQ ID NO 56
<211> LENGTH: 512
<212> TYPE: PRT
<213> ORGANISM: Yarrowia lipolytica
<220> FEATURE:
<221> NAME/KEY: MISC_FEATURE
<222> LOCATION: (139)..(139)
<223> OTHER INFORMATION: Xaa = Ala [A], Asn [N], Cys [C], Gly [G],
      His [H], Leu [L], Met [M], Phe [F], Pro [P], Trp [W] or Val [V]

<400> SEQUENCE: 56

Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Met Lys Leu Xaa Ser Phe Gly Trp Asn
    130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270
```

```
Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Pro
    370                 375                 380

Gly Tyr Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510
```

<210> SEQ ID NO 57
<211> LENGTH: 512
<212> TYPE: PRT
<213> ORGANISM: Yarrowia lipolytica
<220> FEATURE:
<221> NAME/KEY: MISC_FEATURE
<222> LOCATION: (140)..(140)
<223> OTHER INFORMATION: Xaa = Asn [N], Cys [C], His [H], Ile [I],
Leu [L], Phe [F], Pro [P], Trp [W], Tyr [Y] or Val [V]

<400> SEQUENCE: 57

```
Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110
```

```
Ser Gln Phe Phe Pro Glu Thr Tyr Asp Pro Asn Val Ile Asp Ile Thr
        115                 120                 125

Gly Ala Gln Met Val Leu Cys Met Lys Leu Ser Xaa Phe Gly Trp Asn
    130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Pro
    370                 375                 380

Gly Tyr Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510
```

<210> SEQ ID NO 58
<211> LENGTH: 512

<212> TYPE: PRT
<213> ORGANISM: Yarrowia lipolytica
<220> FEATURE:
<221> NAME/KEY: misc
<222> LOCATION: (141)..(141)
<223> OTHER INFORMATION: Xaa = Ala [A], Asn [N], Gly [G], His [H],
Ile [I], Met [M], Pro [P], Ser [S], Thr [T], Trp [W] or Val [V]

<400> SEQUENCE: 58

```
Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Met Lys Leu Ser Ser Xaa Gly Trp Asn
    130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365
```

```
Thr Ile Phe Thr Phe Val Val Ser Ala Phe Trp His Gly Thr Arg Pro
    370                 375                 380

Gly Tyr Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510


<210> SEQ ID NO 59
<211> LENGTH: 512
<212> TYPE: PRT
<213> ORGANISM: Yarrowia lipolytica
<220> FEATURE:
<221> NAME/KEY: MISC_FEATURE
<222> LOCATION: (142)..(142)
<223> OTHER INFORMATION: Xaa = Asn [N], His [H], Ile [I], Leu [L], Met
      [M], Phe [F], Pro [P], Thr [T], Trp [W], Tyr [Y] or Val [V]

<400> SEQUENCE: 59

Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Met Lys Leu Ser Ser Phe Xaa Trp Asn
    130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205
```

-continued

```
Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Pro
    370                 375                 380

Gly Tyr Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510


<210> SEQ ID NO 60
<211> LENGTH: 512
<212> TYPE: PRT
<213> ORGANISM: Yarrowia lipolytica
<220> FEATURE:
<221> NAME/KEY: MISC_FEATURE
<222> LOCATION: (143)..(143)
<223> OTHER INFORMATION: Xaa = Ala [A], Gly [G], His [H], Leu [L],
      Lys [K], Pro [P], Ser [S], Thr [T] or Val [V]

<400> SEQUENCE: 60

Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45
```

-continued

```
Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Met Lys Leu Ser Ser Phe Gly Xaa Asn
    130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Pro
    370                 375                 380

Gly Tyr Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
```

```
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510


<210> SEQ ID NO 61
<211> LENGTH: 512
<212> TYPE: PRT
<213> ORGANISM: Yarrowia lipolytica
<220> FEATURE:
<221> NAME/KEY: MISC_FEATURE
<222> LOCATION: (144)..(144)
<223> OTHER INFORMATION: Xaa = Ala [A], Arg [R], Gly [G], His [H],
      Lys [K], Phe [F], Pro [P], Thr [T] or Val [V]

<400> SEQUENCE: 61

Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Met Lys Leu Ser Ser Phe Gly Trp Xaa
    130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
```

```
305                 310                 315                 320

Gln Asn Val Asp Pro Trp Gly Phe Glu Thr Gly Gln Asn Thr Lys Ala
            325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Pro
    370                 375                 380

Gly Tyr Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
            405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
            485                 490                 495

Lys Lys Asp Ala Lys Glu Glu Val Lys Lys Asp Thr Ile Lys Thr Lys
            500                 505                 510


<210> SEQ ID NO 62
<211> LENGTH: 512
<212> TYPE: PRT
<213> ORGANISM: Yarrowia lipolytica
<220> FEATURE:
<221> NAME/KEY: MISC_FEATURE
<222> LOCATION: (145)..(145)
<223> OTHER INFORMATION: Xaa = Ala [A], Cys [C], Gly [G], Gln [E], His
      [H], Met [M], Phe [F], Pro [P], Ser [S], Thr [T] or Trp [W]

<400> SEQUENCE: 62

Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Met Lys Leu Ser Ser Phe Gly Trp Asn
    130                 135                 140

Xaa Tyr Asp Gly Trp Gln Ile Glu Lys Gly Glu Gln Leu Ser Glu Phe
```

```
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Pro
    370                 375                 380

Gly Tyr Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510
```

<210> SEQ ID NO 63
<211> LENGTH: 512
<212> TYPE: PRT
<213> ORGANISM: Yarrowia lipolytica
<220> FEATURE:
<221> NAME/KEY: misc
<222> LOCATION: (146)..(146)
<223> OTHER INFORMATION: Xaa = Arg [R], Asn [N], Asp [D], Gly [G], Gln [E], Glu [Q], Ile [I], Leu [L], Met [M], Phe [F], Pro [P], Trp [W]] or Val [V]

<400> SEQUENCE: 63

```
Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Met Lys Leu Ser Ser Phe Gly Trp Asn
    130                 135                 140

Val Xaa Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Pro
    370                 375                 380

Gly Tyr Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
```

```
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510


<210> SEQ ID NO 64
<211> LENGTH: 512
<212> TYPE: PRT
<213> ORGANISM: Yarrowia lipolytica
<220> FEATURE:
<221> NAME/KEY: misc
<222> LOCATION: (147)..(147)
<223> OTHER INFORMATION: Xaa = Ala [A], Asn [N], Gly [G], Gln [E], Glu
      [Q], His [H], Phe [F], Ser [S] or Thr [T]

<400> SEQUENCE: 64

Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Met Lys Leu Ser Ser Phe Gly Trp Asn
    130                 135                 140

Val Tyr Xaa Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
```

```
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Pro
    370                 375                 380

Gly Tyr Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510


<210> SEQ ID NO 65
<211> LENGTH: 512
<212> TYPE: PRT
<213> ORGANISM: Yarrowia lipolytica
<220> FEATURE:
<221> NAME/KEY: MISC_FEATURE
<222> LOCATION: (148)..(148)
<223> OTHER INFORMATION: Xaa = Ala [A], Asn [N], His [H], Leu [L],
      Met [M], Phe [F], Ser [S], Thr [T] or Val [V]

<400> SEQUENCE: 65

Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
```

-continued

```
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Met Lys Leu Ser Ser Phe Gly Trp Asn
    130                 135                 140

Val Tyr Asp Xaa Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Pro
    370                 375                 380

Gly Tyr Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510
```

```
<210> SEQ ID NO 66
<211> LENGTH: 512
<212> TYPE: PRT
<213> ORGANISM: Yarrowia lipolytica
<220> FEATURE:
<221> NAME/KEY: MISC_FEATURE
<222> LOCATION: (376)..(376)
<223> OTHER INFORMATION: Xaa = Ala [A], Gly [G], His [H], Leu [L],
      Phe [F], Pro [P], Thr [T] or Val [V]

<400> SEQUENCE: 66

Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Met Lys Leu Ser Ser Phe Gly Trp Asn
    130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350
```

```
Val Tyr Leu Arg Val Val Pro Lys Gly Gln Lys Pro Gly Phe Arg Ala
        355                 360                 365

Thr Ile Phe Thr Phe Val Val Xaa Ala Phe Trp His Gly Thr Arg Pro
    370                 375                 380

Gly Tyr Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510


<210> SEQ ID NO 67
<211> LENGTH: 512
<212> TYPE: PRT
<213> ORGANISM: Yarrowia lipolytica
<220> FEATURE:
<221> NAME/KEY: MISC_FEATURE
<222> LOCATION: (377)..(377)
<223> OTHER INFORMATION: Xaa = Asn [N], Gly [G], His [H], Leu [L],
      Phe [F], Pro [P], Ser [S], Thr [T] or Val [V]

<400> SEQUENCE: 67

Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Met Lys Leu Ser Ser Phe Gly Trp Asn
    130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190
```

```
Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Xaa Phe Trp His Gly Thr Arg Pro
    370                 375                 380

Gly Tyr Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510


<210> SEQ ID NO 68
<211> LENGTH: 512
<212> TYPE: PRT
<213> ORGANISM: Yarrowia lipolytica
<220> FEATURE:
<221> NAME/KEY: MISC_FEATURE
<222> LOCATION: (378)..(378)
<223> OTHER INFORMATION: Xaa = Ala [A], Asn [N], Cys [C], Gly [G],
      His [H], Leu [L], Pro [P], Ser [S], Thr [T], Trp [W] or Tyr [Y]

<400> SEQUENCE: 68

Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30
```

-continued

```
Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Met Lys Leu Ser Ser Phe Gly Trp Asn
    130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Xaa Trp His Gly Thr Arg Pro
    370                 375                 380

Gly Tyr Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445
```

-continued

```
Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510


<210> SEQ ID NO 69
<211> LENGTH: 512
<212> TYPE: PRT
<213> ORGANISM: Yarrowia lipolytica
<220> FEATURE:
<221> NAME/KEY: MISC_FEATURE
<222> LOCATION: (382)..(382)
<223> OTHER INFORMATION: Xaa = Ala [A], Asn [N], Gly [G], Glu [Q],
      His [H], Ile [I], Met [M], Pro [P], Ser [S], Trp [W] or Tyr [Y]

<400> SEQUENCE: 69

Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Met Lys Leu Ser Ser Phe Gly Trp Asn
    130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285
```

-continued

```
Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Xaa Arg Pro
    370                 375                 380

Gly Tyr Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510


<210> SEQ ID NO 70
<211> LENGTH: 512
<212> TYPE: PRT
<213> ORGANISM: Yarrowia lipolytica
<220> FEATURE:
<221> NAME/KEY: MISC_FEATURE
<222> LOCATION: (383)..(383)
<223> OTHER INFORMATION: Xaa = Ala [A], Asn [N], Asp [D], Gly [G],
      Gln [E], Glu [Q], His [H], Ile [I], Leu [L], Lys [K], Met [M],
      Phe [F], Pro [P], Thr [T], Trp [W] or Val [V]

<400> SEQUENCE: 70

Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125
```

```
Gly Ala Gln Met Val Leu Cys Met Lys Leu Ser Ser Phe Gly Trp Asn
    130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Xaa Pro
    370                 375                 380

Gly Tyr Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510
```

<210> SEQ ID NO 71
<211> LENGTH: 512
<212> TYPE: PRT
<213> ORGANISM: Yarrowia lipolytica
<220> FEATURE:

```
<221> NAME/KEY: MISC_FEATURE
<222> LOCATION: (384)..(384)
<223> OTHER INFORMATION: Xaa = Ala [A], Arg [R], Gly [G], His [H],
      Ile [I], Leu [L], Lys [K], Met [M], Phe [F], Ser [S], Thr [T],
      Trp [W], Tyr [Y] or Val [V]

<400> SEQUENCE: 71

Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Met Lys Leu Ser Ser Phe Gly Trp Asn
    130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Xaa
    370                 375                 380
```

Gly Tyr Tyr Leu Thr Phe Val Thr Ala Ala Met Tyr Gln Ser Val Gly
385 390 395 400

Lys Phe Phe Arg Arg Tyr Leu Arg Pro Phe Phe Met Glu Ser Asp Gly
405 410 415

Lys Thr Ala Gly Pro Tyr Lys Ile Tyr Tyr Asp Ile Val Cys Trp Ile
420 425 430

Val Val Gln Thr Ala Phe Gly Tyr Ala Thr Gln Ser Phe Met Ile Leu
435 440 445

Asp Phe Trp Leu Ser Leu Lys Cys Trp Lys Asn Ser Trp Phe Leu Tyr
450 455 460

His Ile Ala Leu Gly Ala Ile Phe Ala Ile Ser Ser Pro Tyr Lys Ala
465 470 475 480

Trp Ala Ile Pro Lys Ile Lys Lys Lys Gln Ala Gly Ala Val Thr Asp
485 490 495

Lys Lys Asp Ala Lys Glu Glu Val Lys Lys Asp Thr Ile Lys Thr Lys
500 505 510

<210> SEQ ID NO 72
<211> LENGTH: 512
<212> TYPE: PRT
<213> ORGANISM: Yarrowia lipolytica
<220> FEATURE:
<221> NAME/KEY: MISC_FEATURE
<222> LOCATION: (385)..(385)
<223> OTHER INFORMATION: Xaa = Ala [A], Asn [N], Cys [C], Gly [G], His [H], Ile [I], Leu [L], Lys [K], Met [M], Phe [F], Ser [S], Thr [T], Trp [W], Tyr [Y] or Val [V]

<400> SEQUENCE: 72

Met Ala Phe Pro Trp Ala Asp Lys Trp Ala Ala Asp Ala Ser Ala Ser
1 5 10 15

Thr Gly Leu Pro Pro Asp Leu Leu Lys Ile Ala Phe Thr Leu Val Met
20 25 30

Ser Tyr Pro Leu Ser Ser Leu Met Lys Arg Leu Pro Asp Asp Ala Lys
35 40 45

Asn Leu Lys Ile Ile Tyr Ile Ile Ser Val Ser Ile Phe Tyr Met Val
50 55 60

Gly Val Phe Ser Leu Tyr Gly Gly Ala Ala Thr Leu Leu Phe Ser Ser
65 70 75 80

Met Gly Thr Phe Phe Ile Thr Gln Trp Lys Ser Pro Tyr Met Pro Trp
85 90 95

Val Asn Phe Gly Phe Val Met Thr His Leu Phe Val Asn His Leu Arg
100 105 110

Ser Gln Phe Phe Pro Glu Thr Tyr Asp Pro Asn Val Ile Asp Ile Thr
115 120 125

Gly Ala Gln Met Val Leu Cys Met Lys Leu Ser Ser Phe Gly Trp Asn
130 135 140

Val Tyr Asp Gly Trp Gln Ile Glu Lys Gly Glu Gln Leu Ser Glu Phe
145 150 155 160

Gln Thr Lys Arg Ala Val Leu Lys His Pro Ser Leu Met Asp Phe Leu
165 170 175

Ala Phe Val Phe Tyr Phe Pro Ser Ile Leu Thr Gly Pro Ser Tyr Asp
180 185 190

Tyr Met Glu Phe His Asn Trp Leu Asp Leu Ser Leu Phe Lys Glu Leu
195 200 205

Glu Lys Asp Lys Asp Pro Lys Arg Ala Ala Arg Arg Lys Arg His Lys 210 215 220

Ile Pro Arg Ser Gly Ile Ala Ala Ser Lys Lys Leu Ala Ala Gly Ile
225 230 235 240

Phe Trp Ile Val Leu Trp Thr Gln Val Asp Ser Arg Ile Ser Thr Ala
245 250 255

Tyr Ala Tyr Ser Asp Ala Phe Thr Lys Glu His Asn Ile Phe Gly Arg
260 265 270

Ile Val Tyr Leu Tyr Met Leu Gly Phe Met Tyr Arg Leu Lys Tyr Tyr
275 280 285

Gly Ala Trp Ser Ile Ser Glu Gly Ala Cys Ile Leu Ser Gly Leu Gly
290 295 300

Phe His Gly Val Asp Pro Lys Thr Gly Lys Tyr Lys Trp Asp Arg Val
305 310 315 320

Gln Asn Val Asp Pro Trp Gly Phe Glu Thr Gly Gln Asn Thr Lys Ala
325 330 335

Leu Leu Glu Ala Trp Asn Gln Asn Thr Asn Lys Trp Leu Arg Asn Tyr
340 345 350

Val Tyr Leu Arg Val Val Pro Lys Gly Gln Lys Pro Gly Phe Arg Ala
355 360 365

Thr Ile Phe Thr Phe Val Val Ser Ala Phe Trp His Gly Thr Arg Pro
370 375 380

Xaa Tyr Tyr Leu Thr Phe Val Thr Ala Ala Met Tyr Gln Ser Val Gly
385 390 395 400

Lys Phe Phe Arg Arg Tyr Leu Arg Pro Phe Phe Met Glu Ser Asp Gly
405 410 415

Lys Thr Ala Gly Pro Tyr Lys Ile Tyr Tyr Asp Ile Val Cys Trp Ile
420 425 430

Val Val Gln Thr Ala Phe Gly Tyr Ala Thr Gln Ser Phe Met Ile Leu
435 440 445

Asp Phe Trp Leu Ser Leu Lys Cys Trp Lys Asn Ser Trp Phe Leu Tyr
450 455 460

His Ile Ala Leu Gly Ala Ile Phe Ala Ile Ser Ser Pro Tyr Lys Ala
465 470 475 480

Trp Ala Ile Pro Lys Ile Lys Lys Lys Gln Ala Gly Ala Val Thr Asp
485 490 495

Lys Lys Asp Ala Lys Glu Glu Val Lys Lys Asp Thr Ile Lys Thr Lys
500 505 510

<210> SEQ ID NO 73
<211> LENGTH: 512
<212> TYPE: PRT
<213> ORGANISM: Yarrowia lipolytica
<220> FEATURE:
<221> NAME/KEY: MISC_FEATURE
<222> LOCATION: (386)..(386)
<223> OTHER INFORMATION: Xaa = Ala [A], Gly [G], His [H], Leu [L], Phe
[F], Pro [P], Ser [S], Thr [T] or Val [V]

<400> SEQUENCE: 73

Met Ala Phe Pro Trp Ala Asp Lys Trp Ala Ala Asp Ala Ser Ala Ser
1 5 10 15

Thr Gly Leu Pro Pro Asp Leu Leu Lys Ile Ala Phe Thr Leu Val Met
20 25 30

Ser Tyr Pro Leu Ser Ser Leu Met Lys Arg Leu Pro Asp Asp Ala Lys
35 40 45

Asn Leu Lys Ile Ile Tyr Ile Ile Ser Val Ser Ile Phe Tyr Met Val

-continued

```
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Met Lys Leu Ser Ser Phe Gly Trp Asn
    130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Pro
    370                 375                 380

Gly Xaa Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480
```

```
Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510


<210> SEQ ID NO 74
<211> LENGTH: 512
<212> TYPE: PRT
<213> ORGANISM: Yarrowia lipolytica
<220> FEATURE:
<221> NAME/KEY: MISC_FEATURE
<222> LOCATION: (387)..(387)
<223> OTHER INFORMATION: Xaa = Ala [A], Gly [G], His [H], Leu [L],
      Phe [F], Pro [P], Ser [S], Thr [T], Trp [W] or Val [V]

<400> SEQUENCE: 74

Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Met Lys Leu Ser Ser Phe Gly Trp Asn
    130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320
```

Gln Asn Val Asp Pro Trp Gly Phe Glu Thr Gly Gln Asn Thr Lys Ala
325 330 335

Leu Leu Glu Ala Trp Asn Gln Asn Thr Asn Lys Trp Leu Arg Asn Tyr
340 345 350

Val Tyr Leu Arg Val Val Pro Lys Gly Gln Lys Pro Gly Phe Arg Ala
355 360 365

Thr Ile Phe Thr Phe Val Val Ser Ala Phe Trp His Gly Thr Arg Pro
370 375 380

Gly Tyr Xaa Leu Thr Phe Val Thr Ala Ala Met Tyr Gln Ser Val Gly
385 390 395 400

Lys Phe Phe Arg Arg Tyr Leu Arg Pro Phe Phe Met Glu Ser Asp Gly
405 410 415

Lys Thr Ala Gly Pro Tyr Lys Ile Tyr Tyr Asp Ile Val Cys Trp Ile
420 425 430

Val Val Gln Thr Ala Phe Gly Tyr Ala Thr Gln Ser Phe Met Ile Leu
435 440 445

Asp Phe Trp Leu Ser Leu Lys Cys Trp Lys Asn Ser Trp Phe Leu Tyr
450 455 460

His Ile Ala Leu Gly Ala Ile Phe Ala Ile Ser Ser Pro Tyr Lys Ala
465 470 475 480

Trp Ala Ile Pro Lys Ile Lys Lys Lys Gln Ala Gly Ala Val Thr Asp
485 490 495

Lys Lys Asp Ala Lys Glu Glu Val Lys Lys Asp Thr Ile Lys Thr Lys
500 505 510

<210> SEQ ID NO 75
<211> LENGTH: 512
<212> TYPE: PRT
<213> ORGANISM: Yarrowia lipolytica
<220> FEATURE:
<221> NAME/KEY: MISC_FEATURE
<222> LOCATION: (388)..(388)
<223> OTHER INFORMATION: Xaa = Ala [A], Gly [G], His [H], Pro [P], Ser [S], Thr [T], Trp [W], Tyr [Y] or Val [V]

<400> SEQUENCE: 75

Met Ala Phe Pro Trp Ala Asp Lys Trp Ala Ala Asp Ala Ser Ala Ser
1 5 10 15

Thr Gly Leu Pro Pro Asp Leu Leu Lys Ile Ala Phe Thr Leu Val Met
20 25 30

Ser Tyr Pro Leu Ser Ser Leu Met Lys Arg Leu Pro Asp Asp Ala Lys
35 40 45

Asn Leu Lys Ile Ile Tyr Ile Ile Ser Val Ser Ile Phe Tyr Met Val
50 55 60

Gly Val Phe Ser Leu Tyr Gly Gly Ala Ala Thr Leu Leu Phe Ser Ser
65 70 75 80

Met Gly Thr Phe Phe Ile Thr Gln Trp Lys Ser Pro Tyr Met Pro Trp
85 90 95

Val Asn Phe Gly Phe Val Met Thr His Leu Phe Val Asn His Leu Arg
100 105 110

Ser Gln Phe Phe Pro Glu Thr Tyr Asp Pro Asn Val Ile Asp Ile Thr
115 120 125

Gly Ala Gln Met Val Leu Cys Met Lys Leu Ser Ser Phe Gly Trp Asn
130 135 140

Val Tyr Asp Gly Trp Gln Ile Glu Lys Gly Glu Gln Leu Ser Glu Phe
145 150 155 160

```
Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Pro
    370                 375                 380

Gly Tyr Tyr Xaa Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510
```

```
<210> SEQ ID NO 76
<211> LENGTH: 512
<212> TYPE: PRT
<213> ORGANISM: Yarrowia lipolytica
<220> FEATURE:
<221> NAME/KEY: MISC_FEATURE
<222> LOCATION: (389)..(389)
<223> OTHER INFORMATION: Xaa = Ala [A], Cys [C], Gly [G], His [H],
      Ile [I], Leu [L], Met [M], Phe [F], Pro [P], Ser [S], Trp [W],
      Tyr [Y] or Val [V]
```

<400> SEQUENCE: 76

```
Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Met Lys Leu Ser Ser Phe Gly Trp Asn
    130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Pro
    370                 375                 380

Gly Tyr Tyr Leu Xaa Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415
```

```
Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510


<210> SEQ ID NO 77
<211> LENGTH: 512
<212> TYPE: PRT
<213> ORGANISM: Yarrowia lipolytica
<220> FEATURE:
<221> NAME/KEY: MISC_FEATURE
<222> LOCATION: (390)..(390)
<223> OTHER INFORMATION: Xaa = Ala [A], Asn [N], Cys [C], Gly [G], His
      [H], Leu [L], Met [M], Pro [P], Ser [S], Thr [T] or Val [V]

<400> SEQUENCE: 77

Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Met Lys Leu Ser Ser Phe Gly Trp Asn
    130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255
```

```
Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Pro
    370                 375                 380

Gly Tyr Tyr Leu Thr Xaa Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510


<210> SEQ ID NO 78
<211> LENGTH: 1539
<212> TYPE: DNA
<213> ORGANISM: Yarrowia lipolytica
<220> FEATURE:
<221> NAME/KEY: CDS
<222> LOCATION: (1)..(1539)

<400> SEQUENCE: 78

atg gcc ttt cct tgg gca gat aag tgg gca gcc gat gcg tct gca tct       48
Met Ala Phe Pro Trp Ala Asp Lys Trp Ala Ala Asp Ala Ser Ala Ser
1               5                   10                  15

aca ggg ctg cct ccg gac ctc ctc aag att gca ttc act ctg gtc atg       96
Thr Gly Leu Pro Pro Asp Leu Leu Lys Ile Ala Phe Thr Leu Val Met
            20                  25                  30

tct tat ccg ctg agt tct ctc atg aaa cgg ctg cca gat gac gcc aaa      144
Ser Tyr Pro Leu Ser Ser Leu Met Lys Arg Leu Pro Asp Asp Ala Lys
        35                  40                  45

aac ctc aag atc atc tat atc atc tcc gtg tcc atc ttc tac atg gtg      192
Asn Leu Lys Ile Ile Tyr Ile Ile Ser Val Ser Ile Phe Tyr Met Val
    50                  55                  60

ggt gtc ttc tcc ctc tat ggc gga gct gcc act ctg ctc ttc tcc tca      240
Gly Val Phe Ser Leu Tyr Gly Gly Ala Ala Thr Leu Leu Phe Ser Ser
65                  70                  75                  80
```

```
atg ggt acc ttc ttc atc acc caa tgg aag agc cct tac atg ccc tgg      288
Met Gly Thr Phe Phe Ile Thr Gln Trp Lys Ser Pro Tyr Met Pro Trp
                85                  90                  95

gtc aat ttt ggt ttt gtc atg acc cat ctc ttc gtc aat cac ctg cgt      336
Val Asn Phe Gly Phe Val Met Thr His Leu Phe Val Asn His Leu Arg
            100                 105                 110

tcg cag ttt ttc ccc gaa aca tac gac ccc aat gtc att gac atc acc      384
Ser Gln Phe Phe Pro Glu Thr Tyr Asp Pro Asn Val Ile Asp Ile Thr
        115                 120                 125

gga gca cag atg gtt ctg tgt tct aag cta tcg tct ttt gga tgg aac      432
Gly Ala Gln Met Val Leu Cys Ser Lys Leu Ser Ser Phe Gly Trp Asn
    130                 135                 140

gtc tac gat gga tgg cag att gag aag ggt gag cag ctc agc gag ttc      480
Val Tyr Asp Gly Trp Gln Ile Glu Lys Gly Glu Gln Leu Ser Glu Phe
145                 150                 155                 160

cag act aaa agg gct gtt ctc aag cac ccc agt ctt atg gac ttc cta      528
Gln Thr Lys Arg Ala Val Leu Lys His Pro Ser Leu Met Asp Phe Leu
                165                 170                 175

gct ttt gtg ttc tac ttc cct tcc att ctg aca ggt cct tct tac gac      576
Ala Phe Val Phe Tyr Phe Pro Ser Ile Leu Thr Gly Pro Ser Tyr Asp
            180                 185                 190

tat atg gag ttc cat aac tgg ctc gat ctc agc ctg ttc aag gag ctg      624
Tyr Met Glu Phe His Asn Trp Leu Asp Leu Ser Leu Phe Lys Glu Leu
        195                 200                 205

gag aaa gat aag gac ccc aag cga gct gct cga cga aag cga cac aag      672
Glu Lys Asp Lys Asp Pro Lys Arg Ala Ala Arg Arg Lys Arg His Lys
    210                 215                 220

atc ccc cga tct gga atc gct gct tcc aag aaa ctc gcc gct ggt atc      720
Ile Pro Arg Ser Gly Ile Ala Ala Ser Lys Lys Leu Ala Ala Gly Ile
225                 230                 235                 240

ttc tgg atc gtt ctg tgg acc cag gtg gac tct cga atc tcc acc gcc      768
Phe Trp Ile Val Leu Trp Thr Gln Val Asp Ser Arg Ile Ser Thr Ala
                245                 250                 255

tac gct tac tca gac gca ttc acc aag gag cac aac atc ttt gga cga      816
Tyr Ala Tyr Ser Asp Ala Phe Thr Lys Glu His Asn Ile Phe Gly Arg
            260                 265                 270

att gtg tac ctc tac atg ctc ggt ttc atg tac cga ctc aag tac tac      864
Ile Val Tyr Leu Tyr Met Leu Gly Phe Met Tyr Arg Leu Lys Tyr Tyr
        275                 280                 285

gga gcc tgg tcc att tcc gag gga gcc tgc atc ttg tct ggc ctc gga      912
Gly Ala Trp Ser Ile Ser Glu Gly Ala Cys Ile Leu Ser Gly Leu Gly
    290                 295                 300

ttc cac ggc gtg gac ccc aaa act ggc aag tac aag tgg gac cgt gtc      960
Phe His Gly Val Asp Pro Lys Thr Gly Lys Tyr Lys Trp Asp Arg Val
305                 310                 315                 320

cag aac gtg gac ccg tgg gga ttc gaa act ggt caa aac aca aag gct     1008
Gln Asn Val Asp Pro Trp Gly Phe Glu Thr Gly Gln Asn Thr Lys Ala
                325                 330                 335

ctg ctg gag gcc tgg aac cag aac act aac aag tgg cta cga aac tat     1056
Leu Leu Glu Ala Trp Asn Gln Asn Thr Asn Lys Trp Leu Arg Asn Tyr
            340                 345                 350

gtg tac ctc cga gtg gtg ccc aaa ggc caa aag cct gga ttc cga gcc     1104
Val Tyr Leu Arg Val Val Pro Lys Gly Gln Lys Pro Gly Phe Arg Ala
        355                 360                 365

act atc ttc aca ttt gtg gtt tcc gcc ttc tgg cat gga act cga cct     1152
Thr Ile Phe Thr Phe Val Val Ser Ala Phe Trp His Gly Thr Arg Pro
    370                 375                 380

ggc tac tat ctc gcg ttt gtg acc gct gcc atg tac cag tct gtt ggt     1200
Gly Tyr Tyr Leu Ala Phe Val Thr Ala Ala Met Tyr Gln Ser Val Gly
```

-continued

```
385                 390                 395                 400

aag ttc ttc cga cga tac ctg cga ccc ttc ttc atg gag tct gat gga      1248
Lys Phe Phe Arg Arg Tyr Leu Arg Pro Phe Phe Met Glu Ser Asp Gly
            405                 410                 415

aag act gcc ggt ccc tat aag atc tac tac gac att gtg tgt tgg atc      1296
Lys Thr Ala Gly Pro Tyr Lys Ile Tyr Tyr Asp Ile Val Cys Trp Ile
            420                 425                 430

gtt gtc caa acc gca ttt gga tac gct acc cag tcc ttt atg att cta      1344
Val Val Gln Thr Ala Phe Gly Tyr Ala Thr Gln Ser Phe Met Ile Leu
        435                 440                 445

gac ttc tgg ctg tcg ctc aag tgt tgg aag aac tcc tgg ttc ctg tac      1392
Asp Phe Trp Leu Ser Leu Lys Cys Trp Lys Asn Ser Trp Phe Leu Tyr
    450                 455                 460

cac att gct ctg ggc gcc atc ttt gca att tct agc ccc tac aag gca      1440
His Ile Ala Leu Gly Ala Ile Phe Ala Ile Ser Ser Pro Tyr Lys Ala
465                 470                 475                 480

tgg gcg att ccc aag atc aag aaa aag cag gct gga gcc gtc act gac      1488
Trp Ala Ile Pro Lys Ile Lys Lys Lys Gln Ala Gly Ala Val Thr Asp
            485                 490                 495

aag aag gac gcc aag gag gag gtg aag aag gac acc atc aag acc aag      1536
Lys Lys Asp Ala Lys Glu Glu Val Lys Lys Asp Thr Ile Lys Thr Lys
            500                 505                 510

taa                                                                  1539


<210> SEQ ID NO 79
<211> LENGTH: 512
<212> TYPE: PRT
<213> ORGANISM: Yarrowia lipolytica

<400> SEQUENCE: 79

Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Ser Lys Leu Ser Ser Phe Gly Trp Asn
    130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205
```

-continued

```
Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Pro
    370                 375                 380

Gly Tyr Tyr Leu Ala Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510


<210> SEQ ID NO 80
<211> LENGTH: 1539
<212> TYPE: DNA
<213> ORGANISM: Yarrowia lipolytica
<220> FEATURE:
<221> NAME/KEY: CDS
<222> LOCATION: (1)..(1539)

<400> SEQUENCE: 80

atg gcc ttt cct tgg gca gat aag tgg gca gcc gat gcg tct gca tct       48
Met Ala Phe Pro Trp Ala Asp Lys Trp Ala Ala Asp Ala Ser Ala Ser
1               5                   10                  15

aca ggg ctg cct ccg gac ctc ctc aag att gca ttc act ctg gtc atg       96
Thr Gly Leu Pro Pro Asp Leu Leu Lys Ile Ala Phe Thr Leu Val Met
            20                  25                  30

tct tat ccg ctg agt tct ctc atg aaa cgg ctg cca gat gac gcc aaa      144
Ser Tyr Pro Leu Ser Ser Leu Met Lys Arg Leu Pro Asp Asp Ala Lys
        35                  40                  45
```

```
aac ctc aag atc atc tat atc atc tcc gtg tcc atc ttc tac atg gtg      192
Asn Leu Lys Ile Ile Tyr Ile Ile Ser Val Ser Ile Phe Tyr Met Val
    50                  55                  60

ggt gtc ttc tcc ctc tat ggc gga gct gcc act ctg ctc ttc tcc tca      240
Gly Val Phe Ser Leu Tyr Gly Gly Ala Ala Thr Leu Leu Phe Ser Ser
65                  70                  75                  80

atg ggt acc ttc ttc atc acc caa tgg aag agc cct tac atg ccc tgg      288
Met Gly Thr Phe Phe Ile Thr Gln Trp Lys Ser Pro Tyr Met Pro Trp
                85                  90                  95

gtc aat ttt ggt ttt gtc atg acc cat ctc ttc gtc aat cac ctg cgt      336
Val Asn Phe Gly Phe Val Met Thr His Leu Phe Val Asn His Leu Arg
            100                 105                 110

tcg cag ttt ttc ccc gaa aca tac gac ccc aat gtc att gac atc acc      384
Ser Gln Phe Phe Pro Glu Thr Tyr Asp Pro Asn Val Ile Asp Ile Thr
        115                 120                 125

gga gca cag atg gtt ctg tgt tct aag cta tcg tct ttt gga tgg aac      432
Gly Ala Gln Met Val Leu Cys Ser Lys Leu Ser Ser Phe Gly Trp Asn
    130                 135                 140

gtc tac gat gga tgg cag att gag aag ggt gag cag ctc agc gag ttc      480
Val Tyr Asp Gly Trp Gln Ile Glu Lys Gly Glu Gln Leu Ser Glu Phe
145                 150                 155                 160

cag act aaa agg gct gtt ctc aag cac ccc agt ctt atg gac ttc cta      528
Gln Thr Lys Arg Ala Val Leu Lys His Pro Ser Leu Met Asp Phe Leu
                165                 170                 175

gct ttt gtg ttc tac ttc cct tcc att ctg aca ggt cct tct tac gac      576
Ala Phe Val Phe Tyr Phe Pro Ser Ile Leu Thr Gly Pro Ser Tyr Asp
            180                 185                 190

tat atg gag ttc cat aac tgg ctc gat ctc agc ctg ttc aag gag ctg      624
Tyr Met Glu Phe His Asn Trp Leu Asp Leu Ser Leu Phe Lys Glu Leu
        195                 200                 205

gag aaa gat aag gac ccc aag cga gct gct cga cga aag cga cac aag      672
Glu Lys Asp Lys Asp Pro Lys Arg Ala Ala Arg Arg Lys Arg His Lys
    210                 215                 220

atc ccc cga tct gga atc gct gct tcc aag aaa ctc gcc gct ggt atc      720
Ile Pro Arg Ser Gly Ile Ala Ala Ser Lys Lys Leu Ala Ala Gly Ile
225                 230                 235                 240

ttc tgg atc gtt ctg tgg acc cag gtg gac tct cga atc tcc acc gcc      768
Phe Trp Ile Val Leu Trp Thr Gln Val Asp Ser Arg Ile Ser Thr Ala
                245                 250                 255

tac gct tac tca gac gca ttc acc aag gag cac aac atc ttt gga cga      816
Tyr Ala Tyr Ser Asp Ala Phe Thr Lys Glu His Asn Ile Phe Gly Arg
            260                 265                 270

att gtg tac ctc tac atg ctc ggt ttc atg tac cga ctc aag tac tac      864
Ile Val Tyr Leu Tyr Met Leu Gly Phe Met Tyr Arg Leu Lys Tyr Tyr
        275                 280                 285

gga gcc tgg tcc att tcc gag gga gcc tgc atc ttg tct ggc ctc gga      912
Gly Ala Trp Ser Ile Ser Glu Gly Ala Cys Ile Leu Ser Gly Leu Gly
    290                 295                 300

ttc cac ggc gtg gac ccc aaa act ggc aag tac aag tgg gac cgt gtc      960
Phe His Gly Val Asp Pro Lys Thr Gly Lys Tyr Lys Trp Asp Arg Val
305                 310                 315                 320

cag aac gtg gac ccg tgg gga ttc gaa act ggt caa aac aca aag gct     1008
Gln Asn Val Asp Pro Trp Gly Phe Glu Thr Gly Gln Asn Thr Lys Ala
                325                 330                 335

ctg ctg gag gcc tgg aac cag aac act aac aag tgg cta cga aac tat     1056
Leu Leu Glu Ala Trp Asn Gln Asn Thr Asn Lys Trp Leu Arg Asn Tyr
            340                 345                 350

gtg tac ctc cga gtg gtg ccc aaa ggc caa aag cct gga ttc cga gcc     1104
Val Tyr Leu Arg Val Val Pro Lys Gly Gln Lys Pro Gly Phe Arg Ala
```

```
        355                 360                 365

act atc ttc aca ttt gtg gtt tcc gcc ttc tgg cat gga act cga cct      1152
Thr Ile Phe Thr Phe Val Val Ser Ala Phe Trp His Gly Thr Arg Pro
    370                 375                 380

ggc tac tat ctc tgc ttt gtg acc gct gcc atg tac cag tct gtt ggt      1200
Gly Tyr Tyr Leu Cys Phe Val Thr Ala Ala Met Tyr Gln Ser Val Gly
385                 390                 395                 400

aag ttc ttc cga cga tac ctg cga ccc ttc ttc atg gag tct gat gga      1248
Lys Phe Phe Arg Arg Tyr Leu Arg Pro Phe Phe Met Glu Ser Asp Gly
                405                 410                 415

aag act gcc ggt ccc tat aag atc tac tac gac att gtg tgt tgg atc      1296
Lys Thr Ala Gly Pro Tyr Lys Ile Tyr Tyr Asp Ile Val Cys Trp Ile
            420                 425                 430

gtt gtc caa acc gca ttt gga tac gct acc cag tcc ttt atg att cta      1344
Val Val Gln Thr Ala Phe Gly Tyr Ala Thr Gln Ser Phe Met Ile Leu
        435                 440                 445

gac ttc tgg ctg tcg ctc aag tgt tgg aag aac tcc tgg ttc ctg tac      1392
Asp Phe Trp Leu Ser Leu Lys Cys Trp Lys Asn Ser Trp Phe Leu Tyr
    450                 455                 460

cac att gct ctg ggc gcc atc ttt gca att tct agc ccc tac aag gca      1440
His Ile Ala Leu Gly Ala Ile Phe Ala Ile Ser Ser Pro Tyr Lys Ala
465                 470                 475                 480

tgg gcg att ccc aag atc aag aaa aag cag gct gga gcc gtc act gac      1488
Trp Ala Ile Pro Lys Ile Lys Lys Lys Gln Ala Gly Ala Val Thr Asp
                485                 490                 495

aag aag gac gcc aag gag gag gtg aag aag gac acc atc aag acc aag      1536
Lys Lys Asp Ala Lys Glu Glu Val Lys Lys Asp Thr Ile Lys Thr Lys
            500                 505                 510

taa                                                                  1539


<210> SEQ ID NO 81
<211> LENGTH: 512
<212> TYPE: PRT
<213> ORGANISM: Yarrowia lipolytica

<400> SEQUENCE: 81

Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Ser Lys Leu Ser Ser Phe Gly Trp Asn
    130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
```

```
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Pro
    370                 375                 380

Gly Tyr Tyr Leu Cys Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510


<210> SEQ ID NO 82
<211> LENGTH: 1539
<212> TYPE: DNA
<213> ORGANISM: Yarrowia lipolytica
<220> FEATURE:
<221> NAME/KEY: CDS
<222> LOCATION: (1)..(1539)

<400> SEQUENCE: 82

atg gcc ttt cct tgg gca gat aag tgg gca gcc gat gcg tct gca tct       48
Met Ala Phe Pro Trp Ala Asp Lys Trp Ala Ala Asp Ala Ser Ala Ser
1               5                   10                  15
```

-continued

```
aca ggg ctg cct ccg gac ctc ctc aag att gca ttc act ctg gtc atg        96
Thr Gly Leu Pro Pro Asp Leu Leu Lys Ile Ala Phe Thr Leu Val Met
            20                  25                  30

tct tat ccg ctg agt tct ctc atg aaa cgg ctg cca gat gac gcc aaa       144
Ser Tyr Pro Leu Ser Ser Leu Met Lys Arg Leu Pro Asp Asp Ala Lys
        35                  40                  45

aac ctc aag atc atc tat atc atc tcc gtg tcc atc ttc tac atg gtg       192
Asn Leu Lys Ile Ile Tyr Ile Ile Ser Val Ser Ile Phe Tyr Met Val
    50                  55                  60

ggt gtc ttc tcc ctc tat ggc gga gct gcc act ctg ctc ttc tcc tca       240
Gly Val Phe Ser Leu Tyr Gly Gly Ala Ala Thr Leu Leu Phe Ser Ser
65                  70                  75                  80

atg ggt acc ttc ttc atc acc caa tgg aag agc cct tac atg ccc tgg       288
Met Gly Thr Phe Phe Ile Thr Gln Trp Lys Ser Pro Tyr Met Pro Trp
                85                  90                  95

gtc aat ttt ggt ttt gtc atg acc cat ctc ttc gtc aat cac ctg cgt       336
Val Asn Phe Gly Phe Val Met Thr His Leu Phe Val Asn His Leu Arg
            100                 105                 110

tcg cag ttt ttc ccc gaa aca tac gac ccc aat gtc att gac atc acc       384
Ser Gln Phe Phe Pro Glu Thr Tyr Asp Pro Asn Val Ile Asp Ile Thr
        115                 120                 125

gga gca cag atg gtt ctg tgt tct aag cta tcg tct ttt gga tgg aac       432
Gly Ala Gln Met Val Leu Cys Ser Lys Leu Ser Ser Phe Gly Trp Asn
    130                 135                 140

gtc tac gat gga tgg cag att gag aag ggt gag cag ctc agc gag ttc       480
Val Tyr Asp Gly Trp Gln Ile Glu Lys Gly Glu Gln Leu Ser Glu Phe
145                 150                 155                 160

cag act aaa agg gct gtt ctc aag cac ccc agt ctt atg gac ttc cta       528
Gln Thr Lys Arg Ala Val Leu Lys His Pro Ser Leu Met Asp Phe Leu
                165                 170                 175

gct ttt gtg ttc tac ttc cct tcc att ctg aca ggt cct tct tac gac       576
Ala Phe Val Phe Tyr Phe Pro Ser Ile Leu Thr Gly Pro Ser Tyr Asp
            180                 185                 190

tat atg gag ttc cat aac tgg ctc gat ctc agc ctg ttc aag gag ctg       624
Tyr Met Glu Phe His Asn Trp Leu Asp Leu Ser Leu Phe Lys Glu Leu
        195                 200                 205

gag aaa gat aag gac ccc aag cga gct gct cga cga aag cga cac aag       672
Glu Lys Asp Lys Asp Pro Lys Arg Ala Ala Arg Arg Lys Arg His Lys
    210                 215                 220

atc ccc cga tct gga atc gct gct tcc aag aaa ctc gcc gct ggt atc       720
Ile Pro Arg Ser Gly Ile Ala Ala Ser Lys Lys Leu Ala Ala Gly Ile
225                 230                 235                 240

ttc tgg atc gtt ctg tgg acc cag gtg gac tct cga atc tcc acc gcc       768
Phe Trp Ile Val Leu Trp Thr Gln Val Asp Ser Arg Ile Ser Thr Ala
                245                 250                 255

tac gct tac tca gac gca ttc acc aag gag cac aac atc ttt gga cga       816
Tyr Ala Tyr Ser Asp Ala Phe Thr Lys Glu His Asn Ile Phe Gly Arg
            260                 265                 270

att gtg tac ctc tac atg ctc ggt ttc atg tac cga ctc aag tac tac       864
Ile Val Tyr Leu Tyr Met Leu Gly Phe Met Tyr Arg Leu Lys Tyr Tyr
        275                 280                 285

gga gcc tgg tcc att tcc gag gga gcc tgc atc ttg tct ggc ctc gga       912
Gly Ala Trp Ser Ile Ser Glu Gly Ala Cys Ile Leu Ser Gly Leu Gly
    290                 295                 300

ttc cac ggc gtg gac ccc aaa act ggc aag tac aag tgg gac cgt gtc       960
Phe His Gly Val Asp Pro Lys Thr Gly Lys Tyr Lys Trp Asp Arg Val
305                 310                 315                 320

cag aac gtg gac ccg tgg gga ttc gaa act ggt caa aac aca aag gct      1008
Gln Asn Val Asp Pro Trp Gly Phe Glu Thr Gly Gln Asn Thr Lys Ala
```

```
                325                 330                 335

ctg ctg gag gcc tgg aac cag aac act aac aag tgg cta cga aac tat      1056
Leu Leu Glu Ala Trp Asn Gln Asn Thr Asn Lys Trp Leu Arg Asn Tyr
            340                 345                 350

gtg tac ctc cga gtg gtg ccc aaa ggc caa aag cct gga ttc cga gcc      1104
Val Tyr Leu Arg Val Val Pro Lys Gly Gln Lys Pro Gly Phe Arg Ala
        355                 360                 365

act atc ttc aca ttt gtg gtt tcc gcc ttc tgg cat gga act cga cct      1152
Thr Ile Phe Thr Phe Val Val Ser Ala Phe Trp His Gly Thr Arg Pro
    370                 375                 380

ggc tac tat ctc agc ttt gtg acc gct gcc atg tac cag tct gtt ggt      1200
Gly Tyr Tyr Leu Ser Phe Val Thr Ala Ala Met Tyr Gln Ser Val Gly
385                 390                 395                 400

aag ttc ttc cga cga tac ctg cga ccc ttc ttc atg gag tct gat gga      1248
Lys Phe Phe Arg Arg Tyr Leu Arg Pro Phe Phe Met Glu Ser Asp Gly
                405                 410                 415

aag act gcc ggt ccc tat aag atc tac tac gac att gtg tgt tgg atc      1296
Lys Thr Ala Gly Pro Tyr Lys Ile Tyr Tyr Asp Ile Val Cys Trp Ile
            420                 425                 430

gtt gtc caa acc gca ttt gga tac gct acc cag tcc ttt atg att cta      1344
Val Val Gln Thr Ala Phe Gly Tyr Ala Thr Gln Ser Phe Met Ile Leu
        435                 440                 445

gac ttc tgg ctg tcg ctc aag tgt tgg aag aac tcc tgg ttc ctg tac      1392
Asp Phe Trp Leu Ser Leu Lys Cys Trp Lys Asn Ser Trp Phe Leu Tyr
    450                 455                 460

cac att gct ctg ggc gcc atc ttt gca att tct agc ccc tac aag gca      1440
His Ile Ala Leu Gly Ala Ile Phe Ala Ile Ser Ser Pro Tyr Lys Ala
465                 470                 475                 480

tgg gcg att ccc aag atc aag aaa aag cag gct gga gcc gtc act gac      1488
Trp Ala Ile Pro Lys Ile Lys Lys Lys Gln Ala Gly Ala Val Thr Asp
                485                 490                 495

aag aag gac gcc aag gag gag gtg aag aag gac acc atc aag acc aag      1536
Lys Lys Asp Ala Lys Glu Glu Val Lys Lys Asp Thr Ile Lys Thr Lys
            500                 505                 510

taa                                                                  1539


<210> SEQ ID NO 83
<211> LENGTH: 512
<212> TYPE: PRT
<213> ORGANISM: Yarrowia lipolytica

<400> SEQUENCE: 83

Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125
```

```
Gly Ala Gln Met Val Leu Cys Ser Lys Leu Ser Ser Phe Gly Trp Asn
    130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Pro
    370                 375                 380

Gly Tyr Tyr Leu Ser Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510
```

<210> SEQ ID NO 84
<211> LENGTH: 1539
<212> TYPE: DNA
<213> ORGANISM: Yarrowia lipolytica
<220> FEATURE:

```
<221> NAME/KEY: CDS
<222> LOCATION: (1)..(1539)

<400> SEQUENCE: 84

atg gcc ttt cct tgg gca gat aag tgg gca gcc gat gcg tct gca tct       48
Met Ala Phe Pro Trp Ala Asp Lys Trp Ala Ala Asp Ala Ser Ala Ser
1               5                   10                  15

aca ggg ctg cct ccg gac ctc ctc aag att gca ttc act ctg gtc atg       96
Thr Gly Leu Pro Pro Asp Leu Leu Lys Ile Ala Phe Thr Leu Val Met
            20                  25                  30

tct tat ccg ctg agt tct ctc atg aaa cgg ctg cca gat gac gcc aaa      144
Ser Tyr Pro Leu Ser Ser Leu Met Lys Arg Leu Pro Asp Asp Ala Lys
        35                  40                  45

aac ctc aag atc atc tat atc atc tcc gtg tcc atc ttc tac atg gtg      192
Asn Leu Lys Ile Ile Tyr Ile Ile Ser Val Ser Ile Phe Tyr Met Val
    50                  55                  60

ggt gtc ttc tcc ctc tat ggc gga gct gcc act ctg ctc ttc tcc tca      240
Gly Val Phe Ser Leu Tyr Gly Gly Ala Ala Thr Leu Leu Phe Ser Ser
65                  70                  75                  80

atg ggt acc ttc ttc atc acc caa tgg aag agc cct tac atg ccc tgg      288
Met Gly Thr Phe Phe Ile Thr Gln Trp Lys Ser Pro Tyr Met Pro Trp
                85                  90                  95

gtc aat ttt ggt ttt gtc atg acc cat ctc ttc gtc aat cac ctg cgt      336
Val Asn Phe Gly Phe Val Met Thr His Leu Phe Val Asn His Leu Arg
            100                 105                 110

tcg cag ttt ttc ccc gaa aca tac gac ccc aat gtc att gac atc acc      384
Ser Gln Phe Phe Pro Glu Thr Tyr Asp Pro Asn Val Ile Asp Ile Thr
        115                 120                 125

gga gca cag atg gtt ctg tgt gtt aag cta tcg tct ttt gga tgg aac      432
Gly Ala Gln Met Val Leu Cys Val Lys Leu Ser Ser Phe Gly Trp Asn
    130                 135                 140

gtc tac gat gga tgg cag att gag aag ggt gag cag ctc agc gag ttc      480
Val Tyr Asp Gly Trp Gln Ile Glu Lys Gly Glu Gln Leu Ser Glu Phe
145                 150                 155                 160

cag act aaa agg gct gtt ctc aag cac ccc agt ctt atg gac ttc cta      528
Gln Thr Lys Arg Ala Val Leu Lys His Pro Ser Leu Met Asp Phe Leu
                165                 170                 175

gct ttt gtg ttc tac ttc cct tcc att ctg aca ggt cct tct tac gac      576
Ala Phe Val Phe Tyr Phe Pro Ser Ile Leu Thr Gly Pro Ser Tyr Asp
            180                 185                 190

tat atg gag ttc cat aac tgg ctc gat ctc agc ctg ttc aag gag ctg      624
Tyr Met Glu Phe His Asn Trp Leu Asp Leu Ser Leu Phe Lys Glu Leu
        195                 200                 205

gag aaa gat aag gac ccc aag cga gct gct cga cga aag cga cac aag      672
Glu Lys Asp Lys Asp Pro Lys Arg Ala Ala Arg Arg Lys Arg His Lys
    210                 215                 220

atc ccc cga tct gga atc gct gct tcc aag aaa ctc gcc gct ggt atc      720
Ile Pro Arg Ser Gly Ile Ala Ala Ser Lys Lys Leu Ala Ala Gly Ile
225                 230                 235                 240

ttc tgg atc gtt ctg tgg acc cag gtg gac tct cga atc tcc acc gcc      768
Phe Trp Ile Val Leu Trp Thr Gln Val Asp Ser Arg Ile Ser Thr Ala
                245                 250                 255

tac gct tac tca gac gca ttc acc aag gag cac aac atc ttt gga cga      816
Tyr Ala Tyr Ser Asp Ala Phe Thr Lys Glu His Asn Ile Phe Gly Arg
            260                 265                 270

att gtg tac ctc tac atg ctc ggt ttc atg tac cga ctc aag tac tac      864
Ile Val Tyr Leu Tyr Met Leu Gly Phe Met Tyr Arg Leu Lys Tyr Tyr
        275                 280                 285

gga gcc tgg tcc att tcc gag gga gcc tgc atc ttg tct ggc ctc gga      912
Gly Ala Trp Ser Ile Ser Glu Gly Ala Cys Ile Leu Ser Gly Leu Gly
```

-continued

```
    290                 295                 300

ttc cac ggc gtg gac ccc aaa act ggc aag tac aag tgg gac cgt gtc      960
Phe His Gly Val Asp Pro Lys Thr Gly Lys Tyr Lys Trp Asp Arg Val
305                 310                 315                 320

cag aac gtg gac ccg tgg gga ttc gaa act ggt caa aac aca aag gct     1008
Gln Asn Val Asp Pro Trp Gly Phe Glu Thr Gly Gln Asn Thr Lys Ala
                325                 330                 335

ctg ctg gag gcc tgg aac cag aac act aac aag tgg cta cga aac tat     1056
Leu Leu Glu Ala Trp Asn Gln Asn Thr Asn Lys Trp Leu Arg Asn Tyr
            340                 345                 350

gtg tac ctc cga gtg gtg ccc aaa ggc caa aag cct gga ttc cga gcc     1104
Val Tyr Leu Arg Val Val Pro Lys Gly Gln Lys Pro Gly Phe Arg Ala
        355                 360                 365

act atc ttc aca ttt gtg gtt tcc gcc ttc tgg cat gga act cga cct     1152
Thr Ile Phe Thr Phe Val Val Ser Ala Phe Trp His Gly Thr Arg Pro
    370                 375                 380

ggc tac tat ctc tgc ttt gtg acc gct gcc atg tac cag tct gtt ggt     1200
Gly Tyr Tyr Leu Cys Phe Val Thr Ala Ala Met Tyr Gln Ser Val Gly
385                 390                 395                 400

aag ttc ttc cga cga tac ctg cga ccc ttc ttc atg gag tct gat gga     1248
Lys Phe Phe Arg Arg Tyr Leu Arg Pro Phe Phe Met Glu Ser Asp Gly
                405                 410                 415

aag act gcc ggt ccc tat aag atc tac tac gac att gtg tgt tgg atc     1296
Lys Thr Ala Gly Pro Tyr Lys Ile Tyr Tyr Asp Ile Val Cys Trp Ile
            420                 425                 430

gtt gtc caa acc gca ttt gga tac gct acc cag tcc ttt atg att cta     1344
Val Val Gln Thr Ala Phe Gly Tyr Ala Thr Gln Ser Phe Met Ile Leu
        435                 440                 445

gac ttc tgg ctg tcg ctc aag tgt tgg aag aac tcc tgg ttc ctg tac     1392
Asp Phe Trp Leu Ser Leu Lys Cys Trp Lys Asn Ser Trp Phe Leu Tyr
    450                 455                 460

cac att gct ctg ggc gcc atc ttt gca att tct agc ccc tac aag gca     1440
His Ile Ala Leu Gly Ala Ile Phe Ala Ile Ser Ser Pro Tyr Lys Ala
465                 470                 475                 480

tgg gcg att ccc aag atc aag aaa aag cag gct gga gcc gtc act gac     1488
Trp Ala Ile Pro Lys Ile Lys Lys Lys Gln Ala Gly Ala Val Thr Asp
                485                 490                 495

aag aag gac gcc aag gag gag gtg aag aag gac acc atc aag acc aag     1536
Lys Lys Asp Ala Lys Glu Glu Val Lys Lys Asp Thr Ile Lys Thr Lys
            500                 505                 510

taa                                                                 1539


<210> SEQ ID NO 85
<211> LENGTH: 512
<212> TYPE: PRT
<213> ORGANISM: Yarrowia lipolytica

<400> SEQUENCE: 85

Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80
```

-continued

Met Gly Thr Phe Phe Ile Thr Gln Trp Lys Ser Pro Tyr Met Pro Trp
85 90 95

Val Asn Phe Gly Phe Val Met Thr His Leu Phe Val Asn His Leu Arg
100 105 110

Ser Gln Phe Phe Pro Glu Thr Tyr Asp Pro Asn Val Ile Asp Ile Thr
115 120 125

Gly Ala Gln Met Val Leu Cys Val Lys Leu Ser Ser Phe Gly Trp Asn
130 135 140

Val Tyr Asp Gly Trp Gln Ile Glu Lys Gly Glu Gln Leu Ser Glu Phe
145 150 155 160

Gln Thr Lys Arg Ala Val Leu Lys His Pro Ser Leu Met Asp Phe Leu
165 170 175

Ala Phe Val Phe Tyr Phe Pro Ser Ile Leu Thr Gly Pro Ser Tyr Asp
180 185 190

Tyr Met Glu Phe His Asn Trp Leu Asp Leu Ser Leu Phe Lys Glu Leu
195 200 205

Glu Lys Asp Lys Asp Pro Lys Arg Ala Ala Arg Arg Lys Arg His Lys
210 215 220

Ile Pro Arg Ser Gly Ile Ala Ala Ser Lys Lys Leu Ala Ala Gly Ile
225 230 235 240

Phe Trp Ile Val Leu Trp Thr Gln Val Asp Ser Arg Ile Ser Thr Ala
245 250 255

Tyr Ala Tyr Ser Asp Ala Phe Thr Lys Glu His Asn Ile Phe Gly Arg
260 265 270

Ile Val Tyr Leu Tyr Met Leu Gly Phe Met Tyr Arg Leu Lys Tyr Tyr
275 280 285

Gly Ala Trp Ser Ile Ser Glu Gly Ala Cys Ile Leu Ser Gly Leu Gly
290 295 300

Phe His Gly Val Asp Pro Lys Thr Gly Lys Tyr Lys Trp Asp Arg Val
305 310 315 320

Gln Asn Val Asp Pro Trp Gly Phe Glu Thr Gly Gln Asn Thr Lys Ala
325 330 335

Leu Leu Glu Ala Trp Asn Gln Asn Thr Asn Lys Trp Leu Arg Asn Tyr
340 345 350

Val Tyr Leu Arg Val Val Pro Lys Gly Gln Lys Pro Gly Phe Arg Ala
355 360 365

Thr Ile Phe Thr Phe Val Val Ser Ala Phe Trp His Gly Thr Arg Pro
370 375 380

Gly Tyr Tyr Leu Cys Phe Val Thr Ala Ala Met Tyr Gln Ser Val Gly
385 390 395 400

Lys Phe Phe Arg Arg Tyr Leu Arg Pro Phe Phe Met Glu Ser Asp Gly
405 410 415

Lys Thr Ala Gly Pro Tyr Lys Ile Tyr Tyr Asp Ile Val Cys Trp Ile
420 425 430

Val Val Gln Thr Ala Phe Gly Tyr Ala Thr Gln Ser Phe Met Ile Leu
435 440 445

Asp Phe Trp Leu Ser Leu Lys Cys Trp Lys Asn Ser Trp Phe Leu Tyr
450 455 460

His Ile Ala Leu Gly Ala Ile Phe Ala Ile Ser Ser Pro Tyr Lys Ala
465 470 475 480

Trp Ala Ile Pro Lys Ile Lys Lys Lys Gln Ala Gly Ala Val Thr Asp
485 490 495

Lys Lys Asp Ala Lys Glu Glu Val Lys Lys Asp Thr Ile Lys Thr Lys

-continued

```
            500                 505                 510

<210> SEQ ID NO 86
<211> LENGTH: 1539
<212> TYPE: DNA
<213> ORGANISM: Yarrowia lipolytica
<220> FEATURE:
<221> NAME/KEY: CDS
<222> LOCATION: (1)..(1539)

<400> SEQUENCE: 86

atg gcc ttt cct tgg gca gat aag tgg gca gcc gat gcg tct gca tct       48
Met Ala Phe Pro Trp Ala Asp Lys Trp Ala Ala Asp Ala Ser Ala Ser
1               5                   10                  15

aca ggg ctg cct ccg gac ctc ctc aag att gca ttc act ctg gtc atg       96
Thr Gly Leu Pro Pro Asp Leu Leu Lys Ile Ala Phe Thr Leu Val Met
            20                  25                  30

tct tat ccg ctg agt tct ctc atg aaa cgg ctg cca gat gac gcc aaa      144
Ser Tyr Pro Leu Ser Ser Leu Met Lys Arg Leu Pro Asp Asp Ala Lys
        35                  40                  45

aac ctc aag atc atc tat atc atc tcc gtg tcc atc ttc tac atg gtg      192
Asn Leu Lys Ile Ile Tyr Ile Ile Ser Val Ser Ile Phe Tyr Met Val
    50                  55                  60

ggt gtc ttc tcc ctc tat ggc gga gct gcc act ctg ctc ttc tcc tca      240
Gly Val Phe Ser Leu Tyr Gly Gly Ala Ala Thr Leu Leu Phe Ser Ser
65                  70                  75                  80

atg ggt acc ttc ttc atc acc caa tgg aag agc cct tac atg ccc tgg      288
Met Gly Thr Phe Phe Ile Thr Gln Trp Lys Ser Pro Tyr Met Pro Trp
                85                  90                  95

gtc aat ttt ggt ttt gtc atg acc cat ctc ttc gtc aat cac ctg cgt      336
Val Asn Phe Gly Phe Val Met Thr His Leu Phe Val Asn His Leu Arg
            100                 105                 110

tcg cag ttt ttc ccc gaa aca tac gac ccc aat gtc att gac atc acc      384
Ser Gln Phe Phe Pro Glu Thr Tyr Asp Pro Asn Val Ile Asp Ile Thr
        115                 120                 125

gga gca cag atg gtt ctg tgt atg aag cta tcg tct ttt gga tgg gct      432
Gly Ala Gln Met Val Leu Cys Met Lys Leu Ser Ser Phe Gly Trp Ala
    130                 135                 140

gtc tac gat gga tgg cag att gag aag ggt gag cag ctc agc gag ttc      480
Val Tyr Asp Gly Trp Gln Ile Glu Lys Gly Glu Gln Leu Ser Glu Phe
145                 150                 155                 160

cag act aaa agg gct gtt ctc aag cac ccc agt ctt atg gac ttc cta      528
Gln Thr Lys Arg Ala Val Leu Lys His Pro Ser Leu Met Asp Phe Leu
                165                 170                 175

gct ttt gtg ttc tac ttc cct tcc att ctg aca ggt cct tct tac gac      576
Ala Phe Val Phe Tyr Phe Pro Ser Ile Leu Thr Gly Pro Ser Tyr Asp
            180                 185                 190

tat atg gag ttc cat aac tgg ctc gat ctc agc ctg ttc aag gag ctg      624
Tyr Met Glu Phe His Asn Trp Leu Asp Leu Ser Leu Phe Lys Glu Leu
        195                 200                 205

gag aaa gat aag gac ccc aag cga gct gct cga cga aag cga cac aag      672
Glu Lys Asp Lys Asp Pro Lys Arg Ala Ala Arg Arg Lys Arg His Lys
    210                 215                 220

atc ccc cga tct gga atc gct gct tcc aag aaa ctc gcc gct ggt atc      720
Ile Pro Arg Ser Gly Ile Ala Ala Ser Lys Lys Leu Ala Ala Gly Ile
225                 230                 235                 240

ttc tgg atc gtt ctg tgg acc cag gtg gac tct cga atc tcc acc gcc      768
Phe Trp Ile Val Leu Trp Thr Gln Val Asp Ser Arg Ile Ser Thr Ala
                245                 250                 255

tac gct tac tca gac gca ttc acc aag gag cac aac atc ttt gga cga      816
Tyr Ala Tyr Ser Asp Ala Phe Thr Lys Glu His Asn Ile Phe Gly Arg
```

```
            260                 265                 270

att gtg tac ctc tac atg ctc ggt ttc atg tac cga ctc aag tac tac      864
Ile Val Tyr Leu Tyr Met Leu Gly Phe Met Tyr Arg Leu Lys Tyr Tyr
        275                 280                 285

gga gcc tgg tcc att tcc gag gga gcc tgc atc ttg tct ggc ctc gga      912
Gly Ala Trp Ser Ile Ser Glu Gly Ala Cys Ile Leu Ser Gly Leu Gly
    290                 295                 300

ttc cac ggc gtg gac ccc aaa act ggc aag tac aag tgg gac cgt gtc      960
Phe His Gly Val Asp Pro Lys Thr Gly Lys Tyr Lys Trp Asp Arg Val
305                 310                 315                 320

cag aac gtg gac ccg tgg gga ttc gaa act ggt caa aac aca aag gct     1008
Gln Asn Val Asp Pro Trp Gly Phe Glu Thr Gly Gln Asn Thr Lys Ala
                325                 330                 335

ctg ctg gag gcc tgg aac cag aac act aac aag tgg cta cga aac tat     1056
Leu Leu Glu Ala Trp Asn Gln Asn Thr Asn Lys Trp Leu Arg Asn Tyr
            340                 345                 350

gtg tac ctc cga gtg gtg ccc aaa ggc caa aag cct gga ttc cga gcc     1104
Val Tyr Leu Arg Val Val Pro Lys Gly Gln Lys Pro Gly Phe Arg Ala
        355                 360                 365

act atc ttc aca ttt gtg gtt tcc gcc ttc tgg cat gga act cga cct     1152
Thr Ile Phe Thr Phe Val Val Ser Ala Phe Trp His Gly Thr Arg Pro
    370                 375                 380

ggc tac tat ctc acc agc gtg acc gct gcc atg tac cag tct gtt ggt     1200
Gly Tyr Tyr Leu Thr Ser Val Thr Ala Ala Met Tyr Gln Ser Val Gly
385                 390                 395                 400

aag ttc ttc cga cga tac ctg cga ccc ttc ttc atg gag tct gat gga     1248
Lys Phe Phe Arg Arg Tyr Leu Arg Pro Phe Phe Met Glu Ser Asp Gly
                405                 410                 415

aag act gcc ggt ccc tat aag atc tac tac gac att gtg tgt tgg atc     1296
Lys Thr Ala Gly Pro Tyr Lys Ile Tyr Tyr Asp Ile Val Cys Trp Ile
            420                 425                 430

gtt gtc caa acc gca ttt gga tac gct acc cag tcc ttt atg att cta     1344
Val Val Gln Thr Ala Phe Gly Tyr Ala Thr Gln Ser Phe Met Ile Leu
        435                 440                 445

gac ttc tgg ctg tcg ctc aag tgt tgg aag aac tcc tgg ttc ctg tac     1392
Asp Phe Trp Leu Ser Leu Lys Cys Trp Lys Asn Ser Trp Phe Leu Tyr
    450                 455                 460

cac att gct ctg ggc gcc atc ttt gca att tct agc ccc tac aag gca     1440
His Ile Ala Leu Gly Ala Ile Phe Ala Ile Ser Ser Pro Tyr Lys Ala
465                 470                 475                 480

tgg gcg att ccc aag atc aag aaa aag cag gct gga gcc gtc act gac     1488
Trp Ala Ile Pro Lys Ile Lys Lys Lys Gln Ala Gly Ala Val Thr Asp
                485                 490                 495

aag aag gac gcc aag gag gag gtg aag aag gac acc atc aag acc aag     1536
Lys Lys Asp Ala Lys Glu Glu Val Lys Lys Asp Thr Ile Lys Thr Lys
            500                 505                 510

taa                                                                 1539


<210> SEQ ID NO 87
<211> LENGTH: 512
<212> TYPE: PRT
<213> ORGANISM: Yarrowia lipolytica

<400> SEQUENCE: 87

Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
```

-continued

```
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Met Lys Leu Ser Ser Phe Gly Trp Ala
    130                 135                 140

Val Tyr Asp Gly Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Pro
    370                 375                 380

Gly Tyr Tyr Leu Thr Ser Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460
```

```
His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510


<210> SEQ ID NO 88
<211> LENGTH: 1539
<212> TYPE: DNA
<213> ORGANISM: Yarrowia lipolytica
<220> FEATURE:
<221> NAME/KEY: CDS
<222> LOCATION: (1)..(1539)

<400> SEQUENCE: 88

atg gcc ttt cct tgg gca gat aag tgg gca gcc gat gcg tct gca tct       48
Met Ala Phe Pro Trp Ala Asp Lys Trp Ala Ala Asp Ala Ser Ala Ser
1               5                   10                  15

aca ggg ctg cct ccg gac ctc ctc aag att gca ttc act ctg gtc atg       96
Thr Gly Leu Pro Pro Asp Leu Leu Lys Ile Ala Phe Thr Leu Val Met
            20                  25                  30

tct tat ccg ctg agt tct ctc atg aaa cgg ctg cca gat gac gcc aaa      144
Ser Tyr Pro Leu Ser Ser Leu Met Lys Arg Leu Pro Asp Asp Ala Lys
        35                  40                  45

aac ctc aag atc atc tat atc atc tcc gtg tcc atc ttc tac atg gtg      192
Asn Leu Lys Ile Ile Tyr Ile Ile Ser Val Ser Ile Phe Tyr Met Val
    50                  55                  60

ggt gtc ttc tcc ctc tat ggc gga gct gcc act ctg ctc ttc tcc tca      240
Gly Val Phe Ser Leu Tyr Gly Gly Ala Ala Thr Leu Leu Phe Ser Ser
65                  70                  75                  80

atg ggt acc ttc ttc atc acc caa tgg aag agc cct tac atg ccc tgg      288
Met Gly Thr Phe Phe Ile Thr Gln Trp Lys Ser Pro Tyr Met Pro Trp
                85                  90                  95

gtc aat ttt ggt ttt gtc atg acc cat ctc ttc gtc aat cac ctg cgt      336
Val Asn Phe Gly Phe Val Met Thr His Leu Phe Val Asn His Leu Arg
            100                 105                 110

tcg cag ttt ttc ccc gaa aca tac gac ccc aat gtc att gac atc acc      384
Ser Gln Phe Phe Pro Glu Thr Tyr Asp Pro Asn Val Ile Asp Ile Thr
        115                 120                 125

gga gca cag atg gtt ctg tgt atg aag cta tcg tct ttt gga tgg aac      432
Gly Ala Gln Met Val Leu Cys Met Lys Leu Ser Ser Phe Gly Trp Asn
    130                 135                 140

gtc tac gat gct tgg cag att gag aag ggt gag cag ctc agc gag ttc      480
Val Tyr Asp Ala Trp Gln Ile Glu Lys Gly Glu Gln Leu Ser Glu Phe
145                 150                 155                 160

cag act aaa agg gct gtt ctc aag cac ccc agt ctt atg gac ttc cta      528
Gln Thr Lys Arg Ala Val Leu Lys His Pro Ser Leu Met Asp Phe Leu
                165                 170                 175

gct ttt gtg ttc tac ttc cct tcc att ctg aca ggt cct tct tac gac      576
Ala Phe Val Phe Tyr Phe Pro Ser Ile Leu Thr Gly Pro Ser Tyr Asp
            180                 185                 190

tat atg gag ttc cat aac tgg ctc gat ctc agc ctg ttc aag gag ctg      624
Tyr Met Glu Phe His Asn Trp Leu Asp Leu Ser Leu Phe Lys Glu Leu
        195                 200                 205

gag aaa gat aag gac ccc aag cga gct gct cga cga aag cga cac aag      672
Glu Lys Asp Lys Asp Pro Lys Arg Ala Ala Arg Arg Lys Arg His Lys
    210                 215                 220

atc ccc cga tct gga atc gct gct tcc aag aaa ctc gcc gct ggt atc      720
Ile Pro Arg Ser Gly Ile Ala Ala Ser Lys Lys Leu Ala Ala Gly Ile
```

```
225                 230                 235                 240

ttc tgg atc gtt ctg tgg acc cag gtg gac tct cga atc tcc acc gcc      768
Phe Trp Ile Val Leu Trp Thr Gln Val Asp Ser Arg Ile Ser Thr Ala
                245                 250                 255

tac gct tac tca gac gca ttc acc aag gag cac aac atc ttt gga cga      816
Tyr Ala Tyr Ser Asp Ala Phe Thr Lys Glu His Asn Ile Phe Gly Arg
            260                 265                 270

att gtg tac ctc tac atg ctc ggt ttc atg tac cga ctc aag tac tac      864
Ile Val Tyr Leu Tyr Met Leu Gly Phe Met Tyr Arg Leu Lys Tyr Tyr
        275                 280                 285

gga gcc tgg tcc att tcc gag gga gcc tgc atc ttg tct ggc ctc gga      912
Gly Ala Trp Ser Ile Ser Glu Gly Ala Cys Ile Leu Ser Gly Leu Gly
    290                 295                 300

ttc cac ggc gtg gac ccc aaa act ggc aag tac aag tgg gac cgt gtc      960
Phe His Gly Val Asp Pro Lys Thr Gly Lys Tyr Lys Trp Asp Arg Val
305                 310                 315                 320

cag aac gtg gac ccg tgg gga ttc gaa act ggt caa aac aca aag gct     1008
Gln Asn Val Asp Pro Trp Gly Phe Glu Thr Gly Gln Asn Thr Lys Ala
                325                 330                 335

ctg ctg gag gcc tgg aac cag aac act aac aag tgg cta cga aac tat     1056
Leu Leu Glu Ala Trp Asn Gln Asn Thr Asn Lys Trp Leu Arg Asn Tyr
            340                 345                 350

gtg tac ctc cga gtg gtg ccc aaa ggc caa aag cct gga ttc cga gcc     1104
Val Tyr Leu Arg Val Val Pro Lys Gly Gln Lys Pro Gly Phe Arg Ala
        355                 360                 365

act atc ttc aca ttt gtg gtt tcc gcc ttc tgg cat gga act cga cct     1152
Thr Ile Phe Thr Phe Val Val Ser Ala Phe Trp His Gly Thr Arg Pro
    370                 375                 380

ggc tac tat ctc acc agc gtg acc gct gcc atg tac cag tct gtt ggt     1200
Gly Tyr Tyr Leu Thr Ser Val Thr Ala Ala Met Tyr Gln Ser Val Gly
385                 390                 395                 400

aag ttc ttc cga cga tac ctg cga ccc ttc ttc atg gag tct gat gga     1248
Lys Phe Phe Arg Arg Tyr Leu Arg Pro Phe Phe Met Glu Ser Asp Gly
                405                 410                 415

aag act gcc ggt ccc tat aag atc tac tac gac att gtg tgt tgg atc     1296
Lys Thr Ala Gly Pro Tyr Lys Ile Tyr Tyr Asp Ile Val Cys Trp Ile
            420                 425                 430

gtt gtc caa acc gca ttt gga tac gct acc cag tcc ttt atg att cta     1344
Val Val Gln Thr Ala Phe Gly Tyr Ala Thr Gln Ser Phe Met Ile Leu
        435                 440                 445

gac ttc tgg ctg tcg ctc aag tgt tgg aag aac tcc tgg ttc ctg tac     1392
Asp Phe Trp Leu Ser Leu Lys Cys Trp Lys Asn Ser Trp Phe Leu Tyr
    450                 455                 460

cac att gct ctg ggc gcc atc ttt gca att tct agc ccc tac aag gca     1440
His Ile Ala Leu Gly Ala Ile Phe Ala Ile Ser Ser Pro Tyr Lys Ala
465                 470                 475                 480

tgg gcg att ccc aag atc aag aaa aag cag gct gga gcc gtc act gac     1488
Trp Ala Ile Pro Lys Ile Lys Lys Lys Gln Ala Gly Ala Val Thr Asp
                485                 490                 495

aag aag gac gcc aag gag gag gtg aag aag gac acc atc aag acc aag     1536
Lys Lys Asp Ala Lys Glu Glu Val Lys Lys Asp Thr Ile Lys Thr Lys
            500                 505                 510

taa                                                                 1539


<210> SEQ ID NO 89
<211> LENGTH: 512
<212> TYPE: PRT
<213> ORGANISM: Yarrowia lipolytica

<400> SEQUENCE: 89
```

-continued

```
Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Met Lys Leu Ser Ser Phe Gly Trp Asn
    130                 135                 140

Val Tyr Asp Ala Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Pro
    370                 375                 380

Gly Tyr Tyr Leu Thr Ser Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415
```

```
Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510


<210> SEQ ID NO 90
<211> LENGTH: 1539
<212> TYPE: DNA
<213> ORGANISM: Yarrowia lipolytica
<220> FEATURE:
<221> NAME/KEY: CDS
<222> LOCATION: (1)..(1539)

<400> SEQUENCE: 90

atg gcc ttt cct tgg gca gat aag tgg gca gcc gat gcg tct gca tct        48
Met Ala Phe Pro Trp Ala Asp Lys Trp Ala Ala Asp Ala Ser Ala Ser
1               5                   10                  15

aca ggg ctg cct ccg gac ctc ctc aag att gca ttc act ctg gtc atg        96
Thr Gly Leu Pro Pro Asp Leu Leu Lys Ile Ala Phe Thr Leu Val Met
            20                  25                  30

tct tat ccg ctg agt tct ctc atg aaa cgg ctg cca gat gac gcc aaa       144
Ser Tyr Pro Leu Ser Ser Leu Met Lys Arg Leu Pro Asp Asp Ala Lys
        35                  40                  45

aac ctc aag atc atc tat atc atc tcc gtg tcc atc ttc tac atg gtg       192
Asn Leu Lys Ile Ile Tyr Ile Ile Ser Val Ser Ile Phe Tyr Met Val
    50                  55                  60

ggt gtc ttc tcc ctc tat ggc gga gct gcc act ctg ctc ttc tcc tca       240
Gly Val Phe Ser Leu Tyr Gly Gly Ala Ala Thr Leu Leu Phe Ser Ser
65                  70                  75                  80

atg ggt acc ttc ttc atc acc caa tgg aag agc cct tac atg ccc tgg       288
Met Gly Thr Phe Phe Ile Thr Gln Trp Lys Ser Pro Tyr Met Pro Trp
                85                  90                  95

gtc aat ttt ggt ttt gtc atg acc cat ctc ttc gtc aat cac ctg cgt       336
Val Asn Phe Gly Phe Val Met Thr His Leu Phe Val Asn His Leu Arg
            100                 105                 110

tcg cag ttt ttc ccc gaa aca tac gac ccc aat gtc att gac atc acc       384
Ser Gln Phe Phe Pro Glu Thr Tyr Asp Pro Asn Val Ile Asp Ile Thr
        115                 120                 125

gga gca cag atg gtt ctg tgt atg aag cta tcg tct ttt gga tgg aac       432
Gly Ala Gln Met Val Leu Cys Met Lys Leu Ser Ser Phe Gly Trp Asn
    130                 135                 140

gtc tac gat aat tgg cag att gag aag ggt gag cag ctc agc gag ttc       480
Val Tyr Asp Asn Trp Gln Ile Glu Lys Gly Glu Gln Leu Ser Glu Phe
145                 150                 155                 160

cag act aaa agg gct gtt ctc aag cac ccc agt ctt atg gac ttc cta       528
Gln Thr Lys Arg Ala Val Leu Lys His Pro Ser Leu Met Asp Phe Leu
                165                 170                 175

gct ttt gtg ttc tac ttc cct tcc att ctg aca ggt cct tct tac gac       576
Ala Phe Val Phe Tyr Phe Pro Ser Ile Leu Thr Gly Pro Ser Tyr Asp
            180                 185                 190

tat atg gag ttc cat aac tgg ctc gat ctc agc ctg ttc aag gag ctg       624
Tyr Met Glu Phe His Asn Trp Leu Asp Leu Ser Leu Phe Lys Glu Leu
```

-continued

```
        195                 200                 205

gag aaa gat aag gac ccc aag cga gct gct cga cga aag cga cac aag      672
Glu Lys Asp Lys Asp Pro Lys Arg Ala Ala Arg Arg Lys Arg His Lys
    210                 215                 220

atc ccc cga tct gga atc gct gct tcc aag aaa ctc gcc gct ggt atc      720
Ile Pro Arg Ser Gly Ile Ala Ala Ser Lys Lys Leu Ala Ala Gly Ile
225                 230                 235                 240

ttc tgg atc gtt ctg tgg acc cag gtg gac tct cga atc tcc acc gcc      768
Phe Trp Ile Val Leu Trp Thr Gln Val Asp Ser Arg Ile Ser Thr Ala
                245                 250                 255

tac gct tac tca gac gca ttc acc aag gag cac aac atc ttt gga cga      816
Tyr Ala Tyr Ser Asp Ala Phe Thr Lys Glu His Asn Ile Phe Gly Arg
            260                 265                 270

att gtg tac ctc tac atg ctc ggt ttc atg tac cga ctc aag tac tac      864
Ile Val Tyr Leu Tyr Met Leu Gly Phe Met Tyr Arg Leu Lys Tyr Tyr
        275                 280                 285

gga gcc tgg tcc att tcc gag gga gcc tgc atc ttg tct ggc ctc gga      912
Gly Ala Trp Ser Ile Ser Glu Gly Ala Cys Ile Leu Ser Gly Leu Gly
    290                 295                 300

ttc cac ggc gtg gac ccc aaa act ggc aag tac aag tgg gac cgt gtc      960
Phe His Gly Val Asp Pro Lys Thr Gly Lys Tyr Lys Trp Asp Arg Val
305                 310                 315                 320

cag aac gtg gac ccg tgg gga ttc gaa act ggt caa aac aca aag gct     1008
Gln Asn Val Asp Pro Trp Gly Phe Glu Thr Gly Gln Asn Thr Lys Ala
                325                 330                 335

ctg ctg gag gcc tgg aac cag aac act aac aag tgg cta cga aac tat     1056
Leu Leu Glu Ala Trp Asn Gln Asn Thr Asn Lys Trp Leu Arg Asn Tyr
            340                 345                 350

gtg tac ctc cga gtg gtg ccc aaa ggc caa aag cct gga ttc cga gcc     1104
Val Tyr Leu Arg Val Val Pro Lys Gly Gln Lys Pro Gly Phe Arg Ala
        355                 360                 365

act atc ttc aca ttt gtg gtt tcc gcc ttc tgg cat gga att cga cct     1152
Thr Ile Phe Thr Phe Val Val Ser Ala Phe Trp His Gly Ile Arg Pro
    370                 375                 380

ggc tac tat ctc acc ttt gtg acc gct gcc atg tac cag tct gtt ggt     1200
Gly Tyr Tyr Leu Thr Phe Val Thr Ala Ala Met Tyr Gln Ser Val Gly
385                 390                 395                 400

aag ttc ttc cga cga tac ctg cga ccc ttc ttc atg gag tct gat gga     1248
Lys Phe Phe Arg Arg Tyr Leu Arg Pro Phe Phe Met Glu Ser Asp Gly
                405                 410                 415

aag act gcc ggt ccc tat aag atc tac tac gac att gtg tgt tgg atc     1296
Lys Thr Ala Gly Pro Tyr Lys Ile Tyr Tyr Asp Ile Val Cys Trp Ile
            420                 425                 430

gtt gtc caa acc gca ttt gga tac gct acc cag tcc ttt atg att cta     1344
Val Val Gln Thr Ala Phe Gly Tyr Ala Thr Gln Ser Phe Met Ile Leu
        435                 440                 445

gac ttc tgg ctg tcg ctc aag tgt tgg aag aac tcc tgg ttc ctg tac     1392
Asp Phe Trp Leu Ser Leu Lys Cys Trp Lys Asn Ser Trp Phe Leu Tyr
    450                 455                 460

cac att gct ctg ggc gcc atc ttt gca att tct agc ccc tac aag gca     1440
His Ile Ala Leu Gly Ala Ile Phe Ala Ile Ser Ser Pro Tyr Lys Ala
465                 470                 475                 480

tgg gcg att ccc aag atc aag aaa aag cag gct gga gcc gtc act gac     1488
Trp Ala Ile Pro Lys Ile Lys Lys Lys Gln Ala Gly Ala Val Thr Asp
                485                 490                 495

aag aag gac gcc aag gag gag gtg aag aag gac acc atc aag acc aag     1536
Lys Lys Asp Ala Lys Glu Glu Val Lys Lys Asp Thr Ile Lys Thr Lys
            500                 505                 510

taa                                                                 1539
```

<210> SEQ ID NO 91
<211> LENGTH: 512
<212> TYPE: PRT
<213> ORGANISM: Yarrowia lipolytica

<400> SEQUENCE: 91

```
Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Met Lys Leu Ser Ser Phe Gly Trp Asn
    130                 135                 140

Val Tyr Asp Asn Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335

Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Ile Arg Pro
```

```
    370                 375                 380

Gly Tyr Tyr Leu Thr Phe Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510


<210> SEQ ID NO 92
<211> LENGTH: 1539
<212> TYPE: DNA
<213> ORGANISM: Yarrowia lipolytica
<220> FEATURE:
<221> NAME/KEY: CDS
<222> LOCATION: (1)..(1539)

<400> SEQUENCE: 92

atg gcc ttt cct tgg gca gat aag tgg gca gcc gat gcg tct gca tct       48
Met Ala Phe Pro Trp Ala Asp Lys Trp Ala Ala Asp Ala Ser Ala Ser
1               5                   10                  15

aca ggg ctg cct ccg gac ctc ctc aag att gca ttc act ctg gtc atg       96
Thr Gly Leu Pro Pro Asp Leu Leu Lys Ile Ala Phe Thr Leu Val Met
            20                  25                  30

tct tat ccg ctg agt tct ctc atg aaa cgg ctg cca gat gac gcc aaa      144
Ser Tyr Pro Leu Ser Ser Leu Met Lys Arg Leu Pro Asp Asp Ala Lys
        35                  40                  45

aac ctc aag atc atc tat atc atc tcc gtg tcc atc ttc tac atg gtg      192
Asn Leu Lys Ile Ile Tyr Ile Ile Ser Val Ser Ile Phe Tyr Met Val
    50                  55                  60

ggt gtc ttc tcc ctc tat ggc gga gct gcc act ctg ctc ttc tcc tca      240
Gly Val Phe Ser Leu Tyr Gly Gly Ala Ala Thr Leu Leu Phe Ser Ser
65                  70                  75                  80

atg ggt acc ttc ttc atc acc caa tgg aag agc cct tac atg ccc tgg      288
Met Gly Thr Phe Phe Ile Thr Gln Trp Lys Ser Pro Tyr Met Pro Trp
                85                  90                  95

gtc aat ttt ggt ttt gtc atg acc cat ctc ttc gtc aat cac ctg cgt      336
Val Asn Phe Gly Phe Val Met Thr His Leu Phe Val Asn His Leu Arg
            100                 105                 110

tcg cag ttt ttc ccc gaa aca tac gac ccc aat gtc att gac atc acc      384
Ser Gln Phe Phe Pro Glu Thr Tyr Asp Pro Asn Val Ile Asp Ile Thr
        115                 120                 125

gga gca cag atg gtt ctg tgt atg aag cta tcg tct ttt gga tgg aac      432
Gly Ala Gln Met Val Leu Cys Met Lys Leu Ser Ser Phe Gly Trp Asn
    130                 135                 140

gtc tac gat aat tgg cag att gag aag ggt gag cag ctc agc gag ttc      480
Val Tyr Asp Asn Trp Gln Ile Glu Lys Gly Glu Gln Leu Ser Glu Phe
145                 150                 155                 160

cag act aaa agg gct gtt ctc aag cac ccc agt ctt atg gac ttc cta      528
Gln Thr Lys Arg Ala Val Leu Lys His Pro Ser Leu Met Asp Phe Leu
```

-continued

```
                165                 170                 175

gct ttt gtg ttc tac ttc cct tcc att ctg aca ggt cct tct tac gac      576
Ala Phe Val Phe Tyr Phe Pro Ser Ile Leu Thr Gly Pro Ser Tyr Asp
            180                 185                 190

tat atg gag ttc cat aac tgg ctc gat ctc agc ctg ttc aag gag ctg      624
Tyr Met Glu Phe His Asn Trp Leu Asp Leu Ser Leu Phe Lys Glu Leu
        195                 200                 205

gag aaa gat aag gac ccc aag cga gct gct cga cga aag cga cac aag      672
Glu Lys Asp Lys Asp Pro Lys Arg Ala Ala Arg Arg Lys Arg His Lys
    210                 215                 220

atc ccc cga tct gga atc gct gct tcc aag aaa ctc gcc gct ggt atc      720
Ile Pro Arg Ser Gly Ile Ala Ala Ser Lys Lys Leu Ala Ala Gly Ile
225                 230                 235                 240

ttc tgg atc gtt ctg tgg acc cag gtg gac tct cga atc tcc acc gcc      768
Phe Trp Ile Val Leu Trp Thr Gln Val Asp Ser Arg Ile Ser Thr Ala
                245                 250                 255

tac gct tac tca gac gca ttc acc aag gag cac aac atc ttt gga cga      816
Tyr Ala Tyr Ser Asp Ala Phe Thr Lys Glu His Asn Ile Phe Gly Arg
            260                 265                 270

att gtg tac ctc tac atg ctc ggt ttc atg tac cga ctc aag tac tac      864
Ile Val Tyr Leu Tyr Met Leu Gly Phe Met Tyr Arg Leu Lys Tyr Tyr
        275                 280                 285

gga gcc tgg tcc att tcc gag gga gcc tgc atc ttg tct ggc ctc gga      912
Gly Ala Trp Ser Ile Ser Glu Gly Ala Cys Ile Leu Ser Gly Leu Gly
    290                 295                 300

ttc cac ggc gtg gac ccc aaa act ggc aag tac aag tgg gac cgt gtc      960
Phe His Gly Val Asp Pro Lys Thr Gly Lys Tyr Lys Trp Asp Arg Val
305                 310                 315                 320

cag aac gtg gac ccg tgg gga ttc gaa act ggt caa aac aca aag gct     1008
Gln Asn Val Asp Pro Trp Gly Phe Glu Thr Gly Gln Asn Thr Lys Ala
                325                 330                 335

ctg ctg gag gcc tgg aac cag aac act aac aag tgg cta cga aac tat     1056
Leu Leu Glu Ala Trp Asn Gln Asn Thr Asn Lys Trp Leu Arg Asn Tyr
            340                 345                 350

gtg tac ctc cga gtg gtg ccc aaa ggc caa aag cct gga ttc cga gcc     1104
Val Tyr Leu Arg Val Val Pro Lys Gly Gln Lys Pro Gly Phe Arg Ala
        355                 360                 365

act atc ttc aca ttt gtg gtt tcc gcc ttc tgg cat gga act cga cct     1152
Thr Ile Phe Thr Phe Val Val Ser Ala Phe Trp His Gly Thr Arg Pro
    370                 375                 380

ggc tac tat ctc acc agc gtg acc gct gcc atg tac cag tct gtt ggt     1200
Gly Tyr Tyr Leu Thr Ser Val Thr Ala Ala Met Tyr Gln Ser Val Gly
385                 390                 395                 400

aag ttc ttc cga cga tac ctg cga ccc ttc ttc atg gag tct gat gga     1248
Lys Phe Phe Arg Arg Tyr Leu Arg Pro Phe Phe Met Glu Ser Asp Gly
                405                 410                 415

aag act gcc ggt ccc tat aag atc tac tac gac att gtg tgt tgg atc     1296
Lys Thr Ala Gly Pro Tyr Lys Ile Tyr Tyr Asp Ile Val Cys Trp Ile
            420                 425                 430

gtt gtc caa acc gca ttt gga tac gct acc cag tcc ttt atg att cta     1344
Val Val Gln Thr Ala Phe Gly Tyr Ala Thr Gln Ser Phe Met Ile Leu
        435                 440                 445

gac ttc tgg ctg tcg ctc aag tgt tgg aag aac tcc tgg ttc ctg tac     1392
Asp Phe Trp Leu Ser Leu Lys Cys Trp Lys Asn Ser Trp Phe Leu Tyr
    450                 455                 460

cac att gct ctg ggc gcc atc ttt gca att tct agc ccc tac aag gca     1440
His Ile Ala Leu Gly Ala Ile Phe Ala Ile Ser Ser Pro Tyr Lys Ala
465                 470                 475                 480

tgg gcg att ccc aag atc aag aaa aag cag gct gga gcc gtc act gac     1488
```

-continued

```
Trp Ala Ile Pro Lys Ile Lys Lys Lys Gln Ala Gly Ala Val Thr Asp
                485                 490                 495

aag aag gac gcc aag gag gag gtg aag aag gac acc atc aag acc aag      1536
Lys Lys Asp Ala Lys Glu Glu Val Lys Lys Asp Thr Ile Lys Thr Lys
            500                 505                 510

taa                                                                  1539


<210> SEQ ID NO 93
<211> LENGTH: 512
<212> TYPE: PRT
<213> ORGANISM: Yarrowia lipolytica

<400> SEQUENCE: 93

Met Ala Phe Pro Trp Ala Asp Lys Trp Ala Ala Asp Ala Ser Ala Ser
1               5                   10                  15

Thr Gly Leu Pro Pro Asp Leu Leu Lys Ile Ala Phe Thr Leu Val Met
            20                  25                  30

Ser Tyr Pro Leu Ser Ser Leu Met Lys Arg Leu Pro Asp Asp Ala Lys
        35                  40                  45

Asn Leu Lys Ile Ile Tyr Ile Ile Ser Val Ser Ile Phe Tyr Met Val
    50                  55                  60

Gly Val Phe Ser Leu Tyr Gly Gly Ala Ala Thr Leu Leu Phe Ser Ser
65                  70                  75                  80

Met Gly Thr Phe Phe Ile Thr Gln Trp Lys Ser Pro Tyr Met Pro Trp
                85                  90                  95

Val Asn Phe Gly Phe Val Met Thr His Leu Phe Val Asn His Leu Arg
            100                 105                 110

Ser Gln Phe Phe Pro Glu Thr Tyr Asp Pro Asn Val Ile Asp Ile Thr
        115                 120                 125

Gly Ala Gln Met Val Leu Cys Met Lys Leu Ser Ser Phe Gly Trp Asn
    130                 135                 140

Val Tyr Asp Asn Trp Gln Ile Glu Lys Gly Glu Gln Leu Ser Glu Phe
145                 150                 155                 160

Gln Thr Lys Arg Ala Val Leu Lys His Pro Ser Leu Met Asp Phe Leu
                165                 170                 175

Ala Phe Val Phe Tyr Phe Pro Ser Ile Leu Thr Gly Pro Ser Tyr Asp
            180                 185                 190

Tyr Met Glu Phe His Asn Trp Leu Asp Leu Ser Leu Phe Lys Glu Leu
        195                 200                 205

Glu Lys Asp Lys Asp Pro Lys Arg Ala Ala Arg Arg Lys Arg His Lys
    210                 215                 220

Ile Pro Arg Ser Gly Ile Ala Ala Ser Lys Lys Leu Ala Ala Gly Ile
225                 230                 235                 240

Phe Trp Ile Val Leu Trp Thr Gln Val Asp Ser Arg Ile Ser Thr Ala
                245                 250                 255

Tyr Ala Tyr Ser Asp Ala Phe Thr Lys Glu His Asn Ile Phe Gly Arg
            260                 265                 270

Ile Val Tyr Leu Tyr Met Leu Gly Phe Met Tyr Arg Leu Lys Tyr Tyr
        275                 280                 285

Gly Ala Trp Ser Ile Ser Glu Gly Ala Cys Ile Leu Ser Gly Leu Gly
    290                 295                 300

Phe His Gly Val Asp Pro Lys Thr Gly Lys Tyr Lys Trp Asp Arg Val
305                 310                 315                 320

Gln Asn Val Asp Pro Trp Gly Phe Glu Thr Gly Gln Asn Thr Lys Ala
                325                 330                 335
```

-continued

```
Leu Leu Glu Ala Trp Asn Gln Asn Thr Asn Lys Trp Leu Arg Asn Tyr
            340                 345                 350

Val Tyr Leu Arg Val Val Pro Lys Gly Gln Lys Pro Gly Phe Arg Ala
        355                 360                 365

Thr Ile Phe Thr Phe Val Val Ser Ala Phe Trp His Gly Thr Arg Pro
    370                 375                 380

Gly Tyr Tyr Leu Thr Ser Val Thr Ala Ala Met Tyr Gln Ser Val Gly
385                 390                 395                 400

Lys Phe Phe Arg Arg Tyr Leu Arg Pro Phe Phe Met Glu Ser Asp Gly
                405                 410                 415

Lys Thr Ala Gly Pro Tyr Lys Ile Tyr Tyr Asp Ile Val Cys Trp Ile
            420                 425                 430

Val Val Gln Thr Ala Phe Gly Tyr Ala Thr Gln Ser Phe Met Ile Leu
        435                 440                 445

Asp Phe Trp Leu Ser Leu Lys Cys Trp Lys Asn Ser Trp Phe Leu Tyr
    450                 455                 460

His Ile Ala Leu Gly Ala Ile Phe Ala Ile Ser Ser Pro Tyr Lys Ala
465                 470                 475                 480

Trp Ala Ile Pro Lys Ile Lys Lys Lys Gln Ala Gly Ala Val Thr Asp
                485                 490                 495

Lys Lys Asp Ala Lys Glu Glu Val Lys Lys Asp Thr Ile Lys Thr Lys
            500                 505                 510
```